United States Patent
Lovejoy et al.

(10) Patent No.: US 8,088,889 B2
(45) Date of Patent: Jan. 3, 2012

(54) TENEURIN C-TERMINAL ASSOCIATED PEPTIDES (TCAP) AND USES THEREOF

(76) Inventors: David Lovejoy, Stouffville (CA); R. Bradley Chewpoy, North Saanich (CA); Dalia Barsyte, Stouffville (CA); Susan Rotzinger, Etobicoke (CA)

( * ) Notice: Subject to any disclaimer, the term of this patent is extended or adjusted under 35 U.S.C. 154(b) by 818 days.

(21) Appl. No.: 10/510,959

(22) PCT Filed: May 2, 2003

(86) PCT No.: PCT/CA03/00622
§ 371 (c)(1),
(2), (4) Date: Aug. 10, 2005

(87) PCT Pub. No.: WO03/093305
PCT Pub. Date: Nov. 13, 2003

(65) Prior Publication Data
US 2006/0035318 A1    Feb. 16, 2006

Related U.S. Application Data

(60) Provisional application No. 60/376,879, filed on May 2, 2002, provisional application No. 60/377,231, filed on May 3, 2002, provisional application No. 60/424,016, filed on Nov. 6, 2002.

(51) Int. Cl.
| | |
|---|---|
| C07K 14/00 | (2006.01) |
| C07K 14/435 | (2006.01) |
| A61K 38/00 | (2006.01) |
| A61P 25/22 | (2006.01) |
| A61P 25/24 | (2006.01) |
| A61P 25/26 | (2006.01) |

(52) U.S. Cl. .......... 530/324; 514/2; 514/17.5; 514/17.6; 514/17.7

(58) Field of Classification Search ....................... None
See application file for complete search history.

(56) References Cited

FOREIGN PATENT DOCUMENTS
WO    WO 01/88088    * 11/2001

OTHER PUBLICATIONS

Guo et al. Proceedings of the National Academy of Sciences, 101(25): 9205-9210, Jun. 2004.*
Rubin et al., Developmental Biology 216:196-209, 1999.*
Baumgartner, S. et al. "Tenm, a Drosophila gene related to tenascin, is a new pair-rule gene", The EMBO Journal, England, vol. 13, No. 16, p. 3728-3740, Aug. 1994.
Chiquet-Ehrismann, R. "Gallus gallus mRNA for teneurin-2, short splice variant (ten2gene) short splice variant; ten2 gene; teneurin-2; Type II transmembrane protein", EMBL (XP002190351).
Dgang, O. et al. "The Drosophila odz/ten-m gene encodes a type I, multiply cleaved heterodimeric transmembrane protein". The Biochemical Journal, England, vol. 363, No. Pt. 3, p. 633-643, May 2002.
Wang, X.Z. et al. "Identification of novel stress-induced genes downstream of chop". The EMBO J., England, vol. 17, No. 13, p. 3619-3630, Jul. 1998.

* cited by examiner

*Primary Examiner* — Lorraine Spector
*Assistant Examiner* — Stacey MacFarlane
(74) *Attorney, Agent, or Firm* — McCarthy Tétrault LLP; Anita Nador

(57) ABSTRACT

The invention provides a novel family of biologically active neuropeptides and the nucleic aid molecules coding for same. The peptides are derived for the C-terminus of the teneurin family peptides (Ten M1-4). These novel peptides, referred to as teneurin C-terminal associated peptides (TCAPs) are active in neuronal communication and are implicated in a number of neuropathologies. They are particularly useful in modulating stress responses and anxiety and in the treatment of cancer.

35 Claims, 30 Drawing Sheets

FIGURE 1

```
5'-tccatctcgggggtgcaacaggaagtgacccggcaagccaaggctttcctgtccttcgag    60
    S  I  S  G  V  Q  Q  E  V  T  R  Q  A  K  A  F  L  S  F  E    20
   aggatgccggagatccagctgagccgccggcgctccaaccgggagaaaccctggctgtgg   120
    R  M  P  E  I  Q  L  S  R  R  R  S  N  R  E  K  P  W  L  W    40
   ttcgccaccgccaagtctctgatcggtaaggtgtcatgttggcggtgacgcagggccgt    180
    F  A  T  A  K  S  L  I  G  K  V  M  L  A  V  T  Q  G  R       60
   gtggtcaccaacgctctgaacatcgccaacgaggactgcatcaaggtcgccgccgtcctc   240
    V  V  T  N  A  L  N  I  A  N  E  D  C  I  K  V  A  A  V  L    80
   aacaatgcgttctacctggaggacctgcacttcacggtggagggacgcgacacgcactac   300
    N  N  A  F  Y  L  E  D  L  H  F  T  V  E  G  R  D  T  H  Y   100
   ttcatcaagaccagcctcccggagagcgacctgggagcgctgaggctgacaagcgggagg   360
    F  I  K  T  S  L  P  E  S  D  L  G  A  L  R  L  T  S  G  R   120
   aagtcgctggagaacggaagtcaacgtgactgtgtcccagtccaccaccgtggtgaacgg   420
    K  S  L  E  N  G  V  N  V  T  V  S  Q  S  T  T  V  V  N  G   140
   cagaaccggcgcttcgccgacgtggagctgcagtacggcgctctagcgctccacgtgcgc   480
    R  T  R  R  F  A  D  V  E  L  Q  Y  G  A  L  A  H  V  R      160
   tatggcatgactctggacgaggagaaggcgcgtgtgctggagcaggccaggcagaaggcg   540
    Y  G  M  T  L  D  E  E  K  A  R  V  L  E  Q  A  R  Q  K  A   180
   ttgtcgagtgcctggtccagggagcaacaacgggtgagggaggggaggaggggtgagg    600
    L  S  S  A  W  S  R  E  Q  Q  R  V  R  E  G  E  E  G  V  R   200
   ctgtggacggaggggagaagaggcagctgctgagcgggaggaaggttctgggctacgac   660
    L  W  T  E  G  E  K  R  Q  L  L  S  G  R  K  V  L  G  Y  D   220
   gggtactacgtcctctccatagagcagtaccccgagctagcagactccgctaacaacatc   720
    G  Y  Y  V  L  S  I  E  Q  Y  P  E  L  A  D  S  A  N  N  I   240
   cagttcctcaggcagagcgaaatagggaagagggtaa    (SEQ.ID.NO.2)          756
    Q  F  L  R  Q  S  E  I  G  K  R  stop  (SEQ.ID.NO.3)          251
                                       cagacagaatcctcggcactggcc   780
   gccaaagagactacccctccaaatcctgccccccaacctccctcgcctccccccttttc   840
   tctaaaaggggagggtccaggctagtgctgtgtttagcgccgactagctgaaacaaac    900
   agtaaaatgtagaatatcttaaactgaactatacctaatactaccactgtggggcctgaa   960
   aatcaaacaaaacggctccaactgacgcaaatgtttgtcccatgtgctatacagcgttga  1020
   atggactgtggactctcttgaaagagagaaaaaaagtcaaaactctcggtttgtgaaa    1080
   ggagaaaaaacgttttttttttttttaaatagacttcctgaatttgctttcggaaaaaa  1140
   tatttttaaaagaaagaagaaatgtgtttacatacgcataacactacaacacgtctggac  1200
   taatagaagaaaagccttctggtttcttacacaggacaacgtctataatctgattctaca  1260
   tcctgacgactgacctttgattgacctttgcgtactgaaaaaggtagtgttgttgttcgc  1320
   agtaggaccatgggtctccaatggtggtaactagacagttaaaaccacttgttgaaacca  1380
   cttgcttgttcttctgcttttctttccaaaagggacaaaacagctcccaccaagtgactt  1440
   ctttaccaatactagatcaaagtgggacgttttgggctcgtgccgaattc-3' (SEQ.ID.NO.1)1490
```

FIGURE 2

```
O.mykiss   Ten M3    SISGVQQEVTRQAKAFLSFERMPEIQLSRRRSNREKPWLWFATAKSLIGK
R.danio    Ten M3    SISGVQQEVMRQAKAFLSFERMPEIQLSRRRSSREKPWLWFATVKSLIGK
M.musculus Ten M3    PIFGVQQQVARQAKAFLSLGKMAEVQVSRRKAGAEQSWLWFATVKSLIGK
H.sapiens  Ten M3    PIFGVQQQVARQAKAFLSLGKMAEVQVSRRRAGGAQSWLWFATVKSLIGK O.mykiss   Ten M3    GVMLAVT QGRVVTNALNIANEDCIKVAAVLNNAFYLEDLHFTVEGRDTH
R.danio    Ten M3    GVMLAITSKGQVATNALNIANEDCIKVVIVLNNAFYLEDLHFTVEGRDTH
M.musculus Ten M3    GVMLAVS QGRVQTNVLNIANEDCIKVAAVLNNAFYLENLHFTIEGKDTH
H.sapiens  Ten M4    GVMLAVS QGRVQTNVLNIANEDCIKVAAVLNNAFYLENLHFTIEGKDTH O.mykiss   Ten M3    YFIKTSLPESDLGALRLTSGRKSLENGVNVTVSQSTTVVNGRTRRFADVE
R.danio    Ten M3    YFIKTSLPESDLGALRLTSGRKSLENGVNVTVSQSTTVVNGRTRRFADVE
M.musculus Ten M3    YFIKTTTPESDLGTLRLTSGRKALENGINVTVSQSTTVVNGRTRRFADVE
H.sapiens  Ten M3    YFIKTTTPESDLGTLRLTSGRKALENGINVTVSQSTTVVNGRTRRFADVE O.mykiss   Ten M3    LQYGALALHVRYGMTLDEEKARVLEQARQKALSSAWSREQQRVREGEEGV
R.danio    Ten M3    LQYGALALHVRYGMTLDEEKARVLEQARQRALSSAWAREQQRVRDGEEGV
M.musculus Ten M3    MQFGALALHVRYGMTLDEEKARILEQARQRALARAWAREQQRVRDGEEGA
H.sapiens  Ten M3    MQFGALALHVRYGMTLDEEKARILEQARQRALARAWAREQQRVRDGEEGA O.mykiss   Ten M3    RLWTEGEKRQLLSGRKVLGYDGYYVLSIEQYPELADSANNIQFLRQSEIG
R.danio    Ten M3    RLWTEGEKRQLLSSGKVLGYDGYYVLSVEQYPELADSANNVQFLRQSEIG
M.musculus Ten M3    RLWTEGEKRQLLSAGKVQGYDGYYVLSVEQYPELADSANNIQFLRQSEIG
H.sapiens  M3        RLWTEGEKRQLLSAGKVQGYDGYYVLSVEQYPELADSANNIQFLRQSEIG O. mykiss   Ten M3    KR (SEQ.ID.NO.3)
R. danio    Ten M3    KR (SEQ.ID.NO.12)
M. musculus Ten M3    KR (SEQ.ID.NO.6)
H. sapiens  Ten M3    RR (SEQ.ID.NO.10)
```

FIGURE 3

```
Mouse Teneurin 1      MILGIQCELQKQLRNFISLDQLPMTPQYNEGRCLEGGKQPRFAAVPSVFG
Mouse Ten eurin M2    LITGVQQTTERHNQAFLALEGQVITKKLHAS  IREKAGHWFATTTPIIG
Mouse Ten eurin M3    PIFGVQQQVARQAKAFLSL GKMAEVQVSRRKAGAEQSWLWFATVKSLIG
Mouse Ten eurin M4    SILGVQCEVQKQLKAFVTLERFDQLYGSTITSCQQAPETKKFASSGSIFG Mouse Teneurin 1      KGIKFAIKEGIVTADIIGVANEDSRRLAAILNNAHYLENLHFTIEGRDTH
Mouse Teneurin 2      KGIMFAIKEGRVTTGVSSIASEDSRKVASVLNNAYYLDKMHYSIEGKDTH
Mouse Teneurin 3      KGVMLAVSQGRVQTNVLNIANEDCIKVAAVLNNAFYLENLHFTIEGKDTH
Mouse Teneurin 4      KGVKFALKDGRVTTDIISVANEDGRRIAAILNNAHYLENLHFTIDGVDTH Mouse Teneurin 1      YFIKLGSLEEDLVLIGNTGGRRILENGVNVTVSQMTSVLNGRTRRFADIQ
Mouse Teneurin 2      YFVKIGAADGDLVTLGTTIGRKVLESGVNVTVSQPTLLVNGRTRRFTNIE
Mouse Teneurin 3      YFIKTTTPESDLGTLRLTSGRKALENGINVTVSQSTTVVNGRTRRFADVE
Mouse Teneurin 4      YFVKPGPSEGDLAILGLSGGRRTLENGVNVTVSQINTML Mouse Teneurin 1      LQHGALCFNIRYGTT   VEEEKNHVLEMARQRAVAQAWTQEQRRLQEGE
Mouse Teneurin 2      FQYSTLLLSIRYGLTPDTLDEEKARVLDQAGQRALGTAWAKEQQKARDGR
Mouse Teneurin 3      MQFGALALHVRYGMT   LDEEKARILEQARQRALARAWAREQQRVRDGE
Mouse Teneurin 4      IQLQYRALCLNTRYGT  TVDEEKVRVLELARQRAVRQAWAREQQRLREGE Mouse Teneurin 1      EGTRVWTEGEKQQLLGTGRVQGYDGYFVLSVEQYLELSDSANNIHFMRQS
Mouse Teneurin 2      EGSRLWTEGEKQQLLSTGRVQGYEGYYVLPVEQYPELADSSSNIQFLRQN
Mouse Teneurin 3      EGARLWTEGEKRQLLSAGKVQGYDGYYVLSVEQYPELADSANNIQFLRQS
Mouse Teneurin 4      EGLRAWTDGEKQQVLNTGRVQGYDGFFVTSVEQYPELSDSANNIHFMRQS Mouse Teneurin 1      EIGRR  (SEQ.ID.NO.4)
Mouse Teneurin 2      EMGKR  (SEQ.ID.NO.5)
Mouse Teneurin 3      EIGKR  (SEQ.ID.NO.6)
Mouse Teneurin 4      EMGRR  (SEQ.ID.NO.7)
```

FIGURE 4

```
Human Ten M1    TILGIQCELQKQLRNFISL     D QLPMTPRYNDGRCLEGGKQ    PRFA
Human Ten M2    LITGVQQTTERHNQAFMALE      GQV ITKKLHASIREKAGHW     FA
Human Ten M3    PIFGVQQQVARQAKAFLSLGKMAEVQV SRRRAGGA    QS   WLW   FA
Human Ten M4    SILGVQCEVQKQLKAFVTLER  FD QL     YGSTITSCLQAPKT    KKFA Human Ten M1    AVPSVFGKGIKFAIKDGIVTADIIGVANEDSRRLAAILNNAHYLENLHFT
Human Ten M2    TTTPIIGKGIMFAIKEGRVTTGVSSIASEDSRKVASVLNNAYYLDKMHYS
Human Ten M3    TVKSLIGKGVMLAVSQGRVQTNVLNIANEDCIKVAAVLNNAFYLENLHFT
Human Ten M4    SSGSVFGKGVKFALKDGRVTTDIISVANEDGRRVAAILNHAHYLENLHFT Human Ten M1    IEGRDTHYFIKLGSLEEDLVLIGNTGGRRILENGVNVTVSQMTSVLNGRT
Human Ten M2    IEGKDTHYFVKIGSADGDLVTLGTTIGRKVLESGVNVTVSQPTLLVNGRT
Human Ten M3    IEGKDTHYFIKTTTPESDLGTLRLTSGRKALENGINVTVSQSTTVVNGRT
Human Ten M4    IDGVDTHYFVKPGPSEGDLAILGLSGGRRTLENGVNVTVSQINTVLSGRT Human Ten M1    RRFADIQLQHGALCFNIRYGTT    VEEEKNHVLEIARQRAVAQAWTKEQ
Human Ten M2    RRFTNIEFQYSTLLLSIRYGLTPDTLDEEKARVLDQARQRALGTAWAKEQ
Human Ten M3    RRFADVEMQFGALALHVRYGMT    LDEEKARILEQARQRALARAWAREQ
Human Ten M4    RRYTDIQLQYGALCLNTRYGTT    LDEEKARVLELARQRAVRQAWAREQ Human Ten M1    RRLQEGEEGIRAWTEGEKQQLLSTGRVQGYDGYFVLSVEQYLELSDSANN
Human Ten M2    QKARDGREGSRLWTEGEKQQLLSTGRVQGYEGYYVLPVEQYPELADSSSN
Human Ten M3    QRVRDGEEGARLWTEGEKRQLLSAGKVQGYDGYYVLSVEQYPELADSANN
Human Ten M4    QRLREGEEGLRAWTEGEKQQVLSTGRVQGYDGFFVISVEQYPELSDSANN Human Ten M1    IHFMRQSEIGRR  (SEQ.ID.NO.8)
Human Ten M2    IQFLRQNEMGKR  (SEQ.ID.NO.9)
Human Ten M3    IQFLRQSEIGRR  (SEQ.ID.NO.10)
Human Ten M4    IHFMRQSEMGRR  (SEQ.ID.NO.11)
```

FIGURE 5

Human TCAP-1

```
cag cag ctt ttg agc act ggg cgg gta caa
ggt tac gat ggg tat ttt gtt ttg tct gtt
gag cag tat tta gaa ctt tct gac agt gcc      (SEQ.ID.NO.76
aat aat att cac ttt atg aga cag agc gaa       +stop codon)
ata ggc agg agg taa
```

Human TCAP-2

```
cag cag ctt ctg agc acc ggg cgc gtg caa
ggg tac gag gga tat tac gtg ctt ccc gtg
gag caa tac cca gag ctt gca gac agt agc      (SEQ.ID.NO.84
agc aac atc cag ttt tta aga cag aat gag       +stop codon)
atg gga aag agg taa
```

Human TCAP-3

```
cgg cag ctg ctg agc gcc ggc aag gtg cag
ggc tac gac ggg tac tac gta ctc tcg gtg
gag cag tac ccc gag ctg gcc gac agc gcc      (SEQ.ID.NO.92
aac aac atc cag ttc ctg cgg cag agc gag       +stop codon)
atc ggc agg agg taa
```

Human TCAP-4

```
cag cag gtg ctg agc aca ggg cgg gtg caa
ggc tac gac ggc ttt ttc gtg atc tct gtc
gag cag tac cca gaa ctg tca gac agc gcc      (SEQ.ID.NO.100
aac aac atc cac ttc atg aga cag agc gag       +stop codon)
atg ggc cgg agg tga
```

Mouse TCAP-1

```
cag cag ctt ttg ggc acc ggg agg gtg cag
ggg tat gat ggg tat ttt gtc ttg tct gtt
gag cag tat tta gaa ctt tca gac agt gcc      (SEQ.ID.NO.44
aac aat att cac ttc atg aga cag agt gaa       +stop codon)
ata ggc agg agg taa
```

FIGURE 5 (CONT'D)

Mouse TCAP-2

```
cag caa ctc ctg agc acg gga cgg gta caa
ggt tat gag ggc tat tac gta ctt ccg gtg
gaa cag tac ccg gag ctg gca gac agt agc      (SEQ.ID.NO.52
agc aac atc cag ttc tta aga cag aat gag       +stop codon)
atg gga aag agg taa
```

Mouse TCAP-3

```
cgg cag ctg ctg agc gct ggc aag gtg cag
ggc tac gat ggg tac tac gta ctg tcg gtg
gag cag tac ccc gag ctg gct gac agt gcc      (SEQ.ID.NO.60
aac aac atc cag ttc ttg cga caa agt gag       +stop codon)
atc ggc aag agg taa
```

Mouse TCAP-4

```
cag cag gtg ctg aac acg ggg cgg gtg caa
ggc tac gac ggc ttc ttt gtg acc tcg gtc
gag cag tac cca gaa ctg tca gac agc gcc      (SEQ.ID.NO.68
aac aat atc cac ttc atg aga cag agc gag       +stop codon)
atg ggc cga agg tga
```

Zebrafish TCAP-3

```
agg cag ttg ctc agc tct ggg aag gtg ctg
ggt tac gat ggt tac tat gta cta tca gtg
gag caa tac cct gaa ctg gcc gac agt gcc      (SEQ.ID.NO.28
aac aat gtc cag ttc ttg agg cag agt gag       +stop codon)
ata ggg aag agg taa
```

Zebrafish TCAP-4

```
cag cag ctc cta agc tct gga cgt gta cag
ggc tac gaa ggc ttc tac ata gta tca gtc
gac cag ttc cca gag ttg act gac aac ata      (SEQ.ID.NO.36
aat aac gtc cat ttc tgg cga cag act gag       +stop codon)
atg gga cgc agg tga
```

Rainbow Trout TCAP-3

```
5'-agg cag ctg ctg agc ggg agg aag gtt ctg
ggc tac gac ggg tac tac gtc ctc tcc ata
gag cag tac ccc gag cta gca gac tcc gct      (SEQ.ID.NO.20
aac aac atc cag ttc ctc agg cag agc gaa       +stop codon)
ata ggg aag agg taa-3'
```

FIGURE 6B

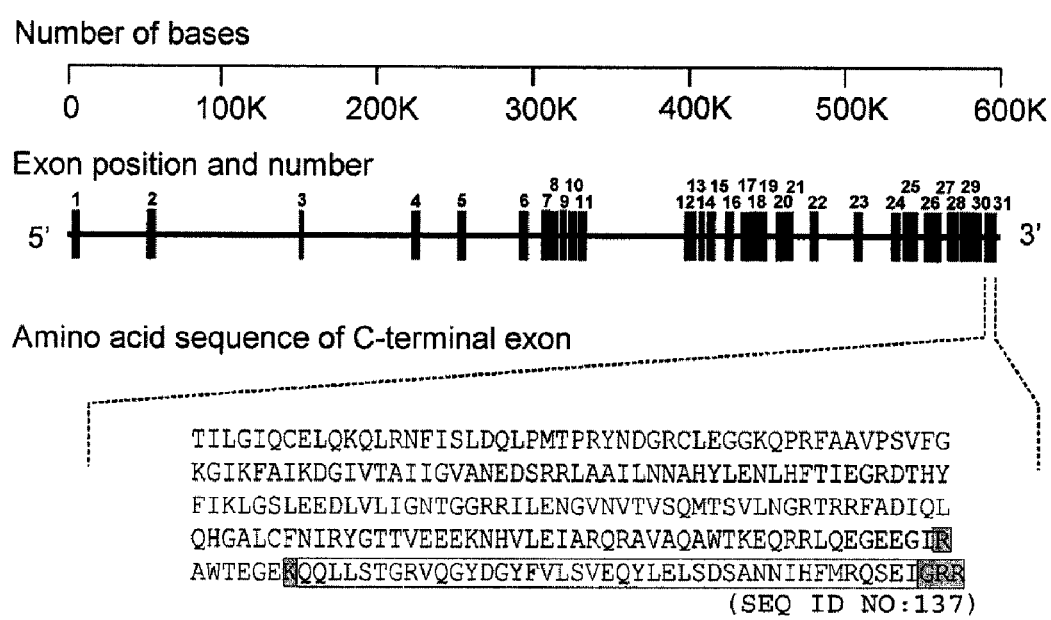

Number of bases

Exon position and number

Amino acid sequence of C-terminal exon

TILGIQCELQKQLRNFISLDQLPMTPRYNDGRCLEGGKQPRFAAVPSVFG
KGIKFAIKDGIVTAIIGVANEDSRRLAAILNNAHYLENLHFTIEGRDTHY
FIKLGSLEEDLVLIGNTGGRRILENGVNVTVSQMTSVLNGRTRRFADIQL
QHGALCFNIRYGTTVEEEKNHVLEIARQRAVAQAWTKEQRRLQEGEEGIR
AWTEGERQQLLSTGRVQGYDGYFVLSVEQYLELSDSANNIHFMRQSEIGRR
(SEQ ID NO:137)

Mammalian TCAP Sequences

| | | Accession Numbers |
|---|---|---|
| human TCAP 1 | QQLLSTGRVQGYDGYFVLSVEQYLELSDSANNIHEMRQSEI-NH2 | nm_014253 (SEQ.ID.NO.69) |
| human TCAP 2 | QQLLSTGRVQGYEGYYVLPVEQYPELADSSSNIQFLRQNEM-NH2 | xm_047995 (SEQ.ID.NO.78) |
| human TCAP 3 | QLLSAGKVQGYDGYYVLSVEQYPEHADSANNIQFLRQSEI-NH2 | ak001336 (SEQ.ID.NO.85) |
| human TCAP 4 | QQVLSTGRVQGYDGFFVISVEQYPELSDSANNIHEMRQSEM-NH2 | ak056531 (SEQ.ID.NO.94) |
| mouse TCAP 1 | QQLLGTGRVQGHDGYFVLSVEQYLELSDSANNIHEMRQSEI-NH2 | nm_011855 (SEQ.ID.NO.37) |
| mouse TCAP 2 | QQLLSTGRVQGYEGYYVLPVEQYPELADSSSNIQFLRQNEM-NH2 | nm_011856 (SEQ.ID.NO.46) |
| mouse TCAP 3 | QLLSAGKVQGYDGYYVLSVEQYPEHADSANNIQFLRQSEI-NH2 | nm_011857 (SEQ.ID.NO.53) |
| mouse TCAP 4 | QQVINTGRVQGYDGFFVTSVEQYPELSDSANNIHEMRQSEM-NH2 | ab025413 (SEQ.ID.NO.66) |
| Rat TCAP 2 | QQLLSTGRVQGYEGYYVLPVEQYPELADSSSNIQFLRQNEM-NH2 | nm_020088 (SEQ.ID.NO.78) |

Avian TCAP Sequences

| | | |
|---|---|---|
| chicken TCAP 1 | QQLLNTGRVQGYEGYYVLPVEQYPELSDSANNIHEMRQSEI-NH2 | aj238613 (SEQ.ID.NO.101) |
| chicken TCAP 2 | QQLLNTGRVQGYEGYYVLPVEQYPFLADSSNIQFLRQNEM-NH2 | aj279031 (SEQ.ID.NO.136) |

Piscine TCAP Sequences

| | | |
|---|---|---|
| Rainbow trout TCAP 3 | QLLSGRKVLGYDGYYVLSIEQYPELADSANNIQFLRQSEI-NH2 | not entered yet (SEQ.ID.NO.13) |
| zebrafish TCAP 3 | QLLSSGKVLGYDGYYVLSVEQYPELADSANNVQFLRQSEI-NH2 | nm_130968 (SEQ.ID.NO.21) |
| zebrafish TCAP 4 | QQLLSSGRVQGVEGFYIVSVDQFPEETDNINVHHWRQTEM-NH2 | ab026980 (SEQ.ID.NO.30) |
| Insect Drospholia | ELVQHGDVDGWNG1DIHSIHKYPQLADOPGNVAFQRDAK | (SEQ.ID.NO.103) |

FIGURE 7A

| Protein name | Species | Truncated Peptide | SEQ ID NO: | % Identical | % Homolog |
|---|---|---|---|---|---|
| Ten-m1/odd Odz1 | M musculus | QLLGTGRVQGYDGYFVLSVEQYLELSDSANNIHFMRQSEI | 37 | 100 | |
| Teneurin-1 | G gallus | QLLNTGRVQGYDGYFVLSVEQYLELSDSANNIHFMRQSEI | 138 | 97 | 97 |
| Odz (odd Oz1/ten-m1) / tenascin M | H sapiens | QLLNTGRVQGYDGYFVLSVEQYLELSDSANNIHFMRQSEI | 69 | 97 | 97 |
| Mouse DOC4-like protein | H sapiens | QLLSTGRVQGYDGYFVLSVEQYLELSDSANNIHFMRQSEI | 69 | 97 | 97 |
| DOC4/Ten-m4 /odd Oz4 | M musculus | QLLNTGRVQGYDGYFVLSVEQYPELSDSANNIHFMRQSE | 61 | 85 | 92 |
| Similar to odd Oz4/ten-m4/ KIAA1302 protein | H sapiens | QLLSTGRVQGYDGYFVLSVEQYPELSDSANNIHFMRQSE | 93 | 85 | 95 |
| Hypothetical protein/DKFZp564O0423.1 (fragment) | H sapiens | QLLSTGRVQGYDGYFVLSVEQYPELSDSANNIHFMRQSE | 93 | 85 | 95 |
| odd Oz/ten-m3/ ODZ3 | M musculus | QLLSAGVQGYDGYVLSVEQYPELDSANNIQFRQSEI | 53 | 80 | 90 |
| Hypothetical protein FLJ10474; FLJ10886, unnamed protein products: AK001336, AK027473, AK001748 | H sapiens | QLLSAGVQGYDGYVLSVEQYPELDSANNIQFRQSEI | 53 | 80 | 90 |
| Putative (AK011924) | M musculus | QLLSAGVQGYDGYVLSVEQYPELDSANNIQFRQSEI | 53 | 80 | 90 |
| N/A | R trout | QLLSGRVHGYDGYVLSEQYPELDSANNIQFRQSEI | 13 | 80 | 90 |
| Ten-m3 | D rerio | QLLGVEGYDGYVLSVEQYPELDSANNQFRQSEI | 21 | 75 | 90 |
| Neurestin alpha | R norvegicus | QLLSTGRVQGYGYVLPVEQYPELDSNIQFRQE | 77 | 70 | 90 |
| Teneurin-2 | G gallus | QLLSTGRVQGYGYVLPVEQYPELDSNIQFRQE | 77 | 70 | 90 |
| Ten-m2/ ODZ2/ odd Oz2 | M musculus | QLLSTGRVQGYGYVLPVEQYPELDSNIQFRQE | 77 | 70 | 90 |
| Odd Oz/ten-m2/ KIAA1127 protein / hypothetical protein DKFZp761F171.1 (fragment) | H sapiens | QLLSTGRVQGYGYVLPVEQYPELDSNIQFRQE | 77 | 70 | 90 |
| Hypothetical protein | H sapiens | QLLSTGRVQGYGYVLPVEQYPELDNIQFRQE | 77 | 70 | 90 |
| Odd Oz/ten-m2 | H sapiens | QLLSTGRVQGYGYVLPVEQYPELDNIQFRQE | 77 | 70 | 90 |
| Ten-m4 | D rerio | QLLSGRVQGYSVQPELDENNHFMRQE | 29 | 57 | 89 |
| odd Oz/tenascin-like protein/Ten-m gene product | D melanogaster | LQHGEVDGGDRSHYRLDDRGNAFQRD | 103 | 30 | 60 |

FIGURE 7B

CRF Peptide Family

| | | |
|---|---|---|
| human CRF | SEEPPISLDLTFHLLREVLEMARAEQLAQQAHSNRKLMEII | (SEQ.ID.NO.104) |
| human urocortin | DNPSLSIDLTFHLLRTLLELARTQSQRERAEQNRIIFDS | (SEQ.ID.NO.105) |
| human urocortin 2 | IVLSLDVPIGLLQILLEQARARAAREQATTNARILARV | (SEQ.ID.NO.106) |
| human urocortin 3 | FTLSLDVPTNIMNLLFNIAKAKNLRAQAAANAHLMAQI | (SEQ.ID.NO.107) |

TCAP Peptide Family

| | | |
|---|---|---|
| human TCAP 1 | QQLESTGRVQGYDGYFVLSVEQYLELSDSANNTHEMRQSEI | (SEQ.ID.NO.70) |
| human TCAP 2 | QQLLSTGRVQGYEGYMVLPVEQYPELADSSSNIQFLRQNEM | (SEQ.ID.NO.78) |
| human TCAP 3 | QLLSAGHVQGYDGYMVLSVEQVPELADSANNIQFLRQSEI | (SEQ.ID.NO.85) |
| human TCAP 4 | QQMLSTGRVQGYDGHFVLSVEQYPELLSDSANNTHEMRQSEM | (SEQ.ID.NO.94) |

FIGURE 8

```
Human CRF Paralogues                                                              SEQ ID NOS human CRF               SEEPPIS  LDLTFHLLREVLEMARAEQLAQQAHSNRKLM EIL           104
human urocortin         DNPSLS   IDLTFHLLRTLLEHARTQSRERAEQNRII   DSW           105
human urocortin 2       IVLS     LDVPIGLLQILLEQARARAAREQATTNARI  ARV           106
human urocortin 3       FTLS     LDVPTNIMNLLFNIAKAKNLRAQAAANAHLM AQI           107

Human TCAP Paralogues human TCAP 1    QQLSTGRVQGYDGYFVLSVEQYLELS DSANNTHEMRQSEL                       70
human TCAP 2    QQLSTGRVQGYEGYYVLPVEQYPELA DSSSNIQFRQNEM                       78
human TCAP 3    QLLSAGKVQGYDGYYVLSVEQYPELA DSANNIQLRQSEL                       85
human TCAP 4    QQVLSTGRVQGYDGFFVLSVEQYPELS DSANNTHEMRQSEM                     94
```

FIGURE 9

```
QLLS      GRKVLGYDGYYVLSIEQYPE    IAPS                  ANNIQFLRQSEI-NH2    O. mykiss TCAP-3   (SEQ.ID.NO.13)
QLLS      TGRVQGYDGYFVLSMEQYLE    LSDS                  ANNIHEMRQSEI-NH2    R. danio TCAP-3    (SEQ.ID.NO.22)
MGMGPSLSIVNPMDVLRQR   LLEIARRR    LRDAEEQI KANKDFI      QQI-NH2             L. migratoria DP   (SEQ.ID.NO.108)
TGAQSLSIVAPLDVLRQR    LMNELNRRR   MRELQGSRIQQNRQLL      LSI-NH2             A. domesticus DP   (SEQ.ID.NO.109)
SPTISITAPIDVLR        KTWEQERARKQMVA                    QNNREFI  NSLN-OH    T. molitor DP      (SEQ.ID.NO.110)
RMPSLSIDLPMSVLRQK     LSNEKERKVHAIRA                    AANRIFL  NDI-NH2    M. sexta DP-I      (SEQ.ID.NO.111)
SLSVNPAVDLLQHR        YMEKVA                            QNNRIFM  NRV-NH2    M. sexta DP-II     (SEQ.ID.NO.112)
TGSGPSLSIVNPLDVLRQR   LLEIARRR                          QNREII   QTI-NH2    P. Americana       (SEQ.ID.NO.113)
SEEPPLSLDLTFHLLR      EVLEMARAEQ  MRQSQDQI AHSNRK       EII-NH2             R. norvegicus CRF  (SEQ.ID.NO.104)
SDDPPLSLDLTFHMLR      QMMEMSRAEQ  LQQQ     AHSNRKMM     EII-NH2             O. keta CRF        (SEQ.ID.NO.114)
DDPPLSIDLTFHLLR       TLEARTQS    QRER     AENRI        DSI-NH2             R. norvegicus UCN  (SEQ.ID.NO.115)
QGPPLSIDLSLELLR       KMIEIEKQEK  EKQQ     AANNRLTL     DTI-NH2             P. sauvageii SVG   (SEQ.ID.NO.116)
NDDPPLSIDLTFHLLR      NMFEMARNEN  QREQ     AGLNRKYL     DEI-NH2             C. carpio UI       (SEQ.ID.NO.117)
VHLSLDVPIGHLR         LLEQARYKA   RNQ      AATNQHL      AHI-NH2             M. musculus UCN2   (SEQ.ID.NO.118)
LTLSLDVPTNIMN         VLLNIAKAKN  LRAK     AAENARIL     AHI-NH2             R. danio UCN2      (SEQ.ID.NO.119)
FTLSLDVPTNIMN         LLENIAKAKN  LRAQ     AAANHLM      AQI-NH2             H. sapiens UCN3    (SEQ.ID.NO.107)
```

FIGURE 11

Whole Mouse Brain

NLT immortalized neurons

Gn11 immortalized neurons

Neuro2a neuroblastoma cells

FIGURE 13
A
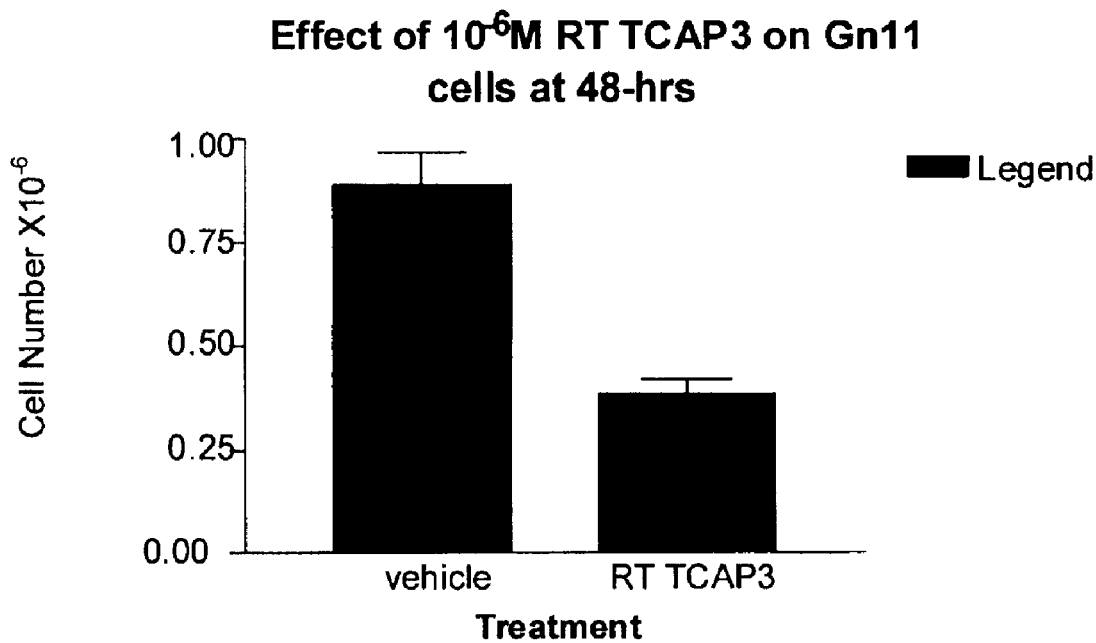
B
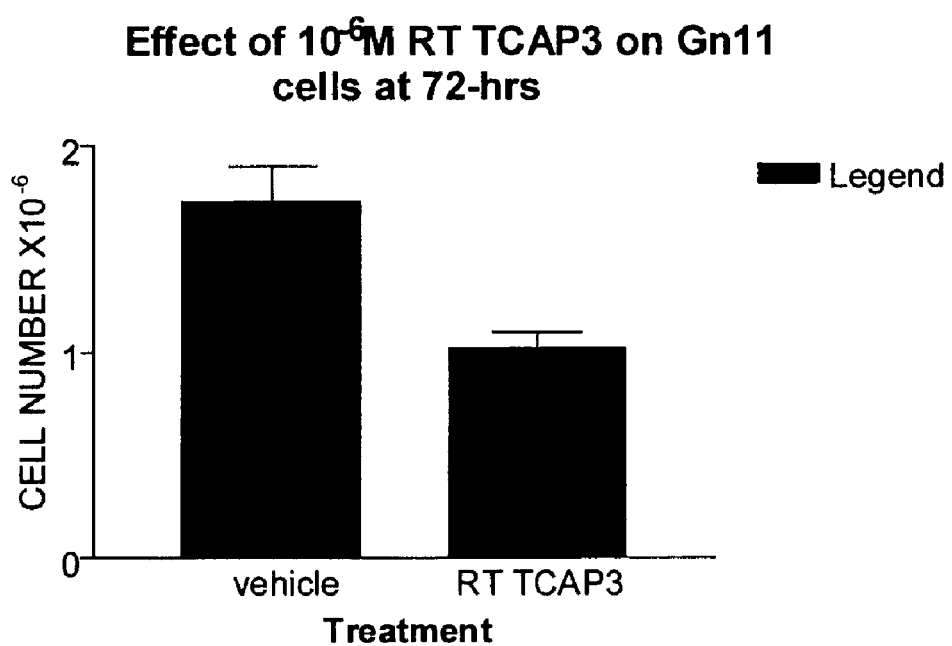

FIGURE 16
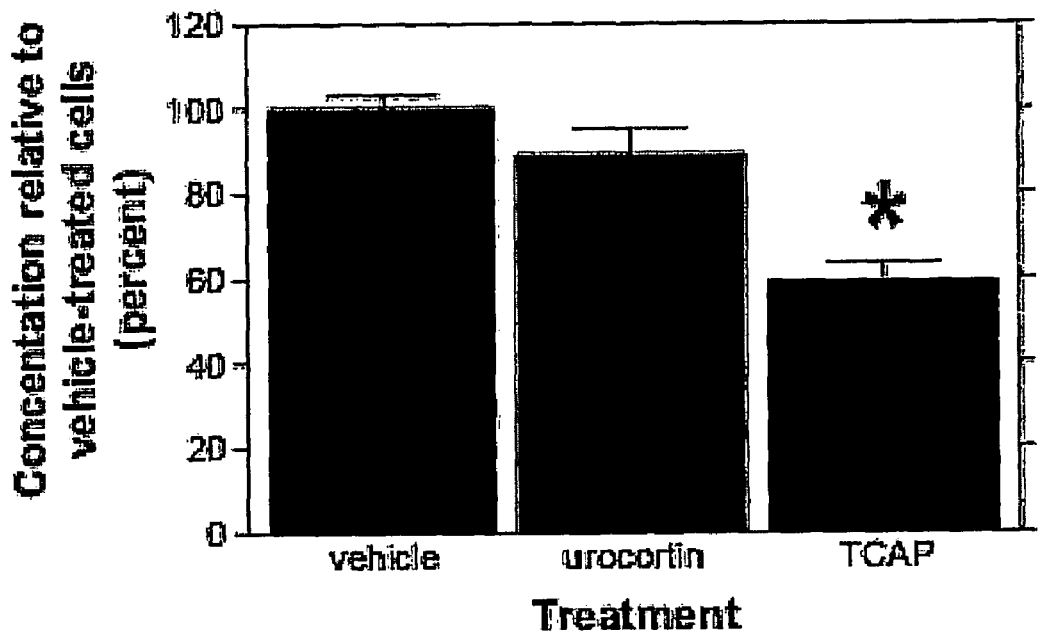
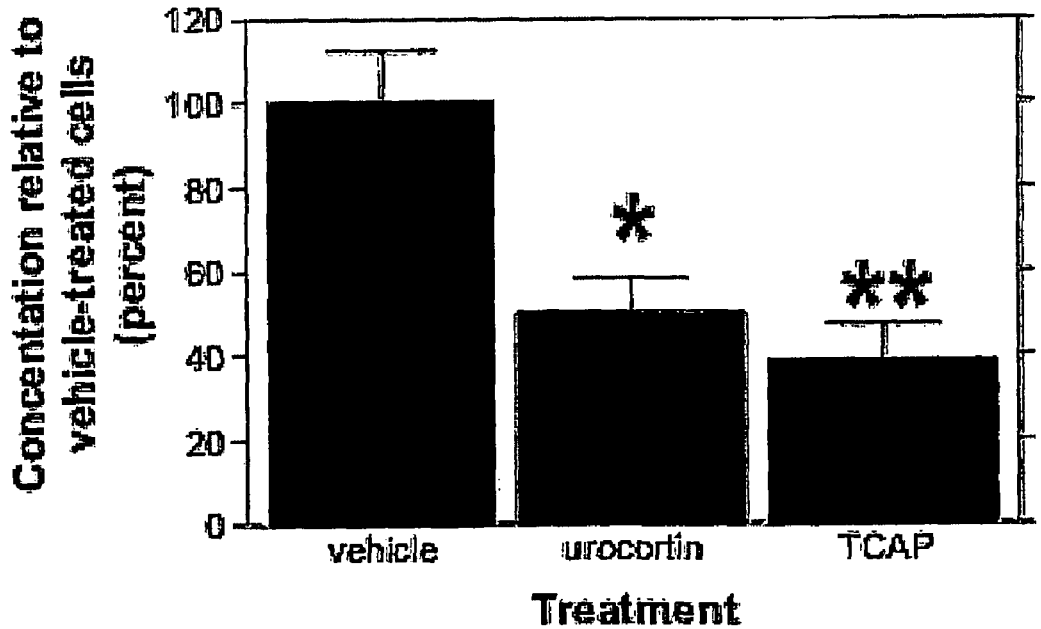

FIGURE 19
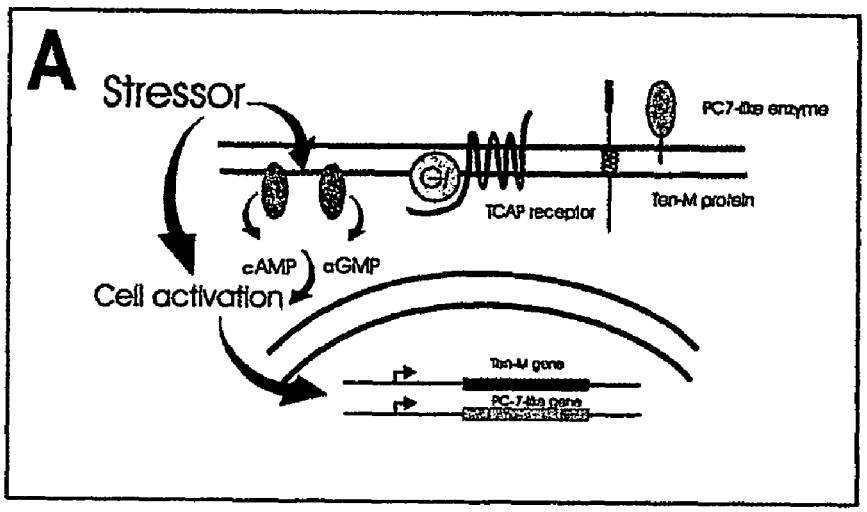
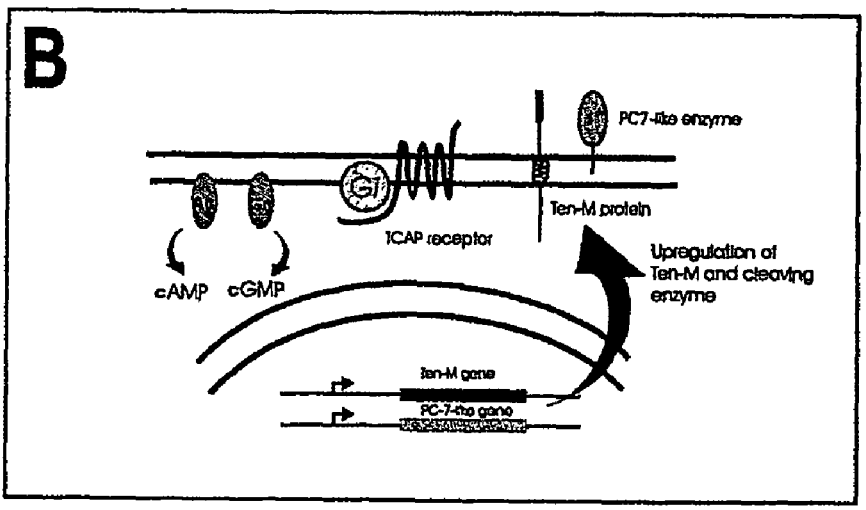
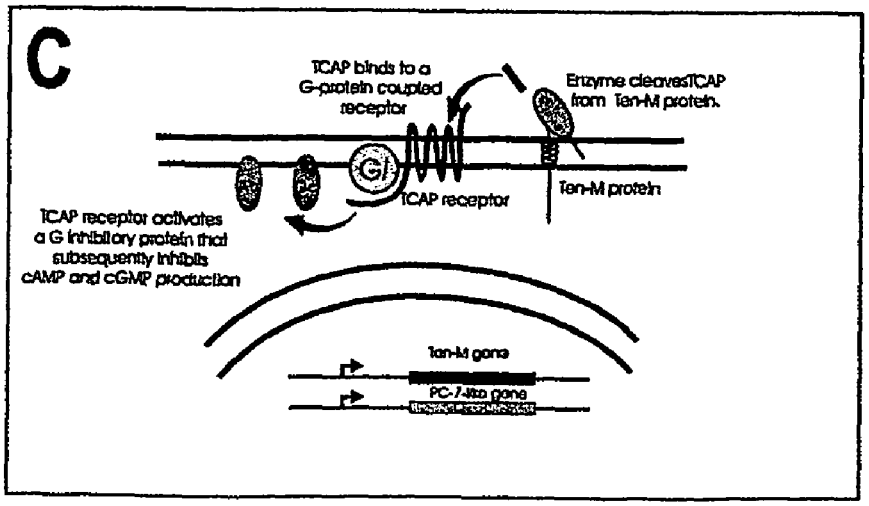

In Situ Hybridization

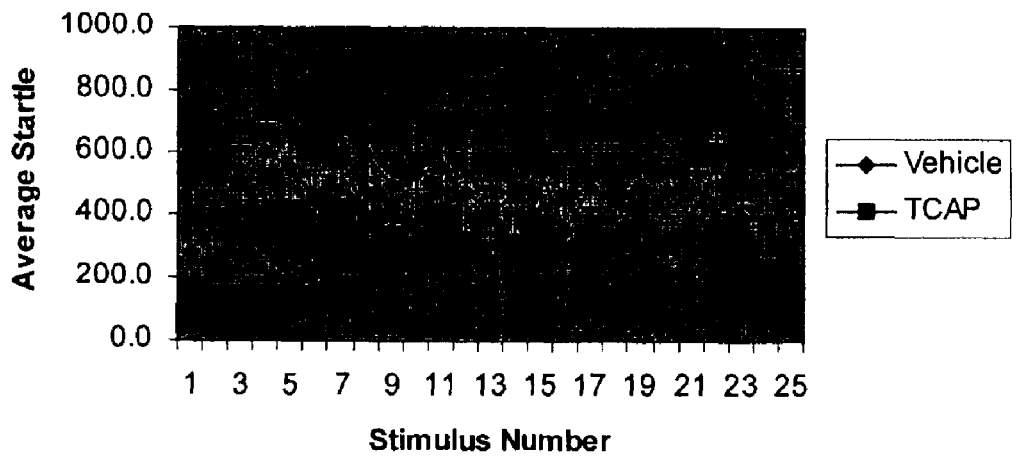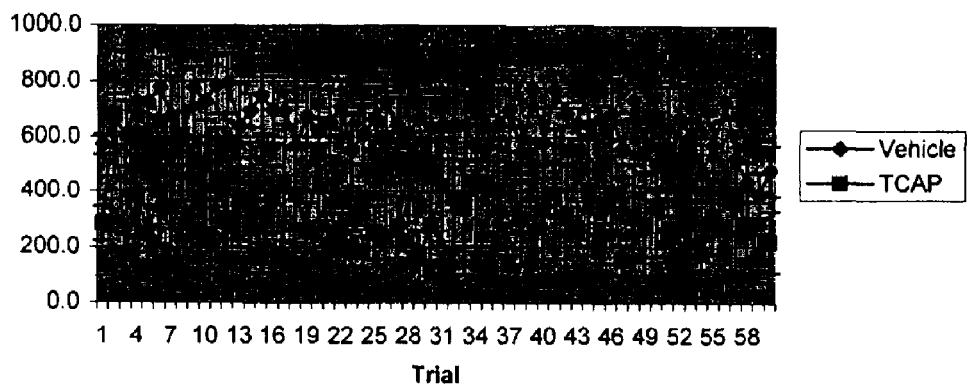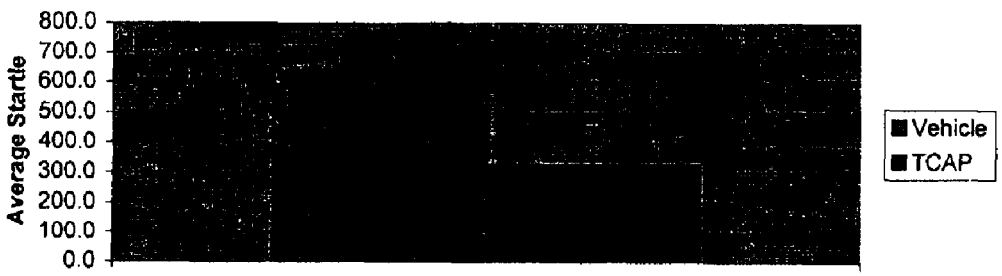
FIGURE 22

Summary of amygdala-injected TCAP-1

SEQUENCE LISTING

<160> NUMBER OF SEQ ID NOS: 138

<210> SEQ ID NO 1
<211> LENGTH: 1490
<212> TYPE: DNA
<213> ORGANISM: Artificial Sequence
<220> FEATURE:
<223> OTHER INFORMATION: Rainbow Trout Ten M3 carboxy termini'

<400> SEQUENCE: 1

```
tccatctcgg gggtgcaaca ggaagtgacc cggcaagcca aggctttcct gtccttcgag      60
aggatgccgg agatccagct gagccgccgg cgctccaacc gggagaaacc ctggctgtgg     120
ttcgccaccg ccaagtctct gatcggtaag ggtgtcatgt tggcggtgac gcagggccgt     180
gtggtcacca acgctctgaa catcgccaac gaggactgca tcaaggtcgc cgccgtcctc     240
aacaatgcgt tctacctgga ggacctgcac ttcacggtgg agggacgcga cacgcactac     300
ttcatcaaga ccagcctccc ggagagcgac ctgggagcgc tgaggctgac aagcgggagg     360
aagtcgctgg agaacggaag tcaacgtgac tgtgtcccag tccaccaccg tggtgaacgg     420
cagaaccggc gcttcgccga cgtggagctg cagtacggcg ctctagcgct ccacgtgcgc     480
tatggcatga ctctggacga ggagaaggcg cgtgtgctgg agcaggccag gcagaaggcg     540
ttgtcgagtg cctggtccag ggagcaacaa cgggtgaggg aggggggagga gggggtgagg     600 ctgtggacga aggggagaa gaggcagctg ctgagcggga ggaaggttct gggctacgac     660
gggtactacg tcctctccat agagcagtac cccgagctag cagactccgc taacaacatc     720
```

```
cagttcctca ggcagagcga aatagggaag aggtaacaga cagaatcctc ggcactggcc    780
gccaaagaga ctacccctc caaatcctgc ccccaacct ccctcgcctc ccccttttc       840 tctaaaaagg gggagggtcc aggctagtgc tgtgtttagc gccgactagc tgaaacaaac    900
agtaaaatgt agaatatctt aaactgaact atacctaata ctaccactgt ggggcctgaa    960
aatcaaacaa aacggctcca actgacgcaa atgtttgtcc catgtgctat acagcgttga    1020
atggactgtg gactctcttg aaaagagaga aaaaaagtc aaaactctcg gtttgtgaaa     1080
ggagaaaaaa acgtttttt ttttttaaa tagacttcct gaatttgctt tcggaaaaaa      1140
tattttaaaa agaaagaaga aatgtgttta catacgcata acactacaac acgtctggac    1200
taatagaaga aaagccttct ggtttcttac acaggacaac gtctataatc tgattctaca    1260
tcctgacgac tgacctttga ttgacctttg cgtactgaaa aaggtagtgt tgttgttcgc    1320
agtaggacca tgggtctcca atggtggtaa ctagacagtt aaaaccactt gttgaaacca    1380
cttgcttgtt cttctgcttt ctttccaaa agggacaaaa cagctcccac caagtgactt     1440
ctttaccaat actagatcaa agtgggacgt tttgggctcg tgccgaattc              1490
```

<210> SEQ ID NO 2  
<211> LENGTH: 756  
<212> TYPE: DNA  
<213> ORGANISM: Artificial Sequence  
<220> FEATURE:  
<223> OTHER INFORMATION: Rainbow Trout Ten M3 coding sequence of carboxy termini of Ten M3

<400> SEQUENCE: 2

```
tccatctcgg gggtgcaaca ggaagtgacc cggcaagcca aggctttcct gtccttcgag    60
aggatgccgg agatccagct gagccgccgg cgctccaacc gggagaaacc ctggctgtgg    120
ttcgccaccg ccaagtctct gatcggtaag ggtgtcatgt tggcggtgac gcagggccgt    180
gtggtcacca acgtctgaa catcgccaac gaggactgca tcaaggtcgc cgccgtcctc    240
aacaatgcgt tctacctgga ggacctgcac ttcacggtgg agggacgcga cacgcactac    300
ttcatcaaga ccagcctccc ggagagcgac ctgggagcgc tgaggctgac aagcggggag    360
aagtcgctgg agaacggaag tcaacgtgac tgtgtcccag tccaccaccg tggtgaacgg    420
cagaaccggc gcttcgccga cgtggagctg cagtacggcg ctctagcgct ccacgtgcgc    480
tatggcatga ctctggacga ggagaaggcg cgtgtgctgg agcaggccag gcagaaggcg    540
ttgtcgagtg cctggtccag ggagcaacaa cgggtgaggg aggggagga ggggtgagg     600 ctgtggacgg agggggagaa gaggcagctg ctgagcggga ggaaggttct gggctacgac    660
gggtactacg tcctctccat agagcagtac cccgagctag cagactccgc taacaacatc    720
cagttcctca ggcagagcga aatagggaag aggtaa                              756
```

<210> SEQ ID NO 3  
<211> LENGTH: 251  
<212> TYPE: PRT  
<213> ORGANISM: Artificial Sequence  
<220> FEATURE:  
<223> OTHER INFORMATION: Rainbow Trout Ten M3 carboxy termini of Ten M3

<400> SEQUENCE: 3

```
Ser Ile Ser Gly Val Gln Gln Glu Val Thr Arg Gln Ala Lys Ala Phe
1               5                   10                  15

Leu Ser Phe Glu Arg Met Pro Glu Ile Gln Leu Ser Arg Arg Arg Ser
            20                  25                  30
```

```
Asn Arg Glu Lys Pro Trp Leu Trp Phe Ala Thr Ala Lys Ser Leu Ile
         35                  40                  45

Gly Lys Gly Val Met Leu Ala Val Thr Gln Gly Arg Val Val Thr Asn
 50                  55                  60

Ala Leu Asn Ile Ala Asn Glu Asp Cys Ile Lys Val Ala Ala Val Leu
 65                  70                  75                  80

Asn Asn Ala Phe Tyr Leu Glu Asp Leu His Phe Thr Val Glu Gly Arg
                 85                  90                  95

Asp Thr His Tyr Phe Ile Lys Thr Ser Leu Pro Glu Ser Asp Leu Gly
             100                 105                 110

Ala Leu Arg Leu Thr Ser Gly Arg Lys Ser Leu Glu Asn Gly Val Asn
         115                 120                 125

Val Thr Val Ser Gln Ser Thr Thr Val Val Asn Gly Arg Thr Arg Arg
130                 135                 140

Phe Ala Asp Val Glu Leu Gln Tyr Gly Ala Leu Ala Leu His Val Arg
145                 150                 155                 160

Tyr Gly Met Thr Leu Asp Glu Glu Lys Ala Arg Val Leu Glu Gln Ala
                165                 170                 175

Arg Gln Lys Ala Leu Ser Ser Ala Trp Ser Arg Glu Gln Gln Arg Val
            180                 185                 190

Arg Glu Gly Glu Glu Gly Val Arg Leu Trp Thr Glu Gly Lys Arg
        195                 200                 205

Gln Leu Leu Ser Gly Arg Lys Val Leu Gly Tyr Asp Gly Tyr Tyr Val
    210                 215                 220

Leu Ser Ile Glu Gln Tyr Pro Glu Leu Ala Asp Ser Ala Asn Asn Ile
225                 230                 235                 240

Gln Phe Leu Arg Gln Ser Glu Ile Gly Lys Arg
                245                 250

<210> SEQ ID NO 4
<211> LENGTH: 252
<212> TYPE: PRT
<213> ORGANISM: Artificial Sequence
<220> FEATURE:
<223> OTHER INFORMATION: Mouse Ten M1

<400> SEQUENCE: 4

Met Ile Leu Gly Ile Gln Cys Glu Leu Gln Lys Gln Leu Arg Asn Phe
 1               5                  10                  15

Ile Ser Leu Asp Gln Leu Pro Met Thr Pro Gln Tyr Asn Glu Gly Arg
                 20                  25                  30

Cys Leu Glu Gly Gly Lys Gln Pro Arg Phe Ala Ala Val Pro Ser Val
         35                  40                  45

Phe Gly Lys Gly Ile Lys Phe Ala Ile Lys Glu Gly Ile Val Thr Ala
 50                  55                  60

Asp Ile Ile Gly Val Ala Asn Glu Asp Ser Arg Arg Leu Ala Ala Ile
 65                  70                  75                  80

Leu Asn Asn Ala His Tyr Leu Glu Asn Leu His Phe Thr Ile Glu Gly
                 85                  90                  95

Arg Asp Thr His Tyr Phe Ile Lys Leu Gly Ser Leu Glu Glu Asp Leu
             100                 105                 110

Val Leu Ile Gly Asn Thr Gly Gly Arg Arg Ile Leu Glu Asn Gly Val
         115                 120                 125

Asn Val Thr Val Ser Gln Met Thr Ser Val Leu Asn Gly Arg Thr Arg
130                 135                 140

Arg Phe Ala Asp Ile Gln Leu Gln His Gly Ala Leu Cys Phe Asn Ile
```

```
                145                 150                 155                 160
Arg Tyr Gly Thr Thr Val Glu Glu Lys Asn His Val Leu Glu Met
                    165                 170                 175

Ala Arg Gln Arg Ala Val Ala Gln Ala Trp Thr Gln Glu Gln Arg Arg
                180                 185                 190

Leu Gln Glu Gly Glu Gly Thr Arg Val Trp Thr Glu Gly Glu Lys
        195                 200                 205

Gln Gln Leu Leu Gly Thr Gly Arg Val Gln Gly Tyr Asp Gly Tyr Phe
        210                 215                 220

Val Leu Ser Val Glu Gln Tyr Leu Glu Leu Ser Asp Ser Ala Asn Asn
225                 230                 235                 240

Ile His Phe Met Arg Gln Ser Glu Ile Gly Arg Arg
                245                 250

<210> SEQ ID NO 5
<211> LENGTH: 253
<212> TYPE: PRT
<213> ORGANISM: Artificial Sequence
<220> FEATURE:
<223> OTHER INFORMATION: Mouse Ten M2

<400> SEQUENCE: 5

Leu Ile Thr Gly Val Gln Gln Thr Thr Glu Arg His Asn Gln Ala Phe
1               5                   10                  15

Leu Ala Leu Glu Gly Gln Val Ile Thr Lys Lys Leu His Ala Ser Ile
                20                  25                  30

Arg Glu Lys Ala Gly His Trp Phe Ala Thr Thr Thr Pro Ile Ile Gly
            35                  40                  45

Lys Gly Ile Met Phe Ala Ile Lys Glu Gly Arg Val Thr Thr Gly Val
        50                  55                  60

Ser Ser Ile Ala Ser Glu Asp Ser Arg Lys Val Ala Ser Val Leu Asn
65                  70                  75                  80

Asn Ala Tyr Tyr Leu Asp Lys Met His Tyr Ser Ile Glu Gly Lys Asp
                85                  90                  95

Thr His Tyr Phe Val Lys Ile Gly Ala Ala Asp Gly Asp Leu Val Thr
            100                 105                 110

Leu Gly Thr Thr Ile Gly Arg Lys Val Leu Glu Ser Gly Val Asn Val
        115                 120                 125

Thr Val Ser Gln Pro Thr Leu Leu Val Asn Gly Arg Thr Arg Phe
    130                 135                 140

Thr Asn Ile Glu Phe Gln Tyr Ser Thr Leu Leu Ser Ile Arg Tyr
145                 150                 155                 160

Gly Leu Thr Pro Asp Thr Leu Asp Glu Glu Lys Ala Arg Val Leu Asp
                165                 170                 175

Gln Ala Gly Gln Arg Ala Leu Gly Thr Ala Trp Ala Lys Glu Gln Gln
            180                 185                 190

Lys Ala Arg Asp Gly Arg Glu Gly Ser Arg Leu Trp Thr Glu Gly Glu
        195                 200                 205

Lys Gln Gln Leu Leu Ser Thr Gly Arg Val Gln Gly Tyr Glu Gly Tyr
    210                 215                 220

Tyr Val Leu Pro Val Glu Gln Tyr Pro Glu Leu Ala Asp Ser Ser Ser
225                 230                 235                 240

Asn Ile Gln Phe Leu Arg Gln Asn Glu Met Gly Lys Arg
                245                 250

<210> SEQ ID NO 6
```

-continued

```
<211> LENGTH: 251
<212> TYPE: PRT
<213> ORGANISM: Artificial Sequence
<220> FEATURE:
<223> OTHER INFORMATION: Mouse Ten M3

<400> SEQUENCE: 6

Pro Ile Phe Gly Val Gln Gln Val Ala Arg Gln Ala Lys Ala Phe
1               5                   10                  15

Leu Ser Leu Gly Lys Met Ala Glu Val Gln Val Ser Arg Arg Lys Ala
            20                  25                  30

Gly Ala Glu Gln Ser Trp Leu Trp Phe Ala Thr Val Lys Ser Leu Ile
        35                  40                  45

Gly Lys Gly Val Met Leu Ala Val Ser Gln Gly Arg Val Gln Thr Asn
    50                  55                  60

Val Leu Asn Ile Ala Asn Glu Asp Cys Ile Lys Val Ala Ala Val Leu
65                  70                  75                  80

Asn Asn Ala Phe Tyr Leu Glu Asn Leu His Phe Thr Ile Glu Gly Lys
                85                  90                  95

Asp Thr His Tyr Phe Ile Lys Thr Thr Thr Pro Glu Ser Asp Leu Gly
            100                 105                 110

Thr Leu Arg Leu Thr Ser Gly Arg Lys Ala Leu Glu Asn Gly Ile Asn
        115                 120                 125

Val Thr Val Ser Gln Ser Thr Val Val Asn Gly Arg Thr Arg Arg
    130                 135                 140

Phe Ala Asp Val Glu Met Gln Phe Gly Ala Leu Ala Leu His Val Arg
145                 150                 155                 160

Tyr Gly Met Thr Leu Asp Glu Glu Lys Ala Arg Ile Leu Glu Gln Ala
                165                 170                 175

Arg Gln Arg Ala Leu Ala Arg Ala Trp Ala Arg Glu Gln Gln Arg Val
            180                 185                 190

Arg Asp Gly Glu Glu Gly Ala Arg Leu Trp Thr Glu Gly Glu Lys Arg
        195                 200                 205

Gln Leu Leu Ser Ala Gly Lys Val Gln Gly Tyr Asp Gly Tyr Tyr Val
    210                 215                 220

Leu Ser Val Glu Gln Tyr Pro Glu Leu Ala Asp Ser Ala Asn Asn Ile
225                 230                 235                 240

Gln Phe Leu Arg Gln Ser Glu Ile Gly Lys Arg
                245                 250

<210> SEQ ID NO 7
<211> LENGTH: 243
<212> TYPE: PRT
<213> ORGANISM: Artificial Sequence
<220> FEATURE:
<223> OTHER INFORMATION: Mouse Ten M4

<400> SEQUENCE: 7

Ser Ile Leu Gly Val Gln Cys Glu Val Gln Lys Gln Leu Lys Ala Phe
1               5                   10                  15

Val Thr Leu Glu Arg Phe Asp Gln Leu Tyr Gly Ser Thr Ile Thr Ser
            20                  25                  30

Cys Gln Gln Ala Pro Glu Thr Lys Lys Phe Ala Ser Ser Gly Ser Ile
        35                  40                  45

Phe Gly Lys Gly Val Lys Phe Ala Leu Lys Asp Gly Arg Val Thr Thr
    50                  55                  60

Asp Ile Ile Ser Val Ala Asn Glu Asp Gly Arg Arg Ile Ala Ala Ile
65                  70                  75                  80
```

```
Leu Asn Asn Ala His Tyr Leu Glu Asn Leu His Phe Thr Ile Asp Gly
                85                  90                  95

Val Asp Thr His Tyr Phe Val Lys Pro Gly Pro Ser Glu Gly Asp Leu
            100                 105                 110

Ala Ile Leu Gly Leu Ser Gly Gly Arg Arg Thr Leu Glu Asn Gly Val
            115                 120                 125

Asn Val Thr Val Ser Gln Ile Asn Thr Met Leu Ile Gln Leu Gln Tyr
        130                 135                 140

Arg Ala Leu Cys Leu Asn Thr Arg Tyr Gly Thr Thr Val Asp Glu Glu
145                 150                 155                 160

Lys Val Arg Val Leu Glu Leu Ala Arg Gln Arg Ala Val Arg Gln Ala
                165                 170                 175

Trp Ala Arg Glu Gln Gln Arg Leu Arg Glu Gly Glu Glu Gly Leu Arg
            180                 185                 190

Ala Trp Thr Asp Gly Glu Lys Gln Gln Val Leu Asn Thr Gly Arg Val
            195                 200                 205

Gln Gly Tyr Asp Gly Phe Phe Val Thr Ser Val Glu Gln Tyr Pro Glu
        210                 215                 220

Leu Ser Asp Ser Ala Asn Asn Ile His Phe Met Arg Gln Ser Glu Met
225                 230                 235                 240

Gly Arg Arg

<210> SEQ ID NO 8
<211> LENGTH: 252
<212> TYPE: PRT
<213> ORGANISM: Artificial Sequence
<220> FEATURE:
<223> OTHER INFORMATION: Human Ten M1

<400> SEQUENCE: 8

Thr Ile Leu Gly Ile Gln Cys Glu Leu Gln Lys Gln Leu Arg Asn Phe
1               5                   10                  15

Ile Ser Leu Asp Gln Leu Pro Met Thr Pro Arg Tyr Asn Asp Gly Arg
            20                  25                  30

Cys Leu Glu Gly Gly Lys Gln Pro Arg Phe Ala Ala Val Pro Ser Val
        35                  40                  45

Phe Gly Lys Gly Ile Lys Phe Ala Ile Lys Asp Gly Ile Val Thr Ala
    50                  55                  60

Asp Ile Ile Gly Val Ala Asn Glu Asp Ser Arg Arg Leu Ala Ala Ile
65                  70                  75                  80

Leu Asn Asn Ala His Tyr Leu Glu Asn Leu His Phe Thr Ile Glu Gly
                85                  90                  95

Arg Asp Thr His Tyr Phe Ile Lys Leu Gly Ser Leu Glu Glu Asp Leu
            100                 105                 110

Val Leu Ile Gly Asn Thr Gly Gly Arg Arg Ile Leu Glu Asn Gly Val
            115                 120                 125

Asn Val Thr Val Ser Gln Met Thr Ser Val Leu Asn Gly Arg Thr Arg
        130                 135                 140

Arg Phe Ala Asp Ile Gln Leu Gln His Gly Ala Leu Cys Phe Asn Ile
145                 150                 155                 160

Arg Tyr Gly Thr Thr Val Glu Glu Glu Lys Asn His Val Leu Glu Ile
                165                 170                 175

Ala Arg Gln Arg Ala Val Ala Gln Ala Trp Thr Lys Glu Gln Arg Arg
            180                 185                 190

Leu Gln Glu Gly Glu Glu Gly Ile Arg Ala Trp Thr Glu Gly Glu Lys
```

-continued

Gln Gln Leu Leu Ser Thr Gly Arg Val Gln Gly Tyr Asp Gly Tyr Phe
            210                 215                 220

Val Leu Ser Val Glu Gln Tyr Leu Glu Leu Ser Asp Ser Ala Asn Asn
225                 230                 235                 240

Ile His Phe Met Arg Gln Ser Glu Ile Gly Arg Arg
                245                 250

<210> SEQ ID NO 9
<211> LENGTH: 253
<212> TYPE: PRT
<213> ORGANISM: Artificial Sequence
<220> FEATURE:
<223> OTHER INFORMATION: Human Ten M2

<400> SEQUENCE: 9

Leu Ile Thr Gly Val Gln Gln Thr Thr Glu Arg His Asn Gln Ala Phe
1               5                   10                  15

Met Ala Leu Glu Gly Gln Val Ile Thr Lys Lys Leu His Ala Ser Ile
            20                  25                  30

Arg Glu Lys Ala Gly His Trp Phe Ala Thr Thr Thr Pro Ile Ile Gly
        35                  40                  45

Lys Gly Ile Met Phe Ala Ile Lys Glu Gly Arg Val Thr Thr Gly Val
    50                  55                  60

Ser Ser Ile Ala Ser Glu Asp Ser Arg Lys Val Ala Ser Val Leu Asn
65                  70                  75                  80

Asn Ala Tyr Tyr Leu Asp Lys Met His Tyr Ser Ile Glu Gly Lys Asp
                85                  90                  95

Thr His Tyr Phe Val Lys Ile Gly Ser Ala Asp Gly Asp Leu Val Thr
            100                 105                 110

Leu Gly Thr Thr Ile Gly Arg Lys Val Leu Glu Ser Gly Val Asn Val
        115                 120                 125

Thr Val Ser Gln Pro Thr Leu Leu Val Asn Gly Arg Thr Arg Arg Phe
    130                 135                 140

Thr Asn Ile Glu Phe Gln Tyr Ser Thr Leu Leu Leu Ser Ile Arg Tyr
145                 150                 155                 160

Gly Leu Thr Pro Asp Thr Leu Asp Glu Glu Lys Ala Arg Val Leu Asp
                165                 170                 175

Gln Ala Arg Gln Arg Ala Leu Gly Thr Ala Trp Ala Lys Glu Gln Gln
            180                 185                 190

Lys Ala Arg Asp Gly Arg Glu Gly Ser Arg Leu Trp Thr Glu Gly Glu
        195                 200                 205

Lys Gln Gln Leu Leu Ser Thr Gly Arg Val Gln Gly Tyr Glu Gly Tyr
    210                 215                 220

Tyr Val Leu Pro Val Glu Gln Tyr Pro Glu Leu Ala Asp Ser Ser Ser
225                 230                 235                 240

Asn Ile Gln Phe Leu Arg Gln Asn Glu Met Gly Lys Arg
                245                 250

<210> SEQ ID NO 10
<211> LENGTH: 251
<212> TYPE: PRT
<213> ORGANISM: Artificial Sequence
<220> FEATURE:
<223> OTHER INFORMATION: Human Ten M3

<400> SEQUENCE: 10

Pro Ile Phe Gly Val Gln Gln Gln Val Ala Arg Gln Ala Lys Ala Phe

```
                 1               5                  10                  15
Leu Ser Leu Gly Lys Met Ala Glu Val Gln Val Ser Arg Arg Ala
             20                  25                  30

Gly Gly Ala Gln Ser Trp Leu Trp Phe Ala Thr Val Lys Ser Leu Ile
         35                  40                  45

Gly Lys Gly Val Met Leu Ala Val Ser Gln Gly Arg Val Gln Thr Asn
     50                  55                  60

Val Leu Asn Ile Ala Asn Glu Asp Cys Ile Lys Val Ala Ala Val Leu
65                  70                  75                  80

Asn Asn Ala Phe Tyr Leu Glu Asn Leu His Phe Thr Ile Glu Gly Lys
                 85                  90                  95

Asp Thr His Tyr Phe Ile Lys Thr Thr Thr Pro Glu Ser Asp Leu Gly
            100                 105                 110

Thr Leu Arg Leu Thr Ser Gly Arg Lys Ala Leu Glu Asn Gly Ile Asn
        115                 120                 125

Val Thr Val Ser Gln Ser Thr Thr Val Val Asn Gly Arg Thr Arg Arg
    130                 135                 140

Phe Ala Asp Val Glu Met Gln Phe Gly Ala Leu Ala Leu His Val Arg
145                 150                 155                 160

Tyr Gly Met Thr Leu Asp Glu Lys Ala Arg Ile Leu Glu Gln Ala
                165                 170                 175

Arg Gln Arg Ala Leu Ala Arg Ala Trp Ala Arg Glu Gln Arg Val
            180                 185                 190

Arg Asp Gly Glu Glu Gly Ala Arg Leu Trp Thr Glu Gly Lys Arg
        195                 200                 205

Gln Leu Leu Ser Ala Gly Lys Val Gln Gly Tyr Asp Gly Tyr Tyr Val
    210                 215                 220

Leu Ser Val Glu Gln Tyr Pro Glu Leu Ala Asp Ser Ala Asn Asn Ile
225                 230                 235                 240

Gln Phe Leu Arg Gln Ser Glu Ile Gly Arg Arg
                245                 250

<210> SEQ ID NO 11
<211> LENGTH: 252
<212> TYPE: PRT
<213> ORGANISM: Artificial Sequence
<220> FEATURE:
<223> OTHER INFORMATION: Human Ten M4

<400> SEQUENCE: 11

Ser Ile Leu Gly Val Gln Cys Glu Val Gln Lys Gln Leu Lys Ala Phe
1               5                   10                  15

Val Thr Leu Glu Arg Phe Asp Gln Leu Tyr Gly Ser Thr Ile Thr Ser
            20                  25                  30

Cys Leu Gln Ala Pro Lys Thr Lys Lys Phe Ala Ser Ser Gly Ser Val
        35                  40                  45

Phe Gly Lys Gly Val Lys Phe Ala Leu Lys Asp Gly Arg Val Thr Thr
    50                  55                  60

Asp Ile Ile Ser Val Ala Asn Glu Asp Gly Arg Arg Val Ala Ala Ile
65                  70                  75                  80

Leu Asn His Ala His Tyr Leu Glu Asn Leu His Phe Thr Ile Asp Gly
                85                  90                  95

Val Asp Thr His Tyr Phe Val Lys Pro Gly Pro Ser Glu Gly Asp Leu
            100                 105                 110

Ala Ile Leu Gly Leu Ser Gly Gly Arg Arg Thr Leu Glu Asn Gly Val
        115                 120                 125
```

Asn Val Thr Val Ser Gln Ile Asn Thr Val Leu Ser Gly Arg Thr Arg
    130                 135                 140

Arg Tyr Thr Asp Ile Gln Leu Gln Tyr Gly Ala Leu Cys Leu Asn Thr
145                 150                 155                 160

Arg Tyr Gly Thr Thr Leu Asp Glu Glu Lys Ala Arg Val Leu Glu Leu
                165                 170                 175

Ala Arg Gln Arg Ala Val Arg Gln Ala Trp Ala Arg Glu Gln Gln Arg
                180                 185                 190

Leu Arg Glu Gly Glu Glu Gly Leu Arg Ala Trp Thr Glu Gly Glu Lys
                195                 200                 205

Gln Gln Val Leu Ser Thr Gly Arg Val Gln Gly Tyr Asp Gly Phe Phe
                210                 215                 220

Val Ile Ser Val Glu Gln Tyr Pro Glu Leu Ser Asp Ser Ala Asn Asn
225                 230                 235                 240

Ile His Phe Met Arg Gln Ser Glu Met Gly Arg Arg
                245                 250

<210> SEQ ID NO 12
<211> LENGTH: 252
<212> TYPE: PRT
<213> ORGANISM: Artificial Sequence
<220> FEATURE:
<223> OTHER INFORMATION: Zebrafish Ten M3

<400> SEQUENCE: 12

Ser Ile Ser Gly Val Gln Gln Glu Val Met Arg Gln Ala Lys Ala Phe
1               5                   10                  15

Leu Ser Phe Glu Arg Met Pro Glu Ile Gln Leu Ser Arg Arg Arg Ser
                20                  25                  30

Ser Arg Glu Lys Pro Trp Leu Trp Phe Ala Thr Val Lys Ser Leu Ile
                35                  40                  45

Gly Lys Gly Val Met Leu Ala Ile Thr Ser Lys Gly Gln Val Ala Thr
50                  55                  60

Asn Ala Leu Asn Ile Ala Asn Glu Asp Cys Ile Lys Val Val Thr Val
65                  70                  75                  80

Leu Asn Asn Ala Phe Tyr Leu Glu Asp Leu His Phe Thr Val Glu Gly
                85                  90                  95

Arg Asp Thr His Tyr Phe Ile Lys Thr Ser Leu Pro Glu Ser Asp Leu
                100                 105                 110

Gly Ala Leu Arg Leu Thr Ser Gly Arg Lys Ser Leu Glu Asn Gly Val
                115                 120                 125

Asn Val Thr Val Ser Gln Ser Thr Thr Val Val Asn Gly Arg Thr Arg
    130                 135                 140

Arg Phe Ala Asp Val Glu Leu Gln Tyr Gly Ala Leu Ala Leu His Val
145                 150                 155                 160

Arg Tyr Gly Met Thr Leu Asp Glu Glu Lys Ala Arg Val Leu Glu Gln
                165                 170                 175

Ala Arg Gln Arg Ala Leu Ser Ser Ala Trp Ala Arg Glu Gln Gln Arg
                180                 185                 190

Val Arg Asp Gly Glu Glu Gly Val Arg Leu Trp Thr Glu Gly Glu Lys
                195                 200                 205

Arg Gln Leu Leu Ser Ser Gly Lys Val Leu Gly Tyr Asp Gly Tyr Tyr
    210                 215                 220

Val Leu Ser Val Glu Gln Tyr Pro Glu Leu Ala Asp Ser Ala Asn Asn
225                 230                 235                 240

-continued

Val Gln Phe Leu Arg Gln Ser Glu Ile Gly Lys Arg
                245                 250

<210> SEQ ID NO 13
<211> LENGTH: 40
<212> TYPE: PRT
<213> ORGANISM: Artificial Sequence
<220> FEATURE:
<223> OTHER INFORMATION: Rainbow Trout TCAP3 (40a.a.)

<400> SEQUENCE: 13

Gln Leu Leu Ser Gly Arg Lys Val Leu Gly Tyr Asp Gly Tyr Tyr Val
1               5                   10                  15

Leu Ser Ile Glu Gln Tyr Pro Glu Leu Ala Asp Ser Ala Asn Asn Ile
            20                  25                  30

Gln Phe Leu Arg Gln Ser Glu Ile
        35                  40

<210> SEQ ID NO 14
<211> LENGTH: 41
<212> TYPE: PRT
<213> ORGANISM: Artificial Sequence
<220> FEATURE:
<223> OTHER INFORMATION: Rainbow Trout TCAP 3 (41a.a.)

<400> SEQUENCE: 14

Arg Gln Leu Leu Ser Gly Arg Lys Val Leu Gly Tyr Asp Gly Tyr Tyr
1               5                   10                  15

Val Leu Ser Ile Glu Gln Tyr Pro Glu Leu Ala Asp Ser Ala Asn Asn
            20                  25                  30

Ile Gln Phe Leu Arg Gln Ser Glu Ile
        35                  40

<210> SEQ ID NO 15
<211> LENGTH: 43
<212> TYPE: PRT
<213> ORGANISM: Artificial Sequence
<220> FEATURE:
<223> OTHER INFORMATION: Rainbow Trout preTCAP3 (43 a.a.)

<400> SEQUENCE: 15

Gln Leu Leu Ser Gly Arg Lys Val Leu Gly Tyr Asp Gly Tyr Tyr Val
1               5                   10                  15

Leu Ser Ile Glu Gln Tyr Pro Glu Leu Ala Asp Ser Ala Asn Asn Ile
            20                  25                  30

Gln Phe Leu Arg Gln Ser Glu Ile Gly Lys Arg
        35                  40

<210> SEQ ID NO 16
<211> LENGTH: 44
<212> TYPE: PRT
<213> ORGANISM: Artificial Sequence
<220> FEATURE:
<223> OTHER INFORMATION: Rainbow Trout preTCAP3 (44 a.a.)

<400> SEQUENCE: 16

Arg Gln Leu Leu Ser Gly Arg Lys Val Leu Gly Tyr Asp Gly Tyr Tyr
1               5                   10                  15

Val Leu Ser Ile Glu Gln Tyr Pro Glu Leu Ala Asp Ser Ala Asn Asn
            20                  25                  30

Ile Gln Phe Leu Arg Gln Ser Glu Ile Gly Lys Arg
        35                  40

```
<210> SEQ ID NO 17
<211> LENGTH: 120
<212> TYPE: DNA
<213> ORGANISM: Artificial Sequence
<220> FEATURE:
<223> OTHER INFORMATION: Rainbow Trout TCAP3 (120 n.a.)

<400> SEQUENCE: 17
cagctgctga gcgggaggaa ggttctgggc tacgacgggt actacgtcct ctccatagag      60
cagtaccccg agctagcaga ctccgctaac aacatccagt tcctcaggca gagcgaaata     120

<210> SEQ ID NO 18
<211> LENGTH: 123
<212> TYPE: DNA
<213> ORGANISM: Artificial Sequence
<220> FEATURE:
<223> OTHER INFORMATION: Rainbow Trout TCAP3 (123 n.a.)

<400> SEQUENCE: 18
aggcagctgc tgagcgggag gaaggttctg ggctacgacg gtactacgt cctctccata      60 gagcagtacc ccgagctagc agactccgct aacaacatcc agttcctcag gcagagcgaa    120
ata                                                                  123

<210> SEQ ID NO 19
<211> LENGTH: 129
<212> TYPE: DNA
<213> ORGANISM: Artificial Sequence
<220> FEATURE:
<223> OTHER INFORMATION: Rainbow Trout preTCAP3 (129 n.a.)

<400> SEQUENCE: 19
cagctgctga gcgggaggaa ggttctgggc tacgacgggt actacgtcct ctccatagag      60
cagtaccccg agctagcaga ctccgctaac aacatccagt tcctcaggca gagcgaaata     120
gggaagagg                                                            129

<210> SEQ ID NO 20
<211> LENGTH: 132
<212> TYPE: DNA
<213> ORGANISM: Artificial Sequence
<220> FEATURE:
<223> OTHER INFORMATION: Rainbow Trout preTCAP3 (132 n.a.)

<400> SEQUENCE: 20
aggcagctgc tgagcgggag gaaggttctg ggctacgacg gtactacgt cctctccata      60 gagcagtacc ccgagctagc agactccgct aacaacatcc agttcctcag gcagagcgaa    120
atagggaaga gg                                                        132

<210> SEQ ID NO 21
<211> LENGTH: 40
<212> TYPE: PRT
<213> ORGANISM: Artificial Sequence
<220> FEATURE:
<223> OTHER INFORMATION: Zebrafish TCAP3 (40 a.a.)

<400> SEQUENCE: 21

Gln Leu Leu Ser Ser Gly Lys Val Leu Gly Tyr Asp Gly Tyr Tyr Val
1               5                   10                  15

Leu Ser Val Glu Gln Tyr Pro Glu Leu Ala Asp Ser Ala Asn Asn Val
            20                  25                  30

Gln Phe Leu Arg Gln Ser Glu Ile
        35                  40
```

-continued

<210> SEQ ID NO 22
<211> LENGTH: 41
<212> TYPE: PRT
<213> ORGANISM: Artificial Sequence
<220> FEATURE:
<223> OTHER INFORMATION: Zebrafish TCAP3 (41 a.a.)

<400> SEQUENCE: 22

Arg Gln Leu Leu Ser Ser Gly Lys Val Leu Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Val Gln Phe Leu Arg Gln Ser Glu Ile
        35                  40

<210> SEQ ID NO 23
<211> LENGTH: 43
<212> TYPE: PRT
<213> ORGANISM: Artificial Sequence
<220> FEATURE:
<223> OTHER INFORMATION: Zebrafish preTCAP3 (43 a.a.)

<400> SEQUENCE: 23

Gln Leu Leu Ser Ser Gly Lys Val Leu Gly Tyr Asp Gly Tyr Tyr Val
1               5                   10                  15

Leu Ser Val Glu Gln Tyr Pro Glu Leu Ala Asp Ser Ala Asn Asn Val
            20                  25                  30

Gln Phe Leu Arg Gln Ser Glu Ile Gly Lys Arg
        35                  40

<210> SEQ ID NO 24
<211> LENGTH: 44
<212> TYPE: PRT
<213> ORGANISM: Artificial Sequence
<220> FEATURE:
<223> OTHER INFORMATION: Zebrafish preTCAP3 (44 a.a.)

<400> SEQUENCE: 24

Arg Gln Leu Leu Ser Ser Gly Lys Val Leu Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Val Gln Phe Leu Arg Gln Ser Glu Ile Gly Lys Arg
        35                  40

<210> SEQ ID NO 25
<211> LENGTH: 120
<212> TYPE: DNA
<213> ORGANISM: Artificial Sequence
<220> FEATURE:
<223> OTHER INFORMATION: Zebrafish TCAP3 (120 n.a.)

<400> SEQUENCE: 25
cagttgctca gctctgggaa ggtgctgggt tacgatggtt actatgtact atcagtggag      60
caataccctg aactggccga cagtgccaac aatgtccagt tcttgaggca gagtgagata     120

<210> SEQ ID NO 26
<211> LENGTH: 123
<212> TYPE: DNA
<213> ORGANISM: Artificial Sequence
<220> FEATURE:
<223> OTHER INFORMATION: Zebrafish TCAP3 (123 n.a.)

<400> SEQUENCE: 26

```
aggcagttgc tcagctctgg gaaggtgctg ggttacgatg gttactatgt actatcagtg    60
gagcaatacc ctgaactggc cgacagtgcc aacaatgtcc agttcttgag gcagagtgag   120
ata                                                                 123
```

<210> SEQ ID NO 27
<211> LENGTH: 129
<212> TYPE: DNA
<213> ORGANISM: Artificial Sequence
<220> FEATURE:
<223> OTHER INFORMATION: Zebrafish TCAP3 (129 n.a.)

<400> SEQUENCE: 27

```
cagttgctca gctctgggaa ggtgctgggt tacgatggtt actatgtact atcagtggag    60
caatacgctg aactggccga cagtgccaac aatgtccagt tcttgaggca gagtgagata   120
gggaagagg                                                           129
```

<210> SEQ ID NO 28
<211> LENGTH: 132
<212> TYPE: DNA
<213> ORGANISM: Artificial Sequence
<220> FEATURE:
<223> OTHER INFORMATION: Zebrafish preTCAP3 (132 n.a.)

<400> SEQUENCE: 28

```
aggcagttgc tcagctctgg gaaggtgctg ggttacgatg gttactatgt actatcagtg    60
gagcaatacc ctgaactggc cgacagtgcc aacaatgtcc agttcttgag gcagagtgag   120
atagggaaga gg                                                       132
```

<210> SEQ ID NO 29
<211> LENGTH: 40
<212> TYPE: PRT
<213> ORGANISM: Artificial Sequence
<220> FEATURE:
<223> OTHER INFORMATION: Zebrafish TCAP4 (40 a.a.)

<400> SEQUENCE: 29

```
Gln Leu Leu Ser Ser Gly Arg Val Gln Gly Tyr Glu Gly Phe Tyr Ile
1               5                   10                  15

Val Ser Val Asp Gln Phe Pro Glu Leu Thr Asp Asn Ile Asn Asn Val
            20                  25                  30

His Phe Trp Arg Gln Thr Glu Met
        35                  40
```

<210> SEQ ID NO 30
<211> LENGTH: 41
<212> TYPE: PRT
<213> ORGANISM: Artificial Sequence
<220> FEATURE:
<223> OTHER INFORMATION: Zebrafish TCAP4 (41 a.a.)

<400> SEQUENCE: 30

```
Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
            20                  25                  30

Val His Phe Trp Arg Gln Thr Glu Met
        35                  40
```

<210> SEQ ID NO 31
<211> LENGTH: 43

<212> TYPE: PRT
<213> ORGANISM: Artificial Sequence
<220> FEATURE:
<223> OTHER INFORMATION: Zebrafish preTCAP4 (43 a.a.)

<400> SEQUENCE: 31

Gln Leu Leu Ser Ser Gly Arg Val Gln Gly Tyr Glu Gly Phe Tyr Ile
1               5                   10                  15

Val Ser Val Asp Gln Phe Pro Glu Leu Thr Asp Asn Ile Asn Asn Val
            20                  25                  30

His Phe Trp Arg Gln Thr Glu Met Gly Arg Arg
        35                  40

<210> SEQ ID NO 32
<211> LENGTH: 44
<212> TYPE: PRT
<213> ORGANISM: Artificial Sequence
<220> FEATURE:
<223> OTHER INFORMATION: Zebrafish preTCAP4 (44 a.a.)

<400> SEQUENCE: 32

Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
            20                  25                  30

Val His Phe Trp Arg Gln Thr Glu Met Gly Arg Arg
            35                  40

<210> SEQ ID NO 33
<211> LENGTH: 120
<212> TYPE: DNA
<213> ORGANISM: Artificial Sequence
<220> FEATURE:
<223> OTHER INFORMATION: Zebrafish TCAP4 (120 n.a.)

<400> SEQUENCE: 33
cagctcctaa gctctggacg tgtacagggc tacgaaggct tctacatagt atcagtcgac      60
cagttcccag agttgactga caacataaat aacgtccatt tctggcgaca gactgagatg     120

<210> SEQ ID NO 34
<211> LENGTH: 123
<212> TYPE: DNA
<213> ORGANISM: Artificial Sequence
<220> FEATURE:
<223> OTHER INFORMATION: Zebrafish TCAP4 (123 n.a.)

<400> SEQUENCE: 34
cagcagctcc taagctctgg acgtgtacag ggctacgaag gcttctacat agtatcagtc      60
gaccagttcc cagagttgac tgacaacata ataacgtcc atttctggcg acagactgag     120
atg                                                                   123

<210> SEQ ID NO 35
<211> LENGTH: 129
<212> TYPE: DNA
<213> ORGANISM: Artificial Sequence
<220> FEATURE:
<223> OTHER INFORMATION: Zebrafish preTCAP4 (129 n.a.)

<400> SEQUENCE: 35
cagctcctaa gctctggacg tgtacagggc tacgaaggct tctacatagt atcagtcgac      60
cagttcccag agttgactga caacataaat aacgtccatt tctggcgaca gactgagatg     120
ggacgcagg                                                             129

<210> SEQ ID NO 36
<211> LENGTH: 132
<212> TYPE: DNA
<213> ORGANISM: Artificial Sequence
<220> FEATURE:
<223> OTHER INFORMATION: Zebrafish preTCAP4 (132 n.a.)

<400> SEQUENCE: 36

```
cagcagctcc taagctctgg acgtgtacag ggctacgaag gcttctacat agtatcagtc    60
gaccagttcc cagagttgac tgacaacata aataacgtcc atttctggcg acagactgag   120
atgggacgca gg                                                       132
```

<210> SEQ ID NO 37
<211> LENGTH: 40
<212> TYPE: PRT
<213> ORGANISM: Artificial Sequence
<220> FEATURE:
<223> OTHER INFORMATION: Mouse TCAP1 (40 a.a.)

<400> SEQUENCE: 37

Gln Leu Leu Gly Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
        35                  40

<210> SEQ ID NO 38
<211> LENGTH: 41
<212> TYPE: PRT
<213> ORGANISM: Artificial Sequence
<220> FEATURE:
<223> OTHER INFORMATION: Mouse TCAP1 (41 a.a.)

<400> SEQUENCE: 38

Gln Gln Leu Leu Gly Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 39
<211> LENGTH: 43
<212> TYPE: PRT
<213> ORGANISM: Artificial Sequence
<220> FEATURE:
<223> OTHER INFORMATION: Mouse preTCAP1 (43 a.a.)

<400> SEQUENCE: 39

Gln Leu Leu Gly Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile Gly Arg Arg
        35                  40

<210> SEQ ID NO 40
<211> LENGTH: 44
<212> TYPE: PRT
<213> ORGANISM: Artificial Sequence
<220> FEATURE:

<223> OTHER INFORMATION: Mouse preTCAP1 (44 a.a.)

<400> SEQUENCE: 40

Gln Gln Leu Leu Gly Thr Gly Arg Val Gln Gly Tyr Asp Gly Tyr Phe
1               5                   10                  15
Val Leu Ser Val Glu Gln Tyr Leu Glu Leu Ser Asp Ser Ala Asn Asn
            20                  25                  30
Ile His Phe Met Arg Gln Ser Glu Ile Gly Arg Arg
        35                  40

<210> SEQ ID NO 41
<211> LENGTH: 120
<212> TYPE: DNA
<213> ORGANISM: Artificial Sequence
<220> FEATURE:
<223> OTHER INFORMATION: Mouse TCAP1 (120 n.a.)

<400> SEQUENCE: 41
cagcttttgg gcaccgggag ggtgcagggg tatgatgggt attttgtctt gtctgttgag      60
cagtatttag aactttcaga cagtgccaac aatattcact tcatgagaca gagtgaaata    120

<210> SEQ ID NO 42
<211> LENGTH: 123
<212> TYPE: DNA
<213> ORGANISM: Artificial Sequence
<220> FEATURE:
<223> OTHER INFORMATION: Mouse TCAP1 (123 n.a.)

<400> SEQUENCE: 42
cagcagcttt tgggcaccgg gagggtgcag gggtatgatg gtattttgt cttgtctgtt       60
gagcagtatt tagaactttc agacagtgcc aacaatattc acttcatgag acagagtgaa    120
ata                                                                  123

<210> SEQ ID NO 43
<211> LENGTH: 129
<212> TYPE: DNA
<213> ORGANISM: Artificial Sequence
<220> FEATURE:
<223> OTHER INFORMATION: Mouse preTCAP1 (129 n.a.)

<400> SEQUENCE: 43
cagcttttgg gcaccgggag ggtgcagggg tatgatgggt attttgtctt gtctgttgag      60
cagtatttag aactttcaga cagtgccaac aatattcact tcatgagaca gagtgaaata    120
ggcaggagg                                                            129

<210> SEQ ID NO 44
<211> LENGTH: 132
<212> TYPE: DNA
<213> ORGANISM: Artificial Sequence
<220> FEATURE:
<223> OTHER INFORMATION: Mouse preTCAP1 (132 n.a.)

<400> SEQUENCE: 44
cagcagcttt tgggcaccgg gagggtgcag gggtatgatg gtattttgt cttgtctgtt       60
gagcagtatt tagaactttc agacagtgcc aacaatattc acttcatgag acagagtgaa    120
ataggcagga gg                                                        132

<210> SEQ ID NO 45
<211> LENGTH: 40
<212> TYPE: PRT
<213> ORGANISM: Artificial Sequence

```
<220> FEATURE:
<223> OTHER INFORMATION: Mouse TCAP2 (40 a.a.)

<400> SEQUENCE: 45

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Asn Ile
            20                  25                  30

Gln Phe Leu Arg Gln Asn Glu Ile
        35                  40

<210> SEQ ID NO 46
<211> LENGTH: 41
<212> TYPE: PRT
<213> ORGANISM: Artificial Sequence
<220> FEATURE:
<223> OTHER INFORMATION: Mouse TCAP2 (41 a.a.)

<400> SEQUENCE: 46

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met
        35                  40

<210> SEQ ID NO 47
<211> LENGTH: 43
<212> TYPE: PRT
<213> ORGANISM: Artificial Sequence
<220> FEATURE:
<223> OTHER INFORMATION: Mouse preTCAP2 (43 a.a)

<400> SEQUENCE: 47

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Asn Ile
            20                  25                  30

Gln Phe Leu Arg Gln Asn Glu Met Gly Lys Arg
        35                  40

<210> SEQ ID NO 48
<211> LENGTH: 44
<212> TYPE: PRT
<213> ORGANISM: Artificial Sequence
<220> FEATURE:
<223> OTHER INFORMATION: Mouse preTCAP2 (44 a.a.)

<400> SEQUENCE: 48

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Ser Asn
            20                  25                  30

Ile Gln Phe Leu Arg Gln Asn Glu Met Gly Lys Arg
        35                  40

<210> SEQ ID NO 49
<211> LENGTH: 120
<212> TYPE: DNA
<213> ORGANISM: Artificial Sequence
<220> FEATURE:
<223> OTHER INFORMATION: Mouse TCAP2 (120 n.a.)

<400> SEQUENCE: 49
```

```
caactcctga gcacgggacg ggtacaaggt tatgagggct attacgtact tccggtggaa    60
cagtacccgg agctggcaga cagtagcagc aacatccagt tcttaagaca gaatgagagg   120
```

<210> SEQ ID NO 50
<211> LENGTH: 123
<212> TYPE: DNA
<213> ORGANISM: Artificial Sequence
<220> FEATURE:
<223> OTHER INFORMATION: Mouse TCAP 2 (123 n.a.)

<400> SEQUENCE: 50

```
cagcaactcc tgagcacggg acgggtacaa ggttatgagg ctattacgt acttccggtg    60 gaacagtacc cggagctggc agacagtagc agcaacatcc agttcttaag acagaatgag   120
atg                                                                 123
```

<210> SEQ ID NO 51
<211> LENGTH: 129
<212> TYPE: DNA
<213> ORGANISM: Artificial Sequence
<220> FEATURE:
<223> OTHER INFORMATION: Mouse preTCAP2 (129 n.a.)

<400> SEQUENCE: 51

```
caactcctga gcacgggacg ggtacaaggt tatgagggct attacgtact tccggtggaa    60
cagtacccgg agctggcaga cagtagcagc aacatccagt tcttaagaca gaatgagatg   120
ggaaagagg                                                           129
```

<210> SEQ ID NO 52
<211> LENGTH: 132
<212> TYPE: DNA
<213> ORGANISM: Artificial Sequence
<220> FEATURE:
<223> OTHER INFORMATION: Mouse preTCAP2 (132 n.a.)

<400> SEQUENCE: 52

```
cagcaactcc tgagcacggg acgggtacaa ggttatgagg ctattacgt acttccggtg    60 gaacagtacc cggagctggc agacagtagc agcaacatcc agttcttaag acagaatgag   120
atgggaaaga gg                                                       132
```

<210> SEQ ID NO 53
<211> LENGTH: 40
<212> TYPE: PRT
<213> ORGANISM: Artificial Sequence
<220> FEATURE:
<223> OTHER INFORMATION: Mouse TCAP3 (40 a.a.)

<400> SEQUENCE: 53

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile
        35                  40

<210> SEQ ID NO 54
<211> LENGTH: 41
<212> TYPE: PRT
<213> ORGANISM: Artificial Sequence
<220> FEATURE:
<223> OTHER INFORMATION: Mouse TCAP3 (41 a..a)

-continued

<400> SEQUENCE: 54

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile
        35                  40

<210> SEQ ID NO 55
<211> LENGTH: 43
<212> TYPE: PRT
<213> ORGANISM: Artificial Sequence
<220> FEATURE:
<223> OTHER INFORMATION: Mouse preTCAP3 (43 a.a.)

<400> SEQUENCE: 55

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile Gly Lys Arg
        35                  40

<210> SEQ ID NO 56
<211> LENGTH: 44
<212> TYPE: PRT
<213> ORGANISM: Artificial Sequence
<220> FEATURE:
<223> OTHER INFORMATION: Mouse preTCAP3 (44 a.a.)

<400> SEQUENCE: 56

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile Gly Lys Arg
        35                  40

<210> SEQ ID NO 57
<211> LENGTH: 120
<212> TYPE: DNA
<213> ORGANISM: Artificial Sequence
<220> FEATURE:
<223> OTHER INFORMATION: Mouse TCAP3 (120 n.a.)

<400> SEQUENCE: 57
cagctgctga gcgctggcaa ggtgcagggc tacgatgggt actacgtact gtcggtggag     60
cagtaccccg agctggctga cagtgccaac aacatccagt tcttgcgaca agtgagatc    120

<210> SEQ ID NO 58
<211> LENGTH: 123
<212> TYPE: DNA
<213> ORGANISM: Artificial Sequence
<220> FEATURE:
<223> OTHER INFORMATION: Mouse TCAP3 (123 n.a.)

<400> SEQUENCE: 58
cggcagctgc tgagcgctgg caaggtgcag ggctacgatg gtactacgt actgtcggtg     60 gagcagtacc ccgagctggc tgacagtgcc aacaacatcc agttcttgcg acaaagtgag   120
atc                                                                 123

<210> SEQ ID NO 59
<211> LENGTH: 129
<212> TYPE: DNA
<213> ORGANISM: Artificial Sequence
<220> FEATURE:
<223> OTHER INFORMATION: Mouse preTCAP3 (129 n.a.)

<400> SEQUENCE: 59
cagctgctga gcgctggcaa ggtgcagggc tacgatgggt actacgtact gtcggtggag    60
cagtaccccg agctggctga cagtgccaac aacatccagt tcttgcgaca aagtgagatc   120
ggcaagagg                                                          129

<210> SEQ ID NO 60
<211> LENGTH: 132
<212> TYPE: DNA
<213> ORGANISM: Artificial Sequence
<220> FEATURE:
<223> OTHER INFORMATION: Mouse preTCAP3 (132 n.a.)

<400> SEQUENCE: 60
cggcagctgc tgagcgctgg caaggtgcag ggctacgatg ggtactacgt actgtcggtg    60
gagcagtacc ccgagctggc tgacagtgcc aacaacatcc agttcttgcg acaaagtgag   120
atcggcaaga gg                                                      132

<210> SEQ ID NO 61
<211> LENGTH: 40
<212> TYPE: PRT
<213> ORGANISM: Artificial Sequence
<220> FEATURE:
<223> OTHER INFORMATION: Mouse TCAP4 (40 a.a.)

<400> SEQUENCE: 61

Gln Val Leu Asn Thr Gly Arg Val Gln Gly Tyr Asp Gly Phe Phe Val
1               5                   10                  15

Thr Ser Val Glu Gln Tyr Pro Glu Leu Ser Asp Ser Ala Asn Asn Ile
            20                  25                  30

His Phe Met Arg Gln Ser Glu Met
        35                  40

<210> SEQ ID NO 62
<211> LENGTH: 41
<212> TYPE: PRT
<213> ORGANISM: Artificial Sequence
<220> FEATURE:
<223> OTHER INFORMATION: Mouse TCAP4 (41 a.a.)

<400> SEQUENCE: 62

Gln Gln Val Leu Asn Thr Gly Arg Val Gln Gly Tyr Asp Gly Phe Phe
1               5                   10                  15

Val Thr Ser Val Glu Gln Tyr Pro Glu Leu Ser Asp Ser Ala Asn Asn
            20                  25                  30

Ile His Phe Met Arg Gln Ser Glu Met
        35                  40

<210> SEQ ID NO 63
<211> LENGTH: 43
<212> TYPE: PRT
<213> ORGANISM: Artificial Sequence
<220> FEATURE:
<223> OTHER INFORMATION: Mouse preTCAP4 (43 a.a.)

<400> SEQUENCE: 63

Gln Val Leu Asn Thr Gly Arg Val Gln Gly Tyr Asp Gly Phe Phe Val

```
                1               5              10              15
Thr Ser Val Glu Gln Tyr Pro Glu Leu Ser Asp Ser Ala Asn Asn Ile
            20                  25                  30

His Phe Met Arg Gln Ser Glu Met Gly Arg Arg
        35                  40

<210> SEQ ID NO 64
<211> LENGTH: 44
<212> TYPE: PRT
<213> ORGANISM: Artificial Sequence
<220> FEATURE:
<223> OTHER INFORMATION: Mouse preTCAP4 (44 a.a.)

<400> SEQUENCE: 64

Gln Gln Val Leu Asn Thr Gly Arg Val Gln Gly Tyr Asp Gly Phe Phe
1               5                   10                  15

Val Thr Ser Val Glu Gln Tyr Pro Glu Leu Ser Asp Ser Ala Asn Asn
            20                  25                  30

Ile His Phe Met Arg Gln Ser Glu Met Gly Arg Arg
        35                  40

<210> SEQ ID NO 65
<211> LENGTH: 120
<212> TYPE: DNA
<213> ORGANISM: Artificial Sequence
<220> FEATURE:
<223> OTHER INFORMATION: Mouse TCAP4 (120 n.a.)

<400> SEQUENCE: 65
caggtgctga acacggggcg ggtgcaaggc tacgacggct tctttgtgac ctcggtcgag      60
cagtacccag aactgtcaga cagcgccaac aatatccact tcatgagaca gagcgagatg     120

<210> SEQ ID NO 66
<211> LENGTH: 123
<212> TYPE: DNA
<213> ORGANISM: Artificial Sequence
<220> FEATURE:
<223> OTHER INFORMATION: Mouse TCAP4 (123 n.a.)

<400> SEQUENCE: 66
cagcaggtgc tgaacacggg gcgggtgcaa ggctacgacg gcttctttgt gacctcggtc      60
gagcagtacc cagaactgtc agacagcgcc aacaatatcc acttcatgag acagagcgag    120
atg                                                                   123

<210> SEQ ID NO 67
<211> LENGTH: 129
<212> TYPE: DNA
<213> ORGANISM: Artificial Sequence
<220> FEATURE:
<223> OTHER INFORMATION: Mouse preTCAP4 (129 n.a.)

<400> SEQUENCE: 67
caggtgctga acacggggcg ggtgcaaggc tacgacggct tctttgtgac ctcggtcgag      60
cagtacccag aactgtcaga cagcgccaac aatatccact tcatgagaca gagcgagatg    120
ggccgaagg                                                             129

<210> SEQ ID NO 68
<211> LENGTH: 132
<212> TYPE: DNA
<213> ORGANISM: Artificial Sequence
<220> FEATURE:
<223> OTHER INFORMATION: Mouse preTCAP4 (132 n.a.)
```

-continued

<400> SEQUENCE: 68
cagcaggtgc tgaacacggg gcgggtgcaa ggctacgacg gcttctttgt gacctcggtc    60
gagcagtacc cagaactgtc agacagcgcc aacaatatcc acttcatgag acagagcgag   120
atgggccgaa gg                                                      132

<210> SEQ ID NO 69
<211> LENGTH: 40
<212> TYPE: PRT
<213> ORGANISM: Artificial Sequence
<220> FEATURE:
<223> OTHER INFORMATION: Human TCAP1 (40 a.a.)

<400> SEQUENCE: 69

Gln Leu Leu Ser Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
        35                  40

<210> SEQ ID NO 70
<211> LENGTH: 41
<212> TYPE: PRT
<213> ORGANISM: Artificial Sequence
<220> FEATURE:
<223> OTHER INFORMATION: Human TCAP1 (41 a.a.)

<400> SEQUENCE: 70

Gln Gln Leu Leu Ser Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 71
<211> LENGTH: 43
<212> TYPE: PRT
<213> ORGANISM: Artificial Sequence
<220> FEATURE:
<223> OTHER INFORMATION: Human preTCAP1 (43 a.a.)

<400> SEQUENCE: 71

Gln Leu Leu Ser Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile Gly Arg Arg
        35                  40

<210> SEQ ID NO 72
<211> LENGTH: 44
<212> TYPE: PRT
<213> ORGANISM: Artificial Sequence
<220> FEATURE:
<223> OTHER INFORMATION: Human preTCAP1 (44 a.a.)

<400> SEQUENCE: 72

Gln Gln Leu Leu Ser Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn

```
                    20                  25                  30
Ile His Phe Met Arg Gln Ser Glu Ile Gly Arg Arg
         35                  40

<210> SEQ ID NO 73
<211> LENGTH: 120
<212> TYPE: DNA
<213> ORGANISM: Artificial Sequence
<220> FEATURE:
<223> OTHER INFORMATION: Human TCAP1 (120 n.a.)

<400> SEQUENCE: 73
cagcttttga gcactgggcg ggtacaaggt tacgatgggt attttgtttt gtctgttgag      60
cagtatttag aactttctga cagtgccaat aatattcact ttatgagaca gagcgaaata     120

<210> SEQ ID NO 74
<211> LENGTH: 123
<212> TYPE: DNA
<213> ORGANISM: Artificial Sequence
<220> FEATURE:
<223> OTHER INFORMATION: Human TCAP1 (123 n.a.)

<400> SEQUENCE: 74
cagcagcttt tgagcactgg gcgggtacaa ggttacgatg gtattttgt tttgtctgtt       60 gagcagtatt tagaactttc tgacagtgcc aataatattc actttatgag acagagcgaa    120
ata                                                                  123

<210> SEQ ID NO 75
<211> LENGTH: 129
<212> TYPE: DNA
<213> ORGANISM: Artificial Sequence
<220> FEATURE:
<223> OTHER INFORMATION: Human preTCAP1 (129 n.a.)

<400> SEQUENCE: 75
cagcttttga gcactgggcg ggtacaaggt tacgatgggt attttgtttt gtctgttgag      60
cagtatttag aactttctga cagtgccaat aatattcact ttatgagaca gagcgaaata    120
ggcaggagg                                                             129

<210> SEQ ID NO 76
<211> LENGTH: 132
<212> TYPE: DNA
<213> ORGANISM: Artificial Sequence
<220> FEATURE:
<223> OTHER INFORMATION: Human preTCAP1 (132 n.a.)

<400> SEQUENCE: 76
cagcagcttt tgagcactgg gcgggtacaa ggttacgatg gtattttgt tttgtctgtt       60 gagcagtatt tagaactttc tgacagtgcc aataatattc actttatgag acagagcgaa    120
ataggcagga gg                                                         132

<210> SEQ ID NO 77
<211> LENGTH: 40
<212> TYPE: PRT
<213> ORGANISM: Artificial Sequence
<220> FEATURE:
<223> OTHER INFORMATION: Human TCAP2 (40 a.a.)

<400> SEQUENCE: 77

Gln Leu Leu Ser Thr Gly Arg Val Gln Gly Tyr Glu Gly Tyr Tyr Val
1               5                  10                  15
```

Leu Pro Val Glu Gln Tyr Pro Glu Leu Ala Asp Ser Ser Asn Ile
            20                  25                  30

Gln Phe Leu Arg Gln Asn Glu Met
        35                  40

<210> SEQ ID NO 78
<211> LENGTH: 41
<212> TYPE: PRT
<213> ORGANISM: Artificial Sequence
<220> FEATURE:
<223> OTHER INFORMATION: Human preTCAP2 (41 a.a.)

<400> SEQUENCE: 78

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Asn
            20                  25                  30

Ile Gln Phe Leu Arg Gln Asn Glu Met
        35                  40

<210> SEQ ID NO 79
<211> LENGTH: 43
<212> TYPE: PRT
<213> ORGANISM: Artificial Sequence
<220> FEATURE:
<223> OTHER INFORMATION: Human preTCAP2 (43 a.a.)

<400> SEQUENCE: 79

Gln Leu Leu Ser Thr Gly Arg Val Gln Gly Tyr Glu Gly Tyr Tyr Val
1               5                   10                  15

Leu Pro Val Glu Gln Tyr Pro Glu Leu Ala Asp Ser Ser Asn Ile
            20                  25                  30

Gln Phe Leu Arg Gln Asn Glu Met Gly Lys Arg
        35                  40

<210> SEQ ID NO 80
<211> LENGTH: 44
<212> TYPE: PRT
<213> ORGANISM: Artificial Sequence
<220> FEATURE:
<223> OTHER INFORMATION: Human preTCAP2 (44 a.a.)

<400> SEQUENCE: 80

Gln Gln Leu Leu Ser Thr Gly Arg Val Gln Gly Tyr Glu Gly Tyr Tyr
1               5                   10                  15

Val Leu Pro Val Glu Gln Tyr Pro Glu Leu Ala Asp Ser Ser Asn
            20                  25                  30

Ile Gln Phe Leu Arg Gln Asn Glu Met Gly Lys Arg
        35                  40

<210> SEQ ID NO 81
<211> LENGTH: 120
<212> TYPE: DNA
<213> ORGANISM: Artificial Sequence
<220> FEATURE:
<223> OTHER INFORMATION: Human TCAP2 (120 n.a.)

<400> SEQUENCE: 81
cagcttctga gcaccgggcg cgtgcaaggg tacgagggat attacgtgct tcccgtggag    60
caatacccag agcttgcaga cagtagcagc aacatccagt ttttaagaca gaatgagatg   120

<210> SEQ ID NO 82
<211> LENGTH: 123

-continued

```
<212> TYPE: DNA
<213> ORGANISM: Artificial Sequence
<220> FEATURE:
<223> OTHER INFORMATION: Human TCAP2 (123 n.a.)

<400> SEQUENCE: 82
cagcagcttc tgagcaccgg gcgcgtgcaa gggtacgagg gatattacgt gcttcccgtg    60
gagcaatacc cagagcttgc agacagtagc agcaacatcc agttttttaag acagaatgag   120 atg                                                                  123

<210> SEQ ID NO 83
<211> LENGTH: 129
<212> TYPE: DNA
<213> ORGANISM: Artificial Sequence
<220> FEATURE:
<223> OTHER INFORMATION: Human preTCAP2 (129 n.a.)

<400> SEQUENCE: 83
cagcttctga gcaccgggcg cgtgcaaggg tacgagggat attacgtgct tcccgtggag    60
caatacccag agcttgcaga cagtagcagc aacatccagt ttttaagaca gaatgagatg   120
ggaaagagg                                                            129

<210> SEQ ID NO 84
<211> LENGTH: 132
<212> TYPE: DNA
<213> ORGANISM: Artificial Sequence
<220> FEATURE:
<223> OTHER INFORMATION: Human preTCAP2 (132 n.a.)

<400> SEQUENCE: 84
cagcagcttc tgagcaccgg gcgcgtgcaa gggtacgagg gatattacgt gcttcccgtg    60
gagcaatacc cagagcttgc agacagtagc agcaacatcc agttttttaag acagaatgag   120 atgggaaaga gg                                                        132

<210> SEQ ID NO 85
<211> LENGTH: 40
<212> TYPE: PRT
<213> ORGANISM: Artificial Sequence
<220> FEATURE:
<223> OTHER INFORMATION: Human TCAP3 (40 a.a.)

<400> SEQUENCE: 85

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile
        35                  40

<210> SEQ ID NO 86
<211> LENGTH: 41
<212> TYPE: PRT
<213> ORGANISM: Artificial Sequence
<220> FEATURE:
<223> OTHER INFORMATION: Human TCAP3 (41 a.a.)

<400> SEQUENCE: 86

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30
```

-continued

```
Ile Gln Phe Leu Arg Gln Ser Glu Ile
        35                  40

<210> SEQ ID NO 87
<211> LENGTH: 43
<212> TYPE: PRT
<213> ORGANISM: Artificial Sequence
<220> FEATURE:
<223> OTHER INFORMATION: Human preTCAP3 (43 a.a.)

<400> SEQUENCE: 87

Gln Leu Leu Ser Ala Gly Lys Val Gln Gly Tyr Asp Gly Tyr Tyr Val
1               5                   10                  15

Leu Ser Val Glu Gln Tyr Pro Glu Leu Ala Asp Ser Ala Asn Asn Ile
            20                  25                  30

Gln Phe Leu Arg Gln Ser Glu Ile Gly Arg Arg
        35                  40

<210> SEQ ID NO 88
<211> LENGTH: 44
<212> TYPE: PRT
<213> ORGANISM: Artificial Sequence
<220> FEATURE:
<223> OTHER INFORMATION: Human preTCAP3 (44 a.a.)

<400> SEQUENCE: 88

Arg Gln Leu Leu Ser Ala Gly Lys Val Gln Gly Tyr Asp Gly Tyr Tyr
1               5                   10                  15

Val Leu Ser Val Glu Gln Tyr Pro Glu Leu Ala Asp Ser Ala Asn Asn
            20                  25                  30

Ile Gln Phe Leu Arg Gln Ser Glu Ile Gly Arg Arg
        35                  40

<210> SEQ ID NO 89
<211> LENGTH: 120
<212> TYPE: DNA
<213> ORGANISM: Artificial Sequence
<220> FEATURE:
<223> OTHER INFORMATION: Human TCAP3 (120 n.a.)

<400> SEQUENCE: 89
cagctgctga gcgccggcaa ggtgcagggc tacgacgggt actacgtact ctcggtggag      60
cagtaccccg agctggccga cagcgccaac aacatccagt tcctgcggca gagcgagatc    120

<210> SEQ ID NO 90
<211> LENGTH: 123
<212> TYPE: DNA
<213> ORGANISM: Artificial Sequence
<220> FEATURE:
<223> OTHER INFORMATION: Human TCAP3 (123 n.a.)

<400> SEQUENCE: 90
cggcagctgc tgagcgccgg caaggtgcag ggctacgacg gtactacgt actctcggtg      60 gagcagtacc ccgagctggc cgacagcgcc aacaacatcc agttcctgcg gcagagcgag    120
atc                                                                  123

<210> SEQ ID NO 91
<211> LENGTH: 129
<212> TYPE: DNA
<213> ORGANISM: Artificial Sequence
<220> FEATURE:
<223> OTHER INFORMATION: Human preTCAP (129 n.a.)

<400> SEQUENCE: 91
```

-continued

```
cagctgctga gcgccggcaa ggtgcagggc tacgacgggt actacgtact ctcggtggag      60
cagtaccccg agctggccga cagcgccaac aacatccagt tcctgcggca gagcgagatc     120
ggcaggagg                                                             129
```

<210> SEQ ID NO 92
<211> LENGTH: 132
<212> TYPE: DNA
<213> ORGANISM: Artificial Sequence
<220> FEATURE:
<223> OTHER INFORMATION: Human preTCAP3 (132 n.a.)

<400> SEQUENCE: 92

```
cggcagctgc tgagcgccgg caaggtgcag ggctacgacg gtactacgt actctcggtg       60 gagcagtacc ccgagctggc cgacagcgcc aacaacatcc agttcctgcg gcagagcgag    120
atcggcagga gg                                                         132
```

<210> SEQ ID NO 93
<211> LENGTH: 40
<212> TYPE: PRT
<213> ORGANISM: Artificial Sequence
<220> FEATURE:
<223> OTHER INFORMATION: Human TCAP4 (40 a.a.)

<400> SEQUENCE: 93

```
Gln Val Leu Ser Thr Gly Arg Val Gln Gly Tyr Asp Gly Phe Phe Val
1               5                   10                  15

Ile Ser Val Glu Gln Tyr Pro Glu Leu Ser Asp Ser Ala Asn Asn Ile
            20                  25                  30

His Phe Met Arg Gln Ser Glu Met
        35                  40
```

<210> SEQ ID NO 94
<211> LENGTH: 41
<212> TYPE: PRT
<213> ORGANISM: Artificial Sequence
<220> FEATURE:
<223> OTHER INFORMATION: Human TCAP4 (41 a.a.)

<400> SEQUENCE: 94

```
Gln Gln Val Leu Ser Thr Gly Arg Val Gln Gly Tyr Asp Gly Phe Phe
1               5                   10                  15

Val Ile Ser Val Glu Gln Tyr Pro Glu Leu Ser Asp Ser Ala Asn Asn
            20                  25                  30

Ile His Phe Met Arg Gln Ser Glu Met
        35                  40
```

<210> SEQ ID NO 95
<211> LENGTH: 43
<212> TYPE: PRT
<213> ORGANISM: Artificial Sequence
<220> FEATURE:
<223> OTHER INFORMATION: Human preTCAP4 (43 a..a)

<400> SEQUENCE: 95

```
Gln Val Leu Ser Thr Gly Arg Val Gln Gly Tyr Asp Gly Phe Phe Val
1               5                   10                  15

Ile Ser Val Glu Gln Tyr Pro Glu Leu Ser Asp Ser Ala Asn Asn Ile
            20                  25                  30

His Phe Met Arg Gln Ser Glu Met Gly Arg Arg
        35                  40
```

<210> SEQ ID NO 96
<211> LENGTH: 44
<212> TYPE: PRT
<213> ORGANISM: Artificial Sequence
<220> FEATURE:
<223> OTHER INFORMATION: Human preTCAP4 (44 a.a.)

<400> SEQUENCE: 96

Gln Gln Val Leu Ser Thr Gly Arg Val Gln Gly Tyr Asp Gly Phe Phe
1               5                   10                  15

Val Ile Ser Val Glu Gln Tyr Pro Glu Leu Ser Asp Ser Ala Asn Asn
            20                  25                  30

Ile His Phe Met Arg Gln Ser Glu Met Gly Arg Arg
        35                  40

<210> SEQ ID NO 97
<211> LENGTH: 120
<212> TYPE: DNA
<213> ORGANISM: Artificial Sequence
<220> FEATURE:
<223> OTHER INFORMATION: Human TCAP4 (120 n.a.)

<400> SEQUENCE: 97
caggtgctga gcacagggcg ggtgcaaggc tacgacggct ttttcgtgat ctctgtcgag      60
cagtacccag aactgtcaga cagcgccaac aacatccact tcatgagaca gagcgagatg    120

<210> SEQ ID NO 98
<211> LENGTH: 123
<212> TYPE: DNA
<213> ORGANISM: Artificial Sequence
<220> FEATURE:
<223> OTHER INFORMATION: Human TCAP4 (123 n.a.)

<400> SEQUENCE: 98
cagcaggtgc tgagcacagg gcgggtgcaa ggctacgacg gcttttttcgt gatctctgtc    60 gagcagtacc cagaactgtc agacagcgcc aacaacatcc acttcatgag acagagcgag   120
atg                                                                 123

<210> SEQ ID NO 99
<211> LENGTH: 129
<212> TYPE: DNA
<213> ORGANISM: Artificial Sequence
<220> FEATURE:
<223> OTHER INFORMATION: Human preTCAP4 (129 n.a.)

<400> SEQUENCE: 99
caggtgctga gcacagggcg ggtgcaaggc tacgacggct ttttcgtgat ctctgtcgag      60
cagtacccag aactgtcaga cagcgccaac aacatccact tcatgagaca gagcgagatg    120
ggccggagg                                                           129

<210> SEQ ID NO 100
<211> LENGTH: 132
<212> TYPE: DNA
<213> ORGANISM: Artificial Sequence
<220> FEATURE:
<223> OTHER INFORMATION: Human preTCAP4 (132 n.a.)

<400> SEQUENCE: 100
cagcaggtgc tgagcacagg gcgggtgcaa ggctacgacg gcttttttcgt gatctctgtc    60 gagcagtacc cagaactgtc agacagcgcc aacaacatcc acttcatgag acagagcgag   120
atgggccgga gg                                                       132

```
<210> SEQ ID NO 101
<211> LENGTH: 41
<212> TYPE: PRT
<213> ORGANISM: Artificial Sequence
<220> FEATURE:
<223> OTHER INFORMATION: G. gallus TCAP-1

<400> SEQUENCE: 101

Gln Gln Leu Leu Asn Thr Gly Arg Val Gln Gly Tyr Asp Gly Tyr Phe
1               5                   10                  15

Val Leu Ser Val Glu Gln Tyr Leu Glu Leu Ser Asp Ser Ala Asn Asn
            20                  25                  30

Ile His Phe Met Arg Gln Ser Glu Ile
        35                  40

<210> SEQ ID NO 102
<211> LENGTH: 41
<212> TYPE: PRT
<213> ORGANISM: Artificial Sequence
<220> FEATURE:
<223> OTHER INFORMATION: Zebrafish TCAP-4

<400> SEQUENCE: 102

Gln Gln Leu Leu Ser Ser Gly Arg Val Gln Gly Tyr Glu Gly Phe Tyr
1               5                   10                  15

Ile Val Ser Val Asp Gln Phe Pro Glu Leu Thr Asp Asn Ile Asn Asn
            20                  25                  30

Val His Phe Trp Arg Gln Thr Glu Met
        35                  40

<210> SEQ ID NO 103
<211> LENGTH: 37
<212> TYPE: PRT
<213> ORGANISM: Artificial Sequence
<220> FEATURE:
<223> OTHER INFORMATION: D. melanogaster Ten-m gene product

<400> SEQUENCE: 103

Glu Leu Val Gln His Gly Asp Val Asp Gly Trp Asn Gly Asp Ile His
1               5                   10                  15

Ser Ile His Lys Tyr Pro Gln Leu Ala Asp Pro Gly Asn Val Ala Phe
            20                  25                  30

Gln Arg Asp Ala Lys
        35

<210> SEQ ID NO 104
<211> LENGTH: 41
<212> TYPE: PRT
<213> ORGANISM: Artificial Sequence
<220> FEATURE:
<223> OTHER INFORMATION: Human CRF TCAP like region

<400> SEQUENCE: 104

Ser Glu Glu Pro Pro Ile Ser Leu Asp Leu Thr Phe His Leu Leu Arg
1               5                   10                  15

Glu Val Leu Glu Met Ala Arg Ala Glu Gln Leu Ala Gln Gln Ala His
            20                  25                  30

Ser Asn Arg Lys Leu Met Glu Ile Ile
        35                  40

<210> SEQ ID NO 105
<211> LENGTH: 40
```

-continued

```
<212> TYPE: PRT
<213> ORGANISM: Artificial Sequence
<220> FEATURE:
<223> OTHER INFORMATION: Human urocortin TCAP-like region

<400> SEQUENCE: 105

Asp Asn Pro Ser Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
            20                  25                  30

Asn Arg Ile Ile Phe Asp Ser Val
        35                  40

<210> SEQ ID NO 106
<211> LENGTH: 38
<212> TYPE: PRT
<213> ORGANISM: Artificial Sequence
<220> FEATURE:
<223> OTHER INFORMATION: Human urocortin 2 TCAP-like region

<400> SEQUENCE: 106

Ile Val Leu Ser Leu Asp Val Pro Ile Gly Leu Leu Gln Ile Leu Leu
1               5                   10                  15

Glu Gln Ala Arg Ala Arg Ala Ala Arg Glu Gln Ala Thr Thr Asn Ala
            20                  25                  30

Arg Ile Leu Ala Arg Val
        35

<210> SEQ ID NO 107
<211> LENGTH: 38
<212> TYPE: PRT
<213> ORGANISM: Artificial Sequence
<220> FEATURE:
<223> OTHER INFORMATION: Human urocortin 3 TCAP=like region

<400> SEQUENCE: 107

Phe Thr Leu Ser Leu Asp Val Pro Thr Asn Ile Met Asn Leu Leu Phe
1               5                   10                  15

Asn Ile Ala Lys Ala Lys Asn Leu Arg Ala Gln Ala Ala Ala Asn Ala
            20                  25                  30

His Leu Met Ala Gln Ile
        35

<210> SEQ ID NO 108
<211> LENGTH: 46
<212> TYPE: PRT
<213> ORGANISM: Artificial Sequence
<220> FEATURE:
<223> OTHER INFORMATION: L. migratoria DP

<400> SEQUENCE: 108

Met Gly Met Gly Pro Ser Leu Ser Ile Val Asn Pro Met Asp Val Leu
1               5                   10                  15

Arg Gln Arg Leu Leu Leu Glu Ile Ala Arg Arg Arg Leu Arg Asp Ala
            20                  25                  30

Glu Glu Gln Ile Lys Ala Asn Lys Asp Phe Leu Gln Gln Ile
        35                  40                  45

<210> SEQ ID NO 109
<211> LENGTH: 46
<212> TYPE: PRT
<213> ORGANISM: Artificial Sequence
<220> FEATURE:
<223> OTHER INFORMATION: A. domesticus DP
```

<400> SEQUENCE: 109

Thr Gly Ala Gln Ser Leu Ser Ile Val Ala Pro Leu Asp Val Leu Arg
1               5                   10                  15

Gln Arg Leu Met Asn Glu Leu Asn Arg Arg Met Arg Glu Leu Gln
            20                  25                  30

Gly Ser Arg Ile Gln Gln Asn Arg Gln Leu Leu Thr Ser Ile
        35                  40                  45

<210> SEQ ID NO 110
<211> LENGTH: 39
<212> TYPE: PRT
<213> ORGANISM: Artificial Sequence
<220> FEATURE:
<223> OTHER INFORMATION: T. molitor DP

<400> SEQUENCE: 110

Ser Pro Thr Ile Ser Ile Thr Ala Pro Ile Asp Val Leu Arg Lys Thr
1               5                   10                  15

Trp Glu Gln Glu Arg Ala Arg Lys Gln Met Val Ala Gln Asn Asn Arg
            20                  25                  30

Glu Phe Leu Asn Ser Leu Asn
        35

<210> SEQ ID NO 111
<211> LENGTH: 41
<212> TYPE: PRT
<213> ORGANISM: Artificial Sequence
<220> FEATURE:
<223> OTHER INFORMATION: M. sexta DP-1

<400> SEQUENCE: 111

Arg Met Pro Ser Leu Ser Ile Asp Leu Pro Met Ser Val Leu Arg Gln
1               5                   10                  15

Lys Leu Ser Leu Glu Lys Glu Arg Lys Val His Ala Leu Arg Ala Ala
            20                  25                  30

Ala Asn Arg Asn Phe Leu Asn Asp Ile
        35                  40

<210> SEQ ID NO 112
<211> LENGTH: 30
<212> TYPE: PRT
<213> ORGANISM: Artificial Sequence
<220> FEATURE:
<223> OTHER INFORMATION: M. sexta DP-II

<400> SEQUENCE: 112

Ser Leu Ser Val Asn Pro Ala Val Asp Ile Leu Gln His Arg Tyr Met
1               5                   10                  15

Glu Lys Val Ala Gln Asn Asn Arg Asn Phe Leu Asn Arg Val
            20                  25                  30

<210> SEQ ID NO 113
<211> LENGTH: 45
<212> TYPE: PRT
<213> ORGANISM: Artificial Sequence
<220> FEATURE:
<223> OTHER INFORMATION: P. Americana

<400> SEQUENCE: 113

Thr Gly Ser Gly Pro Ser Leu Ser Ile Val Asn Pro Leu Asp Val Leu
1               5                   10                  15

Arg Gln Arg Leu Leu Leu Glu Ile Ala Arg Arg Arg Met Arg Gln Ser

```
                    20                  25                  30

Gln Asp Gln Ile Gln Asn Arg Glu Ile Leu Gln Thr Ile
        35                  40                  45

<210> SEQ ID NO 114
<211> LENGTH: 41
<212> TYPE: PRT
<213> ORGANISM: Artificial Sequence
<220> FEATURE:
<223> OTHER INFORMATION: O. keta CRP

<400> SEQUENCE: 114

Ser Asp Asp Pro Pro Ile Ser Leu Asp Leu Thr Phe His Met Leu Arg
1               5                   10                  15

Gln Met Asn Glu Met Ser Arg Ala Glu Gln Leu Gln Gln Gln Ala His
                20                  25                  30

Ser Asn Arg Lys Met Met Glu Ile Phe
        35                  40

<210> SEQ ID NO 115
<211> LENGTH: 40
<212> TYPE: PRT
<213> ORGANISM: Artificial Sequence
<220> FEATURE:
<223> OTHER INFORMATION: R. norvegicus

<400> SEQUENCE: 115

Asp Asp Pro Pro Leu Ser Ile Asp Leu Thr Phe His Leu Leu Arg Thr
1               5                   10                  15

Leu Leu Glu Leu Ala Arg Thr Gln Ser Gln Arg Glu Arg Ala Glu Gln
                20                  25                  30

Asn Arg Ile Ile Phe Asp Ser Val
        35                  40

<210> SEQ ID NO 116
<211> LENGTH: 37
<212> TYPE: PRT
<213> ORGANISM: Artificial Sequence
<220> FEATURE:
<223> OTHER INFORMATION: P. sauvageii

<400> SEQUENCE: 116

Gln Gly Pro Pro Ile Ser Ile Asp Leu Ser Leu Glu Leu Leu Arg Lys
1               5                   10                  15

Met Ile Glu Ile Glu Lys Gln Glu Lys Glu Lys Gln Gln Ala Ala Asn
                20                  25                  30

Asn Arg Leu Leu Leu
        35

<210> SEQ ID NO 117
<211> LENGTH: 41
<212> TYPE: PRT
<213> ORGANISM: Artificial Sequence
<220> FEATURE:
<223> OTHER INFORMATION: C. carpio US

<400> SEQUENCE: 117

Asn Asp Asp Pro Pro Ile Ser Ile Asp Leu Thr Phe His Leu Leu Arg
1               5                   10                  15

Asn Met Ile Glu Met Ala Arg Asn Glu Asn Gln Arg Glu Gln Ala Gly
                20                  25                  30

Leu Asn Arg Lys Tyr Leu Asp Glu Val
        35                  40
```

```
<210> SEQ ID NO 118
<211> LENGTH: 38
<212> TYPE: PRT
<213> ORGANISM: Artificial Sequence
<220> FEATURE:
<223> OTHER INFORMATION: M. Musculus UCN2

<400> SEQUENCE: 118

Val Ile Leu Ser Leu Asp Val Pro Ile Gly Leu Leu Arg Ile Leu Leu
1               5                   10                  15

Glu Gln Ala Arg Tyr Lys Ala Ala Arg Asn Gln Ala Ala Thr Asn Ala
            20                  25                  30

Gln Ile Leu Ala His Val
        35

<210> SEQ ID NO 119
<211> LENGTH: 38
<212> TYPE: PRT
<213> ORGANISM: Artificial Sequence
<220> FEATURE:
<223> OTHER INFORMATION: R. dano UCN2

<400> SEQUENCE: 119

Leu Thr Leu Ser Leu Asp Val Pro Thr Asn Ile Met Asn Val Leu Phe
1               5                   10                  15

Asp Val Ala Lys Ala Lys Asn Leu Arg Ala Lys Ala Ala Glu Asn Ala
            20                  25                  30

Arg Leu Leu Ala His Ile
        35

<210> SEQ ID NO 120
<211> LENGTH: 305
<212> TYPE: DNA
<213> ORGANISM: Artificial Sequence
<220> FEATURE:
<223> OTHER INFORMATION: Hamster 305bp urocortin cDNA probe examples
      "cloning mRNA"

<400> SEQUENCE: 120
attcaccgcc gctcgggatc tgagcctgca ggcgagcggc agcgacggga agaccttccg    60
ctgtccatcg acctcacatt ccacctgcta cggaccctgc tggagatggc ccggacacag   120
agccaacgcg agcgagcaga gcagaaccga atcatactca acgcggtggg caagtgatcg   180
gcccggtgtg ggaccccaaa aggctcgacc ctttcccta cctaccccgg ggctgaagtc   240
acgcgaccga agtcggctta gtcccgcggt gcagcgcctc ccagagttac cctgaacaat   300
cccgc                                                              305

<210> SEQ ID NO 121
<211> LENGTH: 24
<212> TYPE: DNA
<213> ORGANISM: Artificial Sequence
<220> FEATURE:
<223> OTHER INFORMATION: TCAP1 fwd primer

<400> SEQUENCE: 121
acgtcagtgt tgatgggagg acta                                          24

<210> SEQ ID NO 122
<211> LENGTH: 27
<212> TYPE: DNA
<213> ORGANISM: Artificial Sequence
<220> FEATURE:
```

<223> OTHER INFORMATION: TCAP1 rvs primer

<400> SEQUENCE: 122
cctcctgcct atttcactct gtctcat                                27

<210> SEQ ID NO 123
<211> LENGTH: 25
<212> TYPE: DNA
<213> ORGANISM: Artificial Sequence
<220> FEATURE:
<223> OTHER INFORMATION: TCAP2 Fwd primer

<400> SEQUENCE: 123
tcgagggcaa ggacacacac tactt                                  25

<210> SEQ ID NO 124
<211> LENGTH: 26
<212> TYPE: DNA
<213> ORGANISM: Artificial Sequence
<220> FEATURE:
<223> OTHER INFORMATION: TCAP2 rvs primer

<400> SEQUENCE: 124
aagaactgga tgttgctgct actgtc                                 26

<210> SEQ ID NO 125
<211> LENGTH: 25
<212> TYPE: DNA
<213> ORGANISM: Artificial Sequence
<220> FEATURE:
<223> OTHER INFORMATION: TCAP3 fwd primer

<400> SEQUENCE: 125
caacaacgcc ttctacctgg agaac                                  25

<210> SEQ ID NO 126
<211> LENGTH: 21
<212> TYPE: DNA
<213> ORGANISM: Artificial Sequence
<220> FEATURE:
<223> OTHER INFORMATION: TCAP3 rvs primer

<400> SEQUENCE: 126
tgttgttggc actgtcagcc a                                      21

<210> SEQ ID NO 127
<211> LENGTH: 23
<212> TYPE: DNA
<213> ORGANISM: Artificial Sequence
<220> FEATURE:
<223> OTHER INFORMATION: TCAP4 fwd primer

<400> SEQUENCE: 127
tttgcctcca gtggttccat ctt                                    23

<210> SEQ ID NO 128
<211> LENGTH: 24
<212> TYPE: DNA
<213> ORGANISM: Artificial Sequence
<220> FEATURE:
<223> OTHER INFORMATION: TCAP4 rvs primer

<400> SEQUENCE: 128
tggatattgt tggcgctgtc tgac                                   24

<210> SEQ ID NO 129

```
<211> LENGTH: 6
<212> TYPE: PRT
<213> ORGANISM: Artificial Sequence
<220> FEATURE:
<223> OTHER INFORMATION: Conserved motif between CRF and TCAP
      I/L S X X (X)-L/V at amino terminus
<220> FEATURE:
<221> NAME/KEY: MISC_FEATURE
<222> LOCATION: (1)..(1)
<223> OTHER INFORMATION: X=I or L
<220> FEATURE:
<221> NAME/KEY: MISC_FEATURE
<222> LOCATION: (3)..(3)
<223> OTHER INFORMATION: X=T or A
<220> FEATURE:
<221> NAME/KEY: MISC_FEATURE
<222> LOCATION: (4)..(4)
<223> OTHER INFORMATION: X=L, I or G
<220> FEATURE:
<221> NAME/KEY: MISC_FEATURE
<222> LOCATION: (5)..(5)
<223> OTHER INFORMATION: X=D, R or K
<220> FEATURE:
<221> NAME/KEY: MISC_FEATURE
<222> LOCATION: (6)..(6)
<223> OTHER INFORMATION: X=L or V

<400> SEQUENCE: 129

Xaa Ser Xaa Xaa Xaa Xaa
1               5

<210> SEQ ID NO 130
<211> LENGTH: 4
<212> TYPE: PRT
<213> ORGANISM: Artificial Sequence
<220> FEATURE:
<223> OTHER INFORMATION: Conserved motif between CRF and TCAP - In
      middle  L/V-L/I-X-V/aliphatic residue
<220> FEATURE:
<221> NAME/KEY: MISC_FEATURE
<222> LOCATION: (1)..(1)
<223> OTHER INFORMATION: X=V or L
<220> FEATURE:
<221> NAME/KEY: MISC_FEATURE
<222> LOCATION: (2)..(2)
<223> OTHER INFORMATION: X=L, I or F
<220> FEATURE:
<221> NAME/KEY: MISC_FEATURE
<222> LOCATION: (3)..(3)
<223> OTHER INFORMATION: X=E, N, S or P
<220> FEATURE:
<221> NAME/KEY: MISC_FEATURE
<222> LOCATION: (4)..(4)
<223> OTHER INFORMATION: X=M, L Q, I or V

<400> SEQUENCE: 130

Xaa Xaa Xaa Xaa
1

<210> SEQ ID NO 131
<211> LENGTH: 4
<212> TYPE: PRT
<213> ORGANISM: Artificial Sequence
<220> FEATURE:
<223> OTHER INFORMATION: Conserved motif between CRF and TCAP
      N/I/A-H/basic residue -I/L/F/-aliphatic at carboxy terminus
<220> FEATURE:
<221> NAME/KEY: MISC_FEATURE
<222> LOCATION: (2)..(2)
<223> OTHER INFORMATION: X=R, A or I
<220> FEATURE:
<221> NAME/KEY: MISC_FEATURE
<222> LOCATION: (3)..(3)
<223> OTHER INFORMATION: X=H or basic residues, K, I, R or Q
<220> FEATURE:
<221> NAME/KEY: MISC_FEATURE
```

```
<222> LOCATION: (4)..(4)
<223> OTHER INFORMATION: X=I, L or F

<400> SEQUENCE: 131

Asn Xaa Xaa Xaa
1

<210> SEQ ID NO 132
<211> LENGTH: 8964
<212> TYPE: DNA
<213> ORGANISM: Mus musculus
<220> FEATURE:
<221> NAME/KEY: exon
<222> LOCATION: (50)..(8197)

<400> SEQUENCE: 132
aagttctaag aagccggacc gatgtgcaca gagaaggaat gaaggaagt atg gat gtg      58
                                                     Met Asp Val
                                                       1 aag gaa cgc agg cct tac tgc tcc ttg acc aag agc aga cgg gaa aag       106
Lys Glu Arg Arg Pro Tyr Cys Ser Leu Thr Lys Ser Arg Arg Glu Lys
  5              10                  15 gaa agg cgc tat aca aat tcg tcc gcg gac aat gag gag tgt agg gtc       154
Glu Arg Arg Tyr Thr Asn Ser Ser Ala Asp Asn Glu Glu Cys Arg Val
 20                  25                  30                  35 ccc acg cag aag tcc tat agt tcc agt gaa acc ttg aaa gct ttc gat       202
Pro Thr Gln Lys Ser Tyr Ser Ser Ser Glu Thr Leu Lys Ala Phe Asp
                 40                  45                  50 cat gat tat tca cgg ctg ctt tat gga aac aga gta aag gat ttg gtc       250
His Asp Tyr Ser Arg Leu Leu Tyr Gly Asn Arg Val Lys Asp Leu Val
             55                  60                  65 cac aga gaa gcc gac gag tat act aga caa gga cag aat ttt acc cta       298
His Arg Glu Ala Asp Glu Tyr Thr Arg Gln Gly Gln Asn Phe Thr Leu
         70                  75                  80 agg cag tta gga gtg tgt gaa tcc gca act cga aga gga gtg gca ttc       346
Arg Gln Leu Gly Val Cys Glu Ser Ala Thr Arg Arg Gly Val Ala Phe
     85                  90                  95 tgt gcg gaa atg ggg ctc cct cac aga ggt tac tcc atc agt gca ggg       394
Cys Ala Glu Met Gly Leu Pro His Arg Gly Tyr Ser Ile Ser Ala Gly
100                 105                 110                 115 tca gat gcg gat acg gaa aac gaa gca gtg atg tcc cct gag cat gcc       442
Ser Asp Ala Asp Thr Glu Asn Glu Ala Val Met Ser Pro Glu His Ala
                120                 125                 130 atg aga ctt tgg ggc agg ggg gtc aaa tcg ggc cgc agt tcc tgc ctg       490
Met Arg Leu Trp Gly Arg Gly Val Lys Ser Gly Arg Ser Ser Cys Leu
            135                 140                 145 tca agc cgg tcc aac tcc gcc ctc acc ctg aca gac acg gag cac gag       538
Ser Ser Arg Ser Asn Ser Ala Leu Thr Leu Thr Asp Thr Glu His Glu
        150                 155                 160 aac agg tcg gac agt gag agc gag caa cct tca aac aac cca ggg caa       586
Asn Arg Ser Asp Ser Glu Ser Glu Gln Pro Ser Asn Asn Pro Gly Gln
    165                 170                 175 ccc acc ctg cag cct ttg ccg cca tcc cac aag cag cac ccg gcg cag       634
Pro Thr Leu Gln Pro Leu Pro Pro Ser His Lys Gln His Pro Ala Gln
180                 185                 190                 195 cat cac ccg tcc atc act tcc ctc aat aga aac tcc ctg acc aat aga       682
His His Pro Ser Ile Thr Ser Leu Asn Arg Asn Ser Leu Thr Asn Arg
                200                 205                 210 agg aac cag agt ccg gcc ccg ccg gct gct ttg ccc gcc gag ctg caa       730
Arg Asn Gln Ser Pro Ala Pro Pro Ala Ala Leu Pro Ala Glu Leu Gln
            215                 220                 225 acc aca ccc gag tcc gtc cag ctg cag gac agc tgg gtc ctt ggc agt       778
Thr Thr Pro Glu Ser Val Gln Leu Gln Asp Ser Trp Val Leu Gly Ser
```

```
Thr Thr Pro Glu Ser Val Gln Leu Gln Asp Ser Trp Val Leu Gly Ser
        230                 235                 240 aat gta cca ctg gaa agc agg cat ttc cta ttc aaa aca ggg aca ggg      826
Asn Val Pro Leu Glu Ser Arg His Phe Leu Phe Lys Thr Gly Thr Gly
        245                 250                 255 acg acg cca ctg ttc agt acg gca acc ccg gga tac aca atg gca tct      874
Thr Thr Pro Leu Phe Ser Thr Ala Thr Pro Gly Tyr Thr Met Ala Ser
260                 265                 270                 275 ggc tct gtt tat tct ccg cct acc cgg cca ctt cct aga aac acc cta      922
Gly Ser Val Tyr Ser Pro Pro Thr Arg Pro Leu Pro Arg Asn Thr Leu
                280                 285                 290 tca aga agt gct ttt aaa ttc aag aag tct tca aag tac tgc agc tgg      970
Ser Arg Ser Ala Phe Lys Phe Lys Lys Ser Ser Lys Tyr Cys Ser Trp
        295                 300                 305 agg tgc acc gca ctg tgt gct gta ggg gtc tca gtg ctc ctg gcc att     1018
Arg Cys Thr Ala Leu Cys Ala Val Gly Val Ser Val Leu Leu Ala Ile
        310                 315                 320 ctc ctc tcc tat ttt ata gca atg cat cta ttt ggc ctc aac tgg cac     1066
Leu Leu Ser Tyr Phe Ile Ala Met His Leu Phe Gly Leu Asn Trp His
        325                 330                 335 tta cag cag acg gaa aat gac aca ttc gag aat gga aaa gtg aat tct     1114
Leu Gln Gln Thr Glu Asn Asp Thr Phe Glu Asn Gly Lys Val Asn Ser
340                 345                 350                 355 gac acc gtg cca aca aac act gta tcg tta cct tct ggc gac aat gga     1162
Asp Thr Val Pro Thr Asn Thr Val Ser Leu Pro Ser Gly Asp Asn Gly
                360                 365                 370 aaa tta ggt gga ttt aca cat gaa aat aac acc ata gat tcc gga gaa     1210
Lys Leu Gly Gly Phe Thr His Glu Asn Asn Thr Ile Asp Ser Gly Glu
        375                 380                 385 ctt gat att ggc cgg aga gca att caa gag gtt ccc ccc ggg atc ttc     1258
Leu Asp Ile Gly Arg Arg Ala Ile Gln Glu Val Pro Pro Gly Ile Phe
        390                 395                 400 tgg aga tcg cag ctc ttt att gat cag cca cag ttt ctt aag ttc aac     1306
Trp Arg Ser Gln Leu Phe Ile Asp Gln Pro Gln Phe Leu Lys Phe Asn
        405                 410                 415 atc tct ctt cag aag gat gca ttg atc gga gtg tac ggc cgg aag ggc     1354
Ile Ser Leu Gln Lys Asp Ala Leu Ile Gly Val Tyr Gly Arg Lys Gly
420                 425                 430                 435 tta ccg cct tcc cat act cag tac gac ttt gtg gaa cta ctg gat ggt     1402
Leu Pro Pro Ser His Thr Gln Tyr Asp Phe Val Glu Leu Leu Asp Gly
                440                 445                 450 agc agg tta att gcg aga gag cag cgg aac ctg gtg gag tcc gaa aga     1450
Ser Arg Leu Ile Ala Arg Glu Gln Arg Asn Leu Val Glu Ser Glu Arg
        455                 460                 465 gcc ggg cgg cag gcg aga tct gtc agc ctg cac gaa gct ggc ttc atc     1498
Ala Gly Arg Gln Ala Arg Ser Val Ser Leu His Glu Ala Gly Phe Ile
        470                 475                 480 cag tac ttg gat tct gga atc tgg cat ctg gct ttt tat aac gac ggg     1546
Gln Tyr Leu Asp Ser Gly Ile Trp His Leu Ala Phe Tyr Asn Asp Gly
        485                 490                 495 aaa aac cca gag cag gtc tcc ttt aac acg atc gtt ata gag tct gtg     1594
Lys Asn Pro Glu Gln Val Ser Phe Asn Thr Ile Val Ile Glu Ser Val
500                 505                 510                 515 gtg gaa tgc ccc cga aat tgc cat gga aat gga gag tgt gtt tct gga     1642
Val Glu Cys Pro Arg Asn Cys His Gly Asn Gly Glu Cys Val Ser Gly
                520                 525                 530 act tgc cat tgt ttc ccc ggg ttt cta ggt ccg gat tgt tca aga gca     1690
Thr Cys His Cys Phe Pro Gly Phe Leu Gly Pro Asp Cys Ser Arg Ala
        535                 540                 545 gcc tgt ccg gtg ctc tgt agt ggc aac ggg caa tac tcc aag ggc cgc     1738
```

```
Ala Cys Pro Val Leu Cys Ser Gly Asn Gly Gln Tyr Ser Lys Gly Arg
        550                 555                 560 tgc ctg tgc ttc agt ggc tgg aag ggc acc gag tgt gac gtg ccg acg    1786
Cys Leu Cys Phe Ser Gly Trp Lys Gly Thr Glu Cys Asp Val Pro Thr
565                 570                 575 acc cag tgc att gac ccg cag tgc ggg ggt cgt ggg att tgc atc atg    1834
Thr Gln Cys Ile Asp Pro Gln Cys Gly Gly Arg Gly Ile Cys Ile Met
580                 585                 590                 595 ggc tct tgc gct tgt aac tcg gga tac aaa gga gaa aac tgt gag gaa    1882
Gly Ser Cys Ala Cys Asn Ser Gly Tyr Lys Gly Glu Asn Cys Glu Glu
                600                 605                 610 gcg gac tgt cta gac cct gga tgt tct aat cac ggg gtg tgt atc cat    1930
Ala Asp Cys Leu Asp Pro Gly Cys Ser Asn His Gly Val Cys Ile His
            615                 620                 625 ggg gaa tgt cac tgc aat cca ggc tgg ggt ggc agc aac tgt gaa ata    1978
Gly Glu Cys His Cys Asn Pro Gly Trp Gly Gly Ser Asn Cys Glu Ile
        630                 635                 640 ctg aag act atg tgt gca gac cag tgt tca ggc cac ggg act tac ctt    2026
Leu Lys Thr Met Cys Ala Asp Gln Cys Ser Gly His Gly Thr Tyr Leu
645                 650                 655 caa gaa agc ggc tcc tgc act tgc gac cca aat tgg act ggc ccc gac    2074
Gln Glu Ser Gly Ser Cys Thr Cys Asp Pro Asn Trp Thr Gly Pro Asp
660                 665                 670                 675 tgc tca aat gaa ata tgt tca gtg gac tgc ggc tca cac ggc gtc tgc    2122
Cys Ser Asn Glu Ile Cys Ser Val Asp Cys Gly Ser His Gly Val Cys
                680                 685                 690 atg ggg ggc tcc tgt cgc tgt gaa gaa ggc tgg acc ggc ccg gcg tgt    2170
Met Gly Gly Ser Cys Arg Cys Glu Glu Gly Trp Thr Gly Pro Ala Cys
            695                 700                 705 aat cag aga gct tgc cac cct cgc tgt gct gag cac ggg acg tgc aag    2218
Asn Gln Arg Ala Cys His Pro Arg Cys Ala Glu His Gly Thr Cys Lys
        710                 715                 720 gac ggc aag tgc gag tgc agc caa gga tgg aac gga gag cac tgc aca    2266
Asp Gly Lys Cys Glu Cys Ser Gln Gly Trp Asn Gly Glu His Cys Thr
725                 730                 735 att gct cac tat ttg gat aag ata gtt aaa gag ggt tgc ccc ggc ttg    2314
Ile Ala His Tyr Leu Asp Lys Ile Val Lys Glu Gly Cys Pro Gly Leu
740                 745                 750                 755 tgc aac agc aat ggg aga tgc aca ctg gac caa aac ggc tgg cac tgc    2362
Cys Asn Ser Asn Gly Arg Cys Thr Leu Asp Gln Asn Gly Trp His Cys
                760                 765                 770 gtt tgc cag cca ggg tgg aga gga gca ggc tgt gac gta gcc atg gag    2410
Val Cys Gln Pro Gly Trp Arg Gly Ala Gly Cys Asp Val Ala Met Glu
            775                 780                 785 acc ctc tgt aca gac agc aaa gac aac gaa gga gac gga ctc att gac    2458
Thr Leu Cys Thr Asp Ser Lys Asp Asn Glu Gly Asp Gly Leu Ile Asp
        790                 795                 800 tgc atg gat cct gat tgc tgc ctc cag agc tcc tgc caa aac cag ccc    2506
Cys Met Asp Pro Asp Cys Cys Leu Gln Ser Ser Cys Gln Asn Gln Pro
805                 810                 815 tac tgt cgt ggc ttg cct gat cct cag gat atc att agc caa agc ctt    2554
Tyr Cys Arg Gly Leu Pro Asp Pro Gln Asp Ile Ile Ser Gln Ser Leu
820                 825                 830                 835 cag aca cca tct cag caa gct gcc aag tcc ttc tat gac cga atc agt    2602
Gln Thr Pro Ser Gln Gln Ala Ala Lys Ser Phe Tyr Asp Arg Ile Ser
                840                 845                 850 ttc ctg att gga tcg gat agc acc cac gtg ctc cct gga gaa agt ccg    2650
Phe Leu Ile Gly Ser Asp Ser Thr His Val Leu Pro Gly Glu Ser Pro
            855                 860                 865 ttc aat aag agt ctt gcg tcc gtc atc aga ggc caa gta cta aca gct    2698
```

```
        Phe Asn Lys Ser Leu Ala Ser Val Ile Arg Gly Gln Val Leu Thr Ala
                870                 875                 880 gat gga acc cca ctt att ggc gtc aac gtg tcg ttt tta cac tac tcg           2746
Asp Gly Thr Pro Leu Ile Gly Val Asn Val Ser Phe Leu His Tyr Ser
885                 890                 895 gaa tat gga tat acc att acc cgc cag gat gga atg ttt gac ttg gtg           2794
Glu Tyr Gly Tyr Thr Ile Thr Arg Gln Asp Gly Met Phe Asp Leu Val
900                 905                 910                 915 gca aat ggt ggc gct tct ctg act ttg gta ttt gag cgt tcc cca ttc           2842
Ala Asn Gly Gly Ala Ser Leu Thr Leu Val Phe Glu Arg Ser Pro Phe
            920                 925                 930 ctc act cag tac cac act gtg tgg att ccc tgg aat gtc ttt tat gtg           2890
Leu Thr Gln Tyr His Thr Val Trp Ile Pro Trp Asn Val Phe Tyr Val
            935                 940                 945 atg gat acc ctt gtc atg aag aaa gag gag aac gac att ccc agc tgt           2938
Met Asp Thr Leu Val Met Lys Lys Glu Glu Asn Asp Ile Pro Ser Cys
            950                 955                 960 gac ctc agt ggc ttt gtg agg cca agt ccc atc att gtg tct tca ccg           2986
Asp Leu Ser Gly Phe Val Arg Pro Ser Pro Ile Ile Val Ser Ser Pro
            965                 970                 975 tta tcc acc ttc ttc agg tct tcc cct gag gac agc ccc atc atc ccc           3034
Leu Ser Thr Phe Phe Arg Ser Ser Pro Glu Asp Ser Pro Ile Ile Pro
980                 985                 990                 995 gag aca cag gtc ctg cat gaa gaa acc aca att cca gga aca gat               3079
Glu Thr Gln Val Leu His Glu Glu Thr Thr Ile Pro Gly Thr Asp
                1000                1005                1010 ttg aaa ctt tcc tac ctg agt tcc aga gcg gca ggg tac aag tca              3124
Leu Lys Leu Ser Tyr Leu Ser Ser Arg Ala Ala Gly Tyr Lys Ser
                1015                1020                1025 gtt ctt aag att acc atg acc cag gcc gtc ata ccg ttt aac ctc              3169
Val Leu Lys Ile Thr Met Thr Gln Ala Val Ile Pro Phe Asn Leu
                1030                1035                1040 atg aag gtc cat ctg atg gtg gcc gtg gtt ggg aga ctc ttc cag              3214
Met Lys Val His Leu Met Val Ala Val Val Gly Arg Leu Phe Gln
                1045                1050                1055 aag tgg ttt cct gcc tcg cca aac ttg gcc tac acg ttc atc tgg              3259
Lys Trp Phe Pro Ala Ser Pro Asn Leu Ala Tyr Thr Phe Ile Trp
                1060                1065                1070 gat aag acg gac gca tat aat cag aaa gtc tac ggc ttg tca gag              3304
Asp Lys Thr Asp Ala Tyr Asn Gln Lys Val Tyr Gly Leu Ser Glu
                1075                1080                1085 gca gtt gtg tcc gtc gga tac gag tac gag tcg tgc ttg gac ctg              3349
Ala Val Val Ser Val Gly Tyr Glu Tyr Glu Ser Cys Leu Asp Leu
                1090                1095                1100 act ctc tgg gaa aag agg act gcc gtt ttg caa ggc tat gag ttg              3394
Thr Leu Trp Glu Lys Arg Thr Ala Val Leu Gln Gly Tyr Glu Leu
                1105                1110                1115 gat gct tcg aac atg ggc ggc tgg acg ttg gac aag cac cat gta              3439
Asp Ala Ser Asn Met Gly Gly Trp Thr Leu Asp Lys His His Val
                1120                1125                1130 ctg gac gtt cag aac ggt ata cta tac aaa gga aat gga gaa aat              3484
Leu Asp Val Gln Asn Gly Ile Leu Tyr Lys Gly Asn Gly Glu Asn
                1135                1140                1145 cag ttc atc tct cag cag cct ccg gtg gtc agc agc atc atg ggt              3529
Gln Phe Ile Ser Gln Gln Pro Pro Val Val Ser Ser Ile Met Gly
                1150                1155                1160 aat ggt cgg agg cgt agc atc tca tgc cca agt tgc aat ggt caa              3574
Asn Gly Arg Arg Arg Ser Ile Ser Cys Pro Ser Cys Asn Gly Gln
                1165                1170                1175 gct gac ggg aac aaa ctc ctg gca ccc gtg gcg ctt gcc tgt ggg              3619
```

```
                Ala Asp Gly Asn Lys Leu Leu Ala Pro Val Ala Leu Ala Cys Gly
                            1180                1185                1190 atc gac ggc agt cta tac gta ggg gat ttc aat tac gtc cgg cgg          3664
Ile Asp Gly Ser Leu Tyr Val Gly Asp Phe Asn Tyr Val Arg Arg
            1195                1200                1205 ata ttc ccg tct ggg aat gtg aca agt gtt tta gaa cta aga aat          3709
Ile Phe Pro Ser Gly Asn Val Thr Ser Val Leu Glu Leu Arg Asn
            1210                1215                1220 aaa gat ttt aga cat agt agc aac cca gct cac aga tac tac ctg          3754
Lys Asp Phe Arg His Ser Ser Asn Pro Ala His Arg Tyr Tyr Leu
            1225                1230                1235 gct acg gac cca gtc acc gga gat ttg tac gtc tct gat act aac          3799
Ala Thr Asp Pro Val Thr Gly Asp Leu Tyr Val Ser Asp Thr Asn
            1240                1245                1250 acc cgc aga atc tat cgg ccg aaa tca ctc acg gga gcc aaa gac          3844
Thr Arg Arg Ile Tyr Arg Pro Lys Ser Leu Thr Gly Ala Lys Asp
            1255                1260                1265 ctg act aaa aac gct gaa gtg gtg gca ggg acc ggg gaa cag tgc          3889
Leu Thr Lys Asn Ala Glu Val Val Ala Gly Thr Gly Glu Gln Cys
            1270                1275                1280 ctt ccc ttt gac gag gcc agg tgt ggg gat gga ggc aag gct gtg          3934
Leu Pro Phe Asp Glu Ala Arg Cys Gly Asp Gly Gly Lys Ala Val
            1285                1290                1295 gaa gca acg ctc atg agt ccc aaa gga atg gca atc gat aag aac          3979
Glu Ala Thr Leu Met Ser Pro Lys Gly Met Ala Ile Asp Lys Asn
            1300                1305                1310 gga ctg atc tac ttt gtt gat gga acc atg atc aga aag gtt gat          4024
Gly Leu Ile Tyr Phe Val Asp Gly Thr Met Ile Arg Lys Val Asp
            1315                1320                1325 caa aat gga atc ata tca act ctc ctg ggc tcc aac gac ctc acg          4069
Gln Asn Gly Ile Ile Ser Thr Leu Leu Gly Ser Asn Asp Leu Thr
            1330                1335                1340 tca gct cga cct tta acc tgt gat act agc atg cat atc agc cag          4114
Ser Ala Arg Pro Leu Thr Cys Asp Thr Ser Met His Ile Ser Gln
            1345                1350                1355 gtg cgt ctg gaa tgg ccc act gac ctc gcg atc aac ccc atg gat          4159
Val Arg Leu Glu Trp Pro Thr Asp Leu Ala Ile Asn Pro Met Asp
            1360                1365                1370 aac tcc atc tac gtc ctg gat aat aac gta gtt tta cag atc act          4204
Asn Ser Ile Tyr Val Leu Asp Asn Asn Val Val Leu Gln Ile Thr
            1375                1380                1385 gaa aac cgt cag gtc cgc atc gct gcc ggg cgg ccc atg cac tgt          4249
Glu Asn Arg Gln Val Arg Ile Ala Ala Gly Arg Pro Met His Cys
            1390                1395                1400 cag gtc cct gga gtg gaa tac ccg gtg ggg aag cac gcg gtt cag          4294
Gln Val Pro Gly Val Glu Tyr Pro Val Gly Lys His Ala Val Gln
            1405                1410                1415 acc acc ctg gag tca gcc acg gcc att gct gtg tcc tac agc ggg          4339
Thr Thr Leu Glu Ser Ala Thr Ala Ile Ala Val Ser Tyr Ser Gly
            1420                1425                1430 gtc ctt tac atc acg gaa act gat gag aag aag atc aac cga ata          4384
Val Leu Tyr Ile Thr Glu Thr Asp Glu Lys Lys Ile Asn Arg Ile
            1435                1440                1445 agg cag gtc acg aca gac ggg gag atc tcc tta gtg gct ggg ata          4429
Arg Gln Val Thr Thr Asp Gly Glu Ile Ser Leu Val Ala Gly Ile
            1450                1455                1460 cct tcg gaa tgt gac tgc aag aac gac gcc aac tgt gac tgc tac          4474
Pro Ser Glu Cys Asp Cys Lys Asn Asp Ala Asn Cys Asp Cys Tyr
            1465                1470                1475 caa agc gga gac ggc tac gcc aaa gat gcc aaa ctc aat gcg ccg          4519
```

-continued

```
                    Gln Ser Gly Asp Gly Tyr Ala Lys Asp Ala Lys Leu Asn Ala Pro
                            1480                1485                1490 tcc tcc ctg gcc gcc tcg cca gat ggc act ctg tac att gca gat                    4564
Ser Ser Leu Ala Ala Ser Pro Asp Gly Thr Leu Tyr Ile Ala Asp
                1495                1500                1505 ctg gga aat atc agg atc cgg gcc gtt tcg aag aat aaa cct tta                    4609
Leu Gly Asn Ile Arg Ile Arg Ala Val Ser Lys Asn Lys Pro Leu
                1510                1515                1520 ctg aac tca atg aac ttt tac gaa gtt gcc tct cca act gat caa                    4654
Leu Asn Ser Met Asn Phe Tyr Glu Val Ala Ser Pro Thr Asp Gln
                1525                1530                1535 gag ctc tac atc ttt gac atc aac ggt act cac cag tac acc gtg                    4699
Glu Leu Tyr Ile Phe Asp Ile Asn Gly Thr His Gln Tyr Thr Val
                1540                1545                1550 agc ctg gtc acg ggt gac tac cta tat aat ttt agt tac agc aat                    4744
Ser Leu Val Thr Gly Asp Tyr Leu Tyr Asn Phe Ser Tyr Ser Asn
                1555                1560                1565 gac aat gac gtc acc gct gta act gac agc aat ggc aac acc ctc                    4789
Asp Asn Asp Val Thr Ala Val Thr Asp Ser Asn Gly Asn Thr Leu
                1570                1575                1580 cga atc cga agg gat ccg aat cgg atg ccg gtg cgg gtg gtg tct                    4834
Arg Ile Arg Arg Asp Pro Asn Arg Met Pro Val Arg Val Val Ser
                1585                1590                1595 cct gat aac cag gtg ata tgg ttg acc ata ggc acc aac ggg tgt                    4879
Pro Asp Asn Gln Val Ile Trp Leu Thr Ile Gly Thr Asn Gly Cys
                1600                1605                1610 ctg aaa agc atg acc gct cag ggc ctg gaa ctg gtt ttg ttt act                    4924
Leu Lys Ser Met Thr Ala Gln Gly Leu Glu Leu Val Leu Phe Thr
                1615                1620                1625 tac cat ggc aac agt ggg ctt tta gcc acc aaa agt gac gaa act                    4969
Tyr His Gly Asn Ser Gly Leu Leu Ala Thr Lys Ser Asp Glu Thr
                1630                1635                1640 gga tgg aca aca ttt ttt gac tat gac agt gaa ggt cgc ctg acg                    5014
Gly Trp Thr Thr Phe Phe Asp Tyr Asp Ser Glu Gly Arg Leu Thr
                1645                1650                1655 aat gtt acc ttc ccc act ggg gtg gtt aca aac ctg cac ggg gac                    5059
Asn Val Thr Phe Pro Thr Gly Val Val Thr Asn Leu His Gly Asp
                1660                1665                1670 atg gac aag gct atc acg gtg gac atc gag tca tcc agc aga gag                    5104
Met Asp Lys Ala Ile Thr Val Asp Ile Glu Ser Ser Ser Arg Glu
                1675                1680                1685 gaa gat gtc agc atc act tcg aac ttg tcc tcc atc gat tcc ttc                    5149
Glu Asp Val Ser Ile Thr Ser Asn Leu Ser Ser Ile Asp Ser Phe
                1690                1695                1700 tac acc atg gtc caa gac cag tta aga aac agt tac cag att ggg                    5194
Tyr Thr Met Val Gln Asp Gln Leu Arg Asn Ser Tyr Gln Ile Gly
                1705                1710                1715 tat gat ggc tcc ctt aga atc ttc tat gcc agt ggt ctg gac tct                    5239
Tyr Asp Gly Ser Leu Arg Ile Phe Tyr Ala Ser Gly Leu Asp Ser
                1720                1725                1730 cac tac cag aca gag ccc cac gtt ctg gct ggc acg gcg aat ccc                    5284
His Tyr Gln Thr Glu Pro His Val Leu Ala Gly Thr Ala Asn Pro
                1735                1740                1745 aca gta gcc aaa aga aac atg act ctt ccc ggt gag aac ggg cag                    5329
Thr Val Ala Lys Arg Asn Met Thr Leu Pro Gly Glu Asn Gly Gln
                1750                1755                1760 aat ctg gtg gag tgg aga ttc cga aaa gaa caa gcc cag ggc aaa                    5374
Asn Leu Val Glu Trp Arg Phe Arg Lys Glu Gln Ala Gln Gly Lys
                1765                1770                1775 gtc aac gta ttc ggc cgg aag ctc agg gtc aat ggg cgc aac cta                    5419
```

|         |         |         |         |         |         |         |         |         |         |     |
|---------|---------|---------|---------|---------|---------|---------|---------|---------|---------|-----|
| Val     | Asn     | Val     | Phe     | Gly     | Arg     | Lys     | Leu     | Arg     | Val     | Asn Gly Arg Asn Leu |
|         |         |         |         | 1780    |         |         | 1785    |         |         | 1790 |

```
ctc tca gtg gac ttt gat cgg acc acc aag acg gaa aag atc tat              5464
Leu Ser Val Asp Phe Asp Arg Thr Thr Lys Thr Glu Lys Ile Tyr
            1795                1800                1805 gat gac cac cgg aaa ttt ctc ctg agg atc gct tac gac acg tcg              5509
Asp Asp His Arg Lys Phe Leu Leu Arg Ile Ala Tyr Asp Thr Ser
            1810                1815                1820 ggg cac ccg act ctc tgg ctg ccg agt agc aag cta atg gca gtg              5554
Gly His Pro Thr Leu Trp Leu Pro Ser Ser Lys Leu Met Ala Val
            1825                1830                1835 aac gtc acc tac tca tcc acc ggt caa att gcc agc atc cag aga              5599
Asn Val Thr Tyr Ser Ser Thr Gly Gln Ile Ala Ser Ile Gln Arg
            1840                1845                1850 ggg acc acg agc gaa aag gtg gac tat gac agc cag ggg agg atc              5644
Gly Thr Thr Ser Glu Lys Val Asp Tyr Asp Ser Gln Gly Arg Ile
            1855                1860                1865 gta tct cgg gtc ttt gcc gat ggg aaa aca tgg agt tac acg tac              5689
Val Ser Arg Val Phe Ala Asp Gly Lys Thr Trp Ser Tyr Thr Tyr
            1870                1875                1880 ttg gaa aag tcc atg gtt ctt ctc cat agc cag cgg cag tac              5734
Leu Glu Lys Ser Met Val Leu Leu Leu His Ser Gln Arg Gln Tyr
            1885                1890                1895 atc ttc gaa tac gac atg tgg gac cgc ctg tcc gcc atc acc atg              5779
Ile Phe Glu Tyr Asp Met Trp Asp Arg Leu Ser Ala Ile Thr Met
            1900                1905                1910 ccc agt gtg gct cgc cac acc atg cag acc atc cgg tcc att ggc              5824
Pro Ser Val Ala Arg His Thr Met Gln Thr Ile Arg Ser Ile Gly
            1915                1920                1925 tac tac cgc aac atc tac aat ccc cca gaa agc aat gcc tct atc              5869
Tyr Tyr Arg Asn Ile Tyr Asn Pro Pro Glu Ser Asn Ala Ser Ile
            1930                1935                1940 atc acc gac tac aac gag gaa ggg ctg ctt ctg caa aca gct ttc              5914
Ile Thr Asp Tyr Asn Glu Glu Gly Leu Leu Leu Gln Thr Ala Phe
            1945                1950                1955 ctg gga acg agt cgg agg gtc tta ttc aag tat aga agg cag acc              5959
Leu Gly Thr Ser Arg Arg Val Leu Phe Lys Tyr Arg Arg Gln Thr
            1960                1965                1970 agg cta tca gaa att tta tac gac agc aca aga gtc agt ttt acc              6004
Arg Leu Ser Glu Ile Leu Tyr Asp Ser Thr Arg Val Ser Phe Thr
            1975                1980                1985 tac gac gaa aca gcg gga gtc ctg aaa aca gta aac ctt cag agt              6049
Tyr Asp Glu Thr Ala Gly Val Leu Lys Thr Val Asn Leu Gln Ser
            1990                1995                2000 gat ggt ttt att tgc acc att aga tac agg caa att ggt ccc ctg              6094
Asp Gly Phe Ile Cys Thr Ile Arg Tyr Arg Gln Ile Gly Pro Leu
            2005                2010                2015 att gac aga cag att ttc cgc ttc agc gag gat gga atg gta aat              6139
Ile Asp Arg Gln Ile Phe Arg Phe Ser Glu Asp Gly Met Val Asn
            2020                2025                2030 gcg aga ttt gac tat agc tac gac aac agc ttt cga gtg acc agc              6184
Ala Arg Phe Asp Tyr Ser Tyr Asp Asn Ser Phe Arg Val Thr Ser
            2035                2040                2045 atg cag ggt gtc atc aat gaa aca cca ctg ccc att gat cta tac              6229
Met Gln Gly Val Ile Asn Glu Thr Pro Leu Pro Ile Asp Leu Tyr
            2050                2055                2060 cag ttt gat gac atc tct ggc aaa gtc gag cag ttt gga aaa ttc              6274
Gln Phe Asp Asp Ile Ser Gly Lys Val Glu Gln Phe Gly Lys Phe
            2065                2070                2075 gga gtg ata tac tac gac atc aac caa atc att tcc acg gcc gtg              6319
```

```
Gly Val Ile Tyr Tyr Asp Ile Asn Gln Ile Ile Ser Thr Ala Val
            2080            2085            2090 atg act tat aca aag cac ttt gat gct cat ggg cgc atc aag gag       6364
Met Thr Tyr Thr Lys His Phe Asp Ala His Gly Arg Ile Lys Glu
            2095            2100            2105 atc caa tat gag ata ttt agg tca ctc atg tac tgg att aca att       6409
Ile Gln Tyr Glu Ile Phe Arg Ser Leu Met Tyr Trp Ile Thr Ile
            2110            2115            2120 caa tat gat aat atg ggc cgg gta acc aag aga gag att aaa att       6454
Gln Tyr Asp Asn Met Gly Arg Val Thr Lys Arg Glu Ile Lys Ile
            2125            2130            2135 ggg cct ttt gcc aac act acc aaa tac gcg tac gag tac gac gtc       6499
Gly Pro Phe Ala Asn Thr Thr Lys Tyr Ala Tyr Glu Tyr Asp Val
            2140            2145            2150 gat gga cag ctc caa aca gtt tac cta aac gaa aag atc atg tgg       6544
Asp Gly Gln Leu Gln Thr Val Tyr Leu Asn Glu Lys Ile Met Trp
            2155            2160            2165 cgg tac aac tac gac cta aat gga aac ctc cac ttg ctc aac ccc       6589
Arg Tyr Asn Tyr Asp Leu Asn Gly Asn Leu His Leu Leu Asn Pro
            2170            2175            2180 agc agc agc gcc cgc ctg acc cct ctg cgc tat gac ctg cgc gac       6634
Ser Ser Ser Ala Arg Leu Thr Pro Leu Arg Tyr Asp Leu Arg Asp
            2185            2190            2195 aga atc acc cgc ctg ggc gat gtt cag tac cgg ctg gat gaa gat       6679
Arg Ile Thr Arg Leu Gly Asp Val Gln Tyr Arg Leu Asp Glu Asp
            2200            2205            2210 ggt ttc ctg cgt cag agg ggc act gaa att ttt gaa tac agc tcc       6724
Gly Phe Leu Arg Gln Arg Gly Thr Glu Ile Phe Glu Tyr Ser Ser
            2215            2220            2225 aaa ggg ctt ctg act cga gtc tac agt aaa ggc agt ggc tgg aca       6769
Lys Gly Leu Leu Thr Arg Val Tyr Ser Lys Gly Ser Gly Trp Thr
            2230            2235            2240 gtg atc tat cgg tac gac ggc ctg gga aga cgt gtt tct agc aaa       6814
Val Ile Tyr Arg Tyr Asp Gly Leu Gly Arg Arg Val Ser Ser Lys
            2245            2250            2255 acc agc ctg gga cag cac ctt cag ttt ttc tac gcc gac ctg aca       6859
Thr Ser Leu Gly Gln His Leu Gln Phe Phe Tyr Ala Asp Leu Thr
            2260            2265            2270 tac ccc acg aga att act cac gtc tac aac cat tcc agt tca gaa       6904
Tyr Pro Thr Arg Ile Thr His Val Tyr Asn His Ser Ser Ser Glu
            2275            2280            2285 atc acc tcc ctg tac tat gac ctc caa gga cat ctc ttc gcc atg       6949
Ile Thr Ser Leu Tyr Tyr Asp Leu Gln Gly His Leu Phe Ala Met
            2290            2295            2300 gag atc agc agt ggg gat gag ttc tac atc gcc tcg gac aac acg       6994
Glu Ile Ser Ser Gly Asp Glu Phe Tyr Ile Ala Ser Asp Asn Thr
            2305            2310            2315 ggg aca ccg ctg gct gtt ttc agc agc aac ggg ctc atg ctg aaa       7039
Gly Thr Pro Leu Ala Val Phe Ser Ser Asn Gly Leu Met Leu Lys
            2320            2325            2330 cag acc cag tac act gcc tat ggt gag atc tac ttt gac tcc aac       7084
Gln Thr Gln Tyr Thr Ala Tyr Gly Glu Ile Tyr Phe Asp Ser Asn
            2335            2340            2345 gtc gac ttt cag ctg gta att gga ttc cac ggg ggc ttg tat gac       7129
Val Asp Phe Gln Leu Val Ile Gly Phe His Gly Gly Leu Tyr Asp
            2350            2355            2360 ccg ctc acc aaa cta atc cac ttt gga gaa aga gat tat gac att       7174
Pro Leu Thr Lys Leu Ile His Phe Gly Glu Arg Asp Tyr Asp Ile
            2365            2370            2375 ttg gcg gga aga tgg acc aca ccg gac att gaa atc tgg aaa agg       7219
```

-continued

| | | |
|---|---|---|
| Leu Ala Gly Arg Trp Thr Thr Pro Asp Ile Glu Ile Trp Lys Arg<br>2380                            2385                         2390 | |

```
atc gga aag gac cct gct cct ttt aac ctg tat atg ttt cgg aat       7264
Ile Gly Lys Asp Pro Ala Pro Phe Asn Leu Tyr Met Phe Arg Asn
         2395                2400                2405 aac aac ccc gcg agc aaa atc cat gat gtg aaa gat tac atc acg       7309
Asn Asn Pro Ala Ser Lys Ile His Asp Val Lys Asp Tyr Ile Thr
         2410                2415                2420 gat gtt aac agc tgg ctg gtg acg ttt ggc ttc cat ctg cac aat       7354
Asp Val Asn Ser Trp Leu Val Thr Phe Gly Phe His Leu His Asn
         2425                2430                2435 gct att cct gga ttc cct gtt ccc aaa ttt gat tta act gag cct       7399
Ala Ile Pro Gly Phe Pro Val Pro Lys Phe Asp Leu Thr Glu Pro
         2440                2445                2450 tcc tat gag ctt gtg aag agt caa cag tgg gaa gat gtg ccg ccc       7444
Ser Tyr Glu Leu Val Lys Ser Gln Gln Trp Glu Asp Val Pro Pro
         2455                2460                2465 atc ttt gga gtt cag cag caa gtg gca agg caa gcc aag gcc ttc       7489
Ile Phe Gly Val Gln Gln Gln Val Ala Arg Gln Ala Lys Ala Phe
         2470                2475                2480 ttg tcc ctg ggg aag atg gcc gag gtg cag gtg agc cga cgc aaa       7534
Leu Ser Leu Gly Lys Met Ala Glu Val Gln Val Ser Arg Arg Lys
         2485                2490                2495 gct ggc gcc gag cag tcg tgg ctg tgg ttc gcc acg gtc aag tcg       7579
Ala Gly Ala Glu Gln Ser Trp Leu Trp Phe Ala Thr Val Lys Ser
         2500                2505                2510 ctc atc ggc aag ggc gtc atg ctg gcc gtg agc caa ggc cgc gtg       7624
Leu Ile Gly Lys Gly Val Met Leu Ala Val Ser Gln Gly Arg Val
         2515                2520                2525 cag acc aac gtg ctc aac atc gcc aac gag gac tgc atc aag gtg       7669
Gln Thr Asn Val Leu Asn Ile Ala Asn Glu Asp Cys Ile Lys Val
         2530                2535                2540 gcg gcg gtg ctc aac aac gcc ttc tac ctg gag aac ctg cac ttc       7714
Ala Ala Val Leu Asn Asn Ala Phe Tyr Leu Glu Asn Leu His Phe
         2545                2550                2555 acc atc gag ggc aag gac aca cac tac ttc atc aag acc acc aca       7759
Thr Ile Glu Gly Lys Asp Thr His Tyr Phe Ile Lys Thr Thr Thr
         2560                2565                2570 ccc gag agc gac ctg ggc aca ctg cgg ctg acg agc ggt cgc aag       7804
Pro Glu Ser Asp Leu Gly Thr Leu Arg Leu Thr Ser Gly Arg Lys
         2575                2580                2585 gcc ctg gag aac ggg atc aac gtg acc gtg tct cag tcc acc acg       7849
Ala Leu Glu Asn Gly Ile Asn Val Thr Val Ser Gln Ser Thr Thr
         2590                2595                2600 gtg gtg aac ggc agg act cgc agg ttc gcc gac gtg gag atg cag       7894
Val Val Asn Gly Arg Thr Arg Arg Phe Ala Asp Val Glu Met Gln
         2605                2610                2615 ttc ggt gcc ctg gca ctg cat gtg cgc tat ggc atg acg ctg gac       7939
Phe Gly Ala Leu Ala Leu His Val Arg Tyr Gly Met Thr Leu Asp
         2620                2625                2630 gag gag aag gcg cgc att ctg gag cag gcg cgc cag cgc gcg ctc       7984
Glu Glu Lys Ala Arg Ile Leu Glu Gln Ala Arg Gln Arg Ala Leu
         2635                2640                2645 gcc cgg gcg tgg gca cgg gag cag cag cgc gtg cgc gac ggc gag       8029
Ala Arg Ala Trp Ala Arg Glu Gln Gln Arg Val Arg Asp Gly Glu
         2650                2655                2660 gag ggt gcg cgc ctc tgg acg gag ggt gag aaa cgg cag ctg ctg       8074
Glu Gly Ala Arg Leu Trp Thr Glu Gly Glu Lys Arg Gln Leu Leu
         2665                2670                2675 agc gct ggc aag gtg cag ggc tac gat ggg tac tac gta ctg tcg       8119
```

-continued

```
Ser Ala Gly Lys Val Gln Gly Tyr Asp Gly Tyr Tyr Val Leu Ser
            2680                2685                2690 gtg gag cag tac ccc gag ctg gct gac agt gcc aac aac atc cag      8164
Val Glu Gln Tyr Pro Glu Leu Ala Asp Ser Ala Asn Asn Ile Gln
                2695                2700                2705 ttc ttg cga caa agt gag atc ggc aag agg taa ccccgggcc            8207
Phe Leu Arg Gln Ser Glu Ile Gly Lys Arg
                    2710                2715 accctgtgc agattctcct gtagcacaat ccaaaccgga ctctccaaag agccttccaa  8267
aatgacactg ctctgcagac agacacatcg cagatacaca cgcaacacaa accagaaaca 8327 aagacaactt tttttttttt ctgaatgacc ttaaaggtga tcggctttaa agaatatgtt 8387 tacatacgca tatcgctgca ctcaattgga ctggaagtat gagaaaggaa aaaaaagcat 8447 taaaaaaggc aacgttttgc catgacccct ctgtaccttc gaggcactgt atttaacaaa 8507 ggttttaaaa aggaaaaaaa aatgcgtaca atgtttccag atattactga attgtcgacc 8567 tttgcttaca ggaagtaatc tctacttagg atgtgatata tatagatctg ttcattttaa 8627 aatgtggggc aaagttactg tttatagaac ccaactgctt tcccgtgctg ctttgtaaaa 8687 ggacactgga acaagggacg tctgcttcgg cggggattta ataatggatt ttactaacat 8747 ggcttgccct gggagggaaa aactgacgaa tagaatcctt gtcactgata agcaaaggaa 8807 accctgattt ttttgtaaat tatgtgagac aagttgttta tggattttta tatgaattac 8867 aatttactgt acatcaaata ttagtctcag aggagttaat ttatgtaaag tgtttaaaaa 8927 gtttatactt aaaaataaaa tgataaaaac aaaaaaa                         8964

<210> SEQ ID NO 133
<211> LENGTH: 2253
<212> TYPE: DNA
<213> ORGANISM: Homo sapiens
<220> FEATURE:
<221> NAME/KEY: exon
<222> LOCATION: (107)..(1090)

<400> SEQUENCE: 133
gtgccccgga tgtgcccagc tggctcctgg ccccacccct cgggcctttg ggctggacca  60
gccacctctg cctgagacct ccggtcgccg caagaagctg gagagg atg tac agc   115
                                                  Met Tyr Ser
                                                    1 gtt gac cgt gtg tct gac gac atc cct att cgt acc tgg ttc ccc aag  163
Val Asp Arg Val Ser Asp Asp Ile Pro Ile Arg Thr Trp Phe Pro Lys
  5                  10                  15 gaa aat ctt ttc agc ttc cag aca gca acc aca act atg caa gcg gtg  211
Glu Asn Leu Phe Ser Phe Gln Thr Ala Thr Thr Thr Met Gln Ala Val
 20                  25                  30                  35 ttc agg ggc tac gcg gag agg aag cgc cgg aaa cgg gag aat gat tcc  259
Phe Arg Gly Tyr Ala Glu Arg Lys Arg Arg Lys Arg Glu Asn Asp Ser
                 40                  45                  50 gcg tct gta atc cag agg aac ttc cgc aaa cac ctg cgc atg gtc ggc  307
Ala Ser Val Ile Gln Arg Asn Phe Arg Lys His Leu Arg Met Val Gly
             55                  60                  65 agc cgg agg gtg aag gcc cag acg ttc gct gag cgg cgc gag cgg agc  355
Ser Arg Arg Val Lys Ala Gln Thr Phe Ala Glu Arg Arg Glu Arg Ser
         70                  75                  80 ttc agc cgg tcc tgg agc gac ccc acc ccc atg aaa gcc gac act tcc  403
Phe Ser Arg Ser Trp Ser Asp Pro Thr Pro Met Lys Ala Asp Thr Ser
     85                  90                  95 cac gac tcc cga gac agc agt gac ctg cag agc tcc cac tgc acg ctg  451
His Asp Ser Arg Asp Ser Ser Asp Leu Gln Ser Ser His Cys Thr Leu
```

```
                                                                        -continued
        100             105             110             115
gac gag gcc ttc gag gac ctg gac tgg gac act gag aag ggc ctg gag          499
Asp Glu Ala Phe Glu Asp Leu Asp Trp Asp Thr Glu Lys Gly Leu Glu
                    120             125             130 gct gtg gcc tgc gac acc gaa ggc ttc gtg cca cca aag gtc atg ctc          547
Ala Val Ala Cys Asp Thr Glu Gly Phe Val Pro Pro Lys Val Met Leu
                135             140             145 att tcc tcc aag gtg ccc aag gct gag tac atc ccc act atc atc cgc          595
Ile Ser Ser Lys Val Pro Lys Ala Glu Tyr Ile Pro Thr Ile Ile Arg
            150             155             160 cgg gat gac ccc tcc atc atc ccc atc ctc tac gac cat gag cac gca          643
Arg Asp Asp Pro Ser Ile Ile Pro Ile Leu Tyr Asp His Glu His Ala
        165             170             175 acc ttc gag gac atc ctt gag gag ata gag agg aag ctg aac gtc tac          691
Thr Phe Glu Asp Ile Leu Glu Glu Ile Glu Arg Lys Leu Asn Val Tyr
180             185             190             195 cac aag gga gcc aag atc tgg aaa atg ctg att ttc tgc cag gga ggt          739
His Lys Gly Ala Lys Ile Trp Lys Met Leu Ile Phe Cys Gln Gly Gly
                200             205             210 cct gga cac ctc tat ctc ctc aag aac aag gtg gcc acc ttt gcc aaa          787
Pro Gly His Leu Tyr Leu Leu Lys Asn Lys Val Ala Thr Phe Ala Lys
                215             220             225 gtg gag aag gaa gag gac atg att cac ttc tgg aag cgg ctg agc cgc          835
Val Glu Lys Glu Glu Asp Met Ile His Phe Trp Lys Arg Leu Ser Arg
                230             235             240 ctg atg agc aaa gtg aac cca gag ccg aac gtc atc cac atc atg ggc          883
Leu Met Ser Lys Val Asn Pro Glu Pro Asn Val Ile His Ile Met Gly
            245             250             255 tgc tac att ctg ggg aac ccc aat gga gag aag ctg ttc cag aac ctc          931
Cys Tyr Ile Leu Gly Asn Pro Asn Gly Glu Lys Leu Phe Gln Asn Leu
260             265             270             275 agg acc ctc atg act cct tat agg gtc acc ttc gag tca ccc ctg gag          979
Arg Thr Leu Met Thr Pro Tyr Arg Val Thr Phe Glu Ser Pro Leu Glu
                280             285             290 ctc tca gcc caa ggg aag cag atg atc gag acg tac ttt gac ttc cgg         1027
Leu Ser Ala Gln Gly Lys Gln Met Ile Glu Thr Tyr Phe Asp Phe Arg
            295             300             305 ttg tat cgc ctg tgg aag agc cgc cag cac tcg aag ctg ctg gac ttt         1075
Leu Tyr Arg Leu Trp Lys Ser Arg Gln His Ser Lys Leu Leu Asp Phe
        310             315             320 gac gac gtc ctg tga ggggcagagg cctccgccca gtcaccatca ggccactccc         1130
Asp Asp Val Leu
        325 tctgcaccgg gacctggggc tgggccgcct cgtgctcccc gggactgtgt agctccggtc       1190 tcgcctggag ccacttcagg gcacctcaga cgttgctcag gttccccctg tgggttccgg       1250 tcctcgctgc acccgtggcc gcagaggctg cagtccctgg gggcgggag gatcccgccc        1310 tgtggcccgt ggatgctcag cggccaggca ctgacctgcc atgcctcgcc tggaggctca       1370 gctgtgggca tccctccatg gggttcatag aaataagtgc aatttctaca cccccgaaac      1430 aattcaaagg gaagcagcat ttcttgttaa ctagttaagc actatgctgc tagttacagt       1490 gtaggcaccc cggcccagca gcccagcagc ccacatgtgt tcaggaccct ccctgcccac       1550 cccctccctg ccgtatcgat caccagcacc agggtggccc gtgtgcgtgg ggccagcgtc       1610 gccgggctgc ccagcctggc tctgtctaca ctggccgagt ctctgggtct gtctacactg       1670 gccgagtctc cgactgtctg tgctttcact tacactcctc ttgccacccc ccatccctgc       1730 ttacttagac ctcagccggc gccggacccg gtaggggcag tctgggcagc aggaaggaag       1790
```

| | | |
|---|---|---|
| ggcgcagcgt cccctccttc agaggaggct ctgggtgggg cctgctcctc atccccccaa | 1850 | |
| gcccacccag cactctcatt gctgctgttg agttcagctt ttaccagcct cagtgtggag | 1910 | |
| gctccatccc agcacacagg cctggggctt ggcaggggcc cagctggggc tgggccctgg | 1970 | |
| gttttgagaa actcgctggc accacagtgg gcccctggac ccggccgcgc agctggtgga | 2030 | |
| ctgtaggggc tcctgactgg gcacaggagc tcccagcttt tgtccacggc cagcaggatg | 2090 | |
| ggctgtcgtg tatatagctg gggcgagggg gcaggccccc cttgtgcaga gccagggtc | 2150 | |
| tgagggcacc tggctgtgtt cccagctgag ggagggctgg ggcggggcc gggcttggaa | 2210 | |
| cgatgtacga taccctcata gtgaccatta aacctgatcc tcc | 2253 | |

<210> SEQ ID NO 134
<211> LENGTH: 2253
<212> TYPE: DNA
<213> ORGANISM: Danio rerio
<220> FEATURE:
<221> NAME/KEY: exon
<222> LOCATION: (1)..(298)

<400> SEQUENCE: 134

```
gtg ccc cgg atg tgc cca gct ggc tcc tgg ccc cac ccc tcg ggc ctt      48
Val Pro Arg Met Cys Pro Ala Gly Ser Trp Pro His Pro Ser Gly Leu
1               5                   10                  15 tgg gct gga cca gcc acc tct gcc tga gac ctc cgg tcg ccg caa gaa      96
Trp Ala Gly Pro Ala Thr Ser Ala     Asp Leu Arg Ser Pro Gln Glu
            20                  25                  30 gct gga gag gat gta cag cgt tga ccg tgt gtc tga cga cat ccc tat     144
Ala Gly Glu Asp Val Gln Arg     Pro Cys Val     Arg His Pro Tyr
        35                      40                      45 tcg tac ctg gtt ccc caa gga aaa tct ttt cag ctt cca gac agc aac     192
Ser Tyr Leu Val Pro Gln Gly Lys Ser Phe Gln Leu Pro Asp Ser Asn
            50                  55                  60 cac aac tat gca agc ggt gtt cag ggg cta cgc gga gag gaa gcg ccg     240
His Asn Tyr Ala Ser Gly Val Gln Gly Leu Arg Gly Glu Glu Ala Pro
        65                  70                  75 gaa acg gga gaa tga ttc cgc gtc tgt aat cca gag gaa ctt ccg caa     288
Glu Thr Gly Glu     Phe Arg Val Cys Asn Pro Glu Glu Leu Pro Gln
    80                      85                  90 aca cct gcg c atggtcggca gccggagggt gaaggcccag acgttcgctg           338
Thr Pro Ala
        95
```

| | | |
|---|---|---|
| agcggcgcga gcggagcttc agccggtcct ggagcgaccc cacccccatg aaagccgaca | 398 | |
| cttcccacga ctcccgagac agcagtgacc tgcagagctc ccactgcacg ctggacgagg | 458 | |
| ccttcgagga cctggactgg gacactgaga agggcctgga ggctgtggcc tgcgacaccg | 518 | |
| aaggcttcgt gccaccaaag gtcatgctca tttcctccaa ggtgcccaag ctgagtaca | 578 | |
| tccccactat catccgccgg gatgaccct ccatcatccc catcctctac gaccatgagc | 638 | |
| acgcaacctt cgaggacatc cttgaggaga tagaggaa gctgaacgtc taccacaagg | 698 | |
| gagccaagat ctggaaaatg ctgattttct gccaggagg tcctggacac ctctatctcc | 758 | |
| tcaagaacaa ggtggccacc tttgccaaag tggagaagga gaggacatg attcacttct | 818 | |
| ggaagcggct gagccgcctg atgagcaaag tgaacccaga gccgaacgtc atccacatca | 878 | |
| tgggctgcta cattctgggg aaccccaatg agagaaagct gttccagaac ctcaggaccc | 938 | |
| tcatgactcc ttatagggtc accttcgagt caccctgga gctctcagcc caagggaagc | 998 | |
| agatgatcga gacgtacttt gacttccggt tgtatcgcct gtggaagagc cgccagcact | 1058 | |
| cgaagctgct ggactttgac gacgtcctgt gaggggcaga ggcctccgcc cagtcaccat | 1118 | |

```
caggccactc cctctgcacc gggacctggg gctgggccgc ctcgtgctcc ccgggactgt    1178
gtagctccgg tctcgcctgg agccacttca gggcacctca gacgttgctc aggttccccc    1238
tgtgggttcc ggtcctcgct gcacccgtgg ccgcagaggc tgcagtccct gggggccggg    1298
aggatcccgc cctgtggccc gtggatgctc agcggccagg cactgacctg ccatgcctcg    1358
cctggaggct cagctgtggg catccctcca tggggttcat agaaataagt gcaatttcta    1418
cacccccgaa acaattcaaa gggaagcagc atttcttgtt aactagttaa gcactatgct    1478
gctagttaca gtgtaggcac cccggcccag cagcccagca gcccacatgt gttcaggacc    1538
ctccctgccc acccctccc  tgccgtatcg atcaccagca ccagggtggc ccgtgtgcgt    1598
ggggccagcg tcgccgggct gcccagcctg gctctgtcta cactggccga gtctctgggt    1658
ctgtctacac tggccgagtc tccgactgtc tgtgctttca cttacactcc tcttgccacc    1718
ccccatccct gcttacttag acctcagccg gcgccggacc cggtaggggc agtctgggca    1778
gcaggaagga agggcgcagc gtcccctcct tcagaggagg ctctgggtgg ggcctgctcc    1838 tcatccccc  aagcccaccc agcactctca ttgctgctgt tgagttcagc ttttaccagc    1898
ctcagtgtgg aggctccatc ccagcacaca ggcctgggg  ttggcagggg cccagctggg    1958
gctgggccct gggttttgag aaactcgctg gcaccacagt gggcccctgg acccggccgc    2018
gcagctggtg gactgtaggg gctcctgact gggcacagga gctcccagct tttgtccacg    2078
gccagcagga tgggctgtcg tgtatatagc tggggcgagg gggcaggccc ccttgtgca    2138 gagccagggg tctgagggca cctggctgtg ttcccagctg agggagggct ggggcggggg    2198
ccgggcttgg aacgatgtac gataccctca tagtgaccat taaacctgat cctcc         2253
```

<210> SEQ ID NO 135
<211> LENGTH: 40
<212> TYPE: PRT
<213> ORGANISM: Artificial Sequence
<220> FEATURE:
<223> OTHER INFORMATION: TCAP 3 General Motif
<220> FEATURE:
<221> NAME/KEY: MISC_FEATURE
<222> LOCATION: (5)..(5)
<223> OTHER INFORMATION: X=G, S or A
<220> FEATURE:
<221> NAME/KEY: MISC_FEATURE
<222> LOCATION: (6)..(6)
<223> OTHER INFORMATION: X=G or R
<220> FEATURE:
<221> NAME/KEY: MISC_FEATURE
<222> LOCATION: (9)..(9)
<223> OTHER INFORMATION: X=L or Q
<220> FEATURE:
<221> NAME/KEY: MISC_FEATURE
<222> LOCATION: (19)..(19)
<223> OTHER INFORMATION: X=V or I
<220> FEATURE:
<221> NAME/KEY: MISC_FEATURE
<222> LOCATION: (32)..(32)
<223> OTHER INFORMATION: X=V or I

<400> SEQUENCE: 135

Gln Leu Leu Ser Xaa Xaa Lys Val Xaa Gly Tyr Asp Gly Tyr Tyr Val
1               5                   10                  15

Leu Ser Xaa Glu Gln Tyr Pro Glu Leu Ala Asp Ser Ala Asn Asn Xaa
            20                  25                  30

Gln Phe Leu Arg Gln Ser Glu Ile
        35                  40

<210> SEQ ID NO 136

```
<211> LENGTH: 36
<212> TYPE: PRT
<213> ORGANISM: Artificial Sequence
<220> FEATURE:
<223> OTHER INFORMATION: G. gallus TCAP2

<400> SEQUENCE: 136

Thr Gly Arg Val Gln Gly Tyr Glu Gly Tyr Tyr Val Leu Pro Val Glu
1               5                   10                  15

Gln Tyr Pro Glu Leu Ala Asp Ser Ser Asn Ile Gln Phe Leu Arg
            20                  25                  30

Gln Asn Glu Met
            35

<210> SEQ ID NO 137
<211> LENGTH: 251
<212> TYPE: PRT
<213> ORGANISM: Artificial Sequence
<220> FEATURE:
<223> OTHER INFORMATION: Human Ten M1

<400> SEQUENCE: 137

Thr Ile Leu Gly Ile Gln Cys Glu Leu Gln Lys Gln Leu Arg Asn Phe
1               5                   10                  15

Ile Ser Leu Asp Gln Leu Pro Met Thr Pro Arg Tyr Asn Asp Gly Arg
            20                  25                  30

Cys Leu Glu Gly Gly Lys Gln Pro Arg Phe Ala Ala Val Pro Ser Val
        35                  40                  45

Phe Gly Lys Gly Ile Lys Phe Ala Ile Lys Asp Gly Ile Val Thr Ala
    50                  55                  60

Ile Ile Gly Val Ala Asn Glu Asp Ser Arg Arg Leu Ala Ala Ile Leu
65                  70                  75                  80

Asn Asn Ala His Tyr Leu Glu Asn Leu His Phe Thr Ile Glu Gly Arg
                85                  90                  95

Asp Thr His Tyr Phe Ile Lys Leu Gly Ser Leu Glu Glu Asp Leu Val
            100                 105                 110

Leu Ile Gly Asn Thr Gly Gly Arg Arg Ile Leu Glu Asn Gly Val Asn
        115                 120                 125

Val Thr Val Ser Gln Met Thr Ser Val Leu Asn Gly Arg Thr Arg Arg
130                 135                 140

Phe Ala Asp Ile Gln Leu Gln His Gly Ala Leu Cys Phe Asn Ile Arg
145                 150                 155                 160

Tyr Gly Thr Thr Val Glu Glu Lys Asn His Val Leu Glu Ile Ala
                165                 170                 175

Arg Gln Arg Ala Val Ala Gln Ala Trp Thr Lys Glu Gln Arg Arg Leu
            180                 185                 190

Gln Glu Gly Glu Glu Gly Ile Arg Ala Trp Thr Glu Gly Lys Gln
        195                 200                 205

Gln Leu Leu Ser Thr Gly Arg Val Gln Gly Tyr Asp Gly Tyr Phe Val
    210                 215                 220

Leu Ser Val Glu Gln Tyr Leu Glu Leu Ser Asp Ser Ala Asn Asn Ile
225                 230                 235                 240

His Phe Met Arg Gln Ser Glu Ile Gly Arg Arg
                245                 250

<210> SEQ ID NO 138
<211> LENGTH: 40
<212> TYPE: PRT
<213> ORGANISM: Artificial Sequence
```

```
<220> FEATURE:
<223> OTHER INFORMATION: G. gallus TCAP-1

<400> SEQUENCE: 138

Gln Leu Leu Asn Thr Gly Arg Val Gln Gly Tyr Asp Gly Tyr Phe Val
1               5                   10                  15

Leu Ser Val Glu Gln Tyr Leu Glu Leu Ser Asp Ser Ala Asn Asn Ile
            20                  25                  30

His Phe Met Arg Gln Ser Glu Ile
            35                  40
```

TENEURIN C-TERMINAL ASSOCIATED PEPTIDES (TCAP) AND USES THEREOF

RELATED APPLICATIONS

This application claims the benefit and priority of U.S. provisional patent application number, U.S. 60/377,231, Filed May 3, 2002, entitled "Teneurin C-Terminal Associated Peptides (TCAP)" and U.S. 60/424,016, filed Nov. 6, 2002, entitled "Method for Modulating Stress using Teneurin C-Terminal Associated Peptide-1(TCAP-1)". This application also claims priority from U.S. provisional patent application number, U.S. 60/376,879, filed May 2, 2002, entitled, "Immortalized Hypothalamic Neuronal Cell Lines". All of these references are incorporated in their entirety by reference.

FIELD OF THE INVENTION

The invention relates to a novel family of peptides associated with the c-terminal region of the teneurin molecule, to a nucleic acid molecule encoding said peptides and to methods and uses therefore.

BACKGROUND OF THE INVENTION

The aetiology of any neuropathology is a complex interplay of genetic, physiological and environmental factors. Effective treatment of these conditions will ultimately depend upon the understanding of the cognate genes and their products. In recent years, it has become apparent that large families of related genes are responsible for the regulation of neuropathologies involving anxiogenic peptides. The identification and characterization of these gene families and how they interact is an essential step towards ultimately effectively treating the pathology. The aberrant regulation of neuronal growth can manifest as a variety of pathological conditions depending upon the age. Deficits in neuronal growth in foetal or neonatal animals can cause such diseases as learning deficits, mental retardation, autism, or schizophrenia. At later ages in juvenile individuals it may manifest as affective disorders such as panic disorder, depression, anorexia nervosa, obsessive-compulsive disorder later in adults. In adults such neuronal growth problems could lead to neurodegenerative illnesses such as Alzheimer's Disease or Parkinsons's Disease.

The onset of mood disorders, such as depression or post traumatic stress disorder, involve the altered function of multiple loci in the brain that regulate emotionality, memory and motivation (Manji et al., 2001; Drevets, 2001; Nestler et al., 2002). However, many of the cellular signaling molecules that mediate communication within and between these regions are unknown, leading to an incomplete understanding of the origin of such disorders.

Many neuropeptides show the presence of three or four paralogous structures as evidenced by the neuropeptide Y (NPY) (Larhammar, 1996a,b), proopiomelanocortin (POMC) (Danielson, 2000) and recently, the corticotropin releasing factor (CRF) family (Vale et al., 1981, Vaughan et al., 1995; Lovejoy and Balment, 1999; Lewis et al., 2001 Reyes et al., 2001; Hsu and Hseuh, 2001).

A family of neuronal cell surface proteins has been identified that are predominantly expressed in the nervous system. These proteins have been named teneurins (Rubin et al, Developmental Biology 216, 195-209 (1999)). Four basic teneurins have been identified Ten M1, Ten M2, Ten M3, and Ten M4. The Ten-M or Odz proteins were originally discovered in *Drosophilia* (Levine et al., 1994; Baumgartner et al., 1994) and are presently the only known example of a pair-rule gene that is not a transcription factor. The Ten-M gene is initially activated during the blastoderm stage, then down regulated before being expressed at later stages. The highest levels of Ten-M occur in the central nervous system where the protein occurs preferentially on the surface of axons (Levine et al., 1994; Levine et al, 1997). Mutations of the ten-M/Odz gene result in embryonic lethality (Baumgartner et al., 1994; Levine et al., 1994).

Four Ten-M paralogous genes, called Teneurins, exist in vertebrates and encode a Type II transmembrane protein where the carboxy terminus of the protein is displayed on the extracellular face of the cell (Oohashi et al., 1999). The teneurin proteins are about 2800 amino acids long. There is a short stretch of hydrophobic residues at 300 to 400 amino acids after the amino terminus that appear to act as the membrane spanning site. In the cytoplasmic N-terminal portion, is a conserved proline-rich SH3-binding site indicating a potential site where by they bind other proteins. Evidence suggests that the protein may be cleaved from the membrane at a Furin-like cleavage motif (RERR) located around residue 528 in teneurin 2 (Rubin et al., 1999). However, this motif is not present in the other paralogues and therefore a soluble version of the protein may not occur for all paralogues. There are a series of cysteine-rich EGF-like repeats carboxy terminal to this. Homodimerization occurs between Ten M1 forms via interaction between EGF-like modules 2 and 5 (Oohashi et al., 1999).

The ten-m gene appears to be upregulated by stressors. Wang et al (1998) showed that a ten-M like transcript, named DOC4 (downstream of chop) in mammalian cells was upregulated by the transcription factor GADD153/CHOP. This transcription factor is induced by several types of cellular stressors including UV light, alkylating agents or conditions triggering endoplasmic reticulum (ER) stress responses, such as, deprivation of oxygen, glucose or amino acids, or interference of calcium flux across the ER membrane (Zinszner et al, 1998). GADD153 is a small nuclear protein that dimerizes with members of the C/EBP family of transcription factors (Ron and Habener, 1992). It does not appear to homodimerize. GADD153 undergoes a stressor inducible phosphorylation by a p38-type MAP kinase which also enhances the transcriptional activation of GADD153 (Wang et al., 1996). High expressions of GADD153 will lead to cell cycle arrest (Zhan et al. 1994). These studies suggest that the teneurin gene may play a significant role in the regulation of the stress response of neurons and other cells.

Overexpression of teneurin 2 into the mouse neuroblastoma cells (Nb2a) augmented the amount of neurite outgrowth and a tendency to enlarge the growth cones. The number of filamentous actin-containing filopodia was also enhanced in the teneurin 2 overexpressing cells (Rubin et al., 1999). The expression of the teneurin genes have been examined in embryonic zebrafish (Mieda et al, 1999), chicken (Rubin et al., 1999) and mouse (Ben-Zur et al., 2000) although their expression patterns have not been finely resolved. The transcripts are found in a number of peripheral tissues but are found predominantly in the central nervous system. In the embryonic chicken brain, teneurin 1 and 2 are expressed in the retina, telencephalon, the optic tectum and the diencephalons. The mRNA for teneurin 1 was found mainly in the intermediate zone of the dorsal thalamus whereas teneurin 2 was found in the intermediate zone of the thalamus (Rubin et al., 1999). In zebrafish, teneurin 4 is faintly expressed throughout gastrulation, although there is no teneurin 3 expression. Teneurin 3 expression begins at the notochord and the somite around the tailbud stage. In later stages (14 h post fertilization), teneurin 3 is expressed in the somites, notochord and brain while teneurin 4 expression was confined to the brain. Teneurin 3 becomes defined within the optic vesicles and region covering the caudal diencephalons and mesencephalon with the expression strongest in the anterior mesencephalon. Teneurin 4 has its strongest expression toward the midbrain hindbrain border. By 23 h post fertilization, teneurin 3 is expressed in the dorsal part of the tectal primordium and the ventral midbrain while teneurin 4 is expressed in the ventral primordium (Mieda et al., 1999).

Neuropathological conditions tend to be complex and not very well understood. As such, there is a need to better understand the mechanisms involved and to develop a method of diagnosis and treatment of said conditions. There is also a need for the identification and design of therapeutic compounds for said conditions.

SUMMARY OF THE INVENTION

The present invention provides a teneurin c-terminal associated peptide (TCAP), existing as a 40-41-residue sequence on the c-terminal exon of Ten- M 1, 2, 3, or 4 that is correspondingly named TCAP 1, 2, 3, and 4. In another embodiment, the invention provides a peptide that has the amino acid sequence consisting of a 40- or 41 amino acid sequence located at the c-terminus of the teneurin 1-4 peptides, to analogs, species homologues, derivatives, variants, allelic variants, to sequences having substantial sequence identity thereto and to obvious chemical equivalents thereto. In another embodiment the TCAP peptides of the invention can further include an amidation signal sequence at the carboxy terminus (hereinafter referred to as "preTCAP"). Such amidation signal amino acid sequence can include but is not limited to GKR and GRR. The invention also provides fusion proteins comprising the TCAP peptides noted above, to labeled TCAP Peptides and to peptides comprising flanking amino acid sequence of 1-10 amino acids.

In one embodiment the TCAP sequence is a rainbow trout, zebrafish, human, mouse, *G. gallus*, or *D. melanogaster* TCAP. In another embodiment, the TCAP sequence comprises or consists of SEQ. ID. NOS: 13, 14, 21, 22, 29, 30, 37, 38, 45, 46, 53, 54, 61, 62, 69, 70, 77, 78, 85, 86, 93, 94, 101, 103 In yet another embodiment, the TCAP is a mouse or human TCAP. In one embodiment the TCAP has one of the sequence selected from the group consisting of SEQ. ID. NOS: 69, 70, 77, 78, 85, 86, 93, 94 (human) or SEQ. ID. NOS: 37, 38, 45, 46, 53, 54, 61, 62, (mouse).

In one aspect, the invention provides a TCAP consisting of any one of the SEQ. ID. NOS. noted above and an amidation signal sequence at the carboxy terminus. Preferably the amidation signal sequence is selected from the group consisting of GRR or GKR, such as, 15, 16, 23, 24, 31, 32, 39, 40, 47, 48, 55, 56, 63, 64, 71, 72, 79, 80, 97, 88, 95, 96.

Another aspect of the invention relates to an isolated teneurin c-terminal associated peptide that has the amino acid sequence as shown in SEQ. ID. NOS: 13, 14, 21, 22, 29, 30, 37, 38, 45, 46, 53, 54, 61, 62, 69, 70, 77, 78, 85, 86, 93, 94, 101, 103; or a fragment, analog, homolog, derivative or mimetic thereof. In a preferred embodiment, the TCAP peptides of the invention have anxiogenic activity. The invention also encompasses an antibody that can bind a TCAP peptide of the invention.

In another embodiment, the peptide of the invention is a TCAP mouse peptide having the amino acid sequence of: SEQ. ID. NOS: 37, 38, 45, 46, 53, 54, 61, 62.

In another embodiment, the peptide of the invention is a TCAP human peptide having the amino acid sequence of SEQ. ID. NOS: 69, 70, 77, 78, 85, 86, 93, or 94.

In another embodiment the peptides TCAP human and mouse peptides have an amidation signal sequence at the C-terminus.

In another embodiment, the peptide of the invention is a TCAP-1 and has the amino acid sequence of SEQ. ID. NOS.: 37, 38, 69 or 70.

In another embodiment, the peptide of the invention is a TCAP-2 and has the amino acid sequence of SEQ. ID. NOS.: 46, 47, 77, or 78.

In another embodiment, the peptide of the invention is a TCAP-3 and has the following amino acid sequence motif:

QLLSXaa$_1$Xaa$_2$KVXaa$_3$GYDGYVLSXaa$_4$EQYPELAD SANNXaa$_5$QFL RQSEI (SEQ. ID. NO:135), where Xaa$_1$ is G, S, or A; Xaa$_2$ is G or R; Xaa$_3$ is L or Q; Xaa$_4$ and Xaa$_5$ are independently V or I. In one embodiment, the TCAP-3 is a human or mouse TCAP-3. In another embodiment, the TCAP-3 has SEQ. ID. NO: 85, 86, 53, or 54. In another embodiment, the TCAP 3 sequence is SEQ. ID. NO.: 13, 14, 21 or 22.

In another embodiment, the peptide of the invention is a TCAP-4 and has the amino acid sequence SEQ. ID. NOS.: 29, 30, 61, 62, 93, or 94.

In another embodiment the peptides TCAP 1 to TCAP 4 have an amidation signal sequence at the C-terminus.

In yet another embodiment, the present invention provides as isolated nucleic acid molecule encoding a teneurin c-terminal associated peptide (TCAP) of the invention, as noted herein. In yet another embodiment, the isolated nucleic acid molecule of the invention consists of:

(a) a nucleic acid sequence as shown in SEQ. ID. NOS.: 17-20, 25-28, 33-36, 41-44, 49-52, 57-60, 65-68, 73-76, 81-84, 89-92, 97-100 or that wherein T can also be U or that encodes a peptide having an amino acid sequence selected from the group consisting of: SEQ. ID. NOS: 13, 14, 21, 22, 29, 30, 37, 38, 45, 46, 53, 54, 61, 62, 69, 70, 77, 78, 85, 86, 93, 94, 101, 103 or that further has an amidation signal sequence (preferably GKR or GRR), at the carboxy terminus of said peptides, such as 15, 16, 23, 24, 31, 32, 39, 40, 47, 48, 55, 56, 63, 64, 71, 72, 79, 80, 97, 88, 95, 96;

(b) a nucleic acid sequence that is complimentary to a nucleic acid sequence of (a) or (b);

(c) a nucleic acid sequence that has substantial sequence homology to a nucleic acid sequence of (a), or (b);

(d) a nucleic acid sequence that is an analog of a nucleic acid sequence of (a), (b), or (c); or (e) a nucleic acid sequence that hybridizes to a nucleic acid sequence of (a), (b), (c), or (d) under stringent hybridization conditions.

In a preferred embodiment the nucleic acid molecules of the invention encode teneurin c-terminal associated peptide that has anxiogenic activity.

The invention also encompasses antisense oligonucleotides complimentary to a nucleic acid sequence of the invention as well as expression vectors comprising a nucleic acid molecule of the invention and host cells transformed with the aforementioned expression vectors.

A further aspect of the invention relates to a method of identifying substances which can bind with a teneurin c-terminal associated peptide, comprising the steps of incubating a teneurin c-terminal associated peptide and a test substance, under conditions which allow for formation of a complex between the teneurin c-terminal associated peptide and the test substance, and assaying for complexes of the teneurin c-terminal associated peptide and the test substance, for free substance or for non complexed teneurin c-terminal associated peptide, wherein the presence of complexes indicates that the test substance is capable of binding a teneurin c-terminal associated peptide.

The invention also provides a method of identifying a compound that affects the regulation of neuronal growth comprising incubating a test compound with a teneurin c-terminal associated peptide or a nucleic acid encoding a teneurin c-terminal associated peptide; and determining an amount of teneurin c-terminal associated peptide protein activity or expression and comparing with a control, wherein a change in the TCAP peptide activity or expression as compared to the control indicates that the test compound has an effect on the regulation of neuronal growth.

The invention also provides a method of inhibiting cell proliferation comprising administering to a cell, an effective amount of teneurin c-terminal associated peptide that inhibits cell proliferation. In a preferred embodiment, the inhibited cells are selected from the group consisting of neuronal or fibroblast cells.

Another aspect of the invention relates to a method of detecting a condition associated with the aberrant regulation of neuronal growth comprising assaying a sample for a nucleic acid molecule encoding a teneurin c-terminal associated peptide or a fragment thereof or a teneurin c-terminal associated peptide or a fragment thereof.

The invention also relates to a method of treating a condition associated with the aberrant regulation of neuronal growth, for instance cancer, comprising administering to a cell or animal in need thereof, an effective amount of teneurin c-terminal associated peptide or an agent that modulates teneurin c-terminal associated peptide expression and/or activity.

The teneurin-1 mRNA containing the TCAP-1 sequence is expressed in regions of the forebrain and limbic system regulating stress responses and anxiety. TCAP signals through a specific cAMP-dependent G-protein-coupled receptor to modify cell cycle and proliferation in immortalized neurons. Administration of synthetic TCAP-1 into the lateral ventricle or amygdala of rats normalized the acoustic startle response. These peptides, therefore, appear to be an integral part of the neural stress response and likely play a role in the aetiology of some psychiatric illnesses.

In another embodiment, the invention provides a method of modulating the stress response in an animal, preferably in a mammal, preferably a human, by administering to said animal an effective amount of TCAP, preferably TCAP-1 peptide, a nucleic acid molecule coding for said TCAP peptide in a form that can express said peptide in situ or an antagonist or agonist of TCAP expression or activity, to modulate the stress response in said animal. In one embodiment the stress response is an anxiety response.

In another embodiment, the invention provides a method for normalizing the stress or anxiety response in an animal. In another embodiment, the invention provides a method for inducing an anxiogenic response in a low anxiety animal and for inducing an anxiolytic effect in a high anxiety animal.

In another embodiment, the invention provides a method modulating the stress response in an animal by modulating the effect of TCAP expression in an animal by administering to said animal a modulator of said TCAP expression or activity. In one embodiment said modulator is an inhibitor of TCAP expression and/or activity, in another embodiment, said modulator is an antagonist of TCAP expression or activity. In one embodiment said TCAP is TCAP-1.

In yet another embodiment, said invention provides a method of diagnosing an animal with high, normal or low stress response condition by administering to said animal a TCAP, such as TCAP-1 and monitoring whether it has an anxiolytic, anxiogenic or neutral effect on a stress response of the animal.

Other aspects of the invention relate to methods of inducing an anxiogenic response in a subject, methods of inhibiting damages caused by physiological stresses and methods of inhibiting cell death, each comprising administering to a subject an effective amount of teneurin c-terminal associated peptide for affecting the desired result.

Other features and advantages of the present invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which:

FIG. 1 shows a putative 3' exon of the rainbow trout Teneurin 3 gene [SEQ. ID. NO: 2] with an intron region [SEQ. ID. NO: 1] (1490 bp). The exon/intron border as established by sequence comparison with the human ten M1 gene (LocusLink ID# 10178) shown in the genome database. The intron placement was subsequently confirmed by PCR. The exon encodes the carboxy terminal 251 residues of the protein SEQ. ID. NO: 3. Cleavage signals are indicated in the bolded grey regions. The Terminal GKR motif usually signifies a post translation amidation signal. The teneurin-associated c-terminal peptide (TCAP) is shown by the sequence between amino acids 208 and 248 inclusive [SEQ. ID. NOS: 13 and 14].

FIG. 2 shows the alignment of the amino acid sequences encoded by the terminal exon of the rainbow trout (*O. mykiss*) SEQ. ID. NO: 3, zebrafish (*R. danio*) SEQ. ID. NO: 12, mouse (*M. musculus*) SEQ. ID. NO: 6 and human (*H. sapiens*) SEQ. ID. NO: 10 genes. All possess an additional serine insertion in position 58. All show a high sequence similarity with about 94% between trout and zebrafish, 83% between rainbow trout and mouse, and 83% between rainbow trout and human. Within the TCAP portion itself, rainbow trout SEQ. ID. NO: 13 or 14 shares 90% sequence identity with zebrafish SEQ. ID. NO: 21 or 22, 90% sequence identity with mouse SEQ. ID. NO:53 or 54, and 88% with human SEQ. ID. NO. 85 or 86. The preTCAP sequences that include the amidation signal are SEQ. ID. NOS: 15-16 (Rainbow Trout), 23-24 (zebrafish), 55-56 (mouse) and 87-88 (human).

FIG. 3 shows the alignment of the amino acid sequences encoded by the terminal exon of the mouse teneurin 1, 2, 3 and 4) SEQ. ID. NOS: 4, 5, 6, 7 genes. The highest level of sequence similarity occurs among the sequences encoding the TCAP portion of the protein. TCAP-1 SEQ. ID. NO: 37 or 38 is 68% identical to TCAP-2 SEQ. ID. NO: 45 or 46, 76% identical to TCAP-3 SEQ. ID. NO: 53 or 54, and 85% identical to TCAP-4 SEQ. ID. NO: 61 or 62. TCAP-2 is 75% identical with TCAP-3, and 68% identical with TCAP4. TCAP-3 possesses 71% identity with TCAP-4. Teneurin 3 possesses a dibasic cleavage site at the amino terminus of TCAP-3 whereas 1, 2 and 4 all possess monobasic sites suggesting that the cleaved peptide is 40 residues in TCAP-3 but 41 residues in TCAP-1, 2 and 4. However, in one embodiment, both the 41 and 40 amino acid residue TCAP has activity.

FIG. 4 shows the alignment of amino acid sequences encoded by the last exon of the human Teneurin 1, 2, 3 and 4 proteins SEQ. ID. NOS: 8, 9, 10, 11. Like the mouse sequence, the highest degree of sequence similarity occurs in the TCAP portion of the exon. TCAP-3 possesses a dibasic leaved signal whereas the others possess a monobasic site. The greatest variable region occurs with the first 70-80 residues of the exon. Within the TCAP portion itself, TCAP-1 SEQ. ID. NO: 69 or 70 shares 73% identity with TCAP-2 SEQ. ID. NO: 77 or 78, 83% identity with TCAP-3 SEQ. ID. NO: 85 or 86 and 88% identity with TCAP-4 SEQ. ID. NO. 93 or 94. TCAP-2 has 76% identity with TCAP-3 and 71% identity with TCAP4. TCAP-3 has 76% identity with TCAP-4.

FIG. 5 shows the nucleotide coding sequence of the preT-CAP sequences for Human (SEQ. ID. NOS: 76, 84, 92, and 100) and Mouse (SEQ. ID. NOS. 44, 52, 60 and 68) preT-CAP-1 to 4, Zebrafish preTCAP-3 and 4 (SEQ. ID. NOS: 28 and 36), and Rainbow Trout preTCAP-3 (SEQ. ID. NO. 20) with stop codon. The coding region of the corresponding mature TCAP peptides would lack the terminal amidation and stop codon coding sequence (e.g. the last 12 nucleotide bases shown for each sequence). The sequences shown code for the 44 amino acid residue preTCAP sequence with stop codon. However, the 43 amino acid TCAP coding sequnce is identical except with the first three nucleotides absent.

FIG. 6B is a schematic view of the exons on human teneurin 1 and an exploded view of the location of the C-terminal exon and location of TCAP thereon (SEQ ID NO:137). A conserved prohormone convertase-like cleavage motif is shown as grey boxes. It illustrates the structure of Teneurin C-terminal Associated Peptides and their location on the teneurin protein and gene.

FIG. 7A shows the alignment of the human, mouse, rat, chicken, rainbow trout, zebrafish and *drosopholia* TCAP sequences SEQ. ID. NOS: 69, 78, 85, 94, 37, 46, 53, 66, 78, 101, 136, 13, 21, and 103 and 7B shows the alignment of the TCAP sequences from mammals birds insects and nematodes FIG. 7B SEQ. ID. NOS: 37, 138, 69, 61, 93, 53, 85, 13, 21, 77, 29, and 103. In FIG. 7B, non homologous amino acid substitutions are shaded in light grey. Homologous residues are shaded in dark grey.

FIG. 8 shows the alignment of the amino acid sequences of the human CRF family SEQ. ID. NOS: 104-107 with those of the human TCAP family SEQ. ID. NOS: 70, 78, 85, 94. Although overall sequence identity is only about 20-25%, many of the other substitutions reflect potential single base codon changes such as proline to serine, leucine or threonine, or conservative amino acid substitutions such as leucine to valine or isoleucine, aspartic acid to glutamic acid and asparagines to glutamine.

FIG. 9 is a comparison of the sequence identity among CRF family members to that of the identity among TCAP members. The TCAP family members show a much greater sequence identity of 68% compared to the CRF family members of 34% between CRF and U3 and U2, 43% between CRF and urocortin, and 21% between urocortin 1 and 3.

FIG. 10 A is a Grantham Polarity Prediction and FIG. 10B is a Kyte-Doolittle Hydrophobicity Prediction. TCAP shows a highly similar polarity profile, but appears to possess higher levels of total hydrophobicity in the amino terminus.

FIG. 11 shows the alignment of amino acid sequences of representations of TCAP peptides with the insect diuretic peptides and CRF superfamily SEQ. ID. NOS: 13, 22, 104, 107-110. The entire superfamily can be divided into three general regions encompassing an amino terminal portion, a midsection and a carboxy terminal portion. All peptides can be aligned by the presence of conserved motifs within each of the separate sections

FIG. 13 is a bar graph illustrating the inhibition of cell proliferation in Gn11 neuronal cells by $10^{-6}$ M TCAP (Rainbow Trout TCAP-3) at 48 hours (FIG. 13 A) and at 72 hours (FIG. 13B).

FIGS. 16A and 16B are bar graphs illustrating the inhibition of cAMP (16A) and cGMP (16B) accumulation in Gn11 cells by rtTCAP-3(Rainbow Trout TCAP-3). A. $10^{-6}$ M TCAP induced a significant (p<0.01) decrease in cAMP concentrations relative to the vehicle-treated cells. Replications: vehicle, n=10; urocortin, n=8; TCAP, n=11. B. $10^{-6}$ M TCAP induced a significant (p<0.01) decrease in cGMP accumulation in Gn11 cells. The same concentration of rat urocortin also induced a significant (p<0.05) decrease in cGMP concentrations. Three replications were used for each of the treatment groups. Significance was assessed using a one-way analysis of variance with a Dunnett's post-hoc test. An a priori level of significance was established at p=0.05. The original data was transformed to show percent concentration relative to the vehicle-treated cells.

FIG. 18A: Baseline, TCAP peptide (1.0 μl of 0.001 mg/ml, left), post-injection (approx. 90 min.), 850 uA. FIG. 18B: Baseline, TCAP peptide ((1.0 μl of 0.001 mg/ml, right), postinjection (approx. 60 min.), 550 uA. 100 nM TCAP induced a significant decrease in the rats desire to self-administer reward by neural impulse.

FIG. 19 A schematic cellular model for TCAP regulation. A. A stressor in the form of a physiological condition such as low oxygen or pH changes, or an anxiogenic ligand triggers metabolic activation of the cell. B. This causes an upregulation of the Teneurin protein and its cleaving enzyme. C. The enzyme liberates TCAP from Teneurin where it acts in an autocrine and paracrine manner to inhibit cAMP and cGMP production via a G protein coupled receptor.

FIG. 22 are graphs illustrating the mean baseline startle response of all animals in Example 10. FIG. 22A is the average startle response at day 1 after TCAP injection and FIG. 22B is the average startle at the end of the chronic TCAP study, FIG. 22C is the average startle response following TCAP-1.

DETAILED DESCRIPTION OF THE INVENTION

Figure 6A:
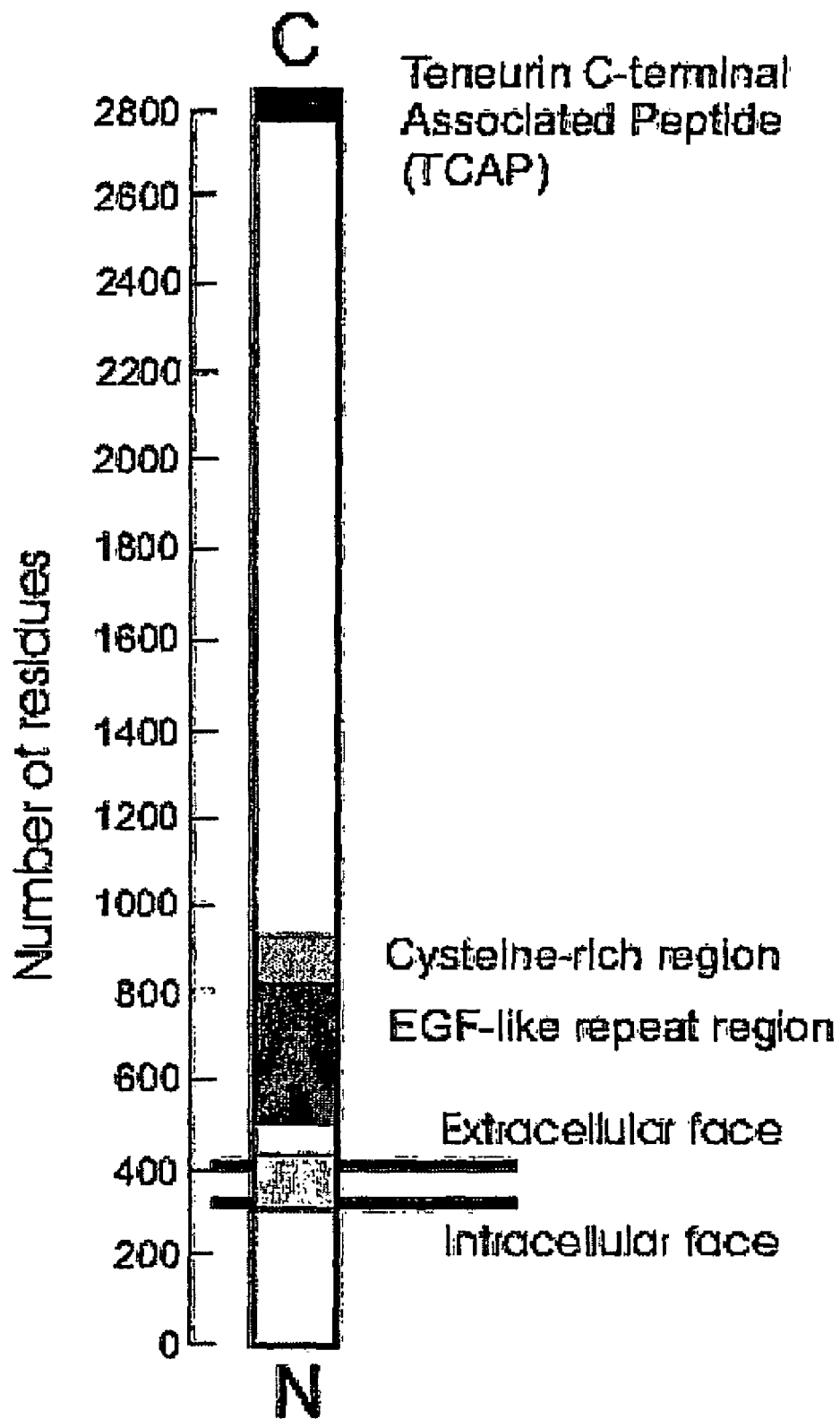
FIG. 6A is a schematic representation of the functional domains within the Teneurin protein.

The inventors have identified a novel peptide sequence which exists as part of a larger protein previously identified as the Ten M proteins or Teneurins. The novel peptides are referred to as teneurin C terminal peptides or TCAP. The genomes or gene transcripts of several vertebrate and invertebrate species were screened by homologous probe hybridization or by PCR. Sequence data from genome sequencing programs allowed the identification of a complement of four paralogous peptides from this family in humans and mice, two paralogues in zebrafish, one in rainbow trout and Drosophila (SEQ ID NO:103). The synthetic TCAP peptide has neuronal communication activity and has been shown to be a modulator of the stress response and anxiety in an animal. TCAP also modulates cell proliferation. In one embodiment, it can inhibit cell proliferation. In another embodiment, TCAP is a potent anxiogenic peptide in rats and highly effective at inhibiting neuronal proliferation in unstressed cells and protecting cells from physiological stresses. As such TCAP and/or modulators of TCAP can be used in the treatment of cancer and neuropathological conditions, including those related to neuronal communication, and/or cell proliferation, for instance, cancer, stress anxiety, food-related disorders, such as anorexia and/or obesity.

The TCAP sequence encodes a cleavable peptide 40 amino acids long flanked by PC7-like cleavage motifs on the amino terminus and an amidation motif on the carboxy terminus. Depending on the cleavage of the PC7-like cleavage site at the N-terminus, the resulting mature TCAP peptide is 40-41 amino acids in length. The TCAP sequence with the carboxy terminus amidation motif is herein referred to as preTCAP. Orthologues in humans, mice, zebrafish and Drosophila as well as three additional paralogous sequences have been identified. A synthetic version of the rainbow trout peptide significantly increases the startle reflex and decreases self-administered brain stimulation in rats. These findings are consistent with the actions of peptides known to induce anxiety in mammals and humans. The peptide is also potent at inhibiting the proliferation of unstressed neuronal and fibroblast cell cultures and inhibiting cell death in these cultures subjected to high pH stress. These findings indicate that TCAP plays a role in the developing and adult brain to modulate and protect neuronal growth and metabolism and therefore be implicated in a number of pathologies including schizophrenia, Parkinson's disease and other mental conditions. In the adult brain the peptide may act to modulate the actions of anxiogenic stimuli and could play a role in depression, anorexia nervosa and other affective disorders.

The term "isolated" as used herein means "altered by the hand of man" from the natural state. If a composition or substance occurs in nature, the isolated form has been changed or removed from its original environment, or both. For example, a polynucleotide or a polypeptide naturally present in a living animal is not "isolated," but the same polynucleotide or polypeptide separated from the coexisting materials of its natural state is "isolated," as the term is employed herein. Thus, a polypeptide or polynucleotide produced and/or contained within a recombinant host cell is considered isolated for purposes of the present invention. Also intended as an "isolated polypeptide" or an "isolated polynucleotide" are polypeptides or polynucleotides that have been purified, partially or substantially, from a recombinant host cell or from a native source. For example, a recombinantly produced version of TCAP peptides and derivatives thereof can be substantially purified by methods known in the art, such as the one-step method described in Smith and Johnson, Gene 67:31-40 (1988).

Nucleic Acid Molecules of the Invention

The present invention provides an isolated nucleic acid molecule consisting of a sequence encoding a teneurin c-terminal associated peptide This peptide is generally referred to as "TCAP" herein. The present invention also provides an isolated nucleic acid molecule encoding a TCAP peptide with a carboxy terminus amidation motif, said peptide herein referred to as "preTCAP".

Isolated nucleic acids substantially free of cellular material or culture medium when produced by recombinant DNA techniques, or chemical precursors, or other chemicals when chemically synthesized are included in this invention.

In a preferred embodiment, the invention provides an isolated nucleic acid sequence comprising or consisting of:
(a) a nucleic acid sequence as shown in SEQ. ID. NOS.: 17-20, 25-28, 33-36, 41-44, 49-52, 57-60, 65-68, 73-76, 81-84, 89-92, 97-100 or that wherein T can also be U or that encodes a peptide having an amino acid sequence selected from the group consisting of: SEQ. ID. NOS: 13, 14, 21, 22, 29, 30, 37, 38, 45, 46, 53, 54, 61, 62, 69, 70, 77, 78, 85, 86, 93, 94, 101, 103 or that further has an amidation signal sequence (preferably GKR or GRR), at the carboxy terminus of said peptides, such as 15, 16, 23, 24, 31, 32, 39, 40, 47, 48, 55, 56, 63, 64, 71, 72, 79, 80, 97, 88, 95, 96;

(b) a nucleic acid sequence that is complimentary to a nucleic acid sequence of (a);

(c) a nucleic acid sequence that has substantial sequence homology to a nucleic acid sequence of (a) or (b);

(d) a nucleic acid sequence that is an analog of a nucleic acid sequence of (a), (b) or (c); or (e) a nucleic acid sequence that hybridizes to a nucleic acid sequence of (a), (b), (c) or (d) under stringent hybridization conditions.

(f) a nucleice acid sequence of (a)-(e) where T is U.

The term "sequence that has substantial sequence homology" means those nucleic acid sequences which have slight or inconsequential sequence variations from the sequences in (a) or (b), i.e., the sequences function in substantially the same manner. The variations may be attributable to local mutations or structural modifications. Nucleic acid sequences having substantial homology include nucleic acid sequences having at least 65%, more preferably at least 85%, and most preferably 90-95% identity with the nucleic acid sequences as listed in (a) above. The term "sequence that hybridizes" means a nucleic acid sequence that can hybridize to a sequence of (a), (b), (c) or (d) under stringent hybridization conditions. Appropriate "stringent hybridization conditions" which promote DNA hybridization are known to those skilled in the art, or may be found in Current Protocols in Molecular Biology, John Wiley & Sons, N.Y. (1989), 6.3.1-6.3.6. For example, the following may be employed: 6.0× sodium chloride/sodium citrate (SSC) at about 45° C., followed by a wash of 2.0×SSC at 50° C.; 0.2×SSC at 50° C. to 65° C.; or 2.0× SSC at 44° C. to 50° C. The stringency may be selected based on the conditions used in the wash step. For example, the salt concentration in the wash step can be selected from a high stringency of about 0.2×SSC at 50° C. In addition, the temperature in the wash step can be at high stringency conditions, at about 65° C.

The term "nucleic acid" is intended to include DNA and RNA and can be either double stranded or single stranded.

The term "a nucleic acid sequence which is an analog" means a nucleic acid sequence which has been modified as compared to the sequence of (a), (b) or (c) wherein the modification does not alter the utility of the sequence as described herein. The modified sequence or analog may have improved properties over the sequence shown in (a), (b) or (c). One example of a modification to prepare an analog is to replace one of the naturally occurring bases (i.e. adenine, guanine, cytosine or thymidine) of the sequence with a modified base such as such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8 amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Another example of a modification is to include modified phosphorous or oxygen heteroatoms in the phosphate backbone, short chain alkyl or cycloalkyl intersugar linkages or short chain heteroatomic or heterocyclic intersugar linkages in the nucleic acid molecule listed in (a) to (e) above. For example, the nucleic acid sequences may contain phosphorothioates, phosphotriesters, methyl phosphonates, and phosphorodithioates.

A further example of an analog of a nucleic acid molecule of the invention is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogs have been shown to be resistant to degradation by enzymes and to have extended lives in vivo and in vitro. PNAs also bind stronger to a complimentary DNA sequence due to the lack of charge repulsion between the PNA strand and the DNA strand. Other nucleic acid analogs may contain nucleotides containing polymer backbones, cyclic backbones, or acyclic backbones. For example, the nucleotides may have morpholino backbone structures (U.S. Pat. No. 5,034,506). The analogs may also contain groups such as reporter groups, a group for improving the pharmacokinetic or pharmacodynamic properties of nucleic acid sequence.

Isolated and purified nucleic acid molecules having sequences which differ from the nucleic acid sequence of the invention due to degeneracy in the genetic code are also within the scope of the invention. Such nucleic acids encode functionally equivalent peptides but differ in sequence from the above mentioned sequences due to degeneracy in the genetic code.

An isolated nucleic acid molecule of the invention which consists of DNA can be isolated by preparing a labeled nucleic acid probe based on all or part of the nucleic acid sequences of the invention and using this labeled nucleic acid probe to screen an appropriate DNA library (e.g. a cDNA or genomic DNA library). For example, a genomic library isolated can be used to isolate a DNA encoding a novel peptide of the invention by screening the library with the labeled probe using standard techniques. Nucleic acids isolated by screening of a cDNA or genomic DNA library can be sequenced by standard techniques.

An isolated nucleic acid molecule of the invention which is DNA can also be isolated by selectively amplifying a nucleic acid encoding a novel peptide of the invention using the polymerase chain reaction (PCR) methods and cDNA or genomic DNA. It is possible to design synthetic oligonucleotide primers from the nucleic acid sequence of the invention for use in PCR. A nucleic acid can be amplified from cDNA or genomic DNA using these oligonucleotide primers and standard PCR amplification techniques. The nucleic acid so amplified can be cloned into an appropriate vector and characterized by DNA sequence analysis. It will be appreciated that cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Invitrogen, Carlsbad, Calif., or AMV reverse transcriptase available from Seikagaku America, Inc., St. Petersburg, Fla.).

An isolated nucleic acid molecule of the invention which is RNA can be isolated by cloning a cDNA encoding a novel peptide of the invention into an appropriate vector which allows for transcription of the cDNA to produce an RNA molecule which encodes a protein of the invention. For example, a cDNA can be cloned downstream of a bacteriophage promoter, (e.g., a T7 promoter) in a vector, cDNA can be transcribed in vitro with T7 polymerase, and the resultant RNA can be isolated by standard techniques.

A nucleic acid molecule of the invention may also be chemically synthesized using standard techniques. Various methods of chemically synthesizing polydeoxynucleotides are known, including solid-phase synthesis which, like peptide synthesis, has been fully automated in commercially available DNA synthesizers (See e.g., Itakura et al. U.S. Pat. No. 4,598,049; Caruthers et al. U.S. Pat. No. 4,458,066; and Itakura U.S. Pat. Nos. 4,401,796 and 4,373,071).

Determination of whether a particular nucleic acid molecule encodes a novel peptide of the invention may be accomplished by expressing the cDNA in an appropriate host cell by standard techniques, and testing the activity of the peptide using the methods as described herein. A cDNA having the activity of a novel peptide of the invention so isolated can be sequenced by standard techniques, such as dideoxynucleotide chain termination or Maxam-Gilbert chemical sequencing, to determine the nucleic acid sequence and the predicted amino acid sequence of the encoded peptide.

The initiation codon and untranslated sequences of nucleic acid molecules of the invention may be determined using currently available computer software designed for the purpose, such as PC/Gene (IntelliGenetics Inc., Calif.). Regulatory elements can be identified using conventional techniques. The function of the elements can be confirmed by using these elements to express a reporter gene which is operatively linked to the elements. These constructs may be introduced into cultured cells using standard procedures. In addition to identifying regulatory elements in DNA, such constructs may also be used to identify proteins interacting with the elements, using techniques known in the art.

The sequence of a nucleic acid molecule of the invention may be inverted relative to its normal presentation for transcription to produce an antisense nucleic acid molecule which are more fully described herein. In particular, the nucleic acid sequences contained in the nucleic acid molecules of the invention or a fragment thereof, may be inverted relative to its normal presentation for transcription to produce antisense nucleic acid molecules.

The invention also provides nucleic acids encoding fusion proteins comprising a novel protein of the invention and a selected protein, or a selectable marker protein (see below).

Also provided are portions of the nucleic acid sequence encoding fragments, functional domains or antigenic determinants of the TCAP peptide. The present invention also provides for the use of portions of the sequence as probes and PCR primers for TCAP as well as for determining functional aspects of the sequence.

One of ordinary skill in the art is now enabled to identify and isolate TCAP encoding nucleic acids or cDNAs that are allelic variants of the disclosed sequences, using standard hybridization screening or PCR techniques.

II. Novel Proteins of the Invention

The invention further broadly contemplates an isolated TCAP peptide. The term "TCAP peptide" as used herein includes all homologs, analogs, fragments or derivatives of the TCAP peptide.

The term "analog" in reference to peptides includes any peptide having an amino acid residue sequence substantially identical to the human or mouse TCAP sequence specifically shown herein in which one or more residues have been conservatively substituted with a functionally similar residue and which displays the ability to mimic TCAP as described herein. Examples of conservative substitutions include the substitution of one non-polar (hydrophobic) residue such as alanine, isoleucine, valine, leucine or methionine for another, the substitution of one polar (hydrophilic) residue for another such as between arginine and lysine, between glutamine and asparagine, between glycine and serine, the substitution of one basic residue such as lysine, arginine or histidine for another, or the substitution of one acidic residue, such as aspartic acid or glutamic acid for another. The phrase "conservative substitution" also includes the use of a chemically derivatized residue in place of a non-derivatized residue provided that such polypeptide displays the requisite activity.

The term "derivative" reference to peptides refers to a peptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

In one embodiment, the isolated TCAP peptide consists of 3841 amino acid residues of the carboxy terminus of a teneurin-like protein with or without an amidation signal at the carboxy terminus. In one embodiment, the amidation signal consists of the amino acid sequence GKR or GRR (preTCAP). In another embodiment, the TCAP peptide comprises sequences substantially identity to the above-noted peptides or comprising an obvious chemical equivalents thereof. It also includes peptides sequence +/− amino acids at the amino and/or carboxy terminus of the above-noted TCAP peptide sequences. In yet another embodiment, the invention includes fusion proteins, comprising the TCAP peptide, labeled TCAP peptides, analogs, homologs and variants thereof.

In one embodiment, the TCAP peptide is a rainbow trout, zebrafish, human, mouse, *G. gallus* or *D. melanogaster* TCAP. In another embodiment, the TCAP peptides have the sequence selected from the group consisting of: SEQ. ID. NOS: 13, 14, 21, 22, 29, 30, 37, 38, 45, 46, 53, 54, 61, 62, 69, 70, 77, 78, 85, 86, 93, 94, 101, 103 or that further has an amidation signal sequence (preferably GKR or GRR), at the carboxy terminus of said peptides, such as 15, 16, 23, 24, 31, 32, 39, 40, 47, 48, 55, 56, 63, 64, 71, 72, 79, 80, 97, 88, 95, 96;

In another embodiment, the peptide of the invention is a TCAP-3 and has the following amino acid sequence motif:
QLLSXaa$_1$Xaa$_2$KVXaa$_3$GYDGYWLSXaa$_4$EQYPELA
DSANNXaa$_5$QFL RQSEI SEQ. ID. NO:135

Where Xaa$_1$ is G, S, or A; Xaa$_2$ is G or R; Xaa$_3$ is L or Q; Xaa$_4$ and Xaa$_5$ are independently V or I. In one embodiment, the TCAP-3 is a human or mouse TCAP-3. In another embodiment, the TCAP-3 has SEQ. ID. NO: 13, 21, 53 or 85.

Within the context of the present invention, a peptide of the invention may include various structural forms of the primary peptide which retain biological activity. For example, a peptide of the invention may be in the form of acidic or basic salts or in neutral form. In addition, individual amino acid residues may be modified by oxidation or reduction.

In addition to the full-length amino acid sequence, the peptide of the present invention may also include truncations, analogs and homologs of the peptide and truncations thereof as described herein. Truncated peptides or fragments may comprise peptides of at least 5, preferably 10 and more preferably 15 amino acid residues of the sequence listed above.

The invention further provides polypeptides comprising at least one functional domain or at least one antigenic determinant of a TCAP peptide.

Analogs of the protein of the invention and/or truncations thereof as described herein, may include, but are not limited to an amino acid sequence containing one or more amino acid substitutions, insertions, deletions and/or mutations. Amino acid substitutions may be of a conserved or non-conserved nature. Conserved amino acid substitutions involve replacing one or more amino acids of the peptides of the invention with amino acids of similar charge, size, and/or hydrophobicity characteristics. When only conserved substitutions are made the resulting analog should be functionally equivalent. Non-conserved substitutions involve replacing one or more amino acids of the amino acid sequence with one or more amino acids which possess dissimilar charge, size, and/or hydrophobicity characteristics.

One or more amino acid insertions may be introduced into the amino acid sequences of the invention. Amino acid insertions may consist of single amino acid residues or sequential amino acids ranging from 2 to 15 amino acids in length. For example, amino acid insertions may be used to destroy target sequences so that the peptide is no longer active. This procedure may be used in vivo to inhibit the activity of the peptide of the invention.

Deletions may consist of the removal of one or more amino acids, or discrete portions from the amino acid sequence of the TCAP peptide. The deleted amino acids may or may not be contiguous.

Analogs of a protein of the invention may be prepared by introducing mutations in the nucleotide sequence encoding the peptide. Mutations may be introduced at particular loci by synthesizing oligonucleotides containing a mutant sequence, flanked by restriction sites enabling ligation to fragments of the native sequence. Following ligation, the resulting reconstructed sequence encodes an analog having the desired amino acid insertion, substitution, or deletion.

Alternatively, oligonucleotide-directed site-specific mutagenesis procedures may be employed to provide an altered gene having particular codons altered according to the substitution, deletion, or insertion required. Deletion or truncation of a peptide of the invention may also be constructed by utilizing convenient restriction endonuclease sites adjacent to the desired deletion. Subsequent to restriction, overhangs may be filled in, and the DNA religated. Exemplary methods of making the alterations set forth above are disclosed by Sambrook et al (Molecular Cloning: A Laboratory Manual, 2nd Ed., Cold Spring Harbor Laboratory Press, 1989).

The peptides of the invention also include homologs of the amino acid sequence of the TCAP peptide, mutated TCAP peptides and/or truncations thereof as described herein. Such homologs are proteins whose amino acid sequences are comprised of amino acid sequences that hybridize under stringent hybridization conditions (see discussion of stringent hybridization conditions herein) with a probe used to obtain a peptide of the invention. Homologs of a peptide of the invention will have the same regions which are characteristic of the protein.

A homologous peptide includes a peptide with an amino acid sequence having at least 70%, preferably 80-95% identity with the amino acid sequence of the TCAP peptide.

The invention also contemplates isoforms of the peptides of the invention. An isoform contains the same number and kinds of amino acids as a peptide of the invention, but the isoform has a different molecular structure. The isoforms contemplated by the present invention are those having the same properties as a peptide of the invention as described herein.

The proteins of the invention (including e.g., truncations, analogs, etc.) may be prepared using recombinant DNA methods. Accordingly, nucleic acid molecules of the present invention having a sequence that encodes a peptide of the invention may be incorporated according to procedures known in the art into an appropriate expression vector that ensures good expression of the peptide. Possible expression vectors include but are not limited to cosmids, plasmids, or modified viruses (e.g., replication defective retroviruses, adenoviruses and adeno-associated viruses), so long as the vector is compatible with the host cell used. The expression "vectors suitable for transformation of a host cell", means that the expression vectors contain a nucleic acid molecule of the invention and regulatory sequences, selected on the basis of the host cells to be used for expression, which are operatively linked to the nucleic acid molecule. "Operatively linked" is intended to mean that the nucleic acid is linked to regulatory sequences in a manner that allows expression of the nucleic acid.

The invention therefore contemplates a recombinant expression vector of the invention containing a nucleic acid molecule of the invention, or a fragment thereof, and the necessary regulatory sequences for the transcription and translation of the inserted peptide-sequence. Suitable regulatory sequences may be derived from a variety of sources, including bacterial, fungal, or viral genes (For example, see the regulatory sequences described in Goeddel, Gene Expression Technology: Methods in Enzymology 185, Academic Press, San Diego, Calif. (1990). Selection of appropriate regulatory sequences is dependent on the host cell chosen, and may be readily accomplished by one of ordinary skill in the art. Examples of such regulatory sequences include: a transcriptional promoter and enhancer or RNA polymerase binding sequence, a ribosomal binding sequence, including a translation initiation signal. Additionally, depending on the host cell chosen and the vector employed, other sequences, such as an origin of replication, additional DNA restriction sites, enhancers, and sequences conferring inducibility of transcription may be incorporated into the expression vector. It will also be appreciated that the necessary regulatory sequences may be supplied by the native peptide and/or its flanking regions.

The invention further provides a recombinant expression vector comprising a DNA nucleic acid molecule of the invention cloned into the expression vector in an antisense orientation. That is, the DNA molecule is operatively linked to a regulatory sequence in a manner that allows for expression, by transcription of the DNA molecule, of an RNA molecule which is antisense to a nucleotide sequence of the invention. Regulatory sequences operatively linked to the antisense nucleic acid can be chosen which direct the continuous expression of the antisense RNA molecule.

The recombinant expression vectors of the invention may also contain a selectable marker gene that facilitates the selection of host cells transformed or transfected with a recombinant molecule of the invention. Examples of selectable marker genes are genes encoding a protein such as G418 and hygromycin which confer resistance to certain drugs, β-galactosidase, chloramphenicol acetyltransferase, or firefly luciferase. Transcription of the selectable marker gene is monitored by changes in the concentration of the selectable marker protein such as β-galactosidase, chloramphenicol acetyltransferase, or firefly luciferase. If the selectable marker gene encodes a protein conferring antibiotic resistance such as neomycin resistance transformant cells can be selected with G418. Cells that have incorporated the selectable marker gene will survive, while the other cells die. This makes it possible to visualize and assay for expression of recombinant expression vectors of the invention and in particular to determine the effect of a mutation on expression and phenotype. It will be appreciated that selectable markers can be introduced on a separate vector from the nucleic acid of interest.

Recombinant expression vectors can be introduced into host cells to produce a transformed host cell. Accordingly, the invention includes a host cell comprising a recombinant expression vector of the invention. The term "transformed host cell" is intended to include prokaryotic and eukaryotic cells which have been transformed or transfected with a recombinant expression vector of the invention. The terms "transformed with", "transfected with", "transformation" and "transfection" are intended to encompass introduction of nucleic acid (e.g. a vector) into a cell by one of many possible techniques known in the art. Prokaryotic cells can be transformed with nucleic acid by, for example, electroporation or calcium-chloride mediated transformation. Nucleic acid can be introduced into mammalian cells via conventional techniques such as calcium phosphate or calcium chloride co-precipitation, DEAE-dextran-mediated transfection, lipofectin, electroporation or microinjection. Suitable methods for transforming and transfecting host cells can be found in Sambrook et al. (Molecular Cloning: A Laboratory Manual, 2nd Edition, Cold Spring Harbor Laboratory press (1989)), and other such laboratory textbooks.

Suitable host cells include a wide variety of prokaryotic and eukaryotic host cells. For example, the peptides of the invention may be expressed in bacterial cells such as *E. coli, Pseudomonas, Bacillus subtillus*, insect cells (using baculovirus), yeast cells or mammalian cells. Other suitable host cells can be found in Goeddel, Gene Expression Technology: Methods in Enzymology 185, Academic Press, San Diego, Calif. (1991).

As an example, to produce TCAP peptides recombinantly, for example, *E. coli* can be used using the T7 RNA polymerase/promoter system using two plasmids or by labeling of plasmid-encoded proteins, or by expression by infection with M13 Phage mGPI-2. *E. coli* vectors can also be used with Phage lamba regulatory sequences, by fusion protein vectors (e.g. lacZ and trpE), by maltose-binding protein fusions, and by glutathione-S-transferase fusion proteins.

Alternatively, a TCAP peptide can be expressed in insect cells using baculoviral vectors, or in mammalian cells using vaccinia virus. For expression in mammalian cells, the cDNA sequence may be ligated to heterologous promoters and introduced into cells, such as COS cells to achieve transient or long-term expression. The stable integration of the chimeric gene construct may be maintained in mammalian cells by biochemical selection, such as neomycin and mycophoenolic acid.

The TCAP DNA sequence can be altered using procedures such as restriction enzyme digestion, fill-in with DNA polymerase, deletion by exonuclease, extension by terminal deoxynucleotide transferase, ligation of synthetic or cloned DNA sequences, site-directed sequence alteration with the use of specific oligonucleotides together with PCR.

The cDNA sequence or portions thereof, or a mini gene consisting of a cDNA with an intron and its own promoter, is introduced into eukaryotic expression vectors by conventional techniques. These vectors permit the transcription of the cDNA in eukaryotic cells by providing regulatory sequences that initiate and enhance the transcription of the cDNA and ensure its proper splicing and polyadenylation. The endogenous TCAP gene promoter can also be used. Different promoters within vectors have different activities which alters the level of expression of the cDNA. In addition, certain promoters can also modulate function such as the glucocorticoid-responsive promoter from the mouse mammary tumor virus.

Some of the vectors listed contain selectable markers or neo bacterial genes that permit isolation of cells by chemical selection. Stable long-term vectors can be maintained in cells as episomal, freely replicating entities by using regulatory elements of viruses. Cell lines can also be produced which have integrated the vector into the genomic DNA. In this manner, the gene product is produced on a continuous basis.

Vectors are introduced into recipient cells by various methods including calcium phosphate, strontium phosphate, electroporation, lipofection, DEAE dextran, microinjection, or by protoplast fusion. Alternatively, the cDNA can be introduced by infection using viral vectors.

TCAP peptides may also be isolated from cells or tissues, including mammalian cells or tissues, in which the peptide is normally expressed.

The protein may be purified by conventional purification methods known to those in the art, such as chromatography methods, high performance liquid chromatography methods or precipitation.

For example, an anti-TCAP antibody (as described below) may be used to isolate a TCAP peptide, which is then purified by standard methods.

The peptides of the invention may also be prepared by chemical synthesis using techniques well known in the chemistry of proteins such as solid phase synthesis (Merrifield, 1964, J. Am. Chem. Assoc. 85:2149-2154) or synthesis in homogenous solution (Houbenweyl, 1987, Methods of Organic Chemistry, ed. E. Wansch, Vol. 15 I and II, Thieme, Stuttgart).

III. Uses

The present invention includes all uses of the nucleic acid molecules, TCAP peptides and preTCAP peptides of the invention including, but not limited to, the preparation of antibodies and antisense oligonucleotides, the preparation of experimental systems to study TCAP, the isolation of substances that can bind or modulate TCAP expression and/or activity as well as the use of the TCAP nucleic acid sequences and peptides and modulators thereof in diagnostic and therapeutic applications. Some of the uses are further described below.

(a) Antibodies

The isolation of the TCAP peptide enables the preparation of antibodies specific for TCAP. Accordingly, the present invention provides an antibody that binds to a TCAP peptide and/or a protein containing a TCAP peptide, such as preTCAP.

Conventional methods can be used to prepare the antibodies. For example, by using a TCAP, polyclonal antisera or monoclonal antibodies can be made using standard methods. A mammal, (e.g., a mouse, hamster, or rabbit) can be immunized with an immunogenic form of the peptide which elicits an antibody response in the mammal. Techniques for conferring immunogenicity on a peptide include conjugation to carriers or other techniques well known in the art. For example, the protein or peptide can be administered in the presence of adjuvant. The progress of immunization can be monitored by detection of antibody titers in plasma or serum. Standard ELISA or other immunoassay procedures can be used with the immunogen as antigen to assess the levels of antibodies. Following immunization, antisera can be obtained and, if desired, polyclonal antibodies isolated from the sera.

To produce monoclonal antibodies, antibody-producing cells (lymphocytes) can be harvested from an immunized animal and fused with myeloma cells by standard somatic cell fusion procedures thus immortalizing these cells and yielding hybridoma cells. Such techniques are well known in the art, (e.g., the hybridoma technique originally developed by Kohler and Milstein (Nature 256, 495-497 (1975)) as well as other techniques such as the human B-cell hybridoma technique (Kozbor et al., Immunol. Today 4, 72 (1983)), the EBV-hybridoma technique to produce human monoclonal antibodies (Cole et al. Monoclonal Antibodies in Cancer Therapy (1985) Allen R. Bliss, Inc., pages 77-96), and screening of combinatorial antibody libraries (Huse et al., Science 246, 1275 (1989)). Hybridoma cells can be screened immunochemically for production of antibodies specifically reactive with the peptide and the monoclonal antibodies can be isolated. Therefore, the invention also contemplates hybridoma cells secreting monoclonal antibodies with specificity for TCAP.

The term "antibody" as used herein is intended to include fragments thereof which also specifically react with TCAP. Antibodies can be fragmented using conventional techniques and the fragments screened for utility in the same manner as described above. For example, F(ab')2 fragments can be generated by treating antibody with pepsin. The resulting F(ab')2 fragment can be further treated to produce Fab' fragments.

Chimeric antibody derivatives, i.e., antibody molecules that combine a non-human animal variable region and a human constant region are also contemplated within the scope of the invention. Chimeric antibody molecules can include, for example, the antigen binding domain from an antibody of a mouse, rat, or other species, with human constant regions. Conventional methods may be used to make chimeric antibodies containing the immunoglobulin variable region which recognizes the gene product of TCAP antigen of the invention (See, for example, Morrison et al., Proc. Natl. Acad. Sci. U.S.A. 81,6851 (1985); Takeda et al., Nature 314, 452 (1985), Cabilly et al., U.S. Pat. No. 4,816,567; Boss et al., U.S. Pat. No. 4,816,397; Tanaguchi et al., European Patent Publication EP171496; European Patent Publication 0173494, United Kingdom patent GB 2177096B). It is expected that chimeric antibodies would be less immunogenic in a human subject than the corresponding non-chimeric antibody.

Monoclonal or chimeric antibodies specifically reactive with a peptide of the invention as described herein can be further humanized by producing human constant region chimeras, in which parts of the variable regions, particularly the conserved framework regions of the antigen-binding domain, are of human origin and only the hypervariable regions are of non-human origin. Such immunoglobulin molecules may be made by techniques known in the art, (e.g., Teng et al., Proc. Natl. Acad. Sci. U.S.A., 80, 7308-7312 (1983); Kozbor et al., Immunology Today, 4, 7279 (1983); Olsson et al., Meth. Enzymol., 92, 3-16 (1982)), and PCT Publication WO92/06193 or EP 0239400). Humanized antibodies can also be commercially produced (Scotgen Limited, 2 Holly Road, Twickenham, Middlesex, Great Britain.)

Specific antibodies, or antibody fragments, reactive against TCAP peptide may also be generated by screening expression libraries encoding immunoglobulin genes, or portions thereof, expressed in bacteria with peptides produced from the nucleic acid molecules encoding TCAP. For example, complete Fab fragments, VH regions and FV regions can be expressed in bacteria using phage expression libraries (See for example Ward et al., Nature 341, 544-546: (1989); Huse et al., Science 246, 1275-1281 (1989); and McCafferty et al. Nature 348, 552-554 (1990)). Alternatively, a SCID-hu mouse, for example the model developed by Genpharm, can be used to produce antibodies or fragments thereof.

(b) Antisense Oligonucleotides

Isolation of a nucleic acid molecule encoding TCAP enables the production of antisense oligonucleotides that can modulate the expression and/or activity of TCAP. Accordingly, the present invention provides an antisense oligonucleotide that is complimentary to a nucleic acid sequence encoding TCAP.

The term "antisense oligonucleotide" as used herein means a nucleotide sequence that is complimentary to its target.

The term "oligonucleotide" refers to an oligomer or polymer of nucleotide or nucleoside monomers consisting of naturally occurring bases, sugars, and intersugar (backbone) linkages. The term also includes modified or substituted oligomers comprising non-naturally occurring monomers or portions thereof, which function similarly. Such modified or substituted oligonucleotides may be preferred over naturally occurring forms because of properties such as enhanced cellular uptake, or increased stability in the presence of nucleases. The term also includes chimeric oligonucleotides which contain two or more chemically distinct regions. For example, chimeric oligonucleotides may contain at least one region of modified nucleotides that confer beneficial properties (e.g. increased nuclease resistance, increased uptake into cells), or two or more oligonucleotides of the invention may be joined to form a chimeric oligonucleotide.

The antisense oligonucleotides of the present invention may be ribonucleic or deoxyribonucleic acids and may contain naturally occurring bases including adenine, guanine, cytosine, thymidine and uracil. The oligonucleotides may also contain modified bases such as xanthine, hypoxanthine, 2-aminoadenine, 6-methyl, 2-propyl and other alkyl adenines, 5-halo uracil, 5-halo cytosine, 6-aza uracil, 6-aza cytosine and 6-aza thymine, pseudo uracil, 4-thiouracil, 8-halo adenine, 8-aminoadenine, 8-thiol adenine, 8-thiolalkyl adenines, 8-hydroxyl adenine and other 8-substituted adenines, 8-halo guanines, 8-amino guanine, 8-thiol guanine, 8-thiolalkyl guanines, 8-hydroxyl guanine and other 8-substituted guanines, other aza and deaza uracils, thymidines, cytosines, adenines, or guanines, 5-trifluoromethyl uracil and 5-trifluoro cytosine.

Other antisense oligonucleotides of the invention may contain modified phosphorous, oxygen heteroatoms in the phosphate backbone, short chain alkyl or cycloalkyl intersugar linkages or short chain heteroatomic or heterocyclic intersugar linkages. For example, the antisense oligonucleotides may contain phosphorothioates, phosphotriesters, methyl phosphonates, and phosphorodithioates. In an embodiment of the invention there are phosphorothioate bonds links between the four to six 3'-terminus bases. In another embodiment phosphorothioate bonds link all the nucleotides.

The antisense oligonucleotides of the invention may also comprise nucleotide analogs that may be better suited as therapeutic or experimental reagents. An example of an oligonucleotide analogue is a peptide nucleic acid (PNA) wherein the deoxyribose (or ribose) phosphate backbone in the DNA (or RNA), is replaced with a polyamide backbone which is similar to that found in peptides (P. E. Nielsen, et al Science 1991, 254, 1497). PNA analogues have been shown to be resistant to degradation by enzymes and to have extended lives in vivo and in vitro. PNAs also bind stronger to a complimentary DNA sequence due to the lack of charge repulsion between the PNA strand and the DNA strand. Other oligonucleotides may contain nucleotides containing polymer backbones, cyclic backbones, or acyclic backbones. For example, the nucleotides may have morpholino backbone structures (U.S. Pat. No. 5,034,506). Oligonucleotides may also contain groups such as reporter groups, a group for improving the pharmacokinetic properties of an oligonucleotide, or a group for improving the pharmacodynamic properties of an antisense oligonucleotide. Antisense oligonucleotides may also have sugar mimetics.

The antisense nucleic acid molecules may be constructed using chemical synthesis and enzymatic ligation reactions using procedures known in the art. The antisense nucleic acid molecules of the invention or a fragment thereof, may be chemically synthesized using naturally occurring nucleotides or variously modified nucleotides designed to increase the biological stability of the molecules or to increase the physical stability of the duplex formed with mRNA or the native gene e.g. phosphorothioate derivatives and acridine substituted nucleotides. The antisense sequences may be produced biologically using an expression vector introduced into cells in the form of a recombinant plasmid, phagemid or attenuated virus in which antisense sequences are produced under the control of a high efficiency regulatory region, the activity of which may be determined by the cell type into which the vector is introduced.

The antisense oligonucleotides may be introduced into tissues or cells using techniques in the art including vectors (retroviral vectors, adenoviral vectors and DNA virus vectors) or physical techniques such as microinjection. The antisense oligonucleotides may be directly administered in vivo or may be used to transfect cells in vitro which are then administered in vivo. In one embodiment, the antisense oligonucleotide may be delivered to macrophages and/or endothelial cells in a liposome formulation.

(c) Diagnostic Assays

The findings by the present inventors that TCAP is involved in inhibiting neuronal cell proliferation, in inducing an anxiogenic response and in inhibiting cell death in cells subject to stress allows development of diagnostic assays, particularly for conditions associated with the aberrant regulation of neuronal growth.

Accordingly, the present invention provides a method of detecting a condition associated with TCAP or preTCAP expression comprising assaying a sample for (a) a nucleic acid molecule encoding a TCAP peptide or a fragment thereof or (b) a TCAP protein or a fragment thereof. The TCAP peptide preferably has a sequence as shown in SEQ. ID. NOS.: 13, 14, 21, 22, 29, 30, 37, 38, 45, 46, 53, 54, 61, 62, 69, 70, 77, 78, 85, 86, 93, 94, 101, 103. In one particular embodiment of the invention the condition is associated with the aberrant regulation of neuronal growth. Neuronal growth may include somatic and process development, mitogenesis or migration. Aberrant regulation of neuronal growth may occur via a disturbance in interneuronal connections and the associated signal molecules. Examples of such conditions include learning deficits, mental retardation, autism, schizophrenia, Alzheimer's Disease, Parkinson's Disease as well as affective disorders such as panic disorder, depression, anorexia nervosa and obsessive-compulsive disorder.

(i) Nucleic Acid Molecules

The nucleic acid molecules encoding TCAP as described herein or fragments thereof, allow those skilled in the art to construct nucleotide probes for use in the detection of nucleotide sequences encoding TCAP or fragments thereof in samples, preferably biological samples such as cells, tissues and bodily fluids. The probes can be useful in detecting the presence of a condition associated with TCAP expression or monitoring the progress of such a condition. Accordingly, the present invention provides a method for detecting a nucleic acid molecule encoding a TCAP comprising contacting the sample with a nucleotide probe capable of hybridizing with the nucleic acid molecule to form a hybridization product, under conditions which permit the formation of the hybridization product, preferably under stringent conditions, and assaying for the hybridization product.

Example of probes that may be used in the above method include fragments of the nucleic acid sequences shown in SEQ. ID. NOS.:-18-20, 25-28, 33-36, 41-44, 49-52, 57-60, 65-68, 73-76, 81-84, 89-92, 97-100 or that wherein T can also be U or that encodes a peptide having an amino acid sequence selected from the group consisting of: SEQ. ID. NOS: 13, 14, 21, 22, 29, 30, 37, 38, 45, 46, 53, 54, 61, 62, 69, 70, 77, 78, 85, 86, 93, 94, 101, 103 or that further has an amidation signal sequence (preferably GKR or GRR), at the carboxy terminus of said peptides, such as 15, 16, 23, 24, 31, 32, 39, 40, 47, 48, 55, 56, 63, 64, 71, 72, 79, 80, 97, 88, 95, 96. A nucleotide probe may be labelled with a detectable substance such as a radioactive label which provides for an adequate signal and has sufficient half-life such as 32P, 3H, 14C or the like. Other detectable substances which may be used include antigens that are recognized by a specific labelled antibody, fluorescent compounds, enzymes, antibodies specific for a labelled antigen, and chemiluminescence. An appropriate label may be selected having regard to the rate of hybridization and binding of the probe to the nucleic acid to be detected and the amount of nucleic acid available for hybridization. Labelled probes may be hybridized to nucleic acids on solid supports such as nitrocellulose filters or nylon membranes as generally described in Sambrook et al, 1989, Molecular Cloning, A Laboratory Manual (2nd ed.). The nucleotide probes may be used to detect genes, preferably in human cells, that hybridize to the nucleic acid molecule of the present invention preferably, nucleic acid molecules which hybridize to the nucleic acid molecule of the invention under stringent hybridization conditions as described herein.

Nucleic acid molecules encoding a TCAP peptide can be selectively amplified in a sample using the polymerase chain reaction (PCR) methods and cDNA or genomic DNA. It is possible to design synthetic oligonucleotide primers from the nucleotide sequence shown in FIGS. 1-5 for use in PCR. A nucleic acid can be amplified from cDNA or genomic DNA using oligonucleotide primers and standard PCR amplification techniques. The amplified nucleic acid can be cloned into an appropriate vector and characterized by DNA sequence analysis. cDNA may be prepared from mRNA, by isolating total cellular mRNA by a variety of techniques, for example, by using the guanidinium-thiocyanate extraction procedure of Chirgwin et al., Biochemistry, 18, 5294-5299 (1979). cDNA is then synthesized from the mRNA using reverse transcriptase (for example, Moloney MLV reverse transcriptase available from Gibco/BRL, Bethesda, Md., or AMV reverse transcriptase available from Seikagaku America, Inc., St. Petersburg, Fla.).

Patients may be screened routinely using probes to detect the presence of a TCAP gene by a variety of techniques. Genomic DNA used for the diagnosis may be obtained from body cells, such as those present in the blood, tissue biopsy, surgical specimen, or autopsy material. The DNA may be isolated and used directly for detection of a specific sequence or may be PCR amplified prior to analysis. RNA or cDNA may also be used. To detect a specific DNA sequence hybridization using specific oligonucleotides, direct DNA sequencing, restriction enzyme digest, RNase protection, chemical cleavage, and ligase-mediated detection are all methods which can be utilized. Oligonucleotides specific to mutant sequences can be chemically synthesized and labelled radioactively with isotopes, or non-radioactively using biotin tags, and hybridized to individual DNA samples immobilized on membranes or other solid-supports by dot-blot or transfer from gels after electrophoresis. The presence or absence of these mutant sequences is then visualized using methods such as autoradiography, fluorometry, or colorimetric reaction. Suitable PCR primers can be generated which are useful for example in amplifying portions of the subject sequence containing identified mutations. Other nucleotide sequence amplification techniques may be used, such as ligation-mediated PCR, anchored PCR and enzymatic amplification as would be understood by those skilled in the art.

Sequence alterations may also generate fortuitous restriction enzyme recognition sites that are revealed by the use of appropriate enzyme digestion followed by gel-blot hybridization. DNA fragments carrying the site (normal or mutant) are detected by their increase or reduction in size, or by the increase or decrease of corresponding restriction fragment numbers. Genomic DNA samples may also be amplified by PCR prior to treatment with the appropriate restriction enzyme and the fragments of different sizes are visualized under UV light in the presence of ethidium bromide after gel electrophoresis.

Genetic testing based on DNA sequence differences may be achieved by detection of alteration in electrophoretic mobility of DNA fragments in gels. Small sequence deletions and insertions can be visualized by high-resolution gel electrophoresis. Small deletions may also be detected as changes in the migration pattern of DNA heteroduplexes in non-denaturing gel electrophoresis. Alternatively, a single base substitution mutation may be detected based on differential primer length in PCR. The PCR products of the normal and mutant gene could be differentially detected in acrylamide gels.

Nuclease protection assays (S1 or ligase-mediated) also reveal sequence changes at specific locations. Alternatively, to confirm or detect a polymorphism restriction mapping changes ligated PCR, ASO, REF-SSCP and SSCP may be used. Both REF-SSCP and SSCP are mobility shift assays that are based upon the change in conformation due to mutations.

DNA fragments may also be visualized by methods in which the individual DNA samples are not immobilized on membranes. The probe and target sequences may be in solution or the probe sequence may be immobilized. Autoradiography, radioactive decay, spectrophotometry, and fluorometry may also be used to identify specific individual genotypes.

(ii) Proteins

The TCAP protein may be detected in a sample using antibodies that bind to the protein as described in detail above. Accordingly, the present invention provides a method for detecting a TCAP protein comprising contacting the sample with an antibody that binds to TCAP and which is capable of being detected after it becomes bound to the TCAP in the sample.

Antibodies specifically reactive with TCAP, or derivatives thereof, such as enzyme conjugates or labeled derivatives, may be used to detect TCAP in various biological materials, for example they may be used in any known immunoassays which rely on the binding interaction between an antigenic determinant of TCAP, and the antibodies. Examples of such assays are radioimmunoassays, enzyme immunoassays (e.g. ELISA), immunofluorescence, immunoprecipitation, latex agglutination, hemagglutination and histochemical tests. Thus, the antibodies may be used to detect and quantify mutated TCAP in a sample in order to determine its role in particular cellular events or pathological states, and to diagnose and treat such pathological states.

In particular, the antibodies of the invention may be used in immuno-histochemical analyses, for example, at the cellular and sub-subcellular level, to detect TCAP, to localize it to particular cells and tissues and to specific subcellular locations, and to quantitate the level of expression.

Cytochemical techniques known in the art for localizing antigens using light and electron microscopy may be used to detect TCAP. Generally, an antibody of the invention may be labelled with a detectable substance and TCAP may be localised in tissue based upon the presence of the detectable substance. Examples of detectable substances include various enzymes, fluorescent materials, luminescent materials and radioactive materials. Examples of suitable enzymes include horseradish peroxidase, biotin, alkaline phosphatase, β-galactosidase, or acetylcholinesterase; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include radioactive iodine I-125, I-131 or 3-H. Antibodies may also be coupled to electron dense substances, such as ferritin or colloidal gold, which are readily visualized by electron microscopy.

Indirect methods may also be employed in which the primary antigen-antibody reaction is amplified by the introduction of a second antibody, having specificity for the antibody reactive against TCAP. By way of example, if the antibody having specificity against TCAP is a rabbit IgG antibody, the second antibody may be goat anti-rabbit gamma-globulin labelled with a detectable substance as described herein.

Where a radioactive label is used as a detectable substance, TCAP may be localized by autoradiography. The results of autoradiography may be quantitated by determining the density of particles in the autoradiographs by various optical methods, or by counting the grains.

(d) Experimental Systems

Eukaryotic expression systems are preferred and can be used for many studies of TCAP encoding genes and gene product(s) including the production of large amounts of the peptide for isolation and purification, to use cells expressing the TCAP peptide as a functional assay system for antibodies generated against the peptide or to test effectiveness of pharmacological agents, to study the function of the normal complete peptide, specific portions of the peptide, or of naturally occurring and artificially produced mutant peptides.

Using the techniques mentioned, the expression vectors containing the TCAP peptide cDNA sequence or portions thereof can be introduced into a variety of mammalian cells from other species or into non-mammalian cells.

The recombinant cloning vector, according to this invention, comprises the selected DNA of the DNA sequences of this invention for expression in a suitable host. The DNA is operatively linked in the vector to an expression control sequence in the recombinant DNA molecule so that TCAP peptide protein can be expressed. The expression control sequence may be selected from the group consisting of sequences that control the expression of genes of eukaryotic cells and their viruses and combinations thereof. The expression control sequence may be selected from the group consisting of the lac system, the trp system, the tac system, the trc system, major operator and promoter regions of phage lambda, the control region of the fd coat protein, early and late promoters of TCAP, promoters derived from polyoma, adenovirus, retrovirus, baculovirus, simian virus, 3-phosphoglycerate kinase promoter, yeast acid phosphatase promoters, yeast alpha-mating factors and combinations thereof.

Expression of the TCAP peptide in heterologous cell systems may also be used to demonstrate structure-function relationships as well as to provide cell lines for the purposes of drug screening. Inserting a TCAP DNA sequence into a plasmid expression vector to transfect cells is a useful method to test the influence of the peptide on various cellular biochemical parameters including the identification of substrates as well as activators and inhibitors of the gene. Plasmid expression vectors containing either the entire coding sequence for TCAP, or for portions thereof, can be used in in vitro mutagenesis experiments that will identify portions of the protein crucial for function. The DNA sequence can be manipulated in studies to understand the expression of the gene and its product. The changes in the sequence may or may not alter the expression pattern in terms of relative quantities, tissue-specificity and functional properties.

The invention also provides methods for examining the function of the TCAP peptide encoded by the nucleic acid molecules of the invention. Cells, tissues, and non-human animals lacking in expression or partially lacking in expression of the peptide may be developed using recombinant molecules of the invention having specific deletion or insertion mutations in the nucleic acid molecule of the invention. A recombinant molecule may be used to inactivate or alter the endogenous gene by homologous recombination, and thereby create a deficient cell, tissue or animal. Such a mutant cell, tissue or animal may be used to define specific cell populations, developmental patterns and in vivo processes, normally dependent on the protein encoded by the nucleic acid molecule of the invention.

Immortalized TCAP responsive cell lines can also be used to identify modulators of TCAP such as noted in Example 13. It can also be used to identify effect of TCAP and TCAP modulators on particular markers. In so far as these markers are associated with the regulation of a medical condition, TCAP and/or the TCAP modulators may be used in the diagnosis, regulation, and/or treatment of said medical condition.

(e) TCAP Modulators

In addition to antibodies and antisense oligonucleotides described above, other substances that modulate TCAP expression or activity may also be identified.

(i) Substances that Bind/Modulate TCAP

Substances that affect TCAP activity can be identified based on their ability to bind to TCAP.

Substances which can bind with the TCAP of the invention may be identified by reacting the TCAP with a substance which potentially binds to TCAP, and assaying for complexes, for free substance, or for non-complexed TCAP, or for activation of TCAP. In particular, a yeast two hybrid assay system may be used to identify proteins which interact with TCAP (Fields, S. and Song, O., 1989, Nature, 340:245-247). Systems of analysis which also may be used include ELISA.

Accordingly, the invention provides a method of identifying substances which can bind with TCAP, comprising the steps of:
1. reacting TCAP and a test substance, under conditions which allow for formation of a complex between the TCAP and the test substance, and
2. assaying for complexes of TCAP and the test substance, for free substance or for non complexed TCAP, wherein the presence of complexes indicates that the test substance is capable of binding TCAP.

In another embodiment the invention provides a method of identifying substances that can modulate TCAP activity, such as by binding to TCAP or a TCAP substrate and thus potentially compete (i.e. inhibit TCAP activity), or enhance TCAP/substrate interaction (i.e enhancing TCAP activity), the method comprising:
1. reacting TCAP and a TCAP substate and a test substance, under conditions which allow for formation of a complex between the TCAP and the TCAP substrate, and
2. assaying for complexes of TCAP and the test substance, TCAP and TCAP substate, TCAP substrate and test substance, for free substance or for non complexed TCAP or TCAP substrate, wherein the presence of complexes with the test substance indicates that the test substance is capable of binding TCAP or TCAP substrate, as the case may be.

In another embodiment, a method of identifying modulators of TCAP comprises the use of a cell line that has known reaction to TCAP that can be monitored and monitoring said reaction in the presence of TCAP and a potential modulator.

The TCAP peptide used in the assay may have the amino acid sequence shown in SEQ. ID. NOS:, 14, 21, 22, 29, 30, 37, 38, 45, 46, 53, 54, 61, 62, 69, 70, 77, 78, 85, 86, 93, 94, 101, 103 or may be a fragment, analog, derivative, homolog or mimetic thereof as described herein.

Conditions which permit the formation of substance and TCAP complexes may be selected having regard to factors such as the nature and amounts of the substance and the peptide.

The substance-peptide complex, free substance or non-complexed peptides may be isolated by conventional isolation techniques, for example, salting out, chromatography, electrophoresis, gel filtration, fractionation, absorption, polyacrylamide gel electrophoresis, agglutination, or combinations thereof. To facilitate the assay of the components, antibody against TCAP or the substance, or labelled TCAP, or a labelled substance may be utilized. The antibodies, proteins, or substances may be labelled with a detectable substance as described above.

TCAP, or the substance used in the method of the invention may be insolubilized. For example, TCAP or substance may be bound to a suitable carrier. Examples of suitable carriers are agarose, cellulose, dextran, Sephadex, Sepharose, carboxymethyl cellulose polystyrene, filter paper, ion-exchange resin, plastic film, plastic tube, glass beads, polyamine-methyl vinyl-ether-maleic acid copolymer, amino acid copolymer, ethylene-maleic acid copolymer, nylon, silk, etc. The carrier may be in the shape of, for example, a tube, test plate, beads, disc, sphere etc.

The insolubilized peptide or substance may be prepared by reacting the material with a suitable insoluble carrier using known chemical or physical methods, for example, cyanogen bromide coupling.

The peptide or substance may also be expressed on the surface of a cell using the methods described herein.

The invention also contemplates assaying for an antagonist or agonist of the action of TCAP.

It will be understood that the agonists and antagonists that can be assayed using the methods of the invention may act on one or more of the binding sites on the protein or substance including agonist binding sites, competitive antagonist binding sites, non-competitive antagonist binding sites or allosteric sites.

The invention also makes it possible to screen for antagonists that inhibit the effects of an agonist of TCAP. Thus, the invention may be used to assay for a substance that competes for the same binding site of TCAP.

(ii) Peptide Mimetics

The present invention also includes peptide mimetics of TCAP. "Peptide mimetics" are structures which serve as substitutes for peptides in interactions between molecules (See Morgan et al (1989), Ann. Reports Med. Chem. 24:243-252 for a review). Peptide mimetics include synthetic structures which may or may not contain amino acids and/or peptide bonds but retain the structural and functional features of a peptide, or enhancer or inhibitor of the invention. Peptide mimetics also include peptoids, oligopeptoids (Simon et al (1972) Proc. Natl. Acad, Sci USA 89:9367); and peptide libraries containing peptides of a designed length representing all possible sequences of amino acids corresponding to a peptide of the invention.

Peptide mimetics may be designed based on information obtained by systematic replacement of L-amino acids by D-amino acids, replacement of side chains with groups having different electronic properties, and by systematic replacement of peptide bonds with amide bond replacements. Local conformational constraints can also be introduced to determine conformational requirements for activity of a candidate peptide mimetic. The mimetics may include isosteric amide bonds, or D-amino acids to stabilize or promote reverse turn conformations and to help stabilize the molecule. Cyclic amino acid analogues may be used to constrain amino acid residues to particular conformational states. The mimetics can also include mimics of inhibitor peptide secondary structures. These structures can model the 3-dimensional orientation of amino acid residues into the known secondary conformations of proteins. Peptoids may also be used which are oligomers of N-substituted amino acids and can be used as motifs for the generation of chemically diverse libraries of novel molecules.

Peptides of the invention may also be used to identify lead compounds for drug development. The structure of the peptides described herein can be readily determined by a number of methods such as NMR and X-ray crystallography. A comparison of the structures of peptides similar in sequence, but differing in the biological activities they elicit in target molecules can provide information about the structure-activity relationship of the target. Information obtained from the examination of structure-activity relationships can be used to design either modified peptides, or other small molecules or lead compounds that can be tested for predicted properties as related to the target molecule. The activity of the lead compounds can be evaluated using assays similar to those described herein.

Information about structure-activity relationships may also be obtained from co-crystallization studies. In these studies, a peptide with a desired activity is crystallized in association with a target molecule, and the X-ray structure of the complex is determined. The structure can then be compared to the structure of the target molecule in its native state, and information from such a comparison may be used to design compounds expected to possess.

(iii) Drug Screening Methods

In accordance with one embodiment, the invention enables a method for screening candidate compounds for their ability to increase or decrease the activity and/or expression of TCAP. The method comprises providing an assay system for assaying TCAP activity, assaying the activity in the presence or absence of the candidate or test compound and determining whether the compound has increased or decreased TCAP activity. Such compounds may be useful in treating conditions associated with aberrant regulation of neuronal growth.

Accordingly, the present invention provides a method for identifying a compound that affects TCAP activity or expression comprising:
(a) incubating a test compound with a TCAP peptide or a nucleic acid encoding a TCAP peptide; and
(b) determining an amount of TCAP peptide activity or expression and comparing with a control (i.e. in the absence of the test substance), wherein a change in the TCAP activity or expression as compared to the control indicates that the test compound has an effect on TCAP activity or expression.

In accordance with a further embodiment, the invention enables a method for screening candidate compounds for their ability to increase or decrease expression of a TCAP peptide. The method comprises putting a cell with a candidate compound, wherein the cell includes a regulatory region of a gene encoding TCAP operably joined to a reporter gene coding region, and detecting a change in expression of the reporter gene.

Such compounds can be selected from protein compounds, chemicals and various drugs that are added to the culture medium. After a period of incubation in the presence of a selected test compound(s), the expression of mutated TCAP can be examined by quantifying the levels of TCAP mRNA using standard Northern blotting procedure, as described in the examples included herein, to determine any changes in expression as a result of the test compound. Cell lines transfected with constructs expressing TCAP can also be used to test the function of compounds developed to modify the protein expression.

(f) Therapeutic Uses

As previously discussed, TCAP of the invention is involved in CAMP, cGMP activity, neuronal growth and neurological development. Accordingly, the present invention provides a method of treating a condition associated with aberrant regulation of cAMP, cGMP, neuronal growth, neuronal communication, or neuronal cell proliferation comprising the administering to a cell or animal in need thereof, an effective amount of agent that modulates TCAP expression and/or activity.

The term "agent that modulates TCAP expression and/or activity" means any substance that can alter the expression and/or activity of TCAP. Examples of agents which may be used to in administration include: a nucleic acid molecule encoding TCAP; the TCAP peptide as well as fragments, analogs, derivatives or homologs thereof; antibodies; antisense nucleic acids; peptide mimetics; and substances isolated using the screening methods described herein that can result in TCAP levels and/or function consistent with a person without the condition.

The term "effective amount" as used herein means an amount effective, at dosages and for periods of time necessary to achieve the desired results.

The term "animal" as used herein includes all members of the animal kingdom that respond to TCAP, preferably mammals, including both human and non-human animals, more preferably humans. In another embodiment, animals include domesticated animals, such as cows, horses, pigs, and sheep, In another embodiment, the animals are from the avian family and include chickens.

In accordance with another embodiment, the present invention enables gene therapy as a potential therapeutic approach to a condition, in which normal copies of the TCAP gene are introduced into patients to successfully code for normal TCAP peptide in several different affected cell types.

Retroviral vectors can be used for somatic cell gene therapy especially because of their high efficiency of infection and stable integration and expression. The targeted cells however must be able to divide and the expression of the levels of normal protein or peptide should be high. A TCAP encoding gene can be cloned into a retroviral vector and driven from its endogenous promoter or from the retroviral long terminal repeat or from a promoter specific for the target cell type of interest (such as lymphoid cells). Other viral vectors that can be used include adeno-associated virus, vaccinia virus, bovine papilloma virus, or a herpesvirus such as Epstein-Barr virus. Gene transfer could also be achieved using non-viral means requiring infection in vitro. This would include calcium phosphate, DEAE dextran, electroporation, cationic or anionic lipid formulations (liposomes) and protoplast fusion. Although these methods are available, many of these are lower efficiency.

Anti-sense based strategies can be employed to inhibit TCAP gene function and as a basis for therapeutic drug design. The principle is based on the hypothesis that sequence specific suppression of gene expression can be achieved by intracellular hybridization between mRNA and a complementary anti-sense species. It is possible to synthesize antisense strand nucleotides that bind the sense strand of RNA or DNA with a high degree of specificity. The formation of a hybrid RNA duplex may interfere with the processing/transport/translation and/or stability of a target mRNA.

Hybridization is required for an antisense effect to occur. Antisense effects have been described using a variety of approaches including the use of antisense oligonucleotides, injection of antisense RNA, DNA and transfection of antisense RNA expression vectors.

Therapeutic antisense nucleotides can be made as oligonucleotides or expressed nucleotides. Oligonucleotides are short single strands of DNA which are usually 15 to 20 nucleic acid bases long. Expressed nucleotides are made using expression vectors such as an adenoviral, retroviral or plasmid vector. The vector is administered to the cells in culture, or to a patient, whose cells then make the antisense nucleotide. Expression vectors can be designed to produce antisense RNA, which can vary in length from a few dozen bases to several thousand.

Antisense effects can be induced by control (sense) sequences. The extent of phenotypic changes is highly variable. Phenotypic effects induced by antisense are based on changes in criteria such as biological endpoints, protein levels, protein activation measurement and target mRNA levels.

(g) Methods and Uses of TCAP For Modulation of Stress Responses, Related Conditions and Anxiety The invention also provides a method of detecting an anxiety disorder in an animal by monitoring the effect of TCAP on said animal. If the anxiety response decreases (anxiolytic) as compared to baseline level, than the animal may have a high anxiety related disorder. If the anxiety response of an animal increases in response to administration of TCAP, then the animal may have a low anxiety disorder.

The invention provides a method for normalizing the anxiety state of an animal by administering TCAP to said animal or up-regulating TCAP expression in said animal.

The invention also provides a method of inducing a desired anxiety state in an animal by:
(a) determining whether the animal is a low or high anxiety animal; and
(b) (i) administering an effective amount of TCAP or TCAP agonist (including a substance or nucleic acid molecule that up regulates TCAP expression) to increase anxiety in a low anxiety animal and decrease anxiety in a high anxiety animal; or
(ii) administering an inhibitor of TCAP or TCAP antagonist (including a substance or nucleic acid molecule, such as a TCAP antisense nucleic acid molecule, that down regulates TCAP expression) to increase anxiety in a high anxiety animal and decrease anxiety in a low anxiety animal.

The invention also provides a method of detecting a modulator of TCAP activity comprising, administering TCAP to an animal with a known anxiety state (high or low anxiety), administering the potential modulator to said animal and comparing the response to TCAP in the presence and absence of said substance. If the animal's response to TCAP is different than that of baseline (Animal with TCAP alone, and no substance), then said substance is a modulator of TCAP activity. Such compounds may be used to treat animals with undesired stress or anxiety levels.

In one embodiment, TCAP is TCAP-1, or analog, derivative or fragment thereof with similar biological activity.

In another embodiment a modulator of TCAP is administered to modulate or regulate the stress response in an animal.

Stress as used herein is any state that is not homeostasis or metabolic balance. Stress is also used to refer to the general state of stressors provoking stress responses (Sapolsky, 1992). Hoemeostasis refers to the normal stability of the internal environment (Sapolsky, 1992). A Stressor is defined as anything that disrupts physiological balance, be it physical or psychological (Sapolsky, 1992). For example, a stressor in the behavioural experimentals herein (Examples 10 and 11) is defined as a 120 dB tone using the acoustic startle test.

Stress Response as used herein is a physiological or behavioural response to stressor(s). For example, in the behavioural experiments (Examples 10 and 11), stress response is the startle response as measured by the acoustic startle testing apparatus (Med Associates, St. Albans, Vt.) following presentation of a 120 dB tone.

Anxiogenic as used herein means a stimulus, internal or external, that increases behavioural measures of anxiety in generally accepted tests. In Examples 10 and 11 herein, the behavioural measure of anxiety is the startle response as measured by the acoustic startle testing apparatus (Med Associates, St. Albans, Vt.) following the presentation of a 120 dB tone. An anxiogenic response is an increase in the startle response. Anxiolytic as used herein means a stimulus, internal or external, that decreases behavioural measures of anxiety in generally accepted tests. In Examples 10 and 11 herein, the behavioural measure of anxiety is the startle response as measured by the acoustic startle testing apparatus (Med Associates, St. Albans, Vt.) following the presentation of a 120 dB tone. An anxiolytic response is a decrease in the startle response.

Anxiety refers to a generalized state of distress that may be prompted by generalized, non-specific cues, and involves physiological arousal, but often without organized functional behaviour (Lang et al., 2000). Animal models of anxiety attempt to represent some aspect of the etiology, symptomatology, or treatment of these disorders (Menard and Treit, 1999). In the present studies, the acoustic startle response was used as a measure of anxiety (Frankland et al., 1996, 1997). This test measures a simple reflex induced by a loud and unexpected auditory stimulus, and can be measured using standardized equipment (Med Associates, St. Albans, Vt.).

High Anxiety as used herein means an animal, e.g., rat, that has a post-vehicle injection startle response that is greater than the baseline response. An average startle response is calculated for the baseline trials and the post-injection (treatment) test periods. The treatment/baseline ratio is then calculated for each animal, e.g., rat. If this ratio is greater than 1, then the animal is classified as high anxiety.

Low Anxiety as used herein means an animal, e.g rat, that has a post-vehicle injection startle response that is less than the baseline response. The treatment/baseline ratio is calculated for each animal, e.g. rat, as above. If this ratio is less than 1, then the animal, e.g. rat, is classified as low anxiety.

Normal Anxiety as used herein means an animal, such as a rat that has a post-vehicle injection startle response that is the same as the baseline response. The treatment/baseline ratio is calculated for each rat as above. If this ratio is equal to 1, then the animal, e.g. rat, is classified as normal anxiety.

(h) The Role of TCAP in the Regulation of Cell Proliferation and in the Treatment of Cancer In one embodiment, the invention provides a method of regulating cell proliferation by administering an effective amount of TCAP to an animal in need thereof. In another embodiment, the TCAP is administered in vivo or in vitro to decreasing and/or inhibiting cell proliferation. In one embodiment the cell is cancerous. In another embodiment the cell is a neuronal tumour cell.

In one embodiment, TCAP or modulators thereof can be used in the treatment of cancer, such as neuroblastomas or other neuronal tumours.

(i) Pharmaceutical Compositions

The above described substances including nucleic acids encoding TCAP, TCAP peptides, antibodies, and antisense oligonucleotides as well as other agents that modulate TCAP activity or expression may be formulated into pharmaceutical compositions for administration to subjects in a biologically compatible form suitable for administration in vivo. By "biologically compatible form suitable for administration in vivo" is meant a form of the substance to be administered in which any toxic effects are outweighed by the therapeutic effects. The substances may be administered to living organisms including humans, and animals.

Thus in one embodiment, the invention provides the use of TCAp or modulator there in the preparation of a medicament for the treatment of TCAP-related or TCAP regulated medical conditions. For instance, in the regulation of cell proliferation (e.g. cancer), stress, anxiety or neuronal communicative disorders.

Administration of a therapeutically effective amount of pharmaceutical compositions of the present invention is defined as an amount effective, at dosages and for periods of time necessary to achieve the desired therapeutic result. For example, a therapeutically effective amount of a substance may vary according to factors such as the disease state, age, sex, and weight of the individual, and the ability of the substance to elicit a desired response in the individual. Dosage regimes may be adjusted to provide the optimum therapeutic response. For example, several divided doses may be administered daily or the dose may be proportionally reduced as indicated by the exigencies of the therapeutic situation.

An active substance may be administered in a convenient manner such as by injection (subcutaneous, intravenous, etc.), oral administration, inhalation, transdermal application, or rectal administration. Depending on the route of administration, the active substance may be coated in a material to protect the compound from the action of enzymes, acids and other natural conditions that may inactivate the compound. If the active substance is a nucleic acid encoding, for example, a TCAP peptide it may be delivered using techniques known in the art.

The compositions described herein can be prepared by per se known methods for the preparation of pharmaceutically acceptable compositions which can be administered to subjects, such that an effective quantity of the active substance is combined in a mixture with a pharmaceutically acceptable vehicle. Suitable vehicles are described, for example, in Remington's Pharmaceutical Sciences (Remington's Pharmaceutical Sciences, Mack Publishing Company, Easton, Pa., USA 1985) or Handbook of Pharmaceutical Additives (compiled by Michael and Irene Ash, Gower Publishing Limited, Aldershot, England (1995)). On this basis, the compositions include, albeit not exclusively, solutions of the substances in association with one or more pharmaceutically acceptable vehicles or diluents, and may be contained in buffered solutions with a suitable pH and/or be iso-osmotic with physiological fluids. In this regard, reference can be made to U.S. Pat. No. 5,843,456. As will also be appreciated by those skilled, administration of substances described herein may be by an inactive viral carrier. In one embodiment TCApP can be administered in a vehicle comprising saline and acetic acid.

(j) Kits

The reagents suitable for carrying out the methods of the invention may be packaged into convenient kits providing the necessary materials, packaged into suitable containers. Such kits may include all the reagents required to detect a nucleic acid molecule or peptide of the invention or conjugates of a nucleic acid molecule or peptide of the invention and another substance, such as a potential modulator of TCAP, and/or the detection of an indicator of TCAP activity, such as cAMP or cGMP, in a sample by means of the methods described herein, and optionally suitable supports useful in performing the methods of the invention.

In one embodiment of the invention, the kit includes primers which are capable of amplifying a nucleic acid molecule of the invention or a predetermined oligonucleotide fragment thereof, all the reagents required to produce the amplified nucleic acid molecule or predetermined fragment hereof in the polymerase chain reaction, and means for assaying the amplified sequences. In one embodiment, the primers can amplify a nucleic acid encoding a TCAP protein, preferably the protein of SEQ. ID. NO.:.

The kit may also include restriction enzymes to digest the PCR products. In another embodiment of the invention the kit contains a nucleotide probe which hybridizes with a nucleic acid molecule of the invention, reagents required for hybridization of the nucleotide probe with the nucleic acid molecule, and directions for its use. In a further embodiment of the invention, the kit includes antibodies of the invention and reagents required for binding of the antibody to a TCAP peptide of the invention in a sample.

Before testing a sample in accordance with the methods described herein, the sample may be concentrated using techniques known in the art, such as centrifugation and filtration. For the hybridization and/or PCR-based methods described herein, nucleic acids may be extracted from cell extracts of the test sample using techniques known in the art.

The following non-limiting examples are illustrative of the present invention:

EXAMPLES

Example 1

Identification of Teneurin C-Terminal Associated Peptide (TCAP)

A. Identification of TCAP mRNA

Cloning of mRNA. A rainbow trout hypothalamic cDNA library was constructed as previously described (Barsyte et al., 1999) using a unidirectional vector (Unizap, Stratagene, La Jolla Calif.). A total of 600,000 clones were screened using a randomly labelled 305-bp hamster urocortin cDNA probe (Robinson et al., 1999) [SEQ. ID. NO 120-5'-att cac cgccgc tcg gga tct gag cct gca ggc gag cgg cag cga cgg gaa gac ctt ccg ctg tcc atc gac ctc aca ftc cac ctg cta cgg acc ctg ctg gag atg gcc cgg aca cag agc caa cgc gag cga gca gag cag aac cga atc ata ctc aac gcg gtg ggc aag tga tcg gcc cgg tgt ggg acc cca aaa ggc tcg acc ctt tcc cct acc tac ccc ggg gct gaa gtc acg cga ccg aag tcg gct tag tcc cgc ggt gca gcg cct ccc aga gtt acc ctg aac aat ccc gc-3'.] Primary, secondary and tertiary screens all utilized the same probe. The size of the clones, positive after the final screen, were determined by restriction analysis then sequenced using automated Big Dye methods.

Five positive clones were isolated from the rainbow trout hypothalamic library. Of these, one represented a partial sequence of a putative rainbow trout Ten-m3 homologue (FIG. 1). The clone was 2986 bases long covering the translated portion of 769 bases]. SEQ. ID. NO. 1 shows a 756 base portion [SEQ. ID. NO. 2 thereof and a 3' untranslated region of 734 bases. The stop codon and translated portion were identified by alignment with the mouse (accession number AB025412)[SEQ. ID. NO: 132], human (accession number AK027474)[SEQ. ID. NO: 133] and zebrafish (accession number AB026976))[SEQ. ID. NO: 134], Ten M3 orthologues. Based on the human gene sequence (Locus Link ID# 10178) using Locus Link on the NICB server, the rainbow trout sequence included the terminal 6 exons of the gene. The final 3' exon encoded a 251 amino acid residue sequence [SEQ. ID. NO. 3] with a 40-41-residue carboxy-terminal sequence [SEQ. ID. NOS. 13 and 14, respectively] suggestive of a bioactive peptide. A putative amidation signal was indicated by the GKR amino acid motif immediately adjacent to the 40-41 residue carboxy terminal sequence and TAA stop codon. 40 residues upstream, a PC-7-like cleavage signal was present immediately followed by a glutamine suggesting that the putative free peptide would begin with a pyroglutamic acid. This cleavage site is not necessarily processed in the normal way and can create a 40 or 41 amino acid residue mature peptide (starting at 43 or 44 amino acid residues upstream from the stop codon).

B. Extraction of Free TCAP Peptide

Tissue Collection: Mouse brains (*Mus musculus*; n=10; 1.8 g) were collected and stored at −80° C. for one month, at which time they were removed and placed immediately into liquid nitrogen. Brain tissue was crushed using a mortar and pestle and powdered in the presence of liquid nitrogen.

Activation of C18 packing material: Bondpack® C18 bulk packing material (1 g; 125 Å; 37-55 μm; Waters Corporation, Milford, Mass., USA) was activated with 100% methanol (5 ml), vortexed and left to stand (5 min.). Excess methanol was removed. C18 was then washed in duplicate with PBS (SmI, pH 7.6). An additional PBS aliquot was added (5 ml), vortexed and centrifuged (5000 rpm; 5 min); the supernatant was discarded.

Tissue Extraction: Acetonitrile (90%) and TFA (0.05%) were added to powdered brains in a 5:1 volume to weight ratio, mixed for 1 hr on an aliquot mixer rocker. The mixture was centrifuged (8000 rpm×20 min.); the supernatant was removed and saved. The remaining solids were back-extracted in acetonitrile (90%) and TFA (0.05%) in 40% of the solvent volume used in the initial extraction, vortexed and centrifuged as described previously. The supernatants were pooled and combined with activated C18 packing material, vortexed, mixed (1 hr) and centrifuged (8000 rpm×10 min). The supernatant was discarded while the pellet was subjected to three successive, independent acetonitrile extractions of 20%, 50% and 90% respectively. Acetonitrile (5 ml) was added to the pellet, vortexed, mixed (20 min) and centrifuged (6000 rpm×10 min.). Resulting supernatant was saved and concentrated to 800 μl on a vacuum concentrator (Brinkman Instruments) for HPLC analysis while the pellet was re-extracted in the same manner.

HPLC Purification of Free TCAP in Brain Extracts

A Beckman model 126 HPLC System Gold (Beckman, Palo Alto, Calif.), attached to a UV detector module 168 and C18 column (3.5 um particle size; Waters Inc) was used to purify the TCAP peptide extracted from mouse brains (n=10).

A single injection (800 ul) was applied to the column through a 1 ml injection loop and carried to the column at a flow rate of 1 ml/min using a dual solvent system (A: 0.05% trifluoroacetic acid (TFA); B: 80% acetonitrile, 0.05% TFA). Following an initial isocratic period of 10 min, mobile phase B was increased from 10% to 60% over 75 min, held isocratically for 5 min and returned to 10% over 5 min. Fractions were collected (1 ml/fraction), aliquoted (500 ul) and concentrated to 50 ul for analysis using mass spectrometry.

Example 2

Detection of the Cleaved TCAP in Cell and Tissue Extracts

HPLC as described in Example 1 can be used to detect TCAP. Mass Spectroscopy can also be used. Other detection methods can also be combined with HPLC, Mass Spectroscopy or used on their own, such as radio immunoassays, ELISAs, capillary electrophoresis, immunofluorescence confocal microscopy. Mass spectrometric methods identify molecules on the basis of a charged molecule's (ion) mass to charge ratio. A precise determination of the molecules mass is then determined allowing for identification of the molecule. Larger peptides can be sequenced by subsequent fragmentation of the peptide in a collision chamber. This causes preferential breaking of the peptide bonds. The amino acid and peptide fragments are identified by their mass to charge ratio. Radioimmunoassays or enzyme-linked immunosorbant assays (ELISA) utilize an antiserum specific for the molecule of interest. The molecule (TCAP) competes with a tagged structurally similar reference molecules to bind the antibody. The bound and unbound fractions are separated from each other and the quantity of remaining tagged TCAP is measured. This measurement is proportional to the amount of unlabeled TCAP present. Capillary electrophoresis can also be used to identify TCAP using an antibody reaction. In this method, the unbound component is separated from the bound component by migration in an electric field. Immunofluorescence confocal microscopy ulitizes a specific antibody bound to TCAP and a secondary antibody that binds to the primary antibody. The secondary antibody is effectively conjugated to an enzyme that catalyzes a fluorescent reaction upon introduction of the appropriate substrate. The amount of fluorescence is proportional to the amount of TCAP and is measured using digital image analysis.

Mass Spectrometry Detection of Peptide

Samples were dissolved in 5 ul of 1:1 (vol/vol) Acetonitrile:water (plus 0.1% (vol/vol) formic acid). Typically, 2-3 ul of each sample was loaded on a glass capillary probe tip and analyzed on a Micromass Q-TOF (hybrid quadrupole time of flight) mass spectrometer (Micromass, Manchester, UK). All spectra were acquired under nanospray, positive-ion mode. For MS measurements the quadrupole RF value was set at 0.5. The scanning region (m/z) was between 200-2000 with a scan time of 1 s and a dwell time of 0.1 s. The data was analyzed using MassLynx program (Micromass, Manchester, UK).

Example 3

Synthesis and Solubilization of Peptide

Rainbow trout TCAP-3 [SEQ. ID. NO: 13], wherein the terminal isoleucine (I) was amidated [to give SEQ. ID. NO. 15] was synthesized on an automated peptide synthesizer, Model Novayn Crystal (NovaBiochem, UK Ltd. Nottingham, UK) on PEG-PS resin using continuous flow Fmoc chemistry (Calbiochem-Novabiochem Group, San Diego, Calif.). Eight times excess diisopropyl ethy amine (Sigma Aldrich Canada Ltd) and four times excess Fmoc-amino acid activated with HATU (O-(7-azabenzotriazol-1-,3,3-tetramethyluronium hexfluorophosphate, Applied Biosystems, Foster City, Calif.) at a 1:1 (mole/mole) ratio were used during the coupling reaction. The reaction time was 1 hour. A solution of 20% piperidine (Sigma-Aldrich Canada Ltd) in N,N-dimethylformide (DMF; Calcdon Laboratories Ltd, Canada was used for the deprotection step in the synthesis cycle. The DMF was purified in-house and used fresh each time as a solvent for the synthesis. The cleavage/deprotection of the final peptide was carried out with trifluoroacetic acid (TFA), thioanisole, 1,2 ethandithiol, m-cresole, triisopropylsilane, and bromotrimethyl silane (Sigma-Aldrich Canada Ltd) at a ratio of 40:10:5:1:1:5. Finally, it was desalted on a Sephadex G-10 column using aqueous 0.1% TFA solution and lyophilized. The peptide structure was confirmed by reverse-phase HPLC, amino acid analysis and atmospheric pressure ionization mass spectrometry. The HPLC and Mass spectrometry can be done as described in Examples 1 and 2 herein. See above method. The same method was used to synthesize mouse TCAP-1.

The peptide was solubilized using a number of different methods, however, the best results were obtained using alpha cyclodextrin. Acetic acid (1 ul) was added to dry TCAP at room temperature, vortexed and left to stand (30 min). Alpha-cyclodextrin (company) was then added in a 4:1 volume to dry weight ratio (0.25 ug/ul), vortexed, and concentrated to 10% of the original volume on an Eppendorf Vacufuge at 30° C. for 2 h and room temperature for the remainder of the process. Distilled, de-ionized water and physiological saline were then added independently in a 1:1 and 3:1, volume to concentrated volume ratio respectively. This solution (0.5 ug/ul) was vortexed and centrifuged (11,000 rpm; 3 min). The supernatant was aliquoted and stored at 4° C. The same method was used to synthesize and solubilize other TCAPS including mouse TCAP-1.

Example 4

Peptide Sequence Relationships and Phylogeny

The rainbow trout Teneurin 3 exon including the TCAP portion shows a high degree of conservation among its orthologues in zebrafish, mouse, and humans (FIG. 2). However the trout sequences also showed high sequence similarity with four mouse Teneurin protein paralogues designated as Teneurin 1 to 4 (FIG. 3) and similarly four human paralogues were found in the sequence data base (FIG. 4). All possess a high degree of similarity among members of the protein family. The Teneurin protein family represents a type II transmembrane protein where the carboxy terminus is displayed on the extracellular face of the plasma membrane (FIGS. 6 A and B). The TCAP portion represents only the C-terminal residues of the protein. The TCAP sequence is highly conserved across vertebrate species and even the *Drosophila* version possesses about 60% sequence identity (accession number AF008228) (FIGS. 7A and B).

FIG. 5 illustrates the preTCAP nucleotide coding sequences for human, mouse, zebrafish and rainbow trout plus the stop codon. The coding sequences for TCAP (40 and 41 amino acid residue sequences) can be easily determined from the figure.

Figure 10:
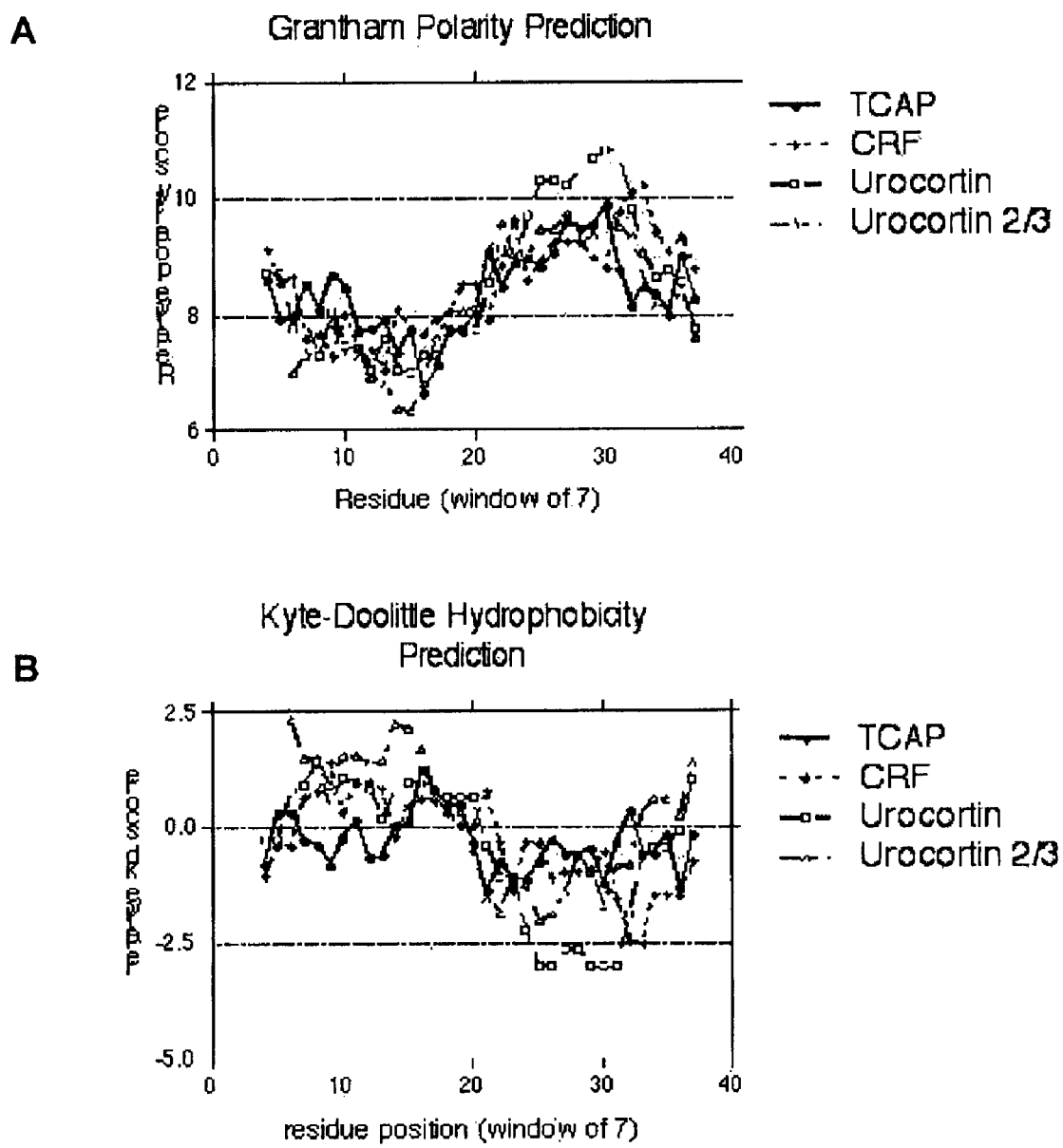
FIG. 10 shows a secondary structure prediction of TCAP (Rainbow Trout TCAP-3) and comparison with CRF-like peptides.

A comparison of the conserved motifs within the primary structure of the TCAP and CRF families show a match (FIG. 9). Conserved motifs of I/L-S-X-X(X)-L/V [SEQ. ID. NO: 129] at the amino terminus, L/V-L/I-X-V/aliphatic residue [SEQ. ID. NO: 130] in the middle and the motif N-I/A-H/basic residue-I/UF-aliphatic residue [SEQ. ID. NO: 131] at the carboxy terminus. A more compelling gage of similarity, however, is shown by the secondary structure predictions (FIG. 10). TCAP shows a highly similar polarity profile in comparison to others in the peptide superfamily. Hydrophobicity, using a Kyte-Doolittle plot shows a general similarity within the middle and carboxy terminal regions, but a more hydrophobic amino terminal region.

Although CRF and urocortin show high sequence similarity for each other and urocortin 2 and 3 show high similarity, the level of identity between these two paralogous lineages is only about 11%. The level of identity among TCAP members is about 60% (FIG. 8). CRF and TCAP belong to a much larger peptide family that also includes the insect diuretic peptides (FIG. 11). Key motifs, outlined in FIG. 9 show alignment when the insect diuretic peptides are included.

Example 5

PCR Expression of Teneurin mRNA

The presence of the Teneurin protein in brain extracts and on cell lines were established using PCR. Primers utilized in this experiment were designed from 3'-ends of the published sequences for mouse Ten-M 1, 2, 3, and 4 [SEQ. ID. NOS: 4-7]. The TCAP-1 forward primer (25mer: 5'-ACGTCAGT-GTTGATGGGAGGACTA-3')[SEQ. ID. NO: 121] is complementary to nucleotides 7938-7962 of Teneurin 1. The Teneurin 1 reverse primer (27mer: 5'-CCTCCTGC-CTATTTCACTCTGTCTCAT-3') [SEQ. ID. NO: 122] is specific for nucleotides 8262-8288 of Teneurin 1. The primers were predicted to generate a Ten-M1 PCR product of 351 bps. The Teneurin 2 forward primer (25mer: 5'-TC-GAGGGCAAGGACACACACTACTT-3') [SEQ. ID. NO: 123] is complementary to nucleotides 7920-7944 of Teneurin 2. The Teneurin 2 reverse primer (26mer: MGAACTGGAT-GTTGCTGCTACTGTC-3') [SEQ. ID. NO: 124] is complementary to nucleotides 8354-8379 of Teneurin 2. The primers were predicted to get a Teneurin 2 PCR product of 460 bps. The Teneurin 3 forward primer (25mer: 5'-CAACAACGC-CTTCTACCTGGAGAAC) [SEQ. ID. NO: 12]5 is complementary to nucleotides 7681-7705 of Teneurin 3. The Teneurin 3 reverse primer (21mer: 5'-TGTTGTTGGCACT-GTCAGCCA-3') [SEQ. ID. NO: 126] is specific for nucleotides 8139-8159. The predicted PCR product for Teneurin 3 primers is 479 bps. The Teneurin 4 forward primer (23mer: 5'-TTTGCCTCCAGTGGTTCCATCTT-3') [SEQ. ID. NO: 127] is complementary to nucleotides 7868-7890 of Teneurin 4. The Teneurin 4 reverse primer (24mer: 5'-TGGATATTGT-TGGCGCTGTCTGAC-3') [SEQ. ID. NO: 128] is complementary to nucleotides 8446-8469 of Teneurin 4. The primers were predicted to generate a Teneurin 4 PCR product of 602 bps.

The total RNA of Gn11 cells was isolated using RNeasy Mini Kit (Qiagen). First strand synthesis was performed by using First-Strand Beads (Amersham Pharmacia Biotech). Briefly, 2 μg of total RNA was mixed with the first strand reaction beads (include buffer, dNTPs, murine reverse transcriptase, RNAguard, and RNase/DNase-free BSA) and 0.2 μg random hexamer pd(N)$_6$ in a volume of 33 μl. Extension was carried out for 60 minutes at 37° C.

The PCR for Teneurin 1,2,3, and 4 was performed respectively using 1 μl cDNA with a final reaction volume of 50 μl containing 0.2 mM each dNTP, 5 μl 10× buffer, 1.5 mM MgCl, 1 ul Taq DNA polymerase, 0.2 μM each Teneurin primer and 0.1 μM each GAPDH primer (forward and reverse primers; The expected GAPDH DNA≈200 bps). The initial denaturation was set over an interval of 3 min at 94° C. After 35 cycles of 1 min. at 94° C., 1 min. at 60° C., and 1 min. at 72° C., a 5 min. extension was performed at 72° C. The PCR products were examined by 1.5% agarose gel electrophoresis. The appropriate size DNAs of Teneurin 1, 2 and 4 were extracted from the gel using DNA extraction kit (MBI-Fermentas). The Teneurin 1, 2 and 4 DNAs recovered from the gel were subcloned by using the TOPO TA Cloning kit (Invitrogen Corporation). Briefly, the pCR® 2.1-TOPO plasmids with Teneurin 1, 2 or 4 DNA were transformed into chemically competent *E. coli* and cultured on LB agar plates and in liquid LB medium successively. The products were purified by using the Perfectprep Plasmid Midi Kit (Eppendorf). Positive results were selected by digesting the plasmids using the restriction endonuclease EcoRI and then by electrophoresis. The positive plasmids were sequenced commercially using T7 sequencing primer (AGTC Corp, Toronto, Canada).

Results

Figure 12:
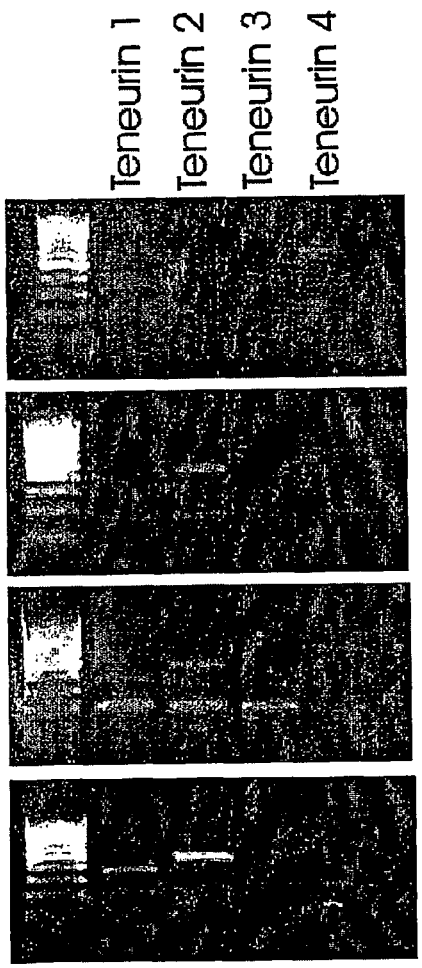
FIG. 12 illustrates expression of Teneurins in mouse brain and cell lines NLT, Gn11, and Nero2a. PCR-amplified products corresponding to Teneurin 1 to 4 were found in whole brain and cell lines. TenM1,2 and 4 were found in whole brain and in the immortalized GnRH-expressing neuronal line, Gn11. Only Teneurin 2 and 4 were found in another GnRH-expressing cell, NLT, however, all four forms were found in the Neuro2a neuroblastoma cell line. The bands on top indicate positive signals for the Teneurin transcripts. The bands at the bottom show a positive signal for glyceraldehydes-3-phosphate dehydrogenase (GAPDH) to indicate the viability of the RNA. A 100-bp DNA ladder is shown at the left of all PCR gels.

A positive amplification product was obtained from adult mouse cells for Teneurin 1, 2 and 4 using PCR (FIG. 12). Similarily, the same products were obtained using mRNA extracted from the immortalized neuronal line, Gn11. A neuronal cell line isolated from the same tumour, NLT, showed expression of only Teneurin 2 and 4. However, a neuroblastoma cell line, Neuro2a appeared to express all four forms of the Teneurin gene family. The Neuro2a is the least differentiated of the cell lines used. A rat fibroblast cell line, TGR1, also showed the presence of paralogues 1, 2 and 4 (data not shown). The identity of the amplication signal was confirmed by sequence analysis. TCAP-1 primers generated a 351 bps sequence and showed 99.43% coincidence with Teneurin 1 DNA. TCAP-2 primers generated a 455 bps sequence and showed 99.56% coincidence with Teneurin 2 DNA. TCAP-4 primers generated a 602 bps sequence and showed 99.83% coincidence with Teneurin 4 DNA. The TCAP 3 primers amplified a 306 bp sequence from mouse neuroblastoma Neuro2a cells. The amplified sequence possesses a 173-bp deletion upstream of the TCAP cleavage signal. This finding indicates that the TCAP-3 primers are specific, but that the Neuro2a cells appear to possess a variant of Teneurin 3.

Example 6

Cell Proliferation Experiments

Several cell lines were utilized initially to establish a model system for which the TCAP could be evaluated. Initially the mouse neuroblastoma cell line, Neuro2a, the human breast cancer cell line MCF-7, mouse GnRH-secreting immortalized neuron lines NLT and Gn11 COS-7 cells, and the rat fibroblast cell line TGR1. Preliminary studies indicated that the cells were responsive to the effects of TCAP Rainbow Trout TCAP-13, SEQ. ID. NO:.13: amidated [SEQ. ID. NO. 15], in that the cells showed a decrease in cell proliferation (data not shown). The studies were performed essentially in accordance with the cell proliferation studies below. Gn11 and TGR1 cells were selected to be used for further studies.

Pharmacological Test of TCAP on fibroblast Cell Lines TGR1 and HO16.4c: 2 plates containing 3×10$^4$TGR1 cells/well and 2 plates containing 3⇌10$^4$HO16.4c cells/well in full-serum medium were prepared for testing. Each 6-wells in the plate was designed as a testing group. 24 hours later, aliquots (20 μl) of drugs) were added in a 12-hours interval after changing the medium using fresh full-serum DMEM. The cells were observed through a microscope per 4-hours. The numbers of the two cell lines were found significantly lower in TCAP groups at 48-hrs and 72-hrs stages. Cells were counted at 48 hours and 72 hours after being treated. Two plates containing 3×10$^4$Gn11 cells/well in full-serum medium were prepared for testing. Each 6-wells in the plate was designed as a testing group. 24 hours later, aliquots (20 μl) of drugs (vehicle:saline+acetic acid; 10$^{-6}$ M TCAP-3) were added in a 12-hours interval after changing the medium using fresh full-serum DMEM. The cells were observed through a microscope per 4-hours. Cells were counted at 48 hours and 72 hours after being treated.

Figure 14:
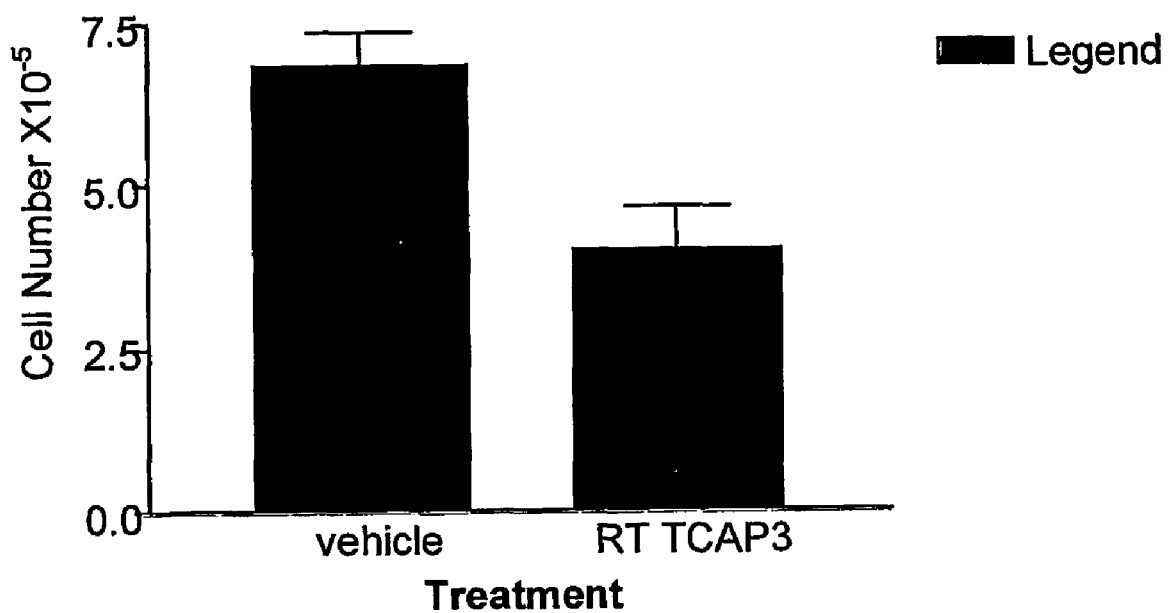
FIG. 14 is a bar graph illustrating the inhibition of cell proliferation in TGR1 (wildtype) fibroblast cells.
Figure 15:
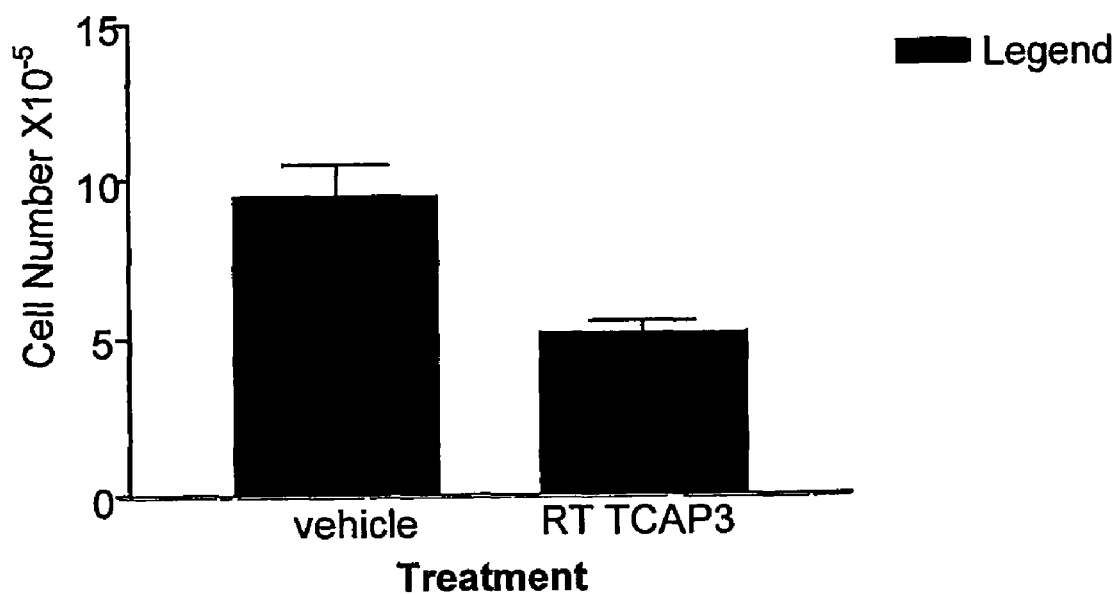
FIG. 15 is a bar graph illustrating the inhibition of cell proliferation in HO16 (c-myc constitutively expressed cells) (14B) by $10^{-6}$ M TCAP (Rainbow Trout TCAP-3) at 48 hours).
Figure 17:
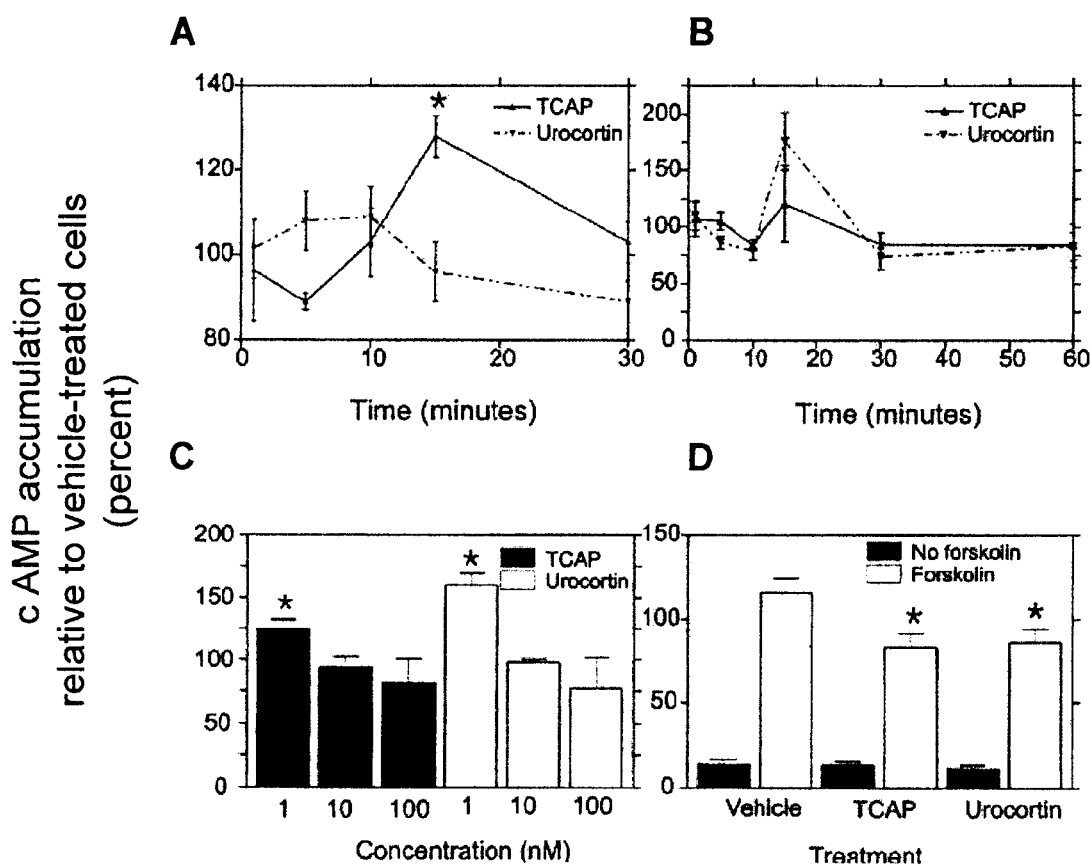
FIG. 17 A-D illustrates TCAP (Rainbow Trout TCAP-3) cAMP regulation in Gn11 cells. 17A illustrates cAMP levels in Gn11 cells treated with $10^{-8}$ M TCAP or urocortin over 30 minutes. 17B illustrates cAMP levels in Gn11 cells in the presence of $10^{-4}$ M 3-isobutyl-1 methyl xanthine (IBMX), a phosphodiesterase inhibitor used to boost cAMP induced by treatment of $10^{-8}$ MTCAP or urocortin. 17C is a bar graph illustrating cAMP accumulation over 30 minutes in Gn11 cells by administration of various concentrations of TCAP or Urocortin in the presence of IBMX. 17D is a bar graph illustrating inhibition of $10^{-6}$ M forskolin-stimulated cAMP by $10^{-8}$ MTCAP or urocortin.

A concentration of 10$^{-6}$ M of TCAP administered at 0, 12 24 and 36 hours decreased the proliferation of a mouse neuronal cell line (Gn11) (FIG. 13A –48 hrs and 13B –72 hrs), a rat fibroblast cell line (TGR1) by 50-60% at 48 hours (FIG. 14) and a HO16.4c cells at 48 hours relative to the vehicle treated cells (FIG. 15).

The ability of TCAP to inhibit cell proliferation in the above-noted cell lines, indicates that the peptide would be useful in the regulations of cell proliferation and associated medical conditions such as in the treatment of cancer TCAP could be used to arrest tumour growth and inhibit metastasis. In a preferred embodiment, TCAP could be used in the treatment of neuronal tumors.

Example 7

Cyclic Nucleotide Experiments

I. A. cAMP and cGMP Assays

Approximately 10$^6$ Gn11 cells were treated with 20 uL of 10$^{-9}$, 10$^{-8}$, or 10$^{-7}$ or 10$^{-6}$M TCAP-1 or TCAP-3 and incubated at 37 C for 10 minutes. Medium and peptide was removed and the cells were lysed using 350 uL of a 0.1 M HCL 0.1% Triton X-100 solution. Using the same concentrated HCl and Triton X-100 solution and a provided standard concentrate, five standard solutions were made up with concentrations of 200, 50, 12.5, 3.12 and 0.78 pmol/ml. All reactions were done in triplicates. Wells were set up for blanks, non-specific binding, total activity (TA), zero binding, five standards, and 12 samples. Using a 96-well IgG coated plate, 50 uL of neutralizing reagent were pipetted into each well except the blanks. 150 uL of the 0.1 M HCL/0.1% Triton solution was pipetted into the NSB wells and 100 uL of this solution was pipetted into the zero binding wells. 100 uL of the standards and 100 uL of the samples were pipetted into their respective wells. 50 uL of conjugate were pipetted into each well except the TA and the blank wells. 50 uL of the cAMP antibody were pipetted into each well except the TA, blank and NSB wells. The plate was allowed to shake overnight. The following morning, the wells were rinsed three times with a 10 times diluted wash buffer solution. 50 uL of conjugate was added to the TA wells and 200 uL of p-Npp substrate was added to each well. The plate was covered again and incubated at room temp for one hour. At this point, 50 uL of stop solution was added to all wells and the absorbance was read at 405 nm using a Spectramax spectrophotometer. Three levels of controls were utlized: A blank tube which provides a measure of any reactivity between p-Npp substrate and IgG coated wells.; TA: measure of activity of alkaline phosphotase in conjugate, if any; NSB: measure of binding of conjugate to plate or to antibody; Bo: measure of binding conjugate to antibody (no sample and conjugate competition).

B. Results

In the first set of experiments, Gn11 cells were treated with $10^{-6}$ M of rtTCAP-3 SEQ. ID. NO:13, amidated [SEQ. ID. NO: 15], see above, rat urocortin or the vehicle, as above (FIG. 16A). TCAP reduced cAMP accumulation in these cells to 58.9±4.8% of the vehicle-treated cells (p<0.01). Urocortin induced a non-significant decrease of 89.2±6.3% of the control cells. In cGMP accumulation experiments, TCAP reduced cGMP accumulation to 38.5±8.8% of the control cells (p<0.01) whereas urocortin caused a decrease to 50.0±8.5% of the control cells. (FIG. 16B)

II. A. cAMP Assays

Gn11 cells were treated when the confluence reached 70%. The cells were treated with $10^{-9}$, $10^{-8}$ or $10^{-7}$ M TCAP, urocortin and vehicle, separately, and incubated in incubator at 37° C. (Details below) Medium was removed and the cells were washed by PBS one time, and then were lysed using 600 uL of 0.1 M HCL solution. After freezing/thawing 3 times, the samples were transferred into microcentrifuge tubes. At the same time, squeezed the cells by 3 ml syringe and 22 G needle 20 times. Centrifuge 400 rpm×5 min, the supernatant of each sample was aspirated and kept in the −20° C. freezer until the cAMP or cGMP assay was carried on. Using the same concentrated HCl and a provided standard concentrate, five standard solutions were made up with concentrations of 200, 50, 12.5, 3.12 and 0.78 pmol/ml. All reactions were done in duplicates. Wells were set up for blanks, non-specific binding (NSB), total activity (TA), zero binding (B0), five standards, and all samples. Using a 96-well IgG coated plate, 50 uL of neutralizing reagent were pipetted into each well except the blanks and TA. 150 uL of the 0.1 M HCL was pipetted into the NSB wells and 100 uL of this solution was pipetted into the zero binding wells. 100 uL of the standards and 100 uL of the samples were pipetted into their respective wells. 50 uL of conjugate were pipetted into each well except the TA and the blank wells. 50 uL of the cAMP antibody were pipetted into each well except the TA, blank and NSB wells. The plate was allowed to shake overnight (18 h) at 200 rpm at 4° C. The next day, the wells were rinsed three times with a 10 times diluted wash buffer solution. After each well was dried thoroughly, 5 uL of conjugate was added to the TA wells and 200 uL of p-Npp substrate was added to each well. The plate was covered again and incubated at room temp for one hour without shaking. At this point, 50 uL of stop solution was added to all wells and the absorbance was read at 405 nm and 580 nm using a Spectramax spectrophotometer. The data of 580 nm were provided the background of each well, which were substracted from the data of 405 nm.

B. Results $10^{-8}$ M TCAP induced a significant increase in cAMP accumulation at 15 minutes after introduction of the peptide and fell to normal limits within 30 minutes of treatment (FIG. 17A). Urocortin was used for the purpose of a positive control. FIG. 17B illustrates cAMP levels in Gn11 cells in the presence of $10^{-4}$ M 3-isobutyl-1 methyl xanthine (IBMX), a phosphodiesterase inhibitor used to boost cAMP induced by treatment of $10^{-8}$ MTCAP or urocortin. FIG. 17C is a bar graph illustrating cAMP accumulation over 30 minutes in Gn11 cells by administration of various concentrations of TCAP or Urocortin in the presence of IBMX. FIG. 17D is a bar graph illustrating inhibition of $10^{-6}$ M forskolin-stimulated cAMP by $10^{-8}$ MTCAP or urocortin.

Example 8

Behavioural Studies

A. Brain Stimulation Reward Behaviour Experiments

Rats can be trained to bar press for electrical stimulation of the lateral hypothalamus which activates cholinergic nuclei of the pontine tegmentum and their projections to dopaminergic paths of the forebrain. Once reliable baseline rates of bar pressing have been established for a given current, the consequences of various drugs for the activity of this cholinergic dopaminergic system can be assessed by making injections of substances intracranially and then observing their effects on rates of self stimulating behaviour. TCAP-3 SEQ. ID. NO: 13, amidated, [SEQ. ID. NO: 15] see above, at a concentrations of 1 nM prepared in physiological saline was injected by canulae into the laterodorsal tegmental nucleus through guide cannulae. The rate of bar pressing was compared to the vehicle treated rats.

B. Results

Figure 18:
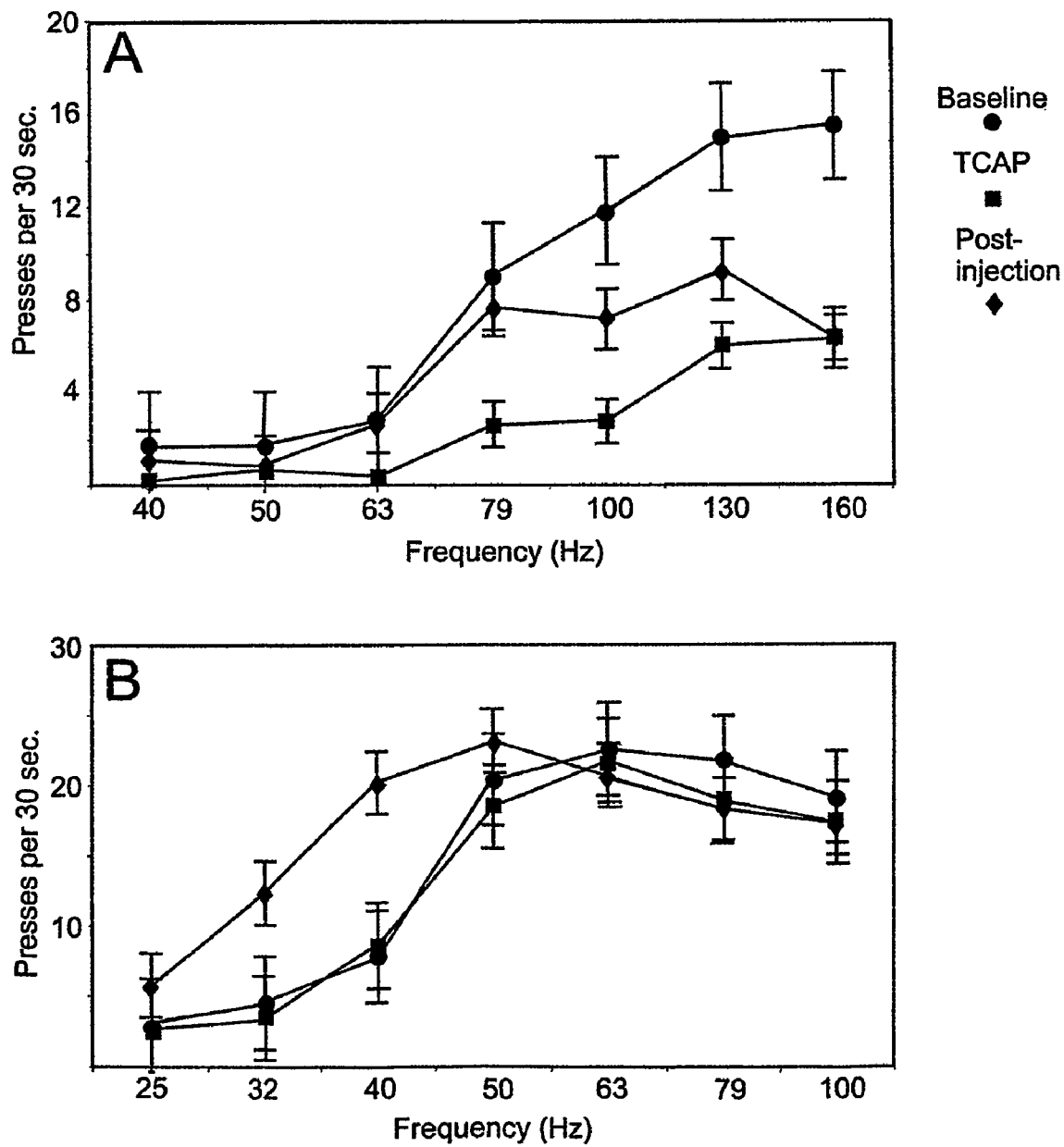
FIGS. 18A and 18B are linear graphs illustrating the effect of TCAP (Rainbow Trout TCAP-3) on the administration of self reward behaviour. The behaviour was indicated by number of bar presses per 30 seconds over a range of pleasurable stimulation (25-100 Hz).

A robust inhibition of self-reward stimulus occurred when TCAP at 1 nM (4.2 pg/ul) was injected into the caudal midbrain of rats (FIG. 18). In both forebrain (lateral ventricle) and midbrain injections the effect was reversible with the rats behaviour returning to normal limits after about 60 minutes.

Example 9

Preliminary In Situ Hybridization Results

The first in situ hybridization data indicate that the Teneurin I gene (TCAP-1) is highly expressed in adult rat brain. The regions of greatest expression occur in the lateral septum, bed nucleus of the stria terminalis ventral medial nucleus of the hypothalamus and ventral premammalary nucleus. Lesser expression occurs in the hippocampus and amygdala. This expression pattern is consistent with peptides regulating the stress response (see above) in emotional and mood disorders. These data indicate that TCAP plays a primary role in stress and anxiety regulation rather than one of neurogenesis and neurodegeneration. The Teneurin 4 (TCAP-4) expression also occurs in the adult brain but Teneurin 1 is stronger.

A. Methods

The methods were performed as previously described (Simmons et al., 1989; Ericsson et al., 1995) using $^{35}$S-labelled antisense and sense (control) probes higher high stringency conditions (50% formamide with final washes at 0.2 SSC at 60 C). The $^{35}$S-labelled cRNA probes were generated from 350 bp cDNA of exon 33 including the TCAP portion by in vitro transcription with the appropriate polymerases (T3 for antisense and T7 for sense).

B. Results

Figure 20:
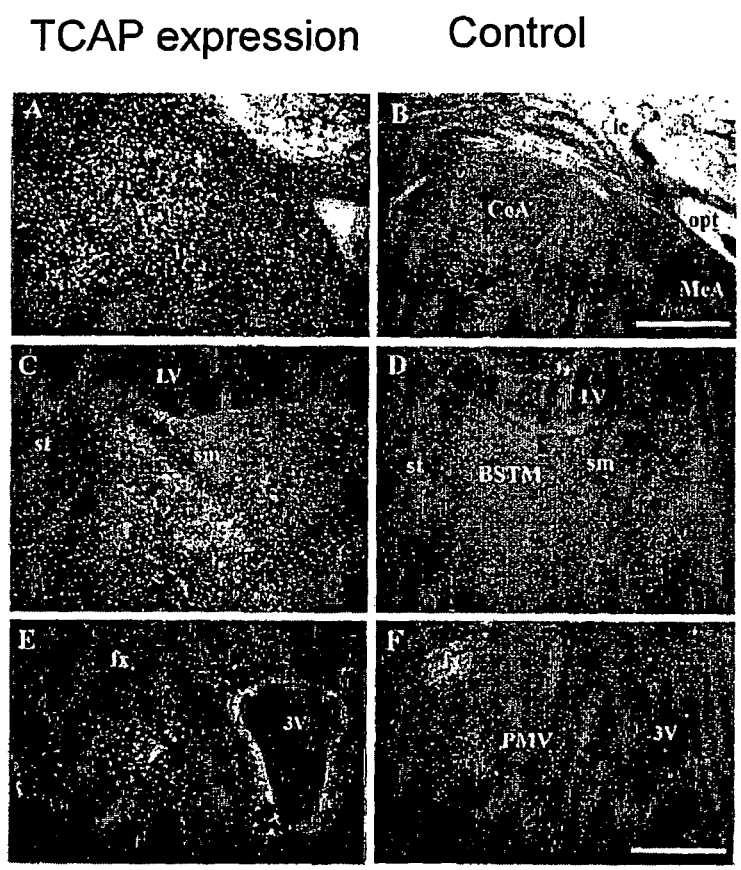
FIG. 20 A-F illustrates the distribution of TCAP-1 mRNA in rat brain nuclei as explained in Example 9.

Results are shown in FIG. 20. On the left column is the expression of TCAP-1 mRNA using the antisense probe, and on the right column, the sense probe. A-B. central nucleus of the amygdala (CeA); C-D. bed nucleus of the stria terminalis, medial (BSTM); E-F: premammilary ventral nucleus (PMV). Abbreviations: 3V, third ventricle; fx, formix; ic, internal capsule; LV, lateral ventricle; MeA, medial nucleus of the amygdala; opt, optic tract; St, stria terminalis. Bars=300 μm (A-B) and 500 μm (C—F)

The in situ hybridization data indicate that the TCAP-1 gene is highly expressed in adult rat brain. The expression of the C-terminal teneurin-1 exon including the TCAP-1 region was restricted to hypothalamic and limbic regions (FIG. 20 A-F). The regions of greatest expression occur in the lateral septum, bed nucleus of the stria terminalis ventral medial nucleus of the hypothalamus and ventral premammalary nucleus. Lesser expression occurs in the hippocampus and amygdala. This distribution is consistent with TCAP playing a modulatory role with emotionality, anxiety and motivation. The presence of TCAP-1 expression in the ventral premammillary nucleus is of particular interest as there are no known CRF receptors found in this region (Li et al., 2002). There was no evidence that the TCAP containing exon was expressed in regions associated with neurogenesis, such as the olfactory lobes or subependymal layers of the lateral ventricles. Despite the previous recognition of the teneurin proteins, their expression in adult brain has never been examined. However, teneurin 1 and 4 expression has been observed in the diencephalon of developing mouse, chick and zebrafish brain (Rubin et al., 1999; Ben-Zur et al, 2000; Mieda et al., 1999).

These data support the hypothesis that TCAP primary role is one of stress and anxiety regulation.

Example 10

Chronic TCAP Study: The Role of TCAP in Modulating the Stress Response

A. Method
1. Wistar Rats were tested in acoustic startle for baseline response (1 hour test consisting of 60 acoustic startle stimuli, 120 dB, 60 sec inter-stimulus interval), and divided into matched groups to receive either TCAP-1 (10 nmol of mouse TCAP-1, amidated [SEQ. ID. NO. 40] in 3 µl vehicle intra-cerebroventricularly) or Vehicle (e.g. saline and acetic acid).
2. Two days later, rats were tested in acoustic startle, 25 stimuli baseline (120 dB, 60 sec inter-stimulus interval), then injected ICV with 10 nmol TCAP-1 or Vehicle, then acute response was measured for 1 h (60 stimuli, 120 dB, 60 sec inter-stimulus interval).
3. 25 days later, rats were given either TCAP-1 (10 nmol in 3 µl or vehicle (3 µl once per day for 5 consecutive days ICV.
4. Rats were left alone for 10 days.
5. On the $10^{th}$ day, rats were tested for acoustic startle response without TCAP-1.

Figure 21A:
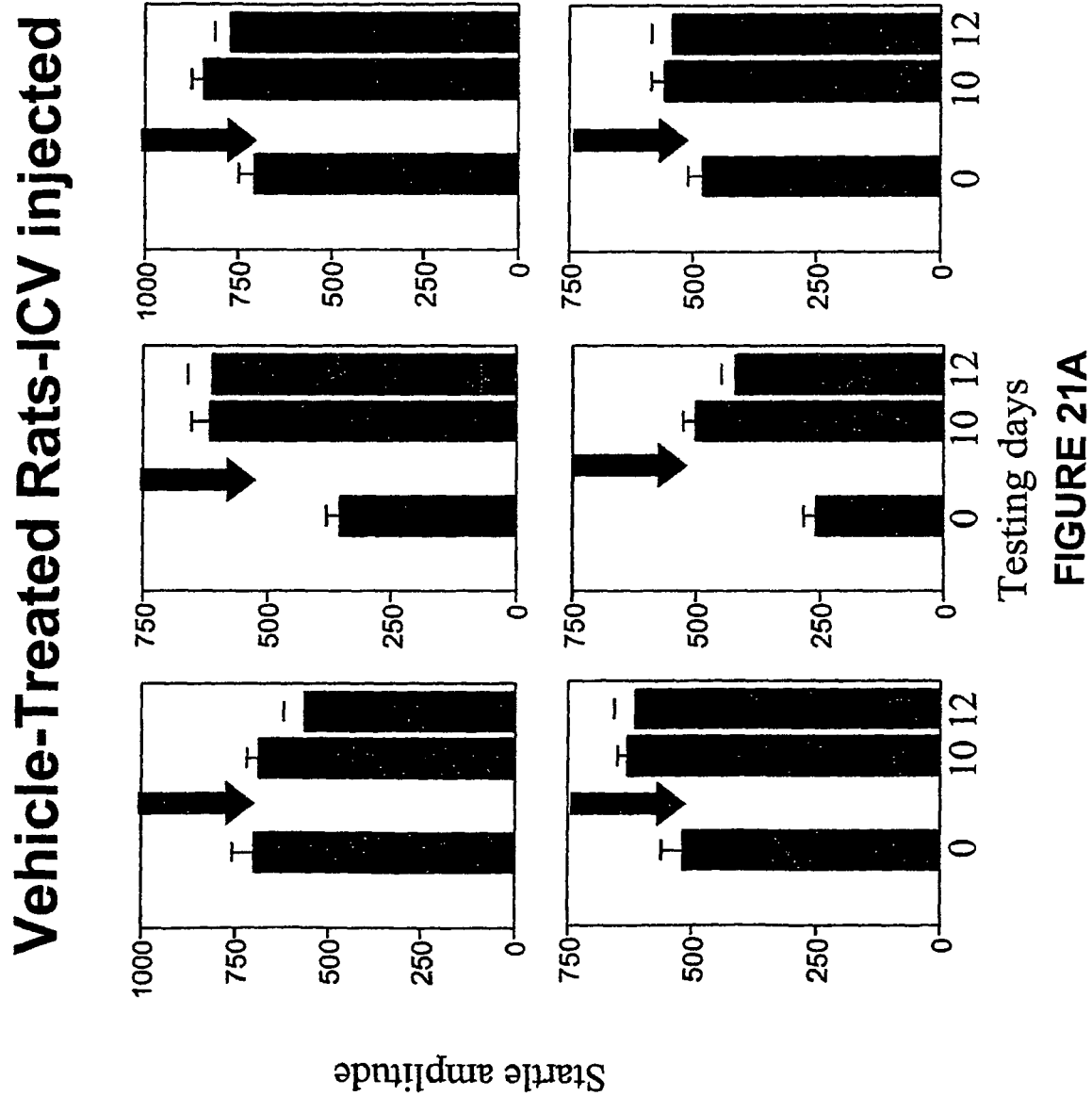
FIG. 21 are bar graphs illustrating the chronic human TCAP-1 response in rats that were (A) vehicle treated ICV injected, (B)TCAP-1 ICV injected as described in Example 10 herein.
Figure 21B:
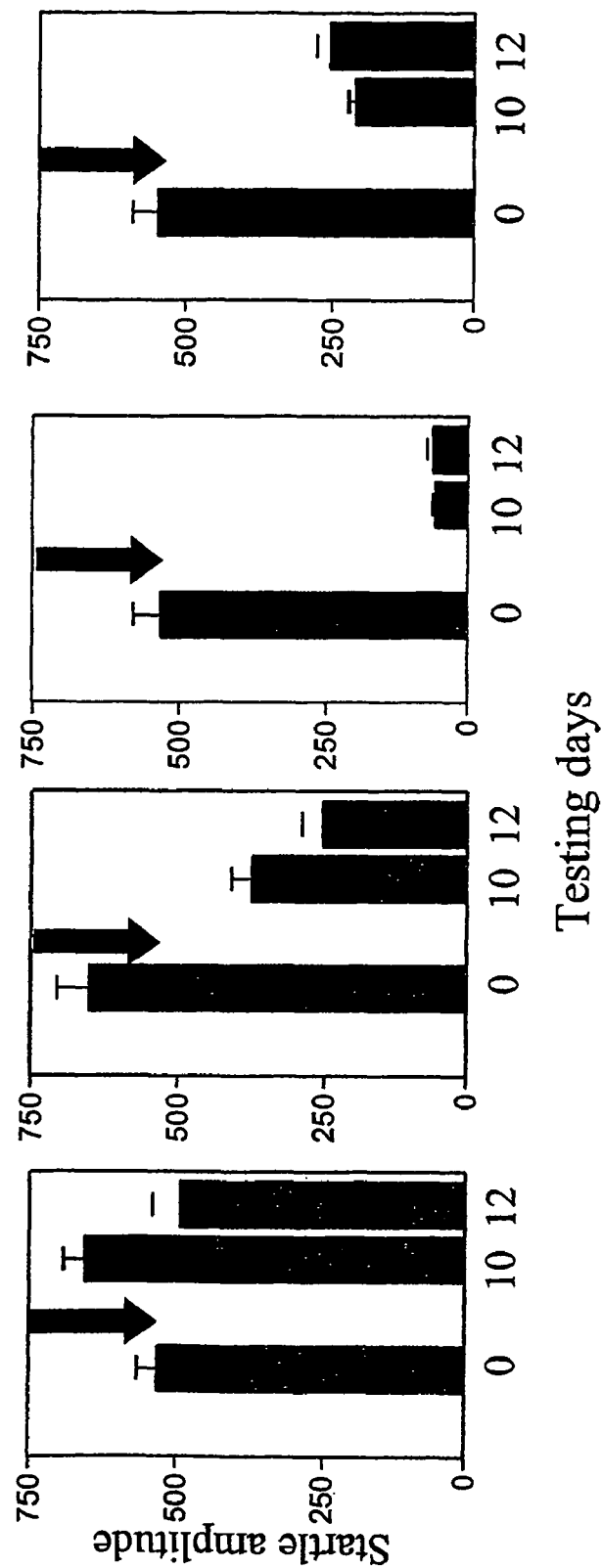

On the 11th day, rats were re-tested for startle response, again without TCAP-1, for 60 minutes (60 stimuli, 60 sec inter-stimulus interval, 120 dB). Re-tested in startle $13^{th}$ and $28^{th}$ days. The vehicle is the mixture of saline and acetic acid into which TCAP-1 was dissolved. When referring to vehicle, this refers to the solution without the addition of TCAP-1.
B. Results Results are shown in FIG. 21 for the 0, 10 and 12 days after the 5 consecutive day ICV of Vehicle (21A) or TCAP-1 (21B). Startle responses for animals in the chronic study are shown in FIG. 22. The average startle response for the two groups (TCAP-1 and Vehicle) on Day 1, before chronic TCAP treatment is shown in FIG. 22A. FIG. 22B shows the average startle response for TCAP and vehicle groups over the 60 trials in the session on the $10^{th}$ day after chronic TCAP treatment. FIG. 22C shows the mean baseline startle responses for all animals for TCAP and vehicle groups averaged across all 60 trials.

Example 11

Acute TCAP Study Acoustic Startle Measurements

A. Method
Male Wistar rats (250-275 g), were surgically implanted with cannulae (23 gauge) bilaterally into the basolateral nuclei of the amydala (AP −2.8, ML +/−5.0, DV −7.2 mm, from bregma). One week later, the animals were habituated to the acoustic startle reflex (ASR) chambers (MED Associates, grid rod cage measuring 7.5"×3.6"×4.2"), consisting of 25 trials of 120 dB stimuli presented randomly with an inter-stimulus interval of 55-65 seconds, duration of 30 msecs and frequency of 5000 Hz. The same stimulus conditions were used for test days, which consisted of a 25 trial baseline, injection with mouse TCAP-1 (with amidation signal)[SEQ. ID. NO. 40] or vehicle (0.25 µl/side, flow rate 0.5 µl/min), and testing for a further 60 trials post-drug. Each rat received vehicle treatment on the first test day then TCAP-1 (e.g. mouse TCAP-1) in a random and counter balanced fashion in subsequent test days, spaced 48 h apart. On the final test day, all rats again received vehicle treatment. Following histological analysis of cannulae placements, the data of eight rats was retained for statistical analysis.

From the data, rats were divided into high and low anxiety groups depending upon their treatment/baseline ratio for the vehicle. Animals that scored less than one were considered low anxiety, those scoring more than one were considered high anxiety. There were four animals in each anxiety group.

Figure 23:
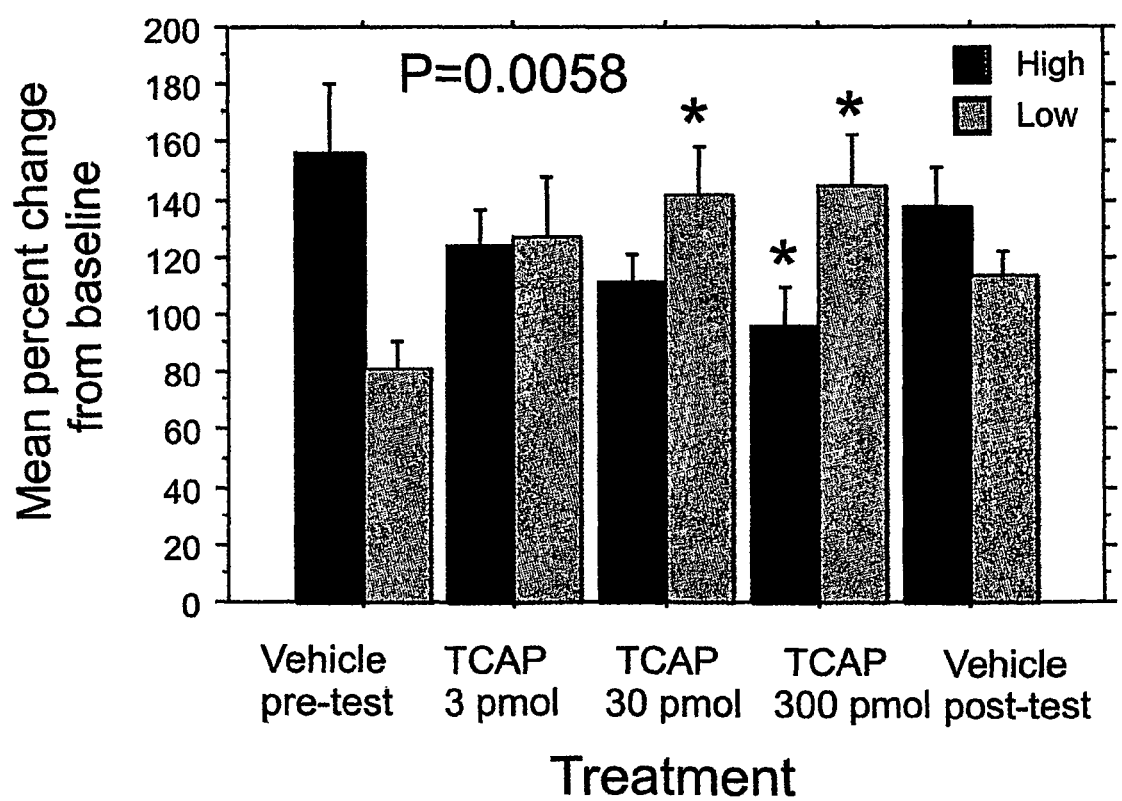
FIG. 23 is the interaction bar plot for treatment with TCAP-1 at various doses for both high and low anxiety response animals as discussed in Example 11 herein.
Figure 24:
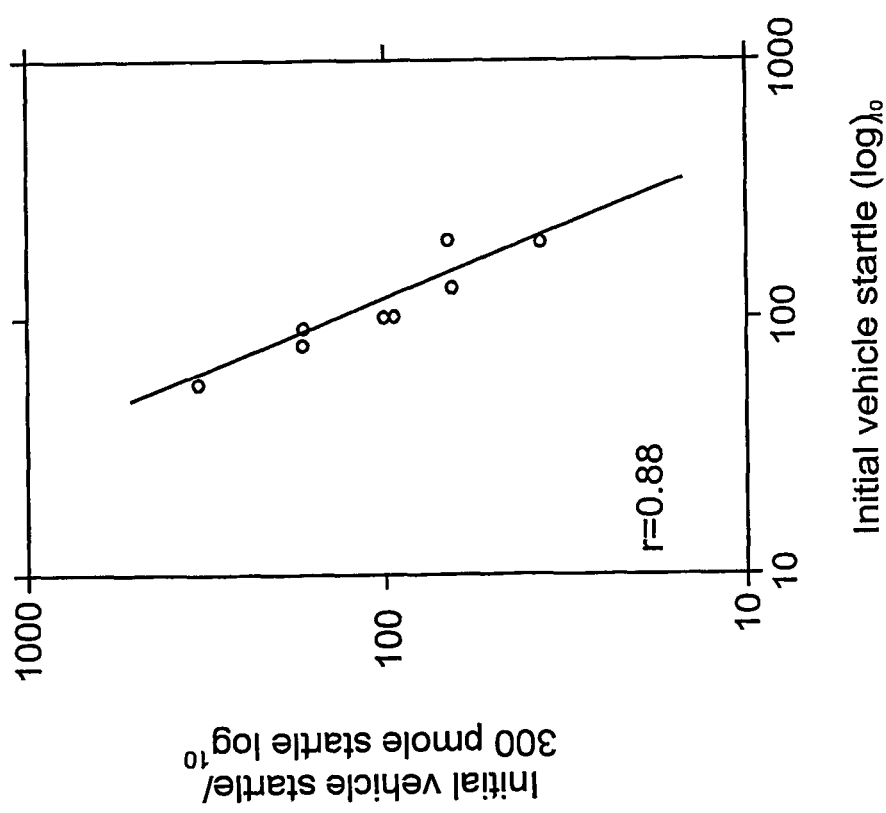
FIG. 24 is the plot of the effect of TCAP-1 amygdala-injected on the startle response of rats as discussed in Example 11 herein.
Figure 25:
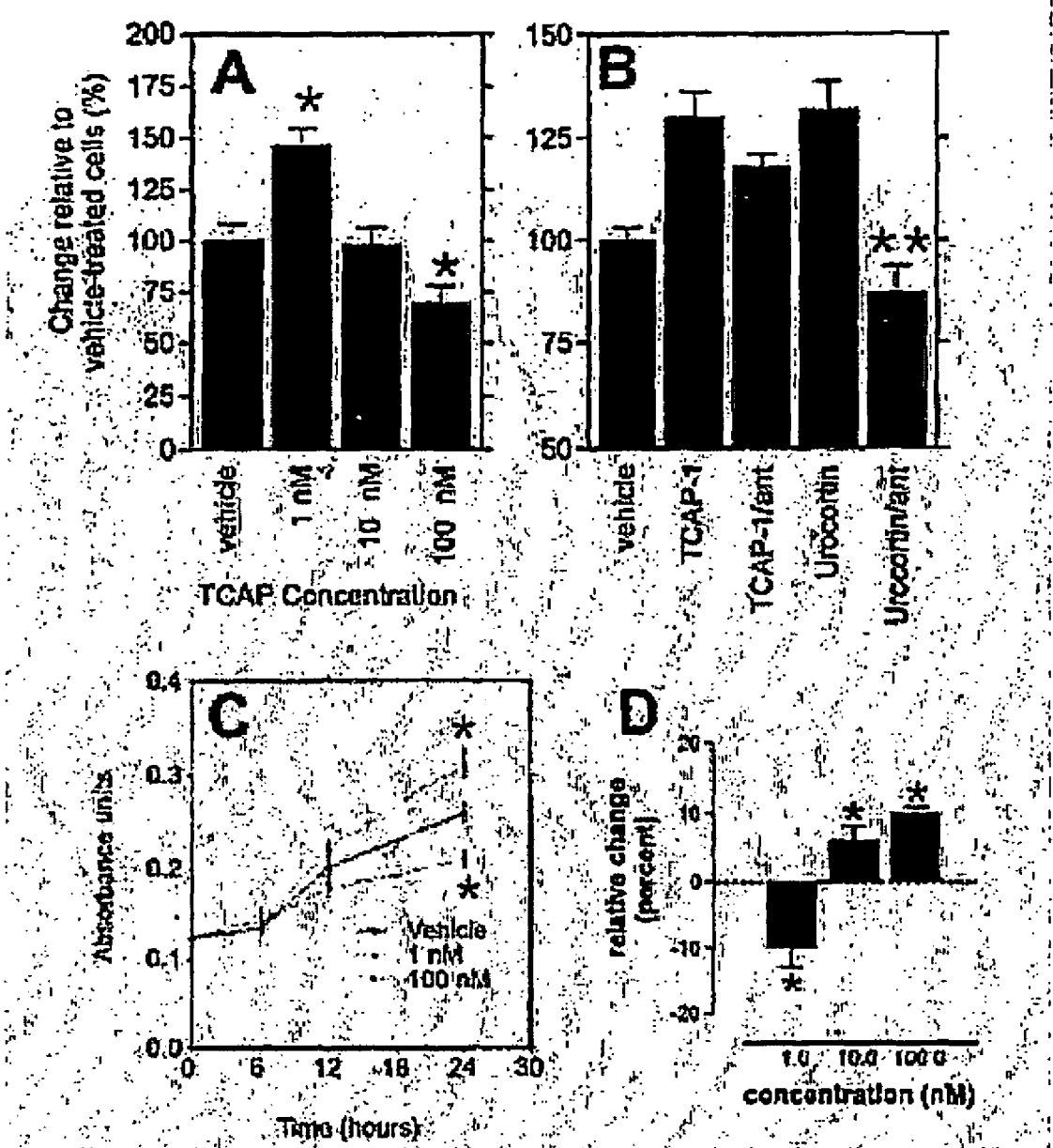
FIG. 25 illustrates activity of TCAP on immortalized neurons. (A) cAMP accumulation in Gn11 cells. 1 nM TCAP increased cAMP ($p<0.05$) whereas 100 nM TCAP decreased ($p<0.05$) cAMP. An intermediate concentration (10 nM) was without effect. (B) Action of CRF-R1 antagonist on cAMP accumulation. A 1 nM mouse TCAP-1, or mouse urocortin increased cAMP accumulation in Gn11 cells. The CRF R1 receptor antagonist PD171729 abolished the action of urocortin on these cells ($p<0.01$) but had no effect on TCAP-mediated cAMP accumulation. (C) Protein assays. Concentrations of 1 to 100 nM TCAP stimulated protein synthesis in Gn11 cells. (D) MTT Assay. 1 nM of mouse TCAP-1 increased MTT activity ($p<0.05$) in Gn11 cells after 48 hours. In contrast, 100 nM of mouse TCAP-1 decreased ($p<0.05$) MTT activity over the same time period. The level of significance was determined using a one-way ANOVA for A and B, and a two-way ANOVA for C and D.

Results are shown in FIGS. 23 and 24. FIG. 23 is a bar graph illustrating the mean treatment/baseline value for both groups for all concentrations of mouse TCAP-1. A repeated measures ANOVA indicated that the level of significant differences between the two anxiety groups was P=0.0078. After TCAP-1 treatment the treatment/baseline ratio of low anxiety was similar to the initial high anxiety value and vice versa. A vehicle injection was performed at the end of the study to show that the effect was due to the TCAP-1 and not to the experience of injection. TCAP 1 concentrations were 3, 30, 300 pmoles. A summary of the effect of amygdala-injected TCAP-1 is illustrated in FIG. 24. It was shown that the effect by TCAP-1 on startle response is inversely proportional to the baseline startle response. As such TCAP-1 can be used to normalize startle behaviour or stress response.

Discussion

Regardless of the mechanism the synthetic TCAP peptide is potent, in vivo at eliciting a behavioural response in rats. Given the strong expression of TCAP in hypothalamic and limbic regions, the synthetic mouse TCAP-1 peptide with amidation signal was micro injected into the basolateral amygdala to determine effects on acoustic startle in rats. Animals possessing a high treatment-to-baseline ratio (>1) showed a significant (p<0.05) decrease in startle magnitude, whereas animals with a low treatment-to-baseline ratio (<1) showed a significant (p, 0.05) and does dependent increase in startle magnitude (FIG. 23). These data indicate that TCAP-1 acts to modulate the effect on startle responses depending on baseline reactivity of the particular animal and can normalize the behaviour associated with acoustic startle. Other neuropeptides that have been demonstrated to increase acoustic startle are CRF (Liang et al., 1992), CCK (Frankland et al., 1997) and SP (Krase et al., 1994/1999). The acoustic startle paradigm is a well-known and extensively used paradigm for assessing the anxiogenic or anxiolytic effects of drugs. This is an ideal paradigm for testing a novel compound since the startle reflex does not involve locomotion, learning, memory, or motivated behaviour of any kind, which could possibly confound the interpretation of the results.

The data presented indicate that TCAP represent a new family of neuropeptides associated with the regulation of anxiety by regulating neuronal function in key regions of the forebrain and limbic system. Previous studies have also suggested a role of the teneurin genes with neural regulation. Human Ten-M1 maps to position Xq25 of the X chromosome (Ben-Zur et al., 1999). This is a region associated with X-linked mental retardation syndromes (Minet et al., 1999). The conditions mapped to this site are characterized by severe mental retardation and may include motor sensory neuropathy, deafness and sometimes seizures and impaired vision.

The regulation of TCAP represent a new target to understand the aetiology of neurological dysfunction and psychiatric illness. The example shows that TCAP can be used in the treatment of stress-reated disorders and in other neuropathological conditions.

Example 12

Activity of TCAP on Immortalized Neurons

A. In Vitro Assays

Gn11 immortalized neurons were cultured as previously reported (Tellam et al., 1998) Direct cAMP measurements were performed with the nonacetylated version of a commercial kit (Assay Designs, Ann Arbor, Mich.). After starved by serum-free DMEM for 1 hr and replaced with fresh DMEM without serum, cells were treated for 15 min with TCAP, urocortin or vehicle±CRFR1 antagonist PD171729 in the continued presence of forskolin (1_M) and IBMX (100_M. Protein assays: Total protein was determined using the BCA protein assay method (Pierce Co). MTT Assays: Gn11 cells were seeded into 96-well plates and cultured in full serum DMEM until the cells were 30% confluent. Vehicle, 1 nM, 10 nM or 100 nM TCAP-1 were added into each group (n=8). (FIG. 25A) The MTT assay (Sigma Chemicals) was performed at 0, 6, 12, 24 and 48 hours. Flow Cytometry: DNA content of the Gn11 cells was quantified by staining with propridium iodide and analyzed on a FACSCAN flow cytometer (Beckman Instruments).

B. Results

Mouse TCAP-1 induced a dose-dependent change in cAMP accumulation in mouse immortalized neurons after 15 minutes. A 1 nM dose increased (p<0.05) cAMP levels 45% over the vehicle-treated cells. In contrast, 100 nM TCAP-1 decreased (p<0.05) cAMP accumulation 40% from control cells (FIG. 25A). However, co-treatment with the specific CRF type 1 receptor antagonist, PD171729 failed to completely abolish TCAP's effects at cAMP accumulation. In contrast, the same concentration of antagonist induced a complete inhibition (p<0.01) of urocortin-stimulated cAMP accumulation in these cells (FIG. 25B). We have previously established that these cells possess a CRF-R1 receptor (Tellam et al., 1998) but not an R2 receptor (data not shown). Concentrations of 1, 10 and 100 nM of TCAP-1 induced a significant increase in total protein concentration after 120 minutes in the same cells (FIG. 25C). Mouse TCAP-1 treatment of these cells also induced a dose-dependent effect on cell metabolism. Cellular activity as indicated by mitochondrial activity (MTT assay) showed a significant (p<0.05) increase in activity at 1 nM concentration, but a decrease at 100 nM concentrations (FIG. 25D). Similarly, 1 nM TCAP reduced (p<0.05) the incidence of G1 phase after 24 hours whereas a 100 nM dose increased (p<0.05) G1 phase as determined by DNA content analysis.

As such α-helical CRF(941) antagonist can modulate TCAP stress response modulating activity.

Example 13

Proteomic Profiling and MicroArray Studies

To determine the effect of TCAP and to develop a cell model system for screening TCAP modulators, diagnostic and conditions related to TCAP and methods of medical treatment, TCAP responsive cell lines were subject to proteomic profiling and microarray analysis. This was done using a non-tumorgenic-derived immortalized murine hypothalamic cell line, N38, which has the marker profile shown in Table 1. The effect of TCAP on other immortalized cell lines can be preformed by adapting the method noted below.

A. TCAP Responsive Immortalized Hypothalamic Cell Lines

The TCAP responsive immortalized cell lines used were prepared by Denise Belsham, University of Toronto, by preparing a culture of embryonic hypothalamic cells; infecting said culture with a retrovirus encoding a viral oncogene, large T Antigen, operably linked to a promoter and a selectable marker; isolating transfected cells from non-transfected cells to obtain a culture of immortalized hypothalamic cells; subcloning said immortalized cells into sub-cloned populations; and screening said subcloned populations for expression of specific neuronal markers; and selecting and further cloning a specific population. The immortalized cell lines can then be screened for TCAP responsiveness.

Figure 26:
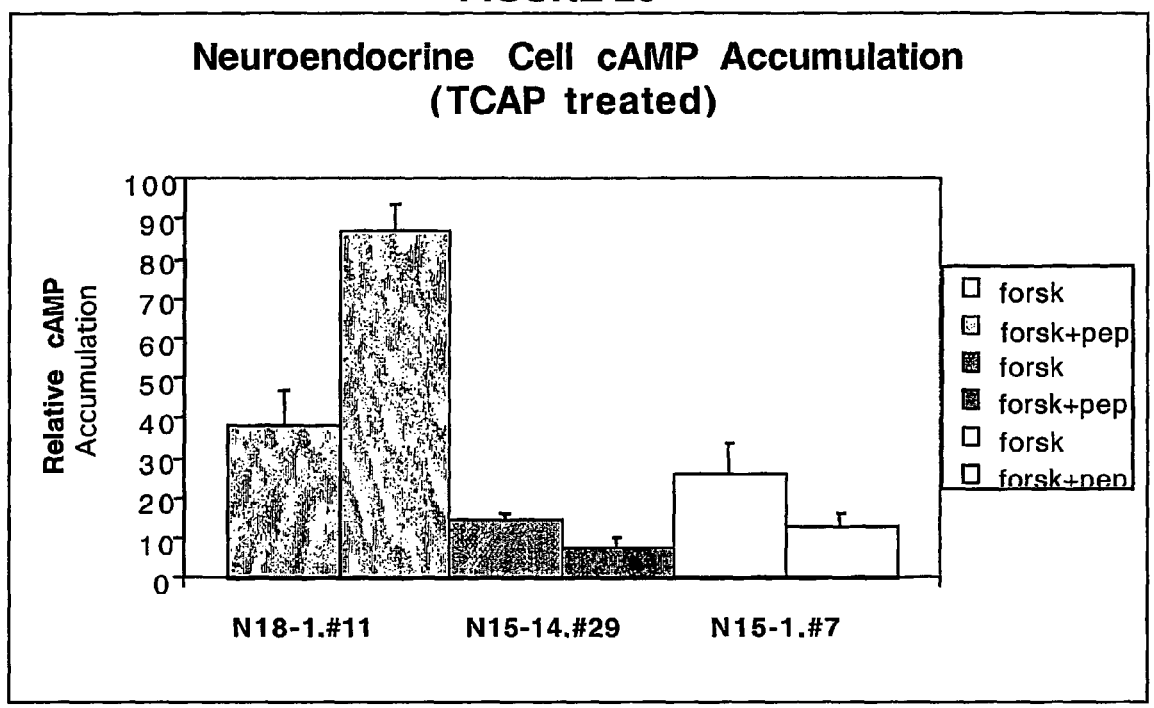
FIG. 26 illustrates the functional cAMP response of murine hypothalamic immortalized cell lines to TCAP (rainbow trout TCAP-3) peptide stimulation.

TCAP responsiveness was screened by measuring the functional cAMP response of the immortalized subclones to TCAP. The results are shown in FIG. 26. N-15-1, #7 (N7), N-18-1, #11 (N22), and N-15-14, #29 (N29) were analyzed for the cAMP response to peptide stimulation. The subclones were split into 24 well plates. Cells were starved for 1 h in DMEM without FBS, then medium was replaced with 0.5 ml fresh DMEM (without FBS) with the compounds as indicated. In FIG. 26, neurons were exposed to $10^{-7}$ M (100 nM) TCAP peptide. All peptides were diluted in DMEM containing IBMX (100 µM). After a 15 min incubation at 37° C., 1 ml of ice-cold ethanol was added to each well. Cells were scraped from the plate and kept at −20° C. until the amounts of intracellular cAMP were determined in triplicate by RIA (Biotechnologies Inc., Stoughton, Mass.) according to the manufacturer's instructions.

B. Proteomic Profiling Using TCAP 3

NPY17 (N38) immortalized neurons were treated with 100 nM TCAP-3 and subjected to proteomic profiling. In this procedure, the nuclei of cells are isolated and the proteins extracted. This method provides an indication of proteins that are up or down regulated by a given treatment. The proteomic profile indicated that the majority of proteins up-regulated were associated with cell cycle, metabolism and the stress response. A. number of cytoskeletal proteins were also upregulated. This observation is of particular importance as many antidepressants have been shown to increase spine density and arborization of neuronal processes. Such events are regulated by cytoskeletal proteins.

| Proteomic profiling Up regulated at 12 hours | |
| --- | --- |
| Protein Processing | Extracellular Matrix |
| Parvulin; protein chaperone | protocadherin gammaB5 talin |
| Transcriptional Regulation | Cytoskeleton |
| Npw28 binding protein<br>Staufen; mRNA targetting<br>histone acetylmethyl transferase helicase<br>Cell Growth, Cycle and Proliferation | alpha actinin4<br>CLP36, actinin4 interaction<br>Cell Signalling |
| MIDA1; cell growth regulator<br>Smad 5; TGFbeta signalling<br>STE20-like kinase; apoptosis<br>Kp78, wnt pathway activation<br>Integrin linked kinase 1, wnt pathway p53 target protein,<br>tumor suppressor IGFBP, growth regulation<br>esp1, cell division<br>sepiapterin reductase<br>TGFbeta Bp1, growth regulation Rad23, uv repair protein | PKC iota |

B. MicroArray Studies
I. Method
RNA Isolation

Total RNA (TRNA) was isolated from 3 independent treated and untreated N38 hypothalmic cell cultures, pooled (to reduce the noise), utilizing Trizol Reagent (GIBCO/BRL) following the manufacturer's protocol. The quality of total RNA was assessed using an Agilent 2100 Bioanalyzer (version A.02.01S1232, Agilent Technologies). Only RNA with the OD ratio of 1.99-2.0 at 260/280 was used.

Oligonucleotide Arrays (Hybridization, Staining, and Scanning)

Hybridizations were performed on the Mouse MU74Av2 GeneChip Set (Affymetrix, Santa Clara, Calif.). Samples were prepared for hybridization according to Affymetrix instructions. Briefly, a primer encoding the T7 RNA polymerase promoter linked to oligo-dT$_{17}$ was used to prime double-stranded cDNA synthesis from each mRNA sample using Superscript II RNase H⁻ reverse transcriptase (Life Technologies, Rockville, Md.). Each purified (Qiaquick kit, Qiagen) double-stranded cDNA was in vitro transcribed using T7 RNA polymerase (T7 kit; Enzo), incorporating biotin-UTP and biotin-CTP (Enzo Biochemicals, New York, N.Y.) into the cRNAs, followed by purification using RNEasy (Qiagen) and quantitated by measuring absorption at 260 nm/280 nm. Samples were fragmented and hybridized to the Chip for 16 h at 45° C. and scanned (GeneArray scanner, Affymetrix). MicroArray Suite Version 5 (MASv5; Affymetrix) was used to scale intensities across the Genechips to 150 fluorescence units, and to determine expression values for each gene on the chip. The expression value for each gene was determined by calculating the average of differences (perfect match intensity minus mismatch intensity) of the probe pairs in use for the gene.

Data Analysis

Gene analysis software: Data analysis was performed using two independent softwares, GeneChip and GeneSpring. To identify differentially expressed transcripts, pairwise comparison analyses were carried out with MicroArray Suite Version 5 MicroArray Suite Version 5 (MASv5; Affymetrix). This approach, which is based on the Mann-Whitney pairwise comparison test, allows the ranking of results by concordance, as well as the calculation of significance (P value) of each identified change in gene expression. Statistically significant genes (P<0.05) were selected for further analysis. Moreover, statistically significant changes in mean expression values were determined by importing the data from MASv5 into GeneSpring 5 (Silicon Genetics, Redwood City, Calif.). A stepwise process was followed, first with normalizations. A per-chip followed by a per-gene normalization in order to facilitate direct comparison of biological differences. Next, a second method of filter using Affymetrix data and p value with cut-off of P<0.005 generated 4,841 genes which were used for subsequent analysis utilizing Hierarchical Clustering, k-means, Self Organization Map (SOM) utilizing GeneSpring 5.0.

II. Results

Further, to demonstrate that the cell lines can be used as a model for studying TCAP responsiveness, modulation, and in screening for TCAP modulators, microarray studies were performed on 1 nM TCAP-1 [SEQ ID NO 5 plus amidation signal GRR at C-terminus] treated N38 hypothalmic cells, which do not possess either CRF receptor subtype (Table 4). RNAs isolated from treated and untreated cells were analyzed on oligonucleotide arrays representing 12,884 mouse genes (Affymetrix, http://www.affymetrix.com). Standard filtering (p<0.005) and hierarchical clustering algorithm (average linage method: GeneSpring software—Silicon Genetics) identified significant changes in the expression of 4, 841/12,885 genes with 166 genes showing 1.5 fold down-regulation and 35 genes up-regulation in the TCAP-1-treated cells compared to the untreated cells. At 16 hours post-treatment, a significant decrease occurred among several genes, notably, GAS5, SDPR and CD95 that have been associated with growth arrest or apoptotic events (45-47). In contrast, upregulated genes including MK167, MOP3 and GDAP10 have been associated with cell proliferation and cell cycle modulation (48-50). A G-protein coupled receptor-related signal transduction pathway is indicated by the regulation of genes, CREM, AKAP8, AKAP95 and PDE6A. Downstream effectors of RAS such as EFK1 and RGL were also down regulated. Downregulation of the A kinase anchoring protein AKAP95 but upregulation of AKAP8 suggests that TCAP may act, in part, by changing the targeting pattern of PKA (51). The upregulation in inducible nitric oxide (INOS), a intracellular voltage-gated chloride channel (CLCN3) and the serotonin transporter (SLC6A4) may reflect the down stream actions of cAMP-mediated signal cascade and indicates the potential for TCAP to be involved in neuronal signaling systems. A role in inter-neuron communication by TCAP is also indicated by the modulation of genes associated with the regulation of vesicle trafficking. Thus, the TCAP responsive cell lines can be used to screen for modulators of neuronal function that affect growth, differentiation and communication.

Summary of Experimental Results

The teneurin c-terminal associated peptide (TCAP) represents the terminal 40 to 41 residues on all four of the known teneurin (Ten M) proteins. On all four of the teneurins, TCAP shows the greatest sequence homology among the entire exon suggesting that it is under the most stringent physiological constraints of the protein. TCAP is a potent inhibitor of neuronal and fibroblast growth possibly by arresting cell cycle. When injected into rat brain it increased the startle reflex and decreased self-administered reward behaviour and was shown to modulate the stress response. These data indicates that TCAP represents a novel neurohormonal system associated with neuronal growth and development.

The finding of a TCAP-like peptide on the carboxy terminus of a type II transmembrane protein is unusual. Assuming that the protein is only expressed on the extracellular face of the cell, then it is likely that the peptide acts in a paracrine manner to regulate the surrounding cells. All Ten M proteins possess a basic residue in positions −1 and −8 upstream from the putative cleavage site from the peptide. Such a basic residue arrangement is recognized by the prohormone convertase 7 (PC7) family of proteases (Saideh and Chretien, 1997), for the processing of peptide prohormones. Assuming this to be the case, then the requisite PC7-like protein would need to be expressed also on the extracellular face of the cell, or perhaps on the extracellular face of an adjacent cell. Alternatively, the protease may be secreted and act in a more mobile fashion. In any case, the release of the cleaved peptide would unlikely to occur in the bolus seen by vesicular release. It is also conceivable that the Ten-M protein is expressed in vesicles of the regulated pathway where intravesicular proteases could cleave the peptide before exocytosis. However, the synthetic peptide shows a strong tendency to aggregate and precipitate at concentrations higher than 2 ug/ul. This is likely due to the high number (15) of leucines, isoleucines, valine, tyrosines and phenylalanine within the peptide. Peptides that have high vesicular concentrations such as the urocortin-like peptide, sauvagine, found in the skin of a neotropical frog, *Phyllomedusa sauvagei*, tend to have a low proportion of hydrophobic residues (Pallai et al., 1983). Thus this physical characteristic of the TCAP peptide supports its preferential release from the cleavage from the extracellular face of the plasma membrane.

The TCAP portion of the Ten-M proteins appears to be the most highly conserved of the terminal exon of the protein. Such high levels of conservation occur when there are many physiological, biochemical constraints acting upon the sequence to inhibit change. Such resistance to change could result from essential interactions with processing or degrading enzymes, receptors, and/or transport proteins. The level of conservation of 90% between the paralogues in vertebrates is high in comparison to the CRF group of peptides to which TCAP appears to be most closely related.

In any case, a number of other bioactive peptides are initially expressed and processed in the same manner as TCAP. Other bioactive peptides such as tumor necrosis factor (TNF) (Utsumi et al., 1995), Apo-2 ligand (Pitti et al., 1996) and fractalkine (Garton et al., 2001) are processed in this manner. These peptides are directed outward at the end of the C-terminus on the extracellular face. Peptides processed and expressed in this manner have the potential for a variety of endocrine or juxtacrine roles. For example they may act as an adhesion molecule for cells displaying the appropriate receptor. Such actions could be particularly important during the migration of neurons in the developing brain, allowing neurons to be directed to a specific target. Alternatively, the peptide may be cleaved via a membrane-bound or extracellular matrix-associated protease to act as a paracrine/autocrine factor to modulate the actions of surrounding cells. Such a mechanism would be important for cells to protect against low oxygen stresses which occur in ischaemia. All three cytokines appear to be processed by a tumor necrosis factor alpha converting enzyme (TACE, ADAM17). This enzyme is also capable of cleaving the cell-surface ectodomain of the amyloid-beta precursor protein (Skovronsky et al. 2001), thus decreasing the generation of amyloid beta suggesting it may have a role in the aetiology of Alzheimer's disease.

The TCAP peptide appears to regulate several physiological events. In a mouse neuronal cell line, Gn11, and a rat fibroblast cell line, TGR1, treatment of TCAP at concentrations of $10^{-9}$ to $10^{-6}$ M could inhibit proliferation in a dose-dependent manner where maximal inhibition occurs at about 60%. There was no evidence of apoptosis or necrosis of the cells and morphology did not differ between treated and untreated cells.

This stress-related studies indicate an ability of the TCAP peptide to inhibit the damage done by environmental stresses on cells that would occur during periods of ischaemia or perhaps various neurodegenerative diseases. Given the decrease of proliferation rate seen in unstressed cells and the apparent increase in stressed cells suggests that TCAP may be acting in part to reduce the metabolic activity of the cell. Other related peptides have a similar effect. For example, urocortin can prevent cell death in primary cardiac myocyte cultures by stimulating the p42/p44 mitogen-activated protein (MAP) kinase pathway (Latchman, 2001). Under stressful conditions such as heat shock (Okosi et al., 1998) or ischaemia (Brar et al., 1999), urocortin mRNA is upregulated in cultured cardiac cells, and is also secreted into the medium (Brar et al., 1999), suggesting that it too, is acting in a paracrine fashion to regulate cell metabolism. This effect is much greater by urocortin than CRF. This is of particular interest given that the urocortin paralogues of the CRF family appear to represent evolutionarily older sequences than CRF (Lovejoy and Balment, 1999). Such paracrine actions on cell metabolism may be then one of the initial and critical functions of the ancestor gene that gave rise to both the TCAP and CRF/urocortin/diuretic group of peptides.

The data obtained so far can be used to delineate a tentative model for the mechanism for TCAP (FIG. 19). Initially, a stressor, such as changes in pH, temperature, or $O_2$ levels, or alternatively, a stress-induced ligand triggers an up-regulation of the Ten-M protein. Such stressors likely act through a number of signal transduction pathways including adenylate cyclase and guanylate cyclase. It is conceivable that the stressor also up-regulates the Ten-M cleaving enzyme such as TACE or PC7. The TCAP ligand is then cleaved from its protein and is free to act in an autocrine and paracrine manner. It binds to a G-protein coupled receptor that subsequently interacts with a G-inhibitory protein. This inhibits cAMP and cGMP production to inhibit activation of the cell. In a dividing neuron this would act to inhibit proliferation or migration, and in an mature non-dividing neuron could manifest as a reduction of synaptic output thereby inhibiting the neurological response of an activated nucleus of cells in the brain.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

TABLE 1

Cell Lines Screening

| MARKER | N-7 | N-22 | N-29 | N-38 |
|---|---|---|---|---|
| T antigen | + | + | + | + |
| NSE | + | + | + | + |
| GFAP | − | − | − | − |
| NT | − | − | − | − |
| ER alpha | + | + | + | + |
| ER beta | + | + | + | + |

TABLE 1-continued

Cell Lines Screening

| MARKER | N-7 | N-22 | N-29 | N-38 |
|---|---|---|---|---|
| Tph | + | + | − | w |
| Socs-3 | + | + | + | + |
| AR | − | − | N/A | + |
| G2R | + | + | + | − |
| CRF | − | − | − | − |
| GnRH | + | + | + | w |
| POMC | − | + | + | − |
| Gal | + | − | w | − |
| Lep Receptor | − | + | + | w |
| Agrp | + | + | + | + |
| Cart | − | − | − | − |
| NPY | − | − | + | + |
| proGlu | − | w | w | − |
| TH | + | − | + | − |
| GHRH | − | + | + | + |
| Avp | + | + | w | w |
| proTRH | − | − | − | − |
| Ucn | − | − | − | − |
| MCH | + | N/A | + | + |
| orexin | − | − | − | − |
| DAT | strong | − | w | − |
| CRFR1 | − | − | − | − |
| CRFR2 | − | − | − | − |
| Aromatase | − | − | − | strong |
| GnRH Receptor | − | − | − | − |
| Insulin receptor | + | + | + | + |
| Oxytocin | + | + | + | + |
| New-1 | − | − | − | − |
| New-2 | − | − | − | − |
| New-4 | − | − | + | − |
| GHS-R | N/A | N/A | N/A | − |
| Leptin | | | | |
| som | | | | |
| NTR | + | w | N/A | − |
| mc3R | | | | |
| mc4R | N/A | N/A | N/A | − |
| NPY-Y1 | | | | |
| NPY-Y2 | | | | |
| CRLR | N/A | N/A | N/A | − |
| Ghrelin | + | + | N/A | + |
| Ghrelin variant | + | − | N/A | − |

The following abbreviations will have their standard scientific abbreviations: T-Ag, Large T-antigen; NSE, neuron-specific enolase; GFAP, glial fibrillary acidic protein; SNTX, syntaxin; ER, estrogen receptor, AR, androgen receptor, LepR, leptin receptor b; Glp-2R (also G2R), glucagon-like peptide 2 receptor, SOCS-3, suppressor of cytokine signaling 3; NPY, neurapeptide Y; AGRP, agoutirelated peptide; POMC, proopiomelanocortin; CART, cocaine and amphetamine regulated transcript; MCH, melanin-concentrating hormone; Ucn, urocortin; NT, neurotensin; Gal, galanin; Orx, orexin; DAT, dopamine transporter; CRFR, corticotrophin-releasing factor receptor, proGlu, proglucagon; GHRH, growth hormone-releasing hormone; GnRH, gonadotropin-releasing hormone; GnRHR, gonadotropin-releasing hormone receptor, CRF, corticotrophin-releasing factor, TRH, thyroid-releasing hormone; AVP, arginine vasopressin; OXY, oxytocin; Arom, aromalase; TPH, tryptophan hydroxylase; TH, tyrosine hydroxylase; TenM-1 (also New-1); TenM-2 (also New-2); TenM-3 (also New-3); and TenM-4 (also New-4), Teneurins 1-4; GHS-R, growth hormone secratogue receptor; Lep, leptin; SOM, somatostatin; NTR, neurotensin receptor, MC3R, melanocortin receptor-3; MC4R, melanocortin receptor-4; NPY-Y1, NPY receptor Y1; NPY-Y2, NPY receptor Y2; CRLR, calcitonin receptor like receptor; nd, not done; na, not done; w, weak expression.

TABLE 2

Genes Regulated by TCAP-1 at 16 hours

| Cluster | Gene | Affimetrix Probe No. | Acc No. GB | Function | Fold change |
|---|---|---|---|---|---|
| Growth/ Differentiation | GAS5 | 98530 | AI849615 | Growth arrest specific transcript | 0.46 |
| | SDPR | 160373 | AI839175 | Serum deprivation response protein | 0.57 |
| | PPAN | 160802 | AA674812 | Peter Pan homologue | 0.62 |
| | CD95 | 102921 | M83649 | Fas antigen | 0.61 |
| | CRD-BP | 102627 | AF061569 | CRD-binding protein | 0.59 |
| | SSG1 | 160298 | AW122012 | Steroid sensitive gene 1 | 0.62 |
| | DIP1/2 | 97353 | AI837497 | DAB2 interacting protein | 0.68 |
| | GBP3 | 103202 | AW047476 | Guanylate binding protein | 0.63 |
| | P202 | 161173 | AV229143 | 202 interferon activatable protein | 0.61 |
| | CAII | 103441 | AI94248 | Casein kinase II | 0.61 |
| | INI1B | 99924 | AW121845 | Integrase interacting protein 1B | 0.48 |
| | MMP1 | 100484 | X66473 | Matrix metalloproteinase 1 | 0.55 |
| | MMP10 | 94724 | Y13185 | Matrix metalloproteinase 10 | 0.59 |
| | PTK7 | 92325 | AI326889 | Receptor protein tyrosine kinase | 1.53 |
| | P204 | 98466 | M31419 | Interferon activatable protein | 1.85 |
| | MKI67 | 161931 | AV309347 | Cell cycle protein regulator | 1.70 |
| | MOP3 | 102382 | AB014494 | Circadian rhythm regulator | 1.57 |
| | ST7 | 160591 | AI504013 | Suppressor of tumourigenicity | 1.97 |
| | GDAP10 | 94192 | Y17860 | Ganglioside induced diff. protein 10 | 1.62 |
| Signalling/ Communication | ERK1 | 101834 | Z14249 | Mitogen activated protein kinase | 0.64 |
| | ALK3 | 92767 | D16250 | Bone morphogenic protein receptor | 0.60 |
| | BMP4 | 93456 | L47480 | Bone morphogenic protein-4 | 0.52 |
| | IL1R | 93914 | M20658 | Interleukin 1 receptor | 0.60 |
| | GR | 98818 | X04435 | Glucocorticoid receptor | 0.66 |
| | BARK1 | 104270 | AA982714 | β adrenergic receptor kinase 1 | 0.61 |
| | CAMIII | 92631 | M19380 | Calmodulin III | 0.53 |
| | PCDHγ | 160976 | AA222943 | protocadherin γ | 0.42 |
| | AKAP95 | 95001 | AB028920 | A kinase anchor protein 95 | 0.60 |
| | TTF-1IP | 161019 | W41560 | TTF-1 interacting peptide | 0.50 |
| | CREMβ1 | 100533 | M60285 | cAMP-responsive element modulator | 1.61 |
| | AKAP8 | 161088 | AV171460 | A kinase anchor protein 8 | 1.58 |
| | PDE6A | 100696 | X60664 | cGMP Phosphodiesterase α | 1.68 |
| | INOS | 104420 | U43428 | Inducible nitric oxide synthetase | 1.50 |
| | FNBX | 92754 | D49920 | Ferredoxin-NADP reductase | 1.61 |
| | SLC6A4 | 161695 | AV230927 | Serotonin transporter | 1.53 |
| | CLCN3 | 94465 | AF029347 | Chloride channel protein 3 | 1.66 |

TABLE 2-continued

Genes Regulated by TCAP-1 at 16 hours

| Cluster | Gene | Affimetrix Probe No. | Acc No. GB | Function | Fold change |
|---|---|---|---|---|---|
| Processing | ARF1 | 95156 | AI1853873 | ADP ribosylation factor 1 | 0.63 |
| | CLM2-B | 93492 | AB013469 | Cytohesin-2 | 0.63 |
| | YIPID | 99675 | AI839766 | Rab-mediated membrane transport | 1.88 |
| | RAB10 | 160149 | AI841543 | Ras oncogene homologue | 1.62 |
| | GP25L2 | 100074 | AW046723 | gp25L brings cargo forward from ER | 1.53 |
| | AP4S1 | 104561 | AI847561 | Adaptor related protein complex | 1.52 |

The change in expression levels is indicated relative to the untreated control cell for the same time period of 16 hours. Values >1.5 fold or <0.70 fold were considered significant.

FULL CITATIONS FOR REFERENCES REFERRED TO IN THE SPECIFICATION

Barsyte et al., (1999), "Rainbow trout (*oncorhynchus mykiss*) urotensin-1: structural differences between the urotensins-1 and urocortins." Gen Comp. Endocrinol. 115, 169-185.

Baumgartner, S. et al., (1994). "A *Drosophilia* gene related to tenascin, is a new pair-rule gene. EMBO J. 13:3728-3740.

Ben-Zur, T. & Wides, R. (1999) Mapping homologs of *Drosophila* odd Oz (odz): Doc4/Odz4 to mouse chromosome 7, Odz1 to mouse chromosome 11; and ODZ3 to human chromosome Xq25. Genomics 58, 102-103.

Ben-Zur, T., Feige, E., Motro, B. & Wides R. (2000) The mammalian Odz gene family: homologs of a *drosphila* pair-rule gene with expression implying distinct yet overlapping developmental roles. Dev. Biol. 217, 107-120.

Brar, B. K., A. Stephanou, et al. (1999). "CRH-like peptides protect cardiac myocytes from lethal ischaemic injury." Molecular and Cellular Endocrinology 158: 55-63.

Brooke, N. M., J. Garcia-Fernandez, et al. (1998). "The para-hox gene cluster is an evolutionary sister of the hox gene cluster." Nature 392: 920-922.

Broqua, P. et al., (1995). "Behavioral effects of neuropeptide Y receptor agonists in the elevated plus-maze and fear-potentiated startle procedures. Behav. Pharmacol. 6:215-222.

Bunger et al., (2000). "Mop3 is an essential component of the master circadian pacemaker in mammals. Cell, 103:1009-1017.

Carroll, S. B. (1995). "Homeotic genes and the evolution of arthropods and chordates." Nature 376: 479-485.

Coast, G. M. (1998). "Insect Diuretic peptides: Structures, evolution and actions." American Zoologist 38: 442-449.

Coccia, E. M. et al., (1992). "Regulation and expression of a growth arrest-specific gene (gas5) during growth differentiation and development. Mol. Cell. Biol. 12:3514-3521.

Copertino, D., G. M. Edelman, et al. (1997). "Multiple promoter elements differentially regulate the expression of the mouse tenascin gene." Proc. Natl. Acad. Sci. U.S.A. 93: 1846-1851.

Danielson P B, Dores R M (1999) Molecular evolution of the opioid/orphanin gene family Gen Comp. Endocrinol 113: 169-186.

Donaldson, C. J., S. W. Sutton, et al. (1996). "Cloning and characterization of human urocortin." Endocrinology 137 (5): 2167-2170.

Drevets, W. C. (2001) Neuroimaging and neuropathological studies of depression: Implications for the cognitive emotional features of mood disorders. Curr. Opin. Neurobiol. 11, 240-249.

Ericsson, A., Liu, C., Hart, R. P. & Sawchenko, P. E. (1995) Type 1 interleukin-1 receptor in the rat brain: Distribution, regulation, and relationship to sites of IL-1 induced cellular activation. J. Comp. Neurol. 361, 681-698.

Erspamer, V., G. Falconieri Erspamer, et al. (1980). "Sauvagine, a new polypeptide from *Phyllomedusa sauvagei* skin." Naunyn-Schmiedeberg's Archives of Pharmacology 312: 265-270.

Fayos, R. et al. (2003). Induction of flexibility through protein-protein interactions. J. Biol. Chem. In press.

Frankland P W, Josselyn S A, Bradwejn J, Vaccarino F J, Yeomans J S. (1996) Intracerebroventricular infusion of the CCKB receptor agonist pentagastrin potentiates acoustic startle. Brain Research; 733(1):129-32

Frankland P W, Josselyn S A, Bradwejn J, Vaccarino F J, Yeomans J S. (1997) Activation of amygdala cholecystokininB receptors potentiates the acoustic startle response in the rat. Journal of Neuroscience 17(5):1838-47.

Garton, K. J. et al, (2001). Tumor necrosis factor-converting enzyme (ADAM17) mediates the cleavage and shedding of fractalkine (CX3CL1). J. Biol. Chem. 276, 37993-38001.

Graner, M. W., T. A. Bunch, et al. (1998). "Splice variants of the Drosphila PS2 integrins differentially interact with RGD-containing fragments of the extracellular proteins tiggrin, Ten-m and D-laminin alpha2." Journal of Biological Chemistry 273.

Greer J. M., Puetz, J., Thomas, K. R. & Capecchi, M. R. (2000). Maintenance of functional equivalence during paralogous gene evolution. Nature 403, 661-665.

Gustavson K. H. et al., (1993). "New X-linked syndrome with severe mental retardation, severely impaired vision, severe hearing defect, epileptic seizures, spasticity, restricted joint mobility, and early death. Am. J. Med. Genet. 45(5): 654-8.

Gustincich, S. et al., (1999). "The human serum response gene (SDPR) maps to 2q32-q33 and codes for a phosphatidylserine-binding protein. Genomics. 57:120-129.

Hsu, S. Y., & Hsuch, A. J. W. (2001). Human stresscopin and stresscopin-related peptide are selective ligands for the coticotropin-releasing hormone receptor. Nature Med. 7, 605-611.

Ichiwara, T., D. McMaster, et al. (1982). "Isolation and amino acid sequence of urotensin-1, a vasoactive and ACTH-releasing neuropeptide from the carp (*Cyprinus carpio*)." Peptides 3: 859-867.

Ishida, I., T. Ichikawa, et al. (1986). "Cloning and sequence analysis of cDNA encoding urotensin-I precursor." Proceedings of the National Academy of Sciences, USA 83: 308-312.

Johnsen, A. H. (1998). Phylogeny of the cholecystokinin/gastrin family. Front. Neuroendocrinol. 19, 73-99.

Kaaijk, P. et al., (2003). "Cell proliferation is related to in vitro drug resistance in childhood acute leukaemia, Br. J. Cancer, 88: 775-781.

Kishimoto, T., R. V. Pearse, et al. (1995). "A sauvagine/corticotropin-releasing factor receptor expressed in heart and skeletal muscle." Proceedings of the National Academy of Sciences, USA. 92: 1108-1112.

Krase, W., Koch, M., & Schnitzler, H. Substance P is involved in the sensitization of the acoustic startle response by footshock in rats. Behav. Brain Res., 63, 81-88 (1994). -1185 (1999).

Lang P J, Davis M, Ohman, A (2000) Fear and anxiety: animal models and human cognitive psychophysiology. Journal of Affective Disorders, 61:137-159.

Larhammar, D. (1996a). "Evolution of neuropeptide Y, peptide YY, and pancreatic polypeptide." Regulatory Peptide 62: 1-11.

Larhammar, D. (1996b). "Structural diversity of receptors for neuropeptide Y, peptide YY and pancreatic polypeptide." Regulatory Peptides 65: 165-174.

Latchman, D. S. (2001). "Urocortin protects against ischemic injury via a MAPK-dependent pathway." Trends in Cell Metabolism 11: 167-169.

Lederis, K., A. Letter, et al. (1983). "Isolation, analysis of structure, synthesis, and biological actions of urotensin I neuropeptides." Can. J. Biochem. Cell. Biol. 61: 602-614.

Lederis, K., J. Fryer, et al. (1985). "Neurohormones from fish tails. II. Actions of urotensin-I in mammals and fishes." Recent Progress in Hormone Research 41: 553-576.

LeFeuvre, R. A., N. J. Rothwell, et al. (1989). "A comparison of the thermogenic effects of CRF, sauvagine and urotensin-I in the rat." Hormones and Metabolism Research 21: 525-526.

Lenz, H. J., L. A. Fisher, et al. (1985). "Corticortropin-releasing factor, sauvagine, and urotensin-I: effects on blood flow." American Journal of Physiology 249: E85-E90.

Levine, A., D. Gartenberg, et al. (2000). "The genetics and molecular structure of the drososphila pair-rule gene odd Oz (odz)." Gene 200, 59-74.

Levine, A. et al. (1994). "A novel Drosophila pair rule gene". Cell, 77:587-598.

Lewis et al., (2001). Identification of urocortin III, an additional member of the corticotropin-releasing factor (CRF) family with high affinity for the CRF 2 receptor. Proc. natn. Acad. Sci. USA. 98, 7570-7575.

Li, C., Vaughan, J., Sawchenko, P. E. & Vale, W. W. (2002). Urocortin III-immunoreactive projections in rat brain: Partial overlap with sites of type 2 corticotropin-releasing factor receptor expression. J. Neurosci. 22, 991-1001.

Liang, K. C. et al., (1992). Lesions of the central nucleus of the amygdala, but not the paraventricular nucleus of the hypothalamus, block the excitatory effects of corticotropin-releasing factor on the acoustic startle reflex. J. Neurosci., 12, 2313-232

Liu, H. et al., (1999). "Isolation of 10 differentially expressed cDNAs in differentiated Neuro2a cells induced through controlled expression of the CD3 syenthetase gene". J. Neurochem. 72:1781-1790.

Lovejoy, D. A. (1996). "Peptide hormone evolution:Functional heterogeneity with GnRH and CRF families." Biochemistry and Cell Biology 74(1): 1-7.

Lovejoy, D. A. & Balment, R. J. (1999). Evolution and physiology of the corticotropin-releasing factor (CRF) family of neuropeptides and vertebrates. Gen. comp. Endocrinol 115, 1-22.

Malmgren H., et al. (1993). "Linkage mapping of a severe X-linked mental retardation syndrome". Am. J. Genet. 52(6):1046-52.

Manji, H. K., Drevets, W. C. & Charney, D. S. (2001). The cellular neurobiology of depression. Nat. Med. 7, 541-547.

Melchiorri, P. and P. Negri (1981). "Action of sauvagine on the mesenteric vascular bed of the dog." Regulatory Peptides 2: 1-13.

Menard J, Treit D (1999) Effects of centrally administered anxiolytic compounds in animal models of anxiety. Neuroscience and Biobehavioral Reviews 23: 591-613.

Mieda, M, Kikuchi, Y., Hirate, Y., Aoki, M. & Okamoto, H. (1999). Compartmentalized expression of zebrafish ten-m3 and ten-m4, homologues of the Drosophila ten(m)/odd Oz gene, in the central nervous system. Mech. Dev. 87, 223-227.

Minet, A. D., Rubin, B. P., Tucker, R. P., Baumgartner, S. & Chiquet-Ehrismann, R. (1999). Teneurin-1, a vertebrate hoomologue of the Drosophila pair-rule gene, Ten-m, is a neuronal protein with a novel type of heparin-binding domain. J. Cell. Sci. 112, 2019-2032.

Montecucchi, P. C., A. Henschen, et al. (1979). "Structure of Sauvagine, a vasoactive peptide from the skin of a frog." Hoppe-Seyler's Z. Physiol. Chem. 360: 1178.

Montminy, M. (1993). Control of transcription and cellular proliferation by cAMP. General and Cell-Type-Specific Gene Expression. M. Karin. Boston, Birkauser: 75-91.

Nestler, E. J. et al., (2002). Neurobiology of Depression. Neuron. 34, 13-25.

Ohno, S., U. Wolf, et al. (1968). "Evolution from fish to mammals by gene duplication." Heredity 59: 169-189.

Ohno, S. (1996). "The notion of the cambrian pananimalia genome." Proc. Natl. Acad. Sci. U.S.A. 93: 8475-8478.

Ohno, S. (1997). "The reason for as well as the consequence of the cambrian explosion in animal evolution." Journal of Molecular Evolution 44 (Suppl. 1): S23-S27.

Okosi, A., B. K. Brar, et al. (1998). "Expression and protective effects of urocortin in cardiac myocytes." Neuropeptides 32: 167-171.

Oohashi, T. et al., (1999). Mouse Ten-m/Odz is a new family of dimeric type II transmembrane proteins expressed in many tissues. J. Cell Biol. 145, 563-577.

Otaki, J. M. and S. Firestein (1999). "Neurestin: Putative transmembrane molecule implicated in neuronal development." Develomental Biology 212: 165-181.

Pallai, P. V., M. Mabilia, et al. (1983). "Structural homology of corticotropin-releasing factor, sauvagine, and urotensin-1: Circular dichroism and prediction studies." Proceedings of the National Academy of Sciences, USA 80: 6770-6774.

Park, J. H., Y. J. Lee, et al. (2000). "Genomic organization and tissue specific expression of rat urocortin." Neuroscience Letters 292: 45-48.

Pitti, R. M. et al., (1996). Induction of apoptosis by Apo-2 ligand, a new member of the tumor necrosis factor cytokine family. J. Biol. Chem. 271, 12687-12690.

Reyes, T. M., K. Lewis, et al. (2001). "Urocortin II: a member of the corticotropin-releasing factor (CRF) neuropeptide family that is selectively bound by type 2 receptors." Proc. Natl. Acad. Sci. U.S.A.: 2843-2848.

Robinson, B. M., et al. (1999). "CRF and Urocortin Genes In Syrian Hamster (Mesocritus auratus); Cloning and Characterization." Peptides, 20, 1177-1185.

Ron D, Habener J F. 1992 CHOP, a novel developmentally regulated nuclear protein that dimerizes with transcription factors C/EBP and LAP and functions as a dominant-negative inhibitor of gene transcription. Genes Dev. 6:439-53.

Rubin, B. P., Tucker, R. P. Martin, D. & Chiquet-Ehrismann, R. (1999) Teneurins: A novel family of neuronal cell surface proteins in vertebrates, homologous to the Drosophila pair-rule gene product Ten-m Dev. Biol. 216, 195-209.

Sapolsky, R M (1992). Neuroendocrinology of the stress response. In: Becker J B, Breedlove S M, Crews D (eds.), *Behavioral Endocrinology*, A Bradford Book, MIT Press, Cambridge, Mass., p. 288.

Schilling, L., C. Kanzler, et al. (1998). "Characterization of the relaxant action of urocortin, a new peptide related to corticotropin-releasing factor in the rat isolated basilar artery." British Journal of Pharmacology 125: 1164-1171.

Seidah N. G. and Chretien M., (1997). "Eukaryotic protein processing: endoproteolysis of precursuor proteins". Curr. Opin. Biotechnol. 8(5):602-7.

Simmons, D. M., Arriza, J. L. & Swanson, L. W. (1989). A complete protocol for in situ hybridization of messenger RNAs in brain and other tissues with radiolabelled single-stranded RNA probes. J. Histotech 12, 169-181.

Sirinathsinghji, D. J. S., L. H. Rees, et al. (1983). "Corticotropin-releasing factor is a potent inhibitor of sexual receptivity in the female rat." Nature 305: 232-234.

Spina, M., E. Merlo-Pich, et al. (1996). "Appetite-suppressing effects of urocortin, a CRF-related peptide." Science 273: 1561-1564.

Stanger, B. Z. (1996). "Looking beneath the surface: the cell death pathway of Fas/Apo-1 (CD95)". Mol. Med. 2:7-20.

Tellam D. J. et al., (1998) Direct regulation of GnRH transcription by CRF-like peptides in an immortalized neuronal cell line. NeuroReport 9, 3135-3140.

Turnbull, A. V., W. Vale, et al. (1996). "Urocortin, a corticotropin-releasing factor-related mammalian peptide, inhibits edema due to thermal injury in rats." European J. of Pharmacology 303: 213-216.

Utsumi T. et al., Human pro-tumor necrosis factor: Molecular determinants of membrane translocation, sorting and maturation. Mol. Cell. Biol. 15, 6395-6405. (1995).

Vale W., Speiss, J., Rivier, C. & Rivier, J. Characterization of a 41-residue ovine hypothalamic peptide that stimulates secretion of corticotropin and B-endorphin. Science 213, 1394-1397 (1981).

Vaughan, J., C. Donaldson, et al. (1995). "Urocortin, a mammalian neuropeptide related to fish urotensin-1 and to corticotropin-releasing factor." Nature 378: 287-292.

Wang, X.-Z., M. Kuroda, et al. (1998). "Identification of novel stress induced genes downstream of chop." EMBO J. 17: 3619-3630.

Wang X. Z. et al., (1996). "Signals from the stressed endoplasmic reticulum induce C/EBP-homologous protein (CHOP/GADD153)." Mol. Cell Biol. 16(8):4273-80.

Xiong, Y. T., L. Y. Xie, et al. (1995). "Signaling properties of mouse and human corticotropin-releasing factor (CRF) receptors-decreased coupling efficiency of human type-II CRF receptor." Endocrinology 136: 1828-1834.

Zhan Q, Lord K A, Alamo I Jr, Hollander M C, Carrier F, Ron D, Kohn K W, Hoffman B, Liebermann D A, Formace A J Jr. 1994 The gadd and MyD genes define a novel set of mammalian genes encoding acidic proteins that synergistically suppress cell growth. Mol Cell Biol. 14:2361-71.

Zhong M. et al., (1999). "The prosegments of furin and PC7 as potent inhibitors of proprotein convertases. In vitro and ex vivo assessment of their efficacy and selectively." J. Biol. Chem. 274(48):33913-20.

Zhou, L., C. J. Donaldson, et al. (1998). "The structures of the mouse and human urocortin genes (Ucn and UCN)." Genomics 50: 23-33.

Zhou, A., Webb, G, Zhu, X. & Steiner, D. F. Proteolytic processing in the secretory pathway. J. Biol. Chem. 274, 20745-20748 (1999).

Zinszner H. et al. (1998). "CHOP is implicated in programmed cell death in response to impaired function of the endoplasmic reticulum. Genes Dev., 12(7):982-95.

We claim:

1. An isolated teneurin c-terminal associated peptide of 38 to 41 amino acids having anxiolytic and/or anxiogenic activity, which consists of:
   (i) the amino acid sequence as shown in SEQ ID NO: 69; or
   (ii) a 38 to 41 amino acid sequence that has at least 95% identity to SEQ ID NO: 69; or
   (iii) a fragment of the carboxy terminal end of (i) or (ii) of at least 38 amino acids; or
   (iv) a 41 amino acid sequence comprising SEQ ID NO: 69, or a pharmaceutically acceptable salt thereof.

2. An isolated teneurin c-terminal associated peptide of claim 1 further comprising an amidation signal sequence at the carboxy terminus selected from the group consisting of GKR and GRR.

3. A pharmaceutical composition comprising the peptide of claim 1 and a pharmaceutically acceptable vehicle.

4. An anxiolytic and/or anxiogenic isolated peptide consisting of a 38-41 amino acid sequence, wherein the amino acid sequence is the 38 to 41 amino acid sequence of the carboxy terminus of human Ten M1 (SEQ ID NO: 8) minus the amidation sequence, or a 38 to 41 amino acid sequence that has at least 95% identity thereto, or pharmaceutically acceptable salt thereof.

5. An isolated peptide of claim 4 further comprising an amidation signal sequence at the carboxy terminus.

6. An isolated peptide of claim 4 selected from SEQ ID NOs: 69 or 70 or having at least 95% identity thereto or a pharmaceutically acceptable salt thereof.

7. An isolated peptide of claim 4 consisting of SEQ ID NO: 69 or having at least 95% identity thereto or a pharmaceutically acceptable salt thereof.

8. An isolated peptide of claim 5, consisting of SEQ ID NO: 71 or 72 or a pharmaceutical acceptable salt thereof.

9. An isolated peptide of claim 4 consisting of SEQ. ID. NO. 69 or a pharmaceutical acceptable salt thereof.

10. An isolated anxiolytic and/or anxiogenic peptide which is a homologue of claim 4 consisting of a 38 to 41 amino acid sequence, wherein the amino acid sequence is the 38 to 41 amino acid sequence of the carboxy terminus of mouse Ten M1 (SEQ ID NO: 4) minus the amidation sequence, or having at least 95% identity thereto or pharmaceutically acceptable salt thereof.

11. An isolated peptide of claim 10 further comprising an amidation signal sequence at the carboxy terminus.

12. An isolated peptide of claim 10 selected from SEQ ID NO: 37 or 38 or having at least 95% identity thereto or a pharmaceutically acceptable salt thereof.

13. An isolated peptide of claim 12 having SEQ ID NO: 37 or having at least 95% identity thereto or a pharmaceutically acceptable salt thereof.

14. An isolated peptide of claim 11, consisting of SEQ ID NO: 39 or 40 or a pharmaceutical acceptable salt thereof.

15. An isolated peptide of claim 10 consisting of SEQ ID NO: 37 or pharmaceutically acceptable salt thereof.

16. A pharmaceutical composition comprising the peptide of claim 4 and a pharmaceutically acceptable vehicle.

17. A pharmaceutical composition comprising the peptide of claim 10 and a pharmaceutically acceptable vehicle.

18. An isolated peptide of claim 1 consisting of 40 to 41 amino acids or a pharmaceutically acceptable salt thereof.

19. A pharmaceutical composition comprising the peptide of claim 2 and a pharmaceutically acceptable vehicle.

20. An isolated peptide of claim 2 consisting of 41 to 44 amino acids or a pharmaceutically acceptable salt thereof.

21. An isolated peptide of claim 4 consisting of 40 to 41 amino acids or a pharmaceutically acceptable salt thereof.

22. An isolated peptide of claim 21 further comprising an amidation signal sequence at the carboxy terminus.

23. An isolated peptide of claim 10 consisting of 40 to 41 amino acids or a pharmaceutically acceptable salt thereof.

24. An isolated peptide of claim 23 further comprising an amidation signal sequence at the carboxy terminus.

25. An isolated peptide of claim 5 selected from SEQ ID NO: 71 or 72 or having at least 95% identity thereto or a pharmaceutically acceptable salt thereof.

26. An isolated peptide of claim 25 having SEQ ID NO: 71 or having at least 95% identity thereto or a pharmaceutically acceptable salt thereof.

27. An isolated peptide of claim 26 consisting of SEQ ID NO: 71 or a pharmaceutical acceptable salt thereof.

28. An isolated peptide of claim 11 selected from SEQ ID NO: 39 or 40 or having at least 95% identity thereto or a pharmaceutically acceptable salt thereof.

29. An isolated peptide of claim 28 having SEQ ID NO: 39 or having at least 95% identity thereto or a pharmaceutically acceptable salt thereof.

30. An isolated peptide of claim 29 consisting of SEQ ID NO: 39 or a pharmaceutical acceptable salt thereof.

31. A pharmaceutical composition comprising the peptide of claim 5 and a pharmaceutically acceptable vehicle.

32. A pharmaceutical composition comprising the peptide of claim 11 and a pharmaceutically acceptable vehicle.

33. A pharmaceutical composition comprising an anxiogenic and/or anxiolyic isolated peptide of any one of SEQ ID NO: 37 to 40, or SEQ ID NO:69 to 72, or having at least 95% identity thereto or a pharmaceutically acceptable salt thereof; and a pharmaceutically acceptable vehicle.

34. A pharmaceutical composition of claim 33 comprising an isolated peptide of any one of SEQ ID NO: 39 or 71 or having at least 95% identity thereto or a pharmaceutically acceptable salt thereof; and a pharmaceutically acceptable vehicle.

35. A pharmaceutical composition of claim 34 comprising an isolated peptide of SEQ ID NO: 39 or having at least 95% identity thereto or a pharmaceutically acceptable salt thereof; and a pharmaceutically acceptable vehicle.

* * * * *